US011492345B2

(12) United States Patent
Reddy et al.

(10) Patent No.: US 11,492,345 B2
(45) Date of Patent: Nov. 8, 2022

(54) COMPOUNDS AND THEIR METHODS OF USE

(71) Applicant: Praxis Precision Medicines, Inc., Cambridge, MA (US)

(72) Inventors: Kiran Reddy, Boston, MA (US); Gabriel Martinez Botella, Wayland, MA (US); Andrew Mark Griffin, L'lle Bizard (CA); Brian Edward Marron, Durham, NC (US)

(73) Assignee: PRAXIS PRECISION MEDICINES, INC., Cambridge, MA (US)

( * ) Notice: Subject to any disclaimer, the term of this patent is extended or adjusted under 35 U.S.C. 154(b) by 0 days.

(21) Appl. No.: 16/485,581

(22) PCT Filed: Feb. 13, 2018

(86) PCT No.: PCT/US2018/018044
§ 371 (c)(1),
(2) Date: Aug. 13, 2019

(87) PCT Pub. No.: WO2018/148745
PCT Pub. Date: Aug. 16, 2018

(65) Prior Publication Data
US 2020/0247793 A1 Aug. 6, 2020

Related U.S. Application Data

(60) Provisional application No. 62/545,549, filed on Aug. 15, 2017, provisional application No. 62/481,468, filed on Apr. 4, 2017, provisional application No. 62/458,317, filed on Feb. 13, 2017.

(51) Int. Cl.
C07D 413/06 (2006.01)
C07D 263/58 (2006.01)
C07D 413/10 (2006.01)
C07D 498/04 (2006.01)

(52) U.S. Cl.
CPC ......... *C07D 413/06* (2013.01); *C07D 263/58* (2013.01); *C07D 413/10* (2013.01); *C07D 498/04* (2013.01)

(58) Field of Classification Search
CPC .............. A61K 31/4184; A61K 31/423; A61K 31/429; A61K 31/4439; A61K 31/497; A61K 31/506; A61K 31/5377; A61K 45/06; C07D 209/34; C07D 235/26; C07D 263/58; C07D 413/06; C07D 413/10; C07D 498/04
See application file for complete search history.

(56) References Cited

U.S. PATENT DOCUMENTS

| 3,845,770 A | 11/1974 | Theeuwes et al. |
| 4,112,095 A | 9/1978 | Allen, Jr. et al. |
| 4,230,705 A | 10/1980 | Allen, Jr. et al. |
| 4,242,515 A | 12/1980 | Trust et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hsieh et al. |
| 5,616,345 A | 4/1997 | Geoghegan et al. |
| 5,905,079 A | 5/1999 | Sargent et al. |
| 6,589,952 B2 | 7/2003 | Bakthavatchalam et al. |
| 7,863,279 B2 | 1/2011 | Even et al. |
| 8,030,305 B2 | 10/2011 | Lu et al. |
| 8,173,654 B2 | 5/2012 | Lu et al. |
| 8,198,448 B2 | 6/2012 | Albrecht et al. |
| 8,212,041 B2 | 7/2012 | Albrecht et al. |
| 8,217,177 B2 | 7/2012 | Albrecht et al. |
| 8,524,900 B2 | 9/2013 | Albrecht et al. |
| 8,937,060 B2 | 1/2015 | Cid-Nunez et al. |
| 8,952,034 B2 | 2/2015 | Corkey et al. |
| 9,066,954 B2 | 6/2015 | Albrecht et al. |
| 9,371,329 B2 | 6/2016 | Corkey et al. |
| 10,280,184 B2 | 5/2019 | Friedman et al. |
| 11,014,931 B2 | 5/2021 | Griffin et al. |
| 11,261,188 B2 | 3/2022 | Reddy et al. |
| 11,278,535 B2 | 3/2022 | Reddy et al. |
| 11,279,700 B2 | 3/2022 | Griffin et al. |
| 2002/0049208 A1 | 4/2002 | Bakthavatchalam et al. |
| 2009/0124609 A1 | 5/2009 | Albrecht et al. |
| 2009/0203707 A1 | 8/2009 | Rajamani et al. |

(Continued)

FOREIGN PATENT DOCUMENTS

| JP | 2017001991 A | 1/2017 |
| WO | WO-2006061428 A2 | 6/2006 |

(Continued)

OTHER PUBLICATIONS

US 8,754,103 B2, 06/2014, Corkey et al. (withdrawn)
Woodland, et al, Discovery of Inhibitors of Trypanosoma brucei by Phenotypic Screening of a Focused Protein Kinase Library, ChemMedChem, 10(11), 1809-1820 (2015). (Year: 2015).*
Fukaya, et al, Identification of a Novel Benzoxazolone Derivative as a Selective, Orally Active 18 kDa Translocator Protein (TSPO) Ligand, J. of Med. Chem., 56, 8191-8195 (2013). (Year: 2013).*
Albright et al. "Synthesis and anxiolytic activity of 6-(substituted-phenyl)-1,2,4-triazolo[4,3-b]pyridazines," J. Med. Chem. (1981) vol. 24, pp. 592-600.
Anderson et al. "Unexpected efficacy of a novel sodium channel modulator in Dravet Syndrome," Scientific Reports. 2017.

(Continued)

Primary Examiner — Erich A Leeser
(74) Attorney, Agent, or Firm — McCarter & English, LLP; Jonathan M. Sparks

(57) ABSTRACT

The present invention is directed to, in part, fused heteroaryl compounds and compositions useful for preventing and/or treating a disease or condition relating to aberrant function of a voltage-gated, sodium ion channel, for example, abnormal late/persistent sodium current. Methods of treating a disease or condition relating to aberrant function of a sodium ion channel including Dravet syndrome or epilepsy are also provided herein.

24 Claims, No Drawings

(56) References Cited

U.S. PATENT DOCUMENTS

| | | | |
|---|---|---|---|
| 2010/0088778 | A1 | 4/2010 | Mulley et al. |
| 2011/0021521 | A1 | 1/2011 | Corkey et al. |
| 2012/0010192 | A1 | 1/2012 | Kobayashi et al. |
| 2012/0065191 | A1 | 3/2012 | Kiss et al. |
| 2012/0245164 | A1 | 9/2012 | Auger et al. |
| 2013/0315895 | A1 | 11/2013 | Farrell et al. |
| 2014/0066443 | A1 | 3/2014 | Beshore et al. |
| 2014/0303158 | A1 | 10/2014 | Corkey et al. |
| 2015/0038503 | A1 | 2/2015 | Bourotte et al. |
| 2015/0344457 | A1 | 12/2015 | Duncan et al. |
| 2016/0159801 | A1 | 6/2016 | Quinn et al. |
| 2016/0235718 | A1 | 8/2016 | Baraban |
| 2016/0297799 | A1 | 10/2016 | Brookings et al. |
| 2016/0317536 | A1 | 11/2016 | Reich et al. |
| 2019/0308938 | A1 | 10/2019 | McCormack et al. |
| 2019/0389868 | A1 | 12/2019 | Reddy et al. |
| 2020/0179358 | A1 | 6/2020 | Reddy et al. |
| 2020/0377499 | A1 | 12/2020 | Griffin et al. |
| 2020/0377506 | A1 | 12/2020 | Reddy et al. |
| 2020/0377507 | A1 | 12/2020 | Griffin et al. |
| 2021/0087197 | A1 | 3/2021 | Griffin et al. |
| 2021/0163488 | A1 | 6/2021 | Griffin et al. |
| 2021/0171530 | A1 | 6/2021 | Reddy et al. |
| 2021/0188839 | A1 | 6/2021 | Reddy et al. |
| 2021/0188852 | A1 | 6/2021 | Reddy et al. |
| 2021/0355118 | A1 | 11/2021 | Reddy et al. |

FOREIGN PATENT DOCUMENTS

| | | | | |
|---|---|---|---|---|
| WO | WO-2007075567 | A1 | 7/2007 | |
| WO | WO-2008008539 | A2 | 1/2008 | |
| WO | WO-2010053757 | A1 | 5/2010 | |
| WO | WO-2010056865 | A1 | 5/2010 | |
| WO | WO-2010074807 | A1 | 7/2010 | |
| WO | WO-2011014462 | A1 | 2/2011 | |
| WO | WO-2011056985 | A2 | 5/2011 | |
| WO | WO-2012003392 | A1 | 1/2012 | |
| WO | WO-2012065546 | A1 | 5/2012 | |
| WO | WO-2012154760 | A1 | 11/2012 | |
| WO | WO-2013006463 | A1 | 1/2013 | |
| WO | WO-2013043925 | A1 | 3/2013 | |
| WO | WO-2014179492 | A1 | 11/2014 | |
| WO | WO-2015095370 | A1 | 6/2015 | |
| WO | WO-2015158283 | A1 | 10/2015 | |
| WO | WO-2015194670 | A1 | 12/2015 | |
| WO | WO-2015197567 | A1 | 12/2015 | |
| WO | WO 2018/067786 | * | 4/2018 | ........... C07D 519/00 |
| WO | WO-2018098491 | A1 | 5/2018 | |
| WO | WO-2018098499 | A1 | 5/2018 | |
| WO | WO-2018098500 | A1 | 5/2018 | |
| WO | WO-2018148745 | A1 | 8/2018 | |
| WO | WO-2018187480 | A1 | 10/2018 | |
| WO | WO-2019035951 | A1 | 2/2019 | |
| WO | WO-2019232209 | A1 | 12/2019 | |
| WO | WO-2020069322 | A1 | 4/2020 | |
| WO | WO-2021 108513 | A1 | 6/2021 | |
| WO | WO-2021 108625 | A1 | 6/2021 | |

OTHER PUBLICATIONS

Anderson et al., "Antiepileptic activity of preferential inhibitors of persistent sodium current," Epilepsia (2014), 55(8), 1274-1283.

Baker et al. "The novel sodium channel modulator GS-458967 (GS967) is an effective treatment in a mouse model of SCN8A encephalopathy," Epilepsia, 2018, 1166-1176.

Barbieri et al. "Late sodium current blocker GS967 inhibits persistent currents induced by familial hemiplegic migraine type 3 mutations of the SCN1A gene," *The Journal of Headache and Pain* (2019) vol. 20, No. 107, pp. 1-13.

Belardinelli et al. "A Novel, Potent, and Selective Inhibitor of Cardiac Late Sodium Current Suppresses Experimental Arrhythmias," *J. Pharmacol. Exp. Ther.* (2013) vol. 344, pp. 23-32.

Guan et al. "Synthesis and anticonvulsant activity of a new 6-alkoxy-[1,2,4]-triazolo[4,3-b]pyridazine," *Eur. J. Med. Chem.* (2010) vol. 45, pp. 1746-1752.

Koltun et al. "Discovery of triazolopyridinone GS-462808, a late sodium current inhibitor (Late INai) of the cardiac Nav1.5 channel with improved efficacy and potency relative to ranolazine," *Bioorg. Med. Chem. Lett.* (2016) vol. 26, pp. 3207-3211.

PUBCHEM-CID 58763997 Create Date: Aug. 19, 2012 (14 pages).
PUBCHEM-CID 597467 Create Date: Mar. 27, 2005 (15 pages).
PUBCHEM-CID 82381512 Create Date: Oct. 20, 2014 (10 pages).
PUBCHEM-CID 89077556 Create Date: Feb. 13, 2015 (11 pages).
STN Chemical Structure Search Results (dated Apr. 14, 2019). (36 pages).
STN Chemical Structure Search Results (dated Apr. 2018). (55 pages).
STN Chemical Structure Search Results (dated Apr. 23, 2019). (45 pages).
STN Chemical Structure Search Results (dated Feb. 2018). (29 pages).
STN Chemical Structure Search Results (dated Jan. 15, 2020). (22 pages).
STN Chemical Structure Search Results (dated Jan. 2018). (23 pages).
STN Chemical Structure Search Results (dated Mar. 20, 2018). (264 pages).
STN Chemical Structure Search Results (dated Mar. 20, 2018). (83 pages).
STN Chemical Structure Search Results (dated Mar. 6, 2017). (480 pages).
STN Chemical Structure Search Results (dated Mar. 6, 2017). (511 pages).
STN Chemical Structure Search Results (dated May 18, 2016). (102 pages).
STN Chemical Structure Search Results (dated Nov. 1, 2017). (107 pages).
STN Chemical Structure Search Results (dated Nov. 21, 2017). (85 pages).
STN Chemical Structure Search Results (dated Nov. 3, 2017). (57 pages).
STN Chemical Structure Search Results (dated Nov. 6, 2017). (123 pages).
STN Chemical Structure Search Results (dated Nov. 6, 2017). (7 pages).

Wengert et al. "Prax330 reduces persistent and resurgent sodium channel currents and neuronal hyperexcitability of subiculum neurons in a mouse model of SCN8A epileptic encephalopathy," *Neuropharmacology* (2019) vol. 158, No. 107699, pp. 1-11.

Written Opinion of the International Searching Authority and International Search Report for PCT/US2017/063507 dated Mar. 29, 2019 (9 pages).
Written Opinion of the International Searching Authority and International Search Report for PCT/US2017/063533 dated Mar. 29, 2019 (10 pages).
Written Opinion of the International Searching Authority and International Search Report for PCT/US2017/063534 dated Mar. 28, 2019 (11 pages).
Written Opinion of the International Searching Authority and International Search Report for PCT/US2018/00224 dated Nov. 5, 2018 (8 pages).
Written Opinion of the International Searching Authority and International Search Report for PCT/US2018/018044 dated May 24, 2018 (10 pages).
Written Opinion of the International Searching Authority and International Search Report for PCT/US2018/026099 dated Aug. 10, 2018 (9 pages).
Written Opinion of the International Searching Authority and International Search Report for PCT/US2019/034653 dated Aug. 9, 2019 (9 pages).
Written Opinion of the International Searching Authority and International Search Report for PCT/US2019/053467 dated Jan. 14, 2020 (9 pages).

Zablocki et al. "Discovery of Dihydrobenzoxazepinone (GS-6615) Late Sodium Current Inhibitor (Late $I_{Na}i$), a Phase II Agent with

(56) References Cited

OTHER PUBLICATIONS

Demonstrated Preclinical Anti-Ischemic and Antiarrhythmic Properties," *Journal of Medicinal Chemistry* (2016) vol. 59, pp. 9005-9017.
Berge et al., (1977). "Pharmaceutical salts," J. Pharmaceutical Sciences, 66(1):1-19.
Burbano et al., (2018). "Characterization of a Novel Knock-in Mouse Model of KCNT1 Epileptic Encephalopathy (P2.273)," Neurology, 90(15 Supplement), 2 pages. Abstract Only.
Cannon, J. G., (1995). "Chapter Nineteen: Analog Design," Burger's Medicinal Chemistry and Drug Discovery, Fifth Edition, vol. I: Principles and Practice, Wiley-lnterscience, pp. 783-802.
Chaplan et al., (1994). "Quantitative assessment of tactile allodynia in the rat paw," J Neurosci Meth., 53:55-63.
Dorwald, F. Z., (2005). "Side Reactions in Organic Synthesis," Wiley: VCH, Weinheim p. IX of Preface p. 1-15.
Flynn et al., (1972). "Correlation and Prediction of Mass Transport across Membranes I: Influence of Alkyl Chain Length on Flux-Determining Properties of Barrier and Diffusant," Journal of Pharmaceutical Sciences, 61(6):838-852.
Hackam et al., (2006). "Translation of research evidence from animals to humans," JAMA, 296(14):1731-1732.
Jordan et al., (2003). "Tamoxifen: a most unlikely pioneering medicine," Nat Rev Drug Discov., 2(3):205-213.
Kearney et al., (2001). "A gain-of-function mutation in the sodium channel gene Scn2a results in seizures and behavioral abnormalities," Neuroscience, 702(2):307-317. Abstract Only.
Kim et al., (1992). "An experimental model for peripheral neuropathy produced by segmental spinal nerve ligation in the rat," Pain, 50:355-363.
Li et al., (2018). "Antisense oligonucleotide therapy for SCN2A gain-of-function epilepsies," American Epilepsy Society, 28 pages.
Patel et al., (2019). "Neuropathy following spinal nerve injury shares features with the irritable nociceptor phenotype: A back-translational study of oxcarbazepine," Eur J Pain, 23:183-197.
Petrou et al., (2018). "Abstract: Antisense oligonucleotide therapy for SCN2A gain-of-function epilepsies," American Epilepsy Society, available online at Khttps://www.aesnet.org/abstractslisting/antisense-oligonucleotide-therapy-for-scn2a-gain-of-function-epilepsies>, 2 pages.
Venkatesh et al., (2000). "Role of the development scientist in compound lead selection and optimization," J Pharm Sci., 89(2):145-54.
Wagnon et al., (2015). "Convulsive seizures and SUDEP in a mouse model of SCN8A epileptic encephalopathy," Human Molecular Genetics, 24(2):506-515.
Wilen et al., (1977). "Strategies in optical resolutions,"Tetrahedron, 33(21):2725-2736.
Zaza et al., (2008). "Pathophysiology and pharmacology of the cardiac 'late sodium current'," Pharmacology & Therapeutics, 119(3):326-339.
Final Office Action received for U.S. Appl. No. 16/638,725 dated Apr. 2, 2021, 8 pages.
International Preliminary Report on Patentability for International Patent Application No. PCT/US2018/018044 filed Feb. 13, 2018, 7 pages.
International Preliminary Report on Patentability for International Patent Application No. PCT/US2018/026099 filed Apr. 4, 2018, 6 pages.
International Preliminary Report on Patentability for International Patent Application No. PCT/US2017/063507 filed Nov. 28, 2017, 6 pages.
International Preliminary Report on Patentability for International Patent Application No. PCT/US2017/063534 filed Nov. 28, 2017, 8 pages.
International Preliminary Report on Patentability for International Patent Application No. PCT/US2018/000224 filed Aug. 15, 2018, 6 pages.
International Search Report and Written Opinion dated Feb. 25, 2021, for PCT Application No. PCT/US2020/062179 filed Nov. 25, 2020, 7 pages.
International Search Report and Written Opinion received for International Patent Application No. PCT/US2020/062317, dated Apr. 6, 2021, 14 pages.
Non-Final Office Action received for U.S. Appl. No. 16/638,725 dated Dec. 11, 2020, 16 pages.
Non-Final Office Action received for U.S. Appl. No. 16/887,906 dated Jun. 10, 2021, 18 pages.
Non-Final Office Action received for U.S. Appl. No. 16/464,483 dated Jun. 30, 2021, 22 pages.
Non-Final Office Action received for U.S. Appl. No. 17/102,586 dated Jan. 26, 2021, 14 pages.
Non-Final Office Action issued in U.S. Appl. No. 16/885,605 dated Jan. 28, 2022, 10 pages.
Restriction Requriement issued in U.S. Appl. No. 16/500,795 dated Dec. 16, 2021 (12 pages).
Non-Final Office Action issued in U.S. Appl. No. 16/500,795, dated Apr. 13, 2022, 31 pages.

\* cited by examiner

COMPOUNDS AND THEIR METHODS OF USE

CROSS REFERENCE TO RELATED APPLICATIONS

This application is the national stage of International (PCT) Patent Application Serial Number PCT/US2018/018044, filed Feb. 13, 2018, which claims priority to and the benefit of U.S. Provisional Patent Application No. 62/458,317, filed Feb. 13, 2017, U.S. Provisional Patent Application No. 62/481,468, filed Apr. 4, 2017, and U.S. Provisional Patent Application No. 62/545,549, filed Aug. 15, 2017, each of which is incorporated herein by reference in its entirety.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339). Accordingly, pharmaceutical compounds that selectively modulate sodium channel activity, e.g., abnormal INaL, are useful in treating such disease states.

SUMMARY OF THE INVENTION

Described herein are fused heteroaryl compounds and compositions useful for preventing and/or treating a disease, disorder, or condition, e.g., a disease, disorder, or condition relating to aberrant function of a sodium ion channel, e.g., abnormal late sodium current (INaL). In one aspect, the present disclosure features compounds of Formula (I):

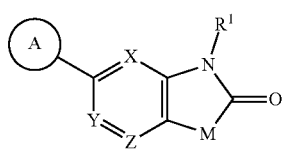

(I)

or a pharmaceutically acceptable salt thereof, wherein each of X, Y, and Z is independently N or CR'; M is O, $C(R^{2a})(R^{2b})$, or $N(R^{2c})$; A is aryl or heteroaryl (e.g., 6-membered aryl or heteroaryl), wherein aryl and heteroaryl are substituted by one or more $R^3$; R' is hydrogen, alkyl, —$OR^c$, or halogen; $R^1$ is hydrogen, alkyl, carbocyclyl, or heterocyclyl, wherein alkyl, carbocyclyl, and heterocyclyl are optionally substituted with one or more $R^4$; each of $R^{2a}$, $R^{2b}$, and $R^{2c}$ is independently hydrogen or alkyl, wherein alkyl is optionally substituted by one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^d$ is independently hydrogen or alkyl, wherein each alkyl is optionally substituted by one or more $R^6$; or two $R^d$, taken together with the atoms to which they are attached, form a ring; each $R^6$ is independently alkyl, carbocyclyl, heterocyclyl, halo, cyano, nitro, or —OH; and each $R^7$ is independently alkyl, halo, or oxo.

In another aspect, the present disclosure provides a compound of formula (I-1):

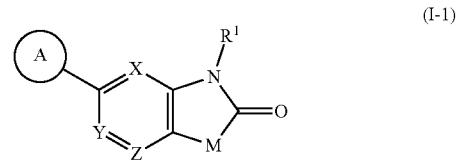

(I-1)

or a pharmaceutically acceptable salt thereof, wherein the variables are as defined herein.

In some embodiments, the present disclosure provides a compound of formula (I-2):

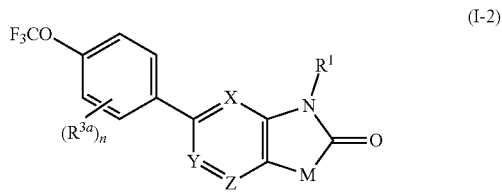

(I-2)

or a pharmaceutically acceptable salt thereof, wherein the variables are as defined herein.

In some embodiments, the present disclosure provides a compound of formula (I-3):

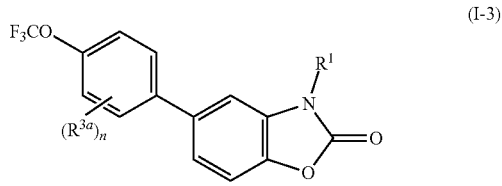

(I-3)

or a pharmaceutically acceptable salt thereof, wherein the variables are as defined herein.

In some embodiments, the present disclosure provides a compound of formula (I-4):

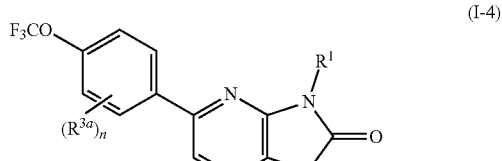

(I-4)

or a pharmaceutically acceptable salt thereof, wherein the variables are as defined herein.

In some embodiments, the present disclosure provides a compound of formula (I-5):

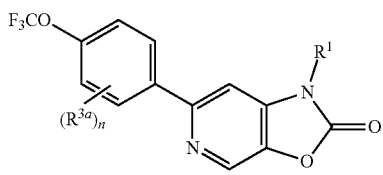

(I-5)

or a pharmaceutically acceptable salt thereof, wherein the variables are as defined herein.

In some embodiments, the present disclosure provides a compound of formula (I-6):

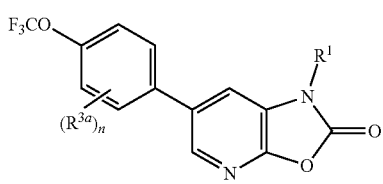

(I-6)

or a pharmaceutically acceptable salt thereof, wherein the variables are as defined herein.

In some embodiments, the present disclosure provides a compound of formula (I-7):

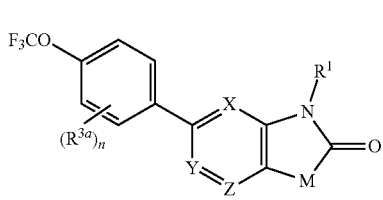

(I-7)

or a pharmaceutically acceptable salt thereof, wherein the variables are as defined herein.

In another aspect, the present disclosure provides a pharmaceutical composition comprising a compound disclosed herein or a pharmaceutically acceptable salt thereof, and a pharmaceutically acceptable carrier.

In another aspect, the present disclosure provides a method of treating a neurological disorder or a psychiatric disorder, wherein the method comprises administering to a subject in need thereof a compound disclosed herein or a pharmaceutically acceptable salt thereof or a pharmaceutical composition disclosed herein.

Other objects and advantages will become apparent to those skilled in the art from a consideration of the ensuing Detailed Description, Examples, and Claims.

DETAILED DESCRIPTION OF THE INVENTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, and $^{14}C$; O may be in any isotopic $^{13}C$, form, including $^{16}O$ and $^{18}O$ and the like.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene,"

and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

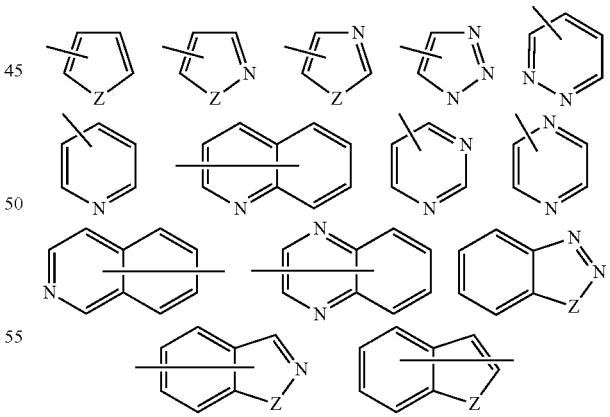

wherein each Z is selected from carbonyl, N, $NR^{65}$, O, and S; and $R^{65}$ is independently hydrogen, $C_1$-$C_8$ alkyl, $C_3$-$C_{10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

As used herein, "halo" or "halogen" refers to fluoro (F), chloro (Cl), bromo (Br), and iodo (I). In certain embodiments, the halo group is either fluoro or chloro.

As used herein, "haloalkyl" refers to an alkyl group substituted with one or more halogen atoms.

As used herein, "nitro" refers to —$NO_2$.

As used herein, "oxo" refers to —C=O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, $SO_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R')_2$, —$SO_2N(R')_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, the present invention features a compound of Formula (I):

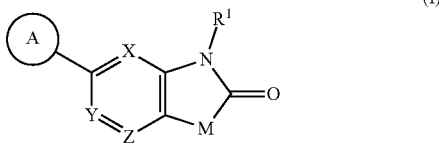

or a pharmaceutically acceptable salt thereof, wherein each of X, Y, and Z is independently N or CR'; M is O, $C(R^{2a})(R^{2b})$, or $N(R^{2c})$; A is aryl or heteroaryl (e.g., 6-membered aryl or heteroaryl), wherein aryl and heteroaryl are substituted by one or more $R^3$; R' is hydrogen, alkyl, —$OR^c$, or halogen; $R^1$ is hydrogen, alkyl, carbocyclyl, or heterocyclyl, wherein alkyl, carbocyclyl, and heterocyclyl are optionally substituted with one or more $R^4$; each of $R^{2a}$, $R^{2b}$, and $R^{2c}$ is independently hydrogen or alkyl, wherein alkyl is optionally substituted by one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^d$ is independently hydrogen or alkyl, wherein each alkyl is optionally substituted by one or more $R^6$; or two $R^d$, taken together with the atoms to which they are attached, form a ring; each $R^6$ is independently alkyl, carbocyclyl, heterocyclyl, halo, cyano, nitro, or —OH; and each $R^7$ is independently alkyl, halo, or oxo.

In some embodiments, X is CR'(e.g., CH). In some embodiments, Y is CR'(e.g., CH). In some embodiments, Z is CR'(e.g., CH). In some embodiments, each of X, Y, and Z is independently CR'(e.g., CH).

In some embodiments, X is N. In some embodiments, X is N and Y is CR'(e.g., CH). In some embodiments, X is N and Z is CR'(e.g., CH). In some embodiments, X is N and each of X and Y is independently CR'(e.g., CH).

In some embodiments, Y is N. In some embodiments, Y is N and X is CR'(e.g., CH). In some embodiments, Y is N and Z is CR'(e.g., CH). In some embodiments, Y is N and each of X and Z is independently CR'(e.g., CH).

In some embodiments, Z is N. In some embodiments, Z is N and X is CR'(e.g., CH). In some embodiments, Z is N and Y is CR'(e.g., CH). In some embodiments, Z is N and each of X and Y is independently CR'(e.g., CH).

In some embodiments, M is O.

In some embodiments, M is $C(R^{2a})(R^{2b})$. In some embodiments, M is $C(R^{2a})(R^{2b})$ and each of $R^{2a}$ and $R^{2b}$ is independently hydrogen.

In some embodiments, M is $N(R^{2c})$. In some embodiments, M is $N(R^{2c})$ and $R^{2c}$ is hydrogen or alkyl (e.g., methyl or ethyl).

In some embodiments, A is aryl. In some embodiments, A is 6-membered aryl (e.g., phenyl). In some embodiments, A is phenyl substituted by 1 $R^3$. In some embodiments, A is phenyl substituted by 1 $R^3$ in the para position.

In some embodiments, A is heteroaryl. In some embodiments, A is 6-membered heteroaryl. In some embodiments, A is nitrogen-containing heteroaryl. In some embodiments, A is pyridyl. In some embodiments, A is pyridyl substituted by 1 $R^3$. In some embodiments, A is pyridyl is substituted by 1 $R^3$ in the para position.

In some embodiments, $R^3$ is alkyl or —$OR^c$. In some embodiments, $R^3$ is —$OR^c$. In some embodiments, $R^c$ is alkyl. In some embodiments, $R^c$ is alkyl substituted by one or more $R^6$. In some embodiments, $R^6$ is halo. In some embodiments, $R^3$ is —$OCH_3$, —$OCF_3$, or —$OCH_2CF_3$. In some embodiments, $R^3$ is —$OCF_3$.

In some embodiments, $R^3$ is alkyl. In some embodiments, $R^3$ is alkyl substituted with $R^5$ (e.g., 1 $R^5$). In some embodiments, $R^5$ is —$OR^c$. In some embodiments, $R^3$ is —$CH_2OCH_3$.

In some embodiments, $R^1$ is hydrogen or alkyl. In some embodiments, $R^1$ is hydrogen.

In some embodiments, $R^1$ is alkyl. In some embodiments, $R^1$ is $C_{1-6}$ alkyl (e.g., methyl, ethyl, propyl, or isopropyl). In some embodiments, $R^1$ is unsubstituted $C_{1-6}$ alkyl (e.g., unsubstituted methyl, unsubstituted ethyl, unsubstituted propyl, or unsubstituted isopropyl). In some embodiments, $R^1$ is $C_{1-6}$ alkyl (e.g., methyl, ethyl, propyl, or isopropyl) substituted with 1-4 $R^4$. In some embodiments, $R^1$ is $C_{1-4}$ alkyl substituted with 1-4 $R^4$.

In some embodiments, $R^4$ is deuterium, halo, —$OR^c$, oxo, carbocyclyl, heteroaryl, —$C(O)OR^c$, or —$C(O)N(R^d)_2$. In some embodiments, R4 is deuterium. In some embodiments, $R^1$ is $CD_3$ or $CD_2CD_3$.

In some embodiments, $R^4$ is halo (e.g., fluoro). In some embodiments, $R^1$ is —$CH_2CF_3$ or $CH_2CHF_2$.

In some embodiments, $R^4$ is —$OR^c$ (e.g., —OH or —$OCH_3$). In some embodiments, $R^1$ is —$CH_2CH_2OCH_3$, $CH_2CH_2OH$, $CH_2CH_2CH(OH)CH_3$, $CH_2CH_2CH_2OH$, or $CH_2CH_2CH_2OCH_3$.

In some embodiments, $R^4$ is carbocyclyl (e.g., cyclopropyl). In some embodiments, $R^1$ is —$CH_2CH_2$-cyclopropyl or —$CH_2$-cyclopropyl.

In some embodiments, $R^4$ is heterocyclyl (e.g., tetrahydropyranyl, tetrahydrofuranyl). In some embodiments, $R^1$ is —$CH_2$-tetrahydropyranyl or —$CH_2$-tetrahydrofuranyl.

In some embodiments, $R^4$ is heteroaryl (e.g., oxadiazolyl, pyrimidinyl). In some embodiments, $R^4$ is heteroaryl (e.g., oxadiazolyl) substituted by 1-4 $R^7$. In some embodiments, $R^1$ is —$CH_2CH_2$-5-methyl-1,3,4-oxadiazole.

In some embodiments, $R^4$ is —$C(O)OR^c$ (e.g., —C(O)OH). In some embodiments, $R^1$ is —$CH_2C(O)OH$.

In some embodiments, $R^4$ is —$C(O)N(R^d)_2$ (e.g., C(O)—$NH(CH_3)_2$, C(O)—$NHCH(CH_3)_2$, C(O)—$NH(CH_3)(CH_2CH_3)$, $C(O)N(CH_3)CH_2CF_3$, or C(O)—N-pyrrolidinyl). In some embodiments, $R^1$ is —$CH_2C(O)NHCH(CH_3)_2$ or —C(O)—N-pyrrolidinyl.

In another aspect, the present invention features a compound of Formula (I-1):

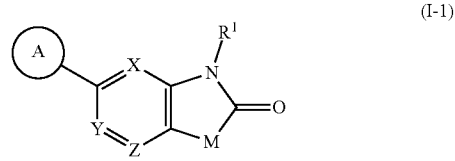

or a pharmaceutically acceptable salt thereof, wherein:

each of X, Y, and Z is independently N or CR';

M is O, C($R^{2a}$)($R^{2b}$), or N($R^{2c}$); A is aryl or heteroaryl (e.g., 6-membered aryl or heteroaryl), wherein aryl and heteroaryl are substituted by one or more $R^3$;

R' is hydrogen, alkyl, —$OR^c$, or halogen;

$R^1$ is hydrogen, alkyl, carbocyclyl, or heterocyclyl, wherein alkyl, carbocyclyl, and heterocyclyl are optionally substituted with one or more $R^4$;

each of $R^{2a}$, $R^{2b}$, and $R^{2c}$ is independently hydrogen or alkyl, wherein alkyl is optionally substituted by one or more $R^4$;

each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$;

each of $R^4$ and $R^5$ is independently deuterium, alkyl, carbocyclyl, heterocyclyl, aryl, heteroaryl, halo, oxo, cyano, nitro, —$OR^c$, —$N(R^d)_2$, —$C(O)R^c$, —$C(O)OR^c$, —$S(O)_2$—$R^e$, —$S(O)_2N(R^d)_2$, or —$C(O)N(R^d)_2$, wherein alkyl, carbocyclyl, heterocyclyl, aryl, and heteroaryl is optionally substituted by one or more $R^7$;

each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$;

each $R^d$ is independently hydrogen or alkyl, wherein each alkyl is optionally substituted by one or more $R^6$; or two $R^d$, taken together with the atoms to which they are attached, form a heterocyclyl optionally substituted with —OH, alkoxy, or alkyl optionally substituted with alkoxy;

each $R^e$ is alkyl;

each $R^6$ is independently alkyl, carbocyclyl, heterocyclyl, halo, cyano, nitro, or —OH;

and each $R^7$ is independently alkyl, halo, oxo, —$C(O)R^c$, or —$C(O)OR^c$.

In some embodiments, the compound is not one of the following:

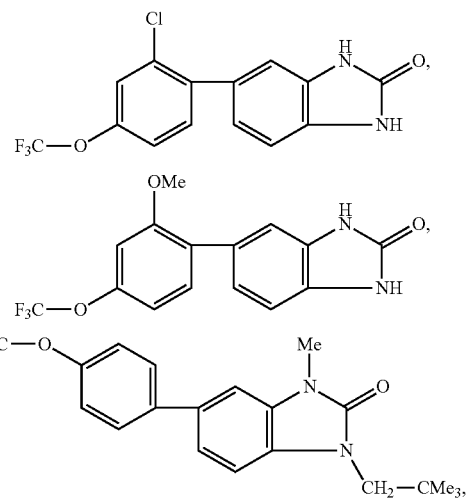

and a pharmaceutically acceptable salt thereof.

In some embodiments, the compound is not one of the following:

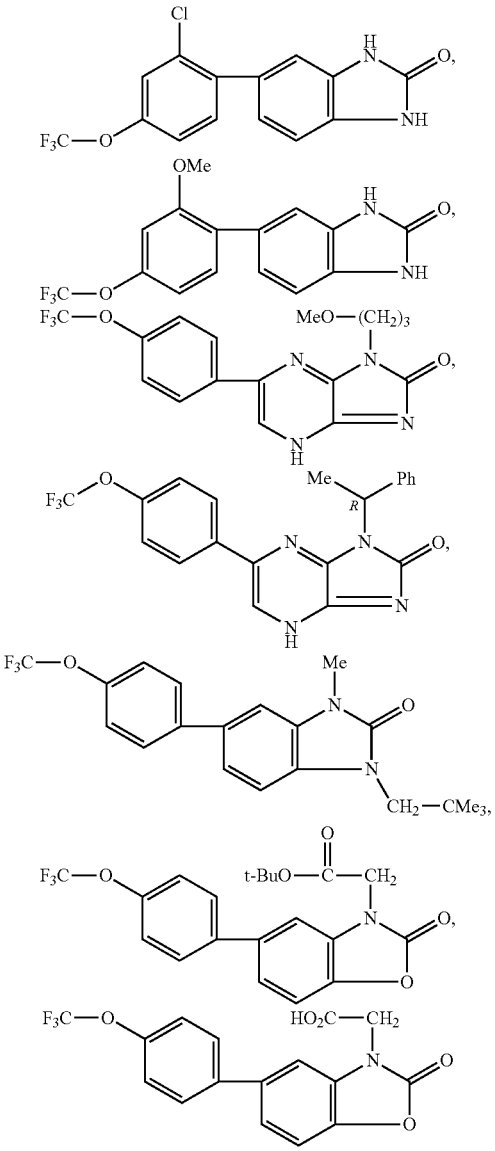

and a pharmaceutically acceptable salt thereof.

In some embodiments, each of X, Y, and Z is independently CR'(e.g., CH).

In other embodiments, M is O.

In certain embodiments, M is C($R^{2a}$)($R^{2b}$) (e.g., $CH_2$).

In some embodiments, M is N($R^{2c}$) (e.g., NH, $NCH_3$).

In certain embodiments, A is aryl (e.g., phenyl).

In other embodiments, A is phenyl substituted by 1 $R^3$ (e.g., wherein $R^3$ is in the para position).

In some embodiments, A is heteroaryl (e.g., pyridyl).

In other embodiments, A is pyridyl substituted by 1 $R^3$ (e.g., wherein $R^3$ is in the para position).

In certain embodiments, $R^3$ is —$OR^c$.

In some embodiments, $R^c$ is alkyl substituted by one or more $R^6$.

In other embodiments, $R^6$ is halo (e.g., fluoro).

In certain embodiments, $R^3$ is —$OCF_3$.

In some embodiments, $R^1$ is alkyl (e.g., substituted with 1-4 $R^4$).

In other embodiments, $R^4$ is deuterium, halo, —$OR^c$, oxo, carbocyclyl, heteroaryl, —$C(O)OR^c$, or —$C(O)N(R^d)_2$.

In certain embodiments, $R^4$ is deuterium, fluoro, tetrahydrofuranyl, tetrahydropyranyl, pyrimidinyl, OH, $C(O)N(CH_3)_2$, $C(O)N(CH_3)(CH_2CH_3)$, $C(O)N(CH_3)(CH_2CF_3)$, or C(O)N— tetrahydropyrrolyl.

In some embodiments, $R^4$ is halo (e.g., fluoro).

In other embodiments, $R^1$ is —$CH_2CF_3$.

In some embodiments, the compound of Formula (I-1) is a compound of Formula (I-2):

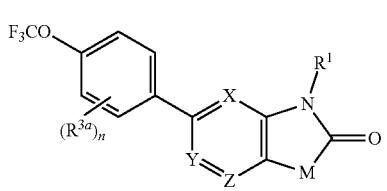

(I-2)

or a pharmaceutically acceptable salt thereof, wherein:
each of X, Y, and Z is independently N or CR';
M is O or $C(R^{2a})(R^{2b})$;
R' is hydrogen, alkyl, —$OR^c$, or halogen;
$R^1$ is hydrogen, alkyl, carbocyclyl, or heterocyclyl, wherein alkyl, carbocyclyl, and heterocyclyl are optionally substituted with one or more $R^4$;
each of $R^{2a}$ and $R^{2b}$ is independently hydrogen or alkyl, wherein alkyl is optionally substituted by one or more $R^4$;
each $R^{3a}$ is independently alkyl, carbocyclyl, heterocyclyl, halo, cyano, nitro, or —$OR^c$, wherein alkyl, carbocyclyl, and heterocyclyl are optionally substituted with one or more $R^5$;
each of $R^4$ and $R^5$ is independently deuterium, alkyl, carbocyclyl, heterocyclyl, aryl, heteroaryl, halo, cyano, nitro, —$C(O)N(R^d)_2$, —$C(O)R^c$, —$C(O)OR^c$, —$S(O)_2$—$R^e$, —$S(O)_2N(R^d)_2$, or —$OR^c$, wherein alkyl, carbocyclyl, heterocyclyl, aryl, and heteroaryl is optionally substituted by one or more $R^7$;
each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$;
each $R^d$ is independently hydrogen or alkyl optionally substituted with one or more halogen;
or two $R^d$, taken together with the atoms to which they are attached, form a heterocyclyl optionally substituted with —OH, alkoxy, or alkyl optionally substituted with alkoxy;
each $R^e$ is alkyl;
each $R^6$ is independently alkyl, carbocyclyl, heterocyclyl, halo, cyano, nitro, or —OH;
each $R^7$ is independently alkyl, oxo, halo, —$C(O)R^c$, or —$C(O)OR^c$; and n is 0, 1, 2, 3, or 4.

In some embodiments, the compound is not one of the following:

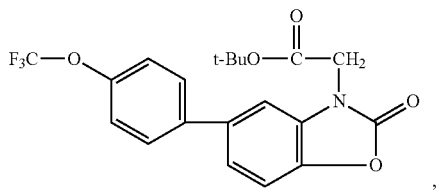

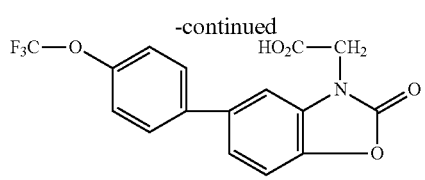

and a pharmaceutically acceptable salt thereof.

In some embodiments, the compound of formula I-2 is a compound of formula I-3:

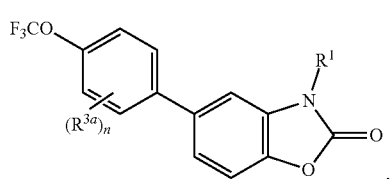

(I-3)

or a pharmaceutically acceptable salt thereof.

In certain embodiments, the compound of formula I-2 is a compound of formula I-4:

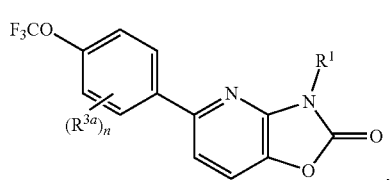

(I-4)

or a pharmaceutically acceptable salt thereof.

In some embodiments, the compound of formula I-2 is a compound of formula I-5:

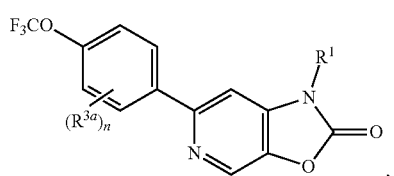

(I-5)

or a pharmaceutically acceptable salt thereof.

In some embodiments, the compound of formula I-2 is a compound of formula I-6:

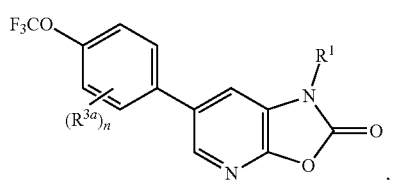

(I-6)

or a pharmaceutically acceptable salt thereof.

In some embodiments of formula I-2, each of X, Y, and Z is CR', wherein R' is hydrogen.

In some embodiments of formula I-2, M is O.

In some embodiments of formula I-2, M is C(R$^{2a}$)(R$^{2b}$).

In some embodiments of formula I-2, R$^1$ is alkyl, wherein alkyl is optionally substituted with one or more R$^4$.

In some embodiments of formula I-2, each of R$^4$ and R$^5$ is independently deuterium, alkyl, carbocyclyl, heterocyclyl, aryl, heteroaryl, halo, cyano, nitro, —C(O)N(R$^d$)$_2$, —C(O)CH$_3$, —C(O)OCH$_3$, —SO$_2$CH$_3$, —S(O)$_2$N(R$^d$)$_2$, or —OR$^c$, wherein alkyl, carbocyclyl, heterocyclyl, aryl, and heteroaryl is optionally substituted by one or more R$^7$.

In some embodiments of formula I-2, each of R$^4$ and R$^5$ is independently deuterium, alkyl, carbocyclyl, heterocyclyl, aryl, heteroaryl, halo, cyano, nitro, —C(O)N(R$^d$)$_2$, —SO$_2$CH$_3$, —S(O)$_2$N(R$^d$)$_2$, or —OR$^c$, wherein alkyl, carbocyclyl, heterocyclyl, aryl, and heteroaryl is optionally substituted by one or more R$^7$.

In some embodiments of formula I-2, each of R$^4$ and R$^5$ is independently deuterium, alkyl, carbocyclyl, heterocyclyl, aryl, heteroaryl, halo, cyano, nitro, or —OR$^c$, wherein alkyl, carbocyclyl, heterocyclyl, aryl, and heteroaryl is optionally substituted by one or more R$^7$.

In some embodiments of formula I-2, n is 0.

In some embodiments, the compound of Formula (I-1) is a compound of Formula (I-7):

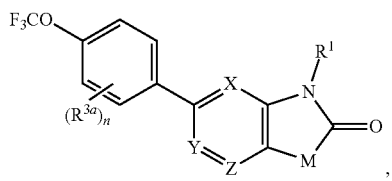

(I-7)

or a pharmaceutically acceptable salt thereof, wherein:
each of X, Y, and Z is independently N or CR';
M is N(R$^{2c}$);
R' is hydrogen, alkyl, —OR$^c$, or halogen;
R$^1$ is hydrogen, alkyl, carbocyclyl, or heterocyclyl, wherein alkyl, carbocyclyl, and heterocyclyl are optionally substituted with one or more R$^4$;
each of R$^{2c}$ is independently hydrogen or alkyl, wherein alkyl is optionally substituted by one or more R$^4$;
each R$^{1a}$ is independently alkyl, carbocyclyl, heterocyclyl, halo, cyano, nitro, or —OR$^c$, wherein alkyl, carbocyclyl, and heterocyclyl are optionally substituted with one or more R$^5$;
each of R$^4$ and R$^5$ is independently deuterium, alkyl, carbocyclyl, heterocyclyl, aryl, heteroaryl, halo, cyano, nitro, —C(O)N(R$^d$)$_2$, —C(O)R$^c$, —C(O)OR$^c$, —S(O)$_2$—R$^e$, —S(O)$_2$N(R$^d$)$_2$, or —OR$^c$, wherein alkyl, carbocyclyl, heterocyclyl, aryl, and heteroaryl is optionally substituted by one or more R$^7$;
each R$^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more R$^6$;
each R$^d$ is independently hydrogen or alkyl optionally substituted with one or more halogen;
or two R$^d$, taken together with the atoms to which they are attached, form a heterocyclyl optionally substituted with —OH, alkoxy, or alkyl optionally substituted with alkoxy;
each R$^e$ is alkyl;
each R$^6$ is independently alkyl, carbocyclyl, heterocyclyl, halo, cyano, nitro, or —OH;
each R$^7$ is independently alkyl, oxo, halo, —C(O)R$^c$, or —C(O)OR$^c$; and n is 0, 1, 2, 3, or 4.

In some embodiments of formula I-7, the compound is not one of the following:

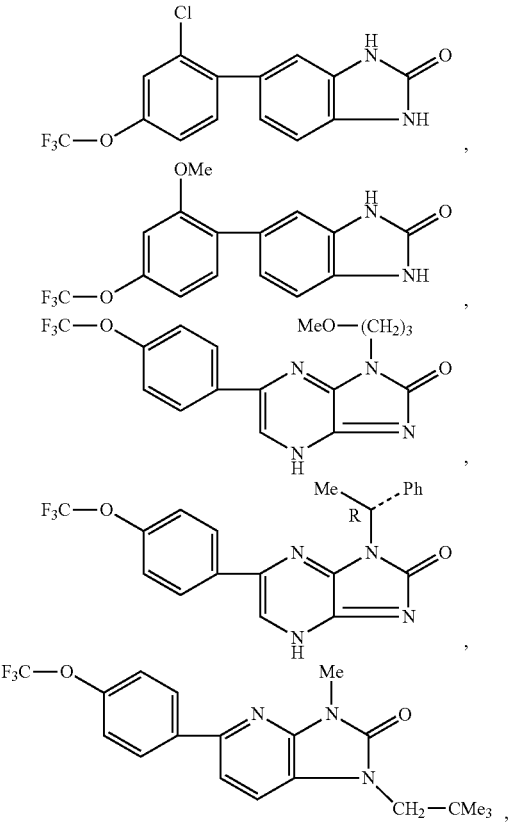

and a pharmaceutically acceptable salt thereof.

In some embodiments of formula I-7, each of X, Y, and Z is CR', wherein R' is hydrogen.

In some embodiments of formula I-7, R$^1$ is alkyl, wherein alkyl is optionally substituted with one or more R$^4$.

In some embodiments, R$^4$ is halo.

In some embodiments of formula I-7, each of R$^4$ and R$^5$ is independently deuterium, alkyl, carbocyclyl, heterocyclyl, aryl, heteroaryl, halo, cyano, nitro, or —OR$^c$, wherein alkyl, carbocyclyl, heterocyclyl, aryl, and heteroaryl is optionally substituted by one or more R$^7$.

In some embodiments of formula I-7, n is 0.

In some embodiments, the compound of Formula (I) is a compound of Formula (I-a):

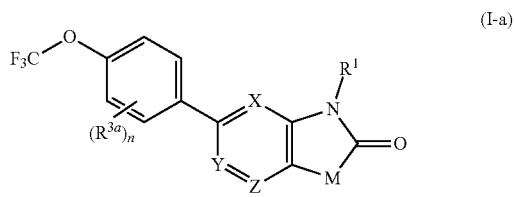

(I-a)

or a pharmaceutically acceptable salt thereof, wherein each of X, Y, and Z is independently N or CR'; M is O, C(R$^{2a}$)(R$^{2b}$), or N(R$^{2c}$); R' is hydrogen, alkyl, —OR$^c$, or halogen (e.g., hydrogen); R$^1$ is hydrogen, alkyl, carbocyclyl, or heterocyclyl, wherein alkyl, carbocyclyl, and heterocyclyl are optionally substituted with one or more $R^4$; each of $R^{2a}$, $R^{1b}$, and $R^{2c}$ is independently hydrogen or alkyl, wherein alkyl is optionally substituted by one or more $R^4$; each $R^{3a}$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, cyano, nitro, —$C(O)N(R^d)_2$, —$C(O)R^c$, —$C(O)OR^c$, —$S(O)_2$—$R^e$, —$S(O)_2N(R^d)_2$, or —$OR^c$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^d$ is independently hydrogen or alkyl optionally substituted with one or more halogen; or two $R^d$, taken together with the atoms to which they are attached, form a heterocyclyl optionally substituted with —OH, alkoxy, or alkyl optionally substituted with alkoxy; each $R^e$ is alkyl;

each $R^6$ is independently alkyl, carbocyclyl, heterocyclyl, halo, cyano, nitro, or —OH; each $R^7$ is independently alkyl, halo, oxo, —$C(O)R^c$, or —$C(O)OR^c$; and n is 0, 1, 2, 3, or 4.

In some embodiments, X is CR'(e.g., CH). In some embodiments, Y is CR'(e.g., CH). In some embodiments, Z is CR'(e.g., CH). In some embodiments, each of X, Y, and Z is independently CR'(e.g., CH).

In some embodiments, M is O.

In some embodiments, M is $C(R^{2a})(R^{2b})$. In some embodiments, M is $C(R^{2a})(R^{2b})$ and each of $R^{2a}$ and $R^{2b}$ is independently hydrogen.

In some embodiments, M is $N(R^{2c})$. In some embodiments, M is $N(R^{2c})$ and $R^{2c}$ is hydrogen or alkyl (e.g., methyl or ethyl).

In some embodiments, n is 0 or 1. In some embodiments, n is 0. In some embodiments, n is 1.

In some embodiments, $R^{1a}$ is alkyl or —$OR^c$. In some embodiments, $R^{1a}$ is alkyl (e.g., ethyl) substituted by one or more $R^5$. In some embodiments, $R^5$ is —$OR^c$. In some embodiments, $R^c$ is alkyl (e.g., methyl). In some embodiments, $R^{1a}$ is —$CH_2CH_2OCH_3$.

In some embodiments, $R^{1a}$ is —$OR^c$. In some embodiments, $R^c$ is alkyl. In some embodiments, $R^{1a}$ is —$OCH_3$.

In some embodiments, $R^{1a}$ is alkyl. In some embodiments, $R^{1a}$ is alkyl substituted with $R^5$ (e.g., 1 $R^5$). In some embodiments, $R^5$ is —$OR^c$. In some embodiments, $R^{1a}$ is —$CH_2OCH_3$.

In some embodiments, $R^1$ is hydrogen or alkyl. In some embodiments, $R^1$ is hydrogen.

In some embodiments, $R^1$ is alkyl. In some embodiments, $R^1$ is $C_{1-6}$ alkyl (e.g., methyl, ethyl, propyl, or isopropyl). In some embodiments, $R^1$ is unsubstituted $C_{1-6}$ alkyl (e.g., unsubstituted methyl, unsubstituted ethyl, unsubstituted propyl, or unsubstituted isopropyl). In some embodiments, $R^1$ is $C_{1-6}$ alkyl (e.g., methyl, ethyl, propyl, or isopropyl) substituted with 1-4 $R^4$. In some embodiments, $R^1$ is $C_{1-4}$ alkyl substituted with 1-4 $R^4$ (e.g., methyl, ethyl, propyl, or isopropyl).

In some embodiments, $R^4$ is deuterium, halo, —$OR^c$, oxo, carbocyclyl, heterocyclyl, —$C(O)OR^c$, or —$C(O)N(R^d)_2$. In some embodiments, $R^4$ is deuterium. In some embodiments, $R^1$ is $CD_3$ or $CD_2CD_3$.

In some embodiments, $R^4$ is halo (e.g., fluoro). In some embodiments, $R^1$ is —$CH_2CF_3$ or $CH_2CHF_2$ In some embodiments, $R^4$ is —$OR^c$ (e.g., —OH or —$OCH_3$). In some embodiments, $R^1$ is —$CH_2CH_2OCH_3$, $CH_2CH_2OH$, $CH_2CH_2CH(OH)CH_3$, $CH_2CH_2CH_2OH$, or $CH_2CH_2CH_2OCH_3$.

In some embodiments, $R^4$ is carbocyclyl (e.g., cyclopropyl). In some embodiments, $R^1$ is —$CH_2CH_2$-cyclopropyl or —$CH_2$-cyclopropyl.

In some embodiments, $R^4$ is heterocyclyl (e.g., tetrahydropyranyl, tetrahydrofuranyl). In some embodiments, $R^1$ is —$CH_2$-tetrahydropyranyl or —$CH_2$-tetrahydrofuranyl.

In some embodiments, $R^4$ is heteroaryl (e.g., oxadiazolyl, pyrimidinyl). In some embodiments, $R^4$ is heteroaryl (e.g., oxadiazolyl) substituted by 1-4 $R^7$. In some embodiments, $R^1$ is —$CH_2CH_2$-5-methyl-1,3,4-oxadiazole.

In some embodiments, $R^4$ is —$C(O)OR^c$ (e.g., —C(O)OH). In some embodiments, $R^1$ is —$CH_2C(O)OH$.

In some embodiments, $R^4$ is —$C(O)N(R^d)_2$ (e.g., C(O)—$NH(CH_3)_2$, C(O)—$NHCH(CH_3)_2$, C(O)—$NH(CH_3)(CH_2CH_3)$, $C(O)N(CH_3)CH_2CF_3$, or C(O)—N-pyrrolidinyl). In some embodiments, $R^1$ is —$CH_2C(O)NHCH(CH_3)_2$ or —C(O)—N-pyrrolidinyl.

In some embodiments, the compound of Formula (I) is a compound of Formula (I-b):

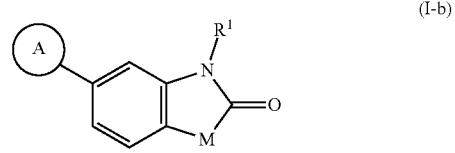

(I-b)

or a pharmaceutically acceptable salt thereof, wherein A is aryl or heteroaryl (e.g., 6-membered aryl or heteroaryl), wherein aryl and heteroaryl are substituted by one or more $R^3$; $R^1$ is hydrogen, alkyl, carbocyclyl, or heterocyclyl, wherein alkyl, carbocyclyl, and heterocyclyl are optionally substituted with one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, cyano, nitro, —$C(O)N(R^d)_2$, —$C(O)R^c$, —$C(O)OR^c$, —$S(O)_2$—$R^e$, —$S(O)_2N(R^d)_2$, or —$OR^c$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^6$ is independently alkyl, carbocyclyl, heterocyclyl, halo, cyano, nitro, or —OH; each $R^d$ is independently hydrogen or alkyl optionally substituted with one or more halogen; or two $R^d$, taken together with the atoms to which they are attached, form a heterocyclyl optionally substituted with —OH, alkoxy, or alkyl optionally substituted with alkoxy; each $R^e$ is alkyl; each $R^7$ is independently alkyl, halo, oxo, —$C(O)R^c$, or —$C(O)OR^c$; and n is 0, 1, 2, 3, or 4.

In some embodiments, A is aryl. In some embodiments, A is 6-membered aryl (e.g., phenyl). In some embodiments, A is phenyl substituted by 1 $R^3$. In some embodiments, A is phenyl substituted by 1 $R^3$ in the para position.

In some embodiments, A is heteroaryl. In some embodiments, A is 6-membered heteroaryl. In some embodiments, A is nitrogen-containing heteroaryl. In some embodiments, A is pyridyl. In some embodiments, A is pyridyl substituted by 1 $R^3$. In some embodiments, A is pyridyl is substituted by 1 $R^3$ in the para position In some embodiments, $R^3$ is alkyl or —$OR^c$. In some embodiments, $R^3$ is —$OR^c$. In some embodiments, $R^c$ is alkyl. In some embodiments, $R^c$ is alkyl substituted by one or more $R^6$. In some embodiments, $R^6$ is halo. In some embodiments, $R^3$ is —$OCH_3$, —$OCF_3$, or —$OCH_2CF_3$. In some embodiments, $R^3$ is —$OCF_3$.

In some embodiments, $R^3$ is alkyl. In some embodiments, $R^3$ is alkyl substituted with $R^5$ (e.g., 1 $R^5$). In some embodiments, $R^5$ is —$OR^c$. In some embodiments, $R^3$ is —$CH_2OCH_3$.

In some embodiments, $R^1$ is hydrogen or alkyl. In some embodiments, $R^1$ is hydrogen.

In some embodiments, $R^1$ is alkyl. In some embodiments, $R^1$ is $C_{1-6}$ alkyl (e.g., methyl, ethyl, propyl, or isopropyl). In some embodiments, $R^1$ is unsubstituted $C_{1-6}$ alkyl (e.g., unsubstituted methyl, unsubstituted ethyl, unsubstituted propyl, or unsubstituted isopropyl). In some embodiments, $R^1$ is $C_{1-6}$ alkyl (e.g., methyl, ethyl, propyl, or isopropyl) substituted with 1-4 $R^4$. In some embodiments, $R^1$ is $C_{1-4}$ alkyl substituted with 1-4 $R^4$ (e.g., methyl, ethyl, propyl, or isopropyl).

In some embodiments, $R^4$ is deuterium, halo, —$OR^c$, oxo, carbocyclyl, heteroaryl, —$C(O)OR^c$, or —$C(O)N(R^d)_2$. In some embodiments, $R^4$ is deuterium. In some embodiments, $R^1$ is $CD_3$ or $CD_2CD_3$.

In some embodiments, $R^4$ is halo (e.g., fluoro). In some embodiments, $R^1$ is —$CH_2CF_3$ or $CH_2CHF_2$.

In some embodiments, $R^4$ is —$OR^c$ (e.g., —OH or —$OCH_3$). In some embodiments, $R^1$ is —$CH_2CH_2OCH_3$, $CH_2CH_2OH$, $CH_2CH_2CH(OH)CH_3$, $CH_2CH_2CH_2OH$, or $CH_2CH_2CH_2OCH_3$.

In some embodiments, $R^4$ is carbocyclyl (e.g., cyclopropyl). In some embodiments, $R^1$ is —$CH_2CH_2$-cyclopropyl or —$CH_2$-cyclopropyl.

In some embodiments, $R^4$ is heterocyclyl (e.g., tetrahydropyranyl, tetrahydrofuranyl). In some embodiments, $R^1$ is —$CH_2$-tetrahydropyranyl or —$CH_2$-tetrahydrofuranyl.

In some embodiments, $R^4$ is heteroaryl (e.g., oxadiazolyl, pyrimidinyl). In some embodiments, $R^4$ is heteroaryl (e.g., oxadiazolyl) substituted by 1-4 $R^7$. In some embodiments, $R^1$ is —$CH_2CH_2$-5-methyl-1,3,4-oxadiazole.

In some embodiments, $R^4$ is —$C(O)OR^c$ (e.g., —$C(O)OH$). In some embodiments, $R^1$ is —$CH_2C(O)OH$.

In some embodiments, $R^4$ is —$C(O)N(R^d)_2$ (e.g., C(O)—$NH(CH_3)_2$, C(O)—$NHCH(CH_3)_2$, C(O)—$NH(CH_3)(CH_2CH_3)$, C(O)N($CH_3$)$CH_2CF_3$, or C(O)—N-pyrrolidinyl). In some embodiments, $R^1$ is —$CH_2C(O)NHCH(CH_3)_2$ or —C(O)—N-pyrrolidinyl.

In some embodiments, the compound of Formula (I) is a compound of Formula (I-c):

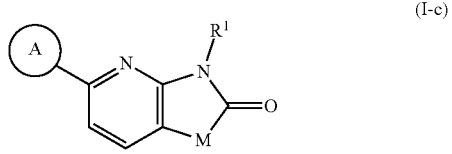

(I-c)

or a pharmaceutically acceptable salt thereof, wherein A is aryl or heteroaryl (e.g., 6-membered aryl or heteroaryl), wherein aryl and heteroaryl are substituted by one or more $R^3$; $R^1$ is hydrogen, alkyl, carbocyclyl, or heterocyclyl, wherein alkyl, carbocyclyl, and heterocyclyl are optionally substituted with one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, cyano, nitro, —$C(O)N(R^d)_2$, —$C(O)R^c$, —$C(O)OR^c$, —$S(O)_2$—$R^e$, —$S(O)_2N(R^d)_2$, or —$OR^c$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^6$ is independently alkyl, carbocyclyl, heterocyclyl, halo, cyano, nitro, or —OH; each $R^d$ is independently hydrogen or alkyl optionally substituted with one or more halogen; or two $R^d$, taken together with the atoms to which they are attached, form a heterocyclyl optionally substituted with —OH, alkoxy, or alkyl optionally substituted with alkoxy; each $R^e$ is alkyl; each $R^7$ is independently alkyl, halo, oxo, —$C(O)R^c$, or —$C(O)OR^c$; and n is 0, 1, 2, 3, or 4.

In some embodiments, A is aryl. In some embodiments, A is 6-membered aryl (e.g., phenyl). In some embodiments, A is phenyl substituted by 1 $R^3$. In some embodiments, A is phenyl substituted by 1 $R^3$ in the para position.

In some embodiments, A is heteroaryl. In some embodiments, A is 6-membered heteroaryl. In some embodiments, A is nitrogen-containing heteroaryl. In some embodiments, A is pyridyl. In some embodiments, A is pyridyl substituted by 1 $R^3$. In some embodiments, A is pyridyl is substituted by 1 $R^3$ in the para position In some embodiments, $R^3$ is alkyl or —$OR^c$. In some embodiments, $R^3$ is —$OR^c$. In some embodiments, $R^c$ is alkyl. In some embodiments, $R^c$ is alkyl substituted by one or more $R^6$. In some embodiments, $R^6$ is halo. In some embodiments, $R^3$ is —$OCH_3$, —$OCF_3$, or —$OCH_2CF_3$. In some embodiments, $R^3$ is —$OCF_3$.

In some embodiments, $R^3$ is alkyl. In some embodiments, $R^3$ is alkyl substituted with $R^5$ (e.g., 1 $R^5$). In some embodiments, $R^5$ is —$OR^c$. In some embodiments, $R^3$ is —$CH_2OCH_3$.

In some embodiments, $R^1$ is hydrogen or alkyl. In some embodiments, $R^1$ is hydrogen.

In some embodiments, $R^1$ is alkyl. In some embodiments, $R^1$ is $C_{1-6}$ alkyl (e.g., methyl, ethyl, propyl, or isopropyl). In some embodiments, $R^1$ is unsubstituted $C_{1-6}$ alkyl (e.g., unsubstituted methyl, unsubstituted ethyl, unsubstituted propyl, or unsubstituted isopropyl). In some embodiments, $R^1$ is $C_{1-6}$ alkyl (e.g., methyl, ethyl, propyl, or isopropyl) substituted with 1-4 $R^4$. In some embodiments, $R^1$ is $C_{1-4}$ alkyl substituted with 1-4 $R^4$ (e.g., methyl, ethyl, propyl, or isopropyl).

In some embodiments, $R^4$ is deuterium, halo, —$OR^c$, oxo, carbocyclyl, heteroaryl, —$C(O)OR^c$, or —$C(O)N(R^d)_2$. In some embodiments, $R^4$ is deuterium. In some embodiments, $R^1$ is $CD_3$ or $CD_2CD_3$.

In some embodiments, $R^4$ is halo (e.g., fluoro). In some embodiments, $R^1$ is —$CH_2CF_3$ or $CH_2CHF_2$.

In some embodiments, $R^4$ is —$OR^c$ (e.g., —OH or —$OCH_3$). In some embodiments, $R^1$ is —$CH_2CH_2OCH_3$, $CH_2CH_2OH$, $CH_2CH_2CH(OH)CH_3$, $CH_2CH_2CH_2OH$, or $CH_2CH_2CH_2OCH_3$.

In some embodiments, $R^4$ is carbocyclyl (e.g., cyclopropyl). In some embodiments, $R^1$ is —$CH_2CH_2$-cyclopropyl or —$CH_2$-cyclopropyl.

In some embodiments, $R^4$ is heterocyclyl (e.g., tetrahydropyranyl, tetrahydrofuranyl). In some embodiments, $R^1$ is —CH$_2$-tetrahydropyranyl or —CH$_2$-tetrahydrofuranyl.

In some embodiments, $R^4$ is heteroaryl (e.g., oxadiazolyl, pyrimidinyl). In some embodiments, $R^4$ is heteroaryl (e.g., oxadiazolyl) substituted by 1-4 $R^7$. In some embodiments, $R^1$ is —CH$_2$CH$_2$-5-methyl-1,3,4-oxadiazole.

In some embodiments, $R^4$ is —C(O)OR$^c$ (e.g., —C(O)OH). In some embodiments, $R^1$ is —CH$_2$C(O)OH.

In some embodiments, $R^4$ is —C(O)N(R$^d$)$_2$ (e.g., C(O)—NH(CH$_3$)$_2$, C(O)—NHCH(CH$_3$)$_2$, C(O)—NH(CH$_3$)(CH$_2$CH$_3$), C(O)N(CH$_3$)CH$_2$CF$_3$, or C(O)—N-pyrrolidinyl). In some embodiments, $R^1$ is —CH$_2$C(O)NHCH(CH$_3$)$_2$ or —C(O)—N-pyrrolidinyl.

In some embodiments, the compound of Formula (I) is a compound of Formula (I-d):

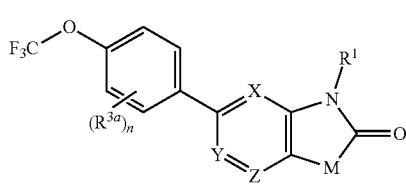

(I-d)

or a pharmaceutically acceptable salt thereof, wherein each of X, Y, and Z is independently N or CR'; R' is hydrogen, alkyl, —OR$^c$, or halogen (e.g., hydrogen); $R^1$ is hydrogen, alkyl, carbocyclyl, or heterocyclyl, wherein alkyl, carbocyclyl, and heterocyclyl are optionally substituted with one or more $R^4$; each $R^{1a}$ is independently alkyl, carbocyclyl, heterocyclyl, halo, cyano, nitro, or —OR$^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, cyano, nitro, —C(O)N(R$^d$)$_2$, —C(O)R$^c$, —C(O)OR$^c$, —S(O)$_2$—R$^e$, —S(O)$_2$N(R$^d$)$_2$, or —OR$^c$; each R$^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each R$^d$ is independently hydrogen or alkyl optionally substituted with one or more halogen; or two R$^d$, taken together with the atoms to which they are attached, form a heterocyclyl optionally substituted with —OH, alkoxy, or alkyl optionally substituted with alkoxy; each R$^e$ is alkyl; each $R^6$ is independently alkyl, carbocyclyl, heterocyclyl, halo, cyano, nitro, or —OH; and n is 0, 1, 2, 3, or 4.

In some embodiments, X is CR'(e.g., CH). In some embodiments, Y is CR'(e.g., CH). In some embodiments, Z is CR'(e.g., CH). In some embodiments, each of X, Y, and Z is independently CR'(e.g., CH).

In some embodiments, n is 0 or 1. In some embodiments, n is 0. In some embodiments, n is 1.

In some embodiments, $R^{1a}$ is alkyl or —OR$^c$. In some embodiments, $R^{1a}$ is alkyl (e.g., ethyl) substituted by one or more $R^5$. In some embodiments, $R^5$ is —OR$^c$. In some embodiments, R$^c$ is alkyl (e.g., methyl). In some embodiments, $R^{1a}$ is —CH$_2$CH$_2$OCH$_3$.

In some embodiments, $R^{1a}$ is —OR$^c$. In some embodiments, R$^c$ is alkyl. In some embodiments, $R^{1a}$ is —OCH$_3$.

In some embodiments, $R^{1a}$ is alkyl. In some embodiments, $R^{1a}$ is alkyl substituted with $R^5$ (e.g., 1 $R^5$). In some embodiments, $R^5$ is —OR$^c$. In some embodiments, $R^{1a}$ is —CH$_2$OCH$_3$.

In some embodiments, $R^1$ is hydrogen or alkyl. In some embodiments, $R^1$ is hydrogen.

In some embodiments, $R^1$ is alkyl. In some embodiments, $R^1$ is $C_{1-6}$ alkyl (e.g., methyl, ethyl, propyl, or isopropyl). In some embodiments, $R^1$ is unsubstituted $C_{1-6}$ alkyl (e.g., unsubstituted methyl, unsubstituted ethyl, unsubstituted propyl, or unsubstituted isopropyl). In some embodiments, $R^1$ is $C_{1-6}$ alkyl (e.g., methyl, ethyl, propyl, or isopropyl) substituted with 1-4 $R^4$. In some embodiments, $R^1$ is $C_{1-4}$ alkyl substituted with 1-4 $R^4$ (e.g., methyl, ethyl, propyl, or isopropyl).

In some embodiments, $R^4$ is deuterium, halo, —OR$^c$, oxo, carbocyclyl, heteroaryl, —C(O)OR$^c$, or —C(O)N(R$^d$)$_2$. In some embodiments, $R^4$ is deuterium. In some embodiments, $R^1$ is CD$_3$ or CD$_2$CD$_3$.

In some embodiments, $R^4$ is halo (e.g., fluoro). In some embodiments, $R^1$ is —CH$_2$CF$_3$ or CH$_2$CHF$_2$.

In some embodiments, $R^4$ is —OR$^c$ (e.g., —OH or —OCH$_3$). In some embodiments, $R^1$ is —CH$_2$CH$_2$OCH$_3$, CH$_2$CH$_2$OH, CH$_2$CH$_2$CH(OH)CH$_3$, CH$_2$CH$_2$CH$_2$OH, or CH$_2$CH$_2$CH$_2$OCH$_3$.

In some embodiments, $R^4$ is carbocyclyl (e.g., cyclopropyl). In some embodiments, $R^1$ is —CH$_2$CH$_2$-cyclopropyl or —CH$_2$-cyclopropyl.

In some embodiments, $R^4$ is heterocyclyl (e.g., tetrahydropyranyl, tetrahydrofuranyl). In some embodiments, $R^1$ is —CH$_2$-tetrahydropyranyl or —CH$_2$-tetrahydrofuranyl.

In some embodiments, $R^4$ is heteroaryl (e.g., oxadiazolyl, pyrimidinyl). In some embodiments, $R^4$ is heteroaryl (e.g., oxadiazolyl) substituted by 1-4 $R^7$. In some embodiments, $R^1$ is —CH$_2$CH$_2$-5-methyl-1,3,4-oxadiazole.

In some embodiments, $R^4$ is —C(O)OR$^c$ (e.g., —C(O)OH). In some embodiments, $R^1$ is —CH$_2$C(O)OH.

In some embodiments, $R^4$ is —C(O)N(R$^d$)$_2$ (e.g., C(O)—NH(CH$_3$)$_2$, C(O)—NHCH(CH$_3$)$_2$, C(O)—NH(CH$_3$)(CH$_2$CH$_3$), C(O)N(CH$_3$)CH$_2$CF$_3$, or C(O)—N-pyrrolidinyl). In some embodiments, $R^1$ is —CH$_2$C(O)NHCH(CH$_3$)$_2$ or —C(O)—N-pyrrolidinyl.

In any and all aspects, in some embodiments, the compound of Formulae (I), (I-1), (I-2), (I-3), (I-4), (I-5), (I-6), (I-7), (I-a), (I-b), (I-c), or (I-d) is selected from:

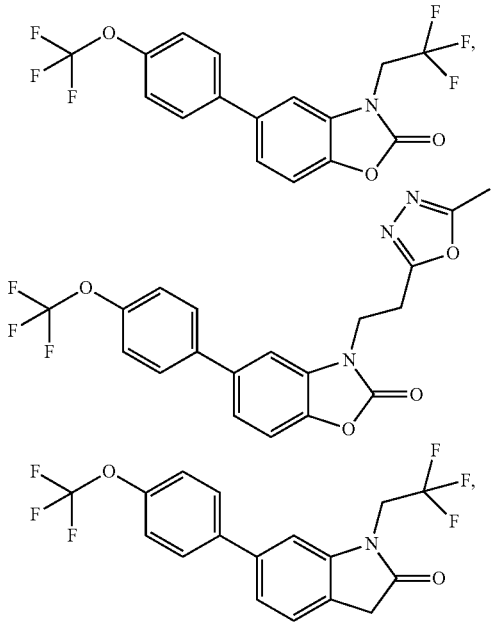

27
-continued
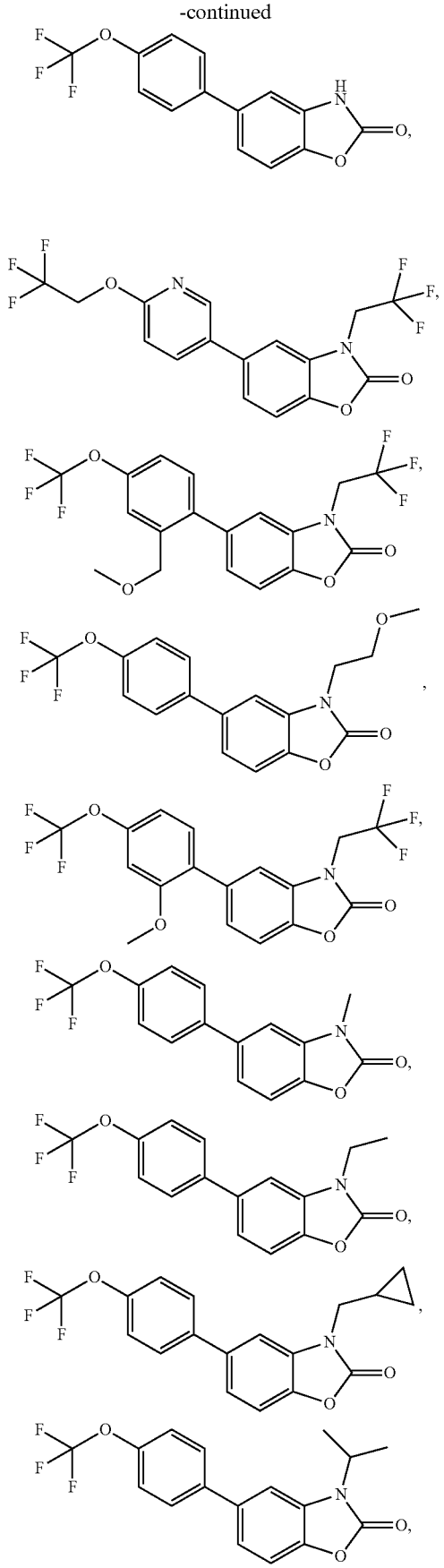
28
-continued
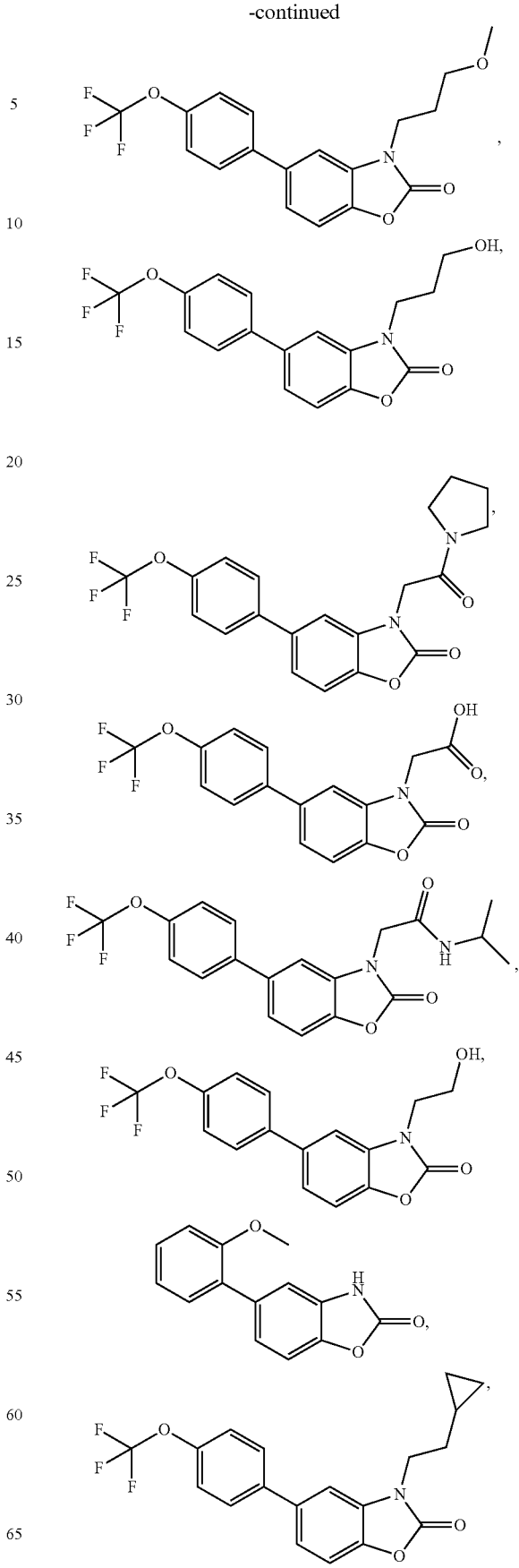

-continued
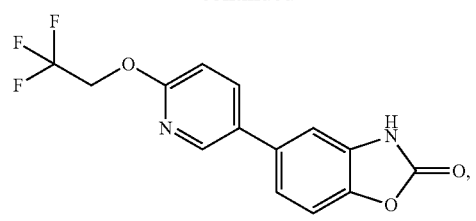
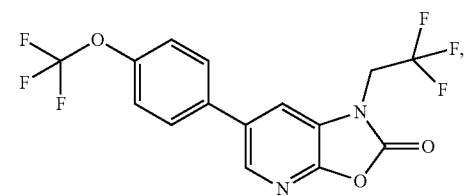
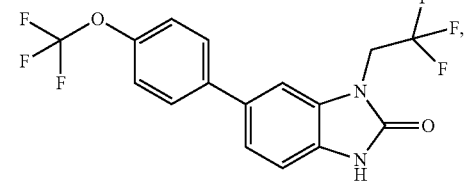
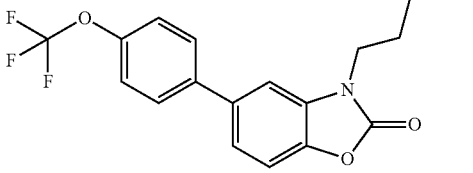
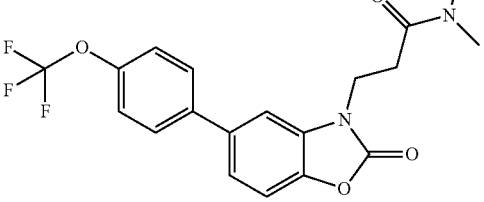
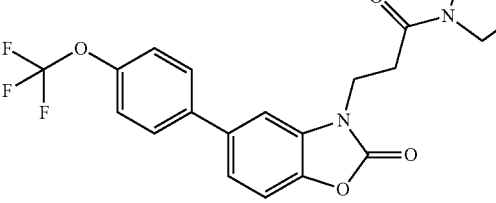
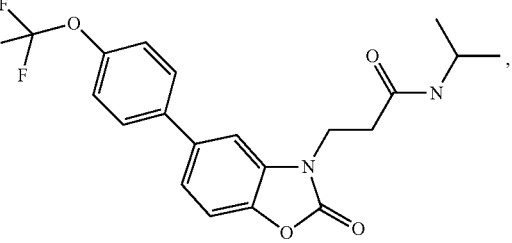
-continued
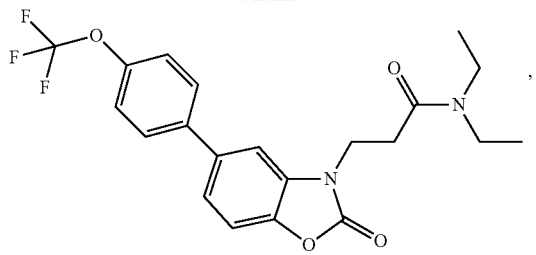
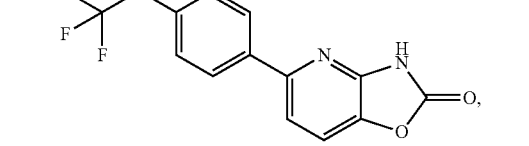
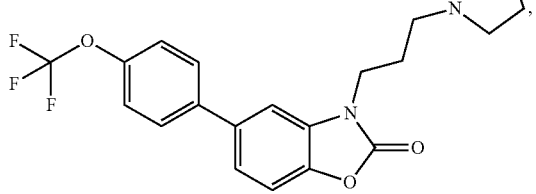
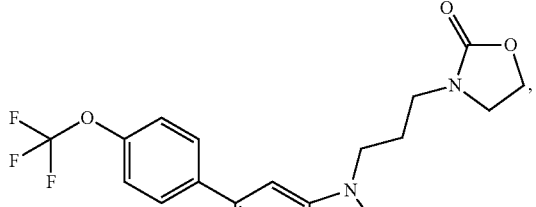
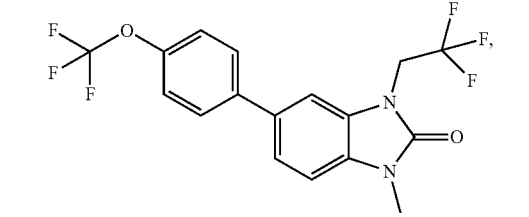
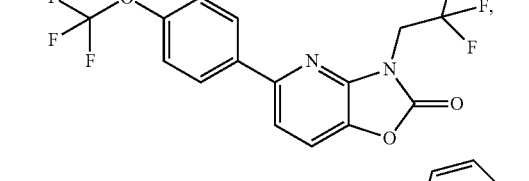
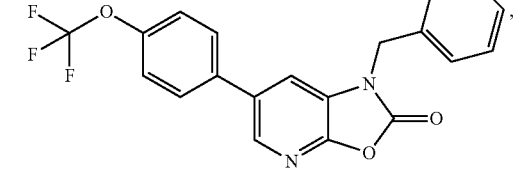

-continued
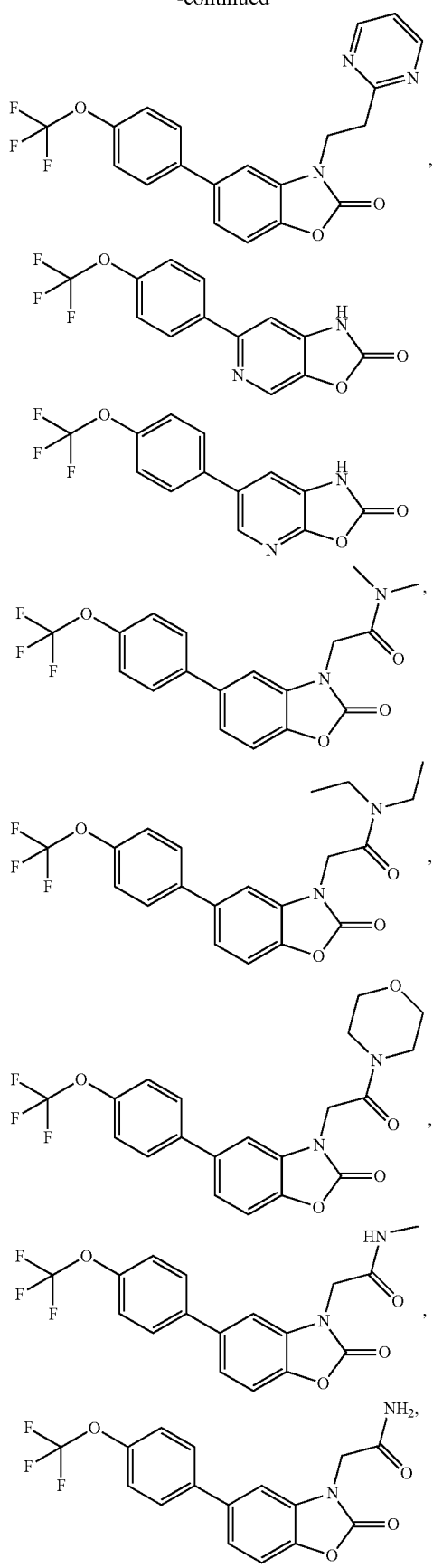
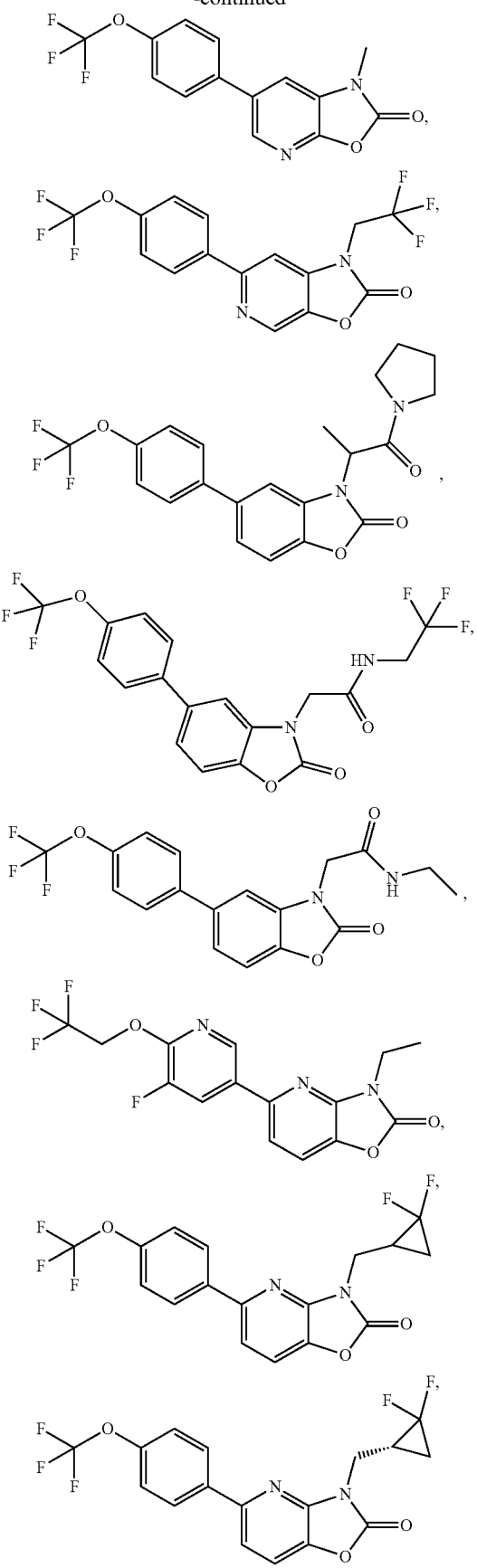

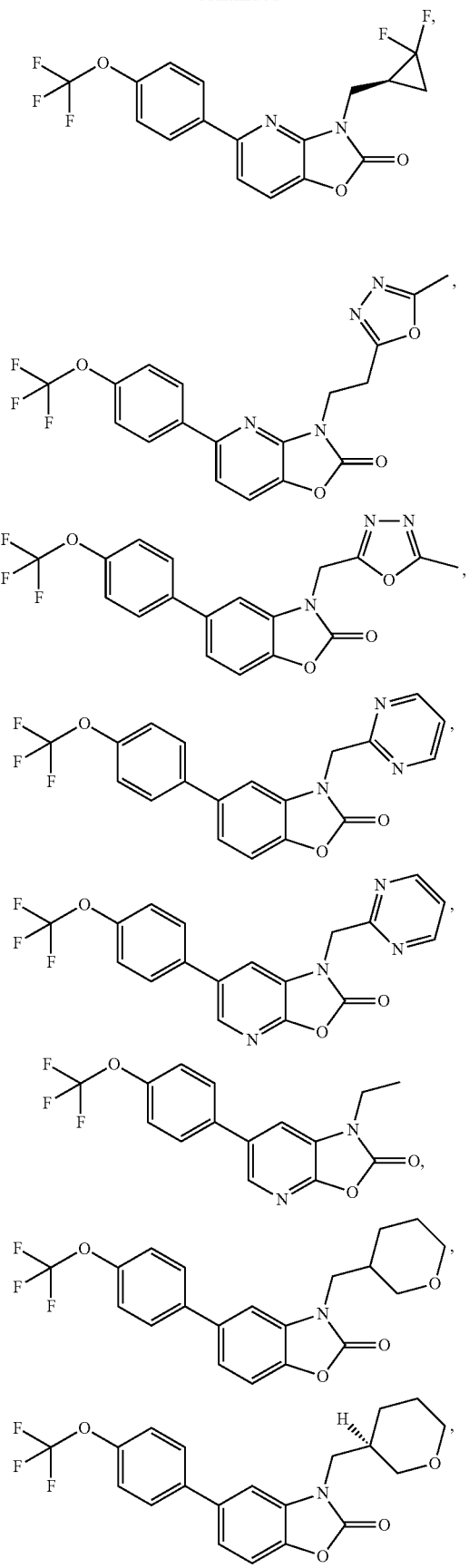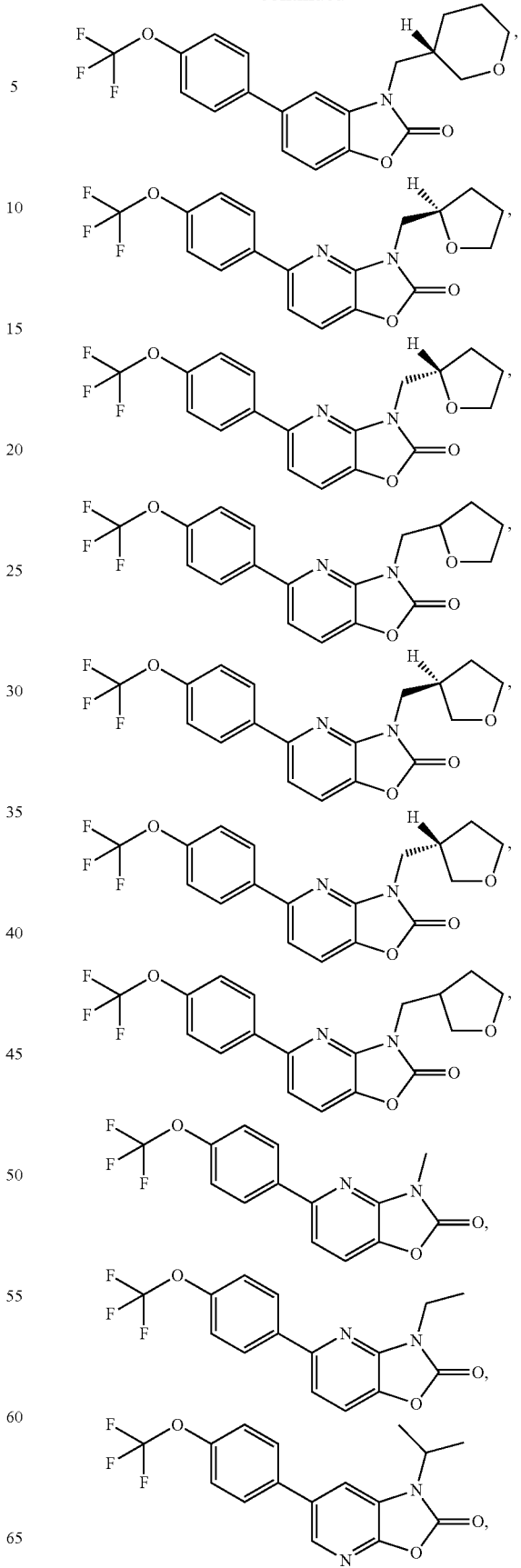

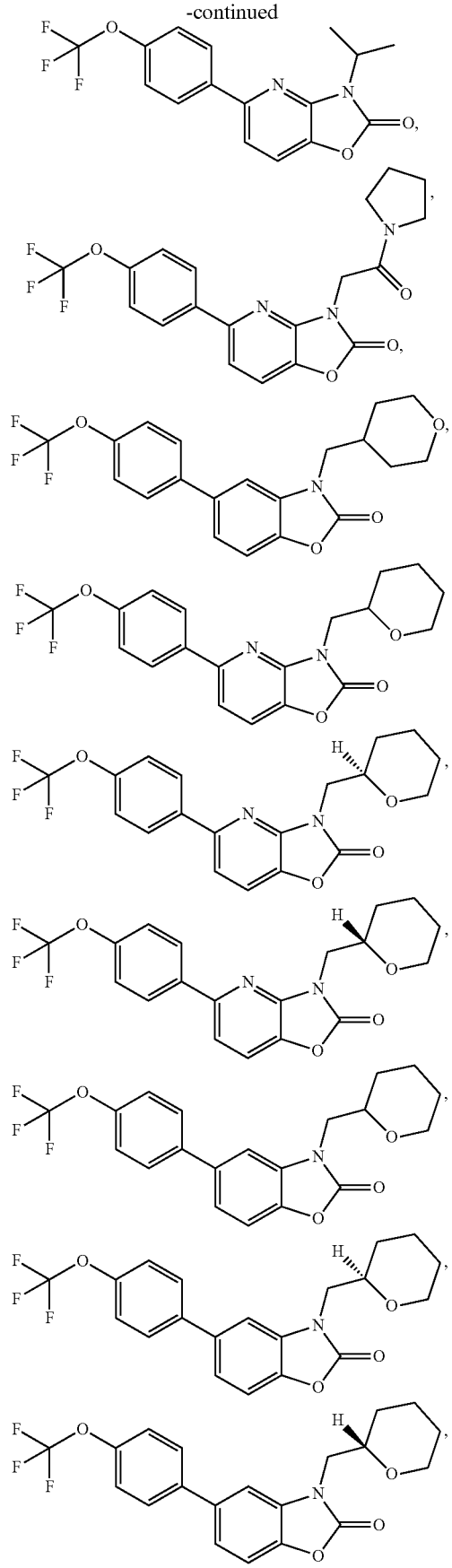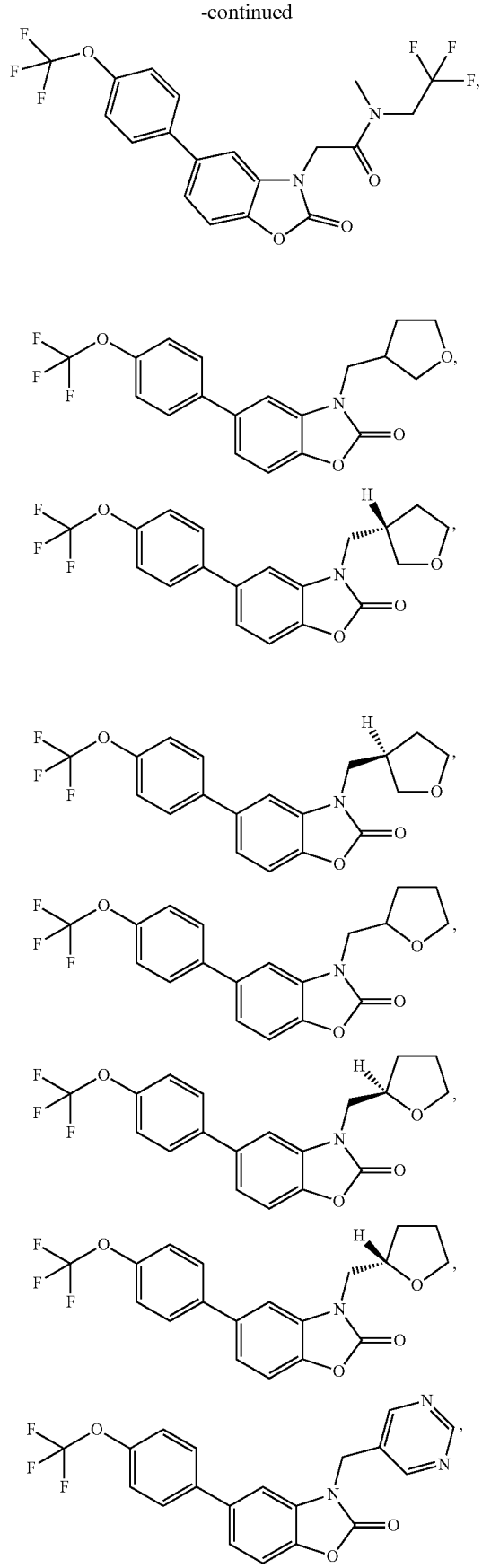

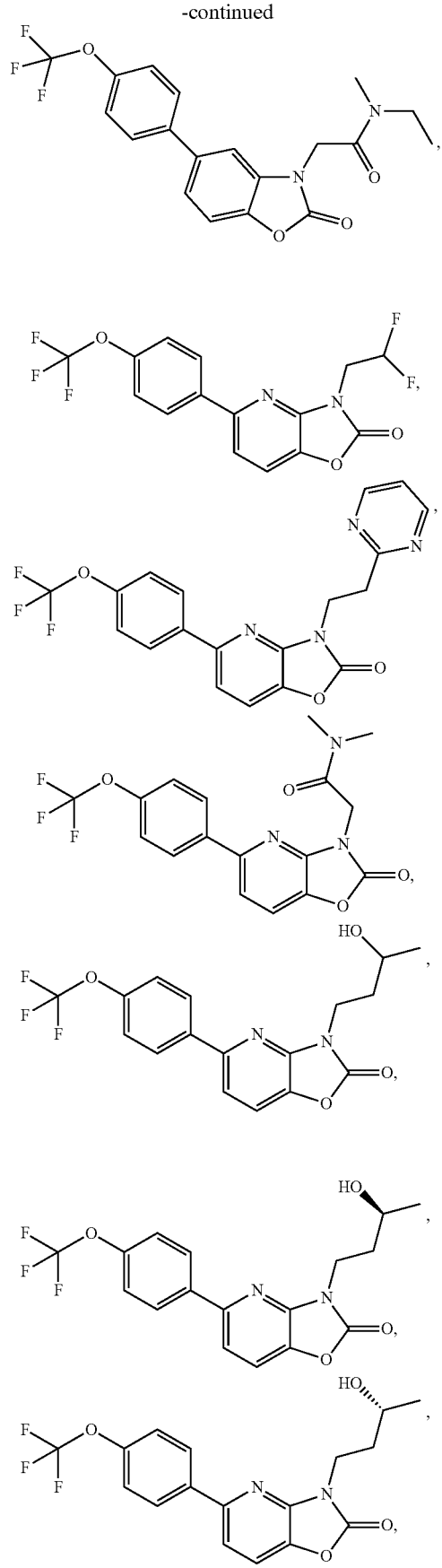
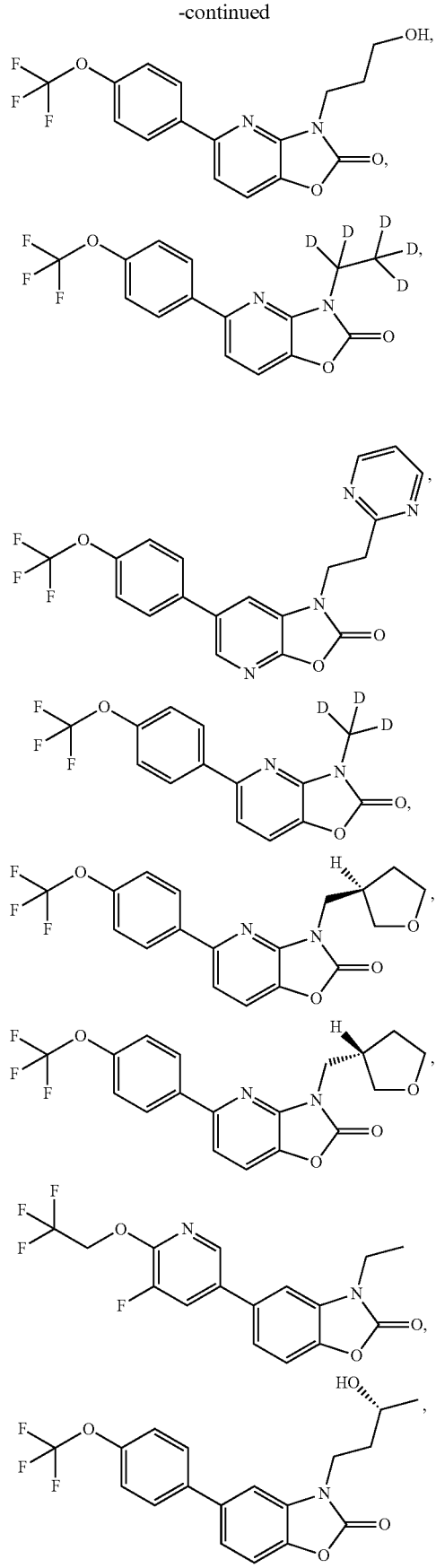

39
-continued
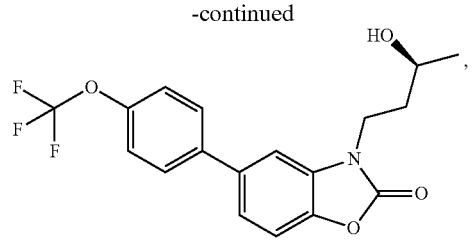
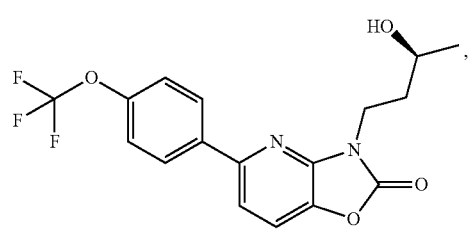
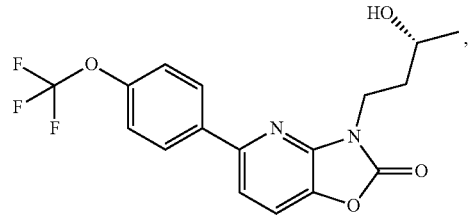
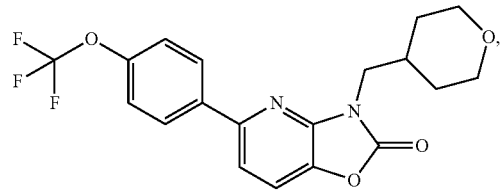
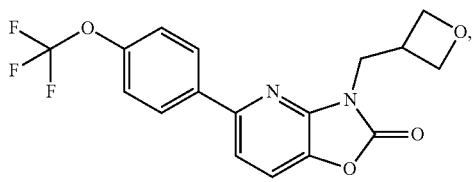
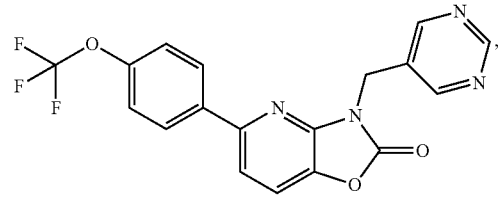
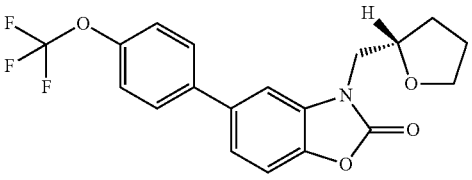
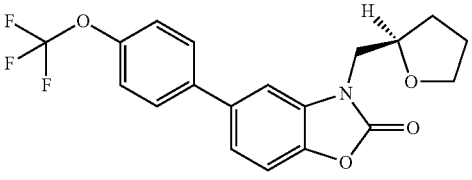
40
-continued
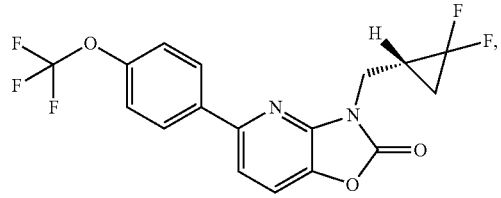
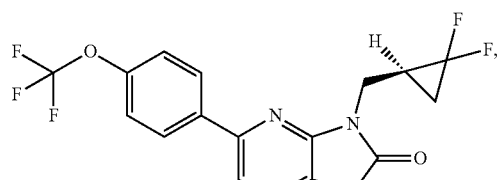
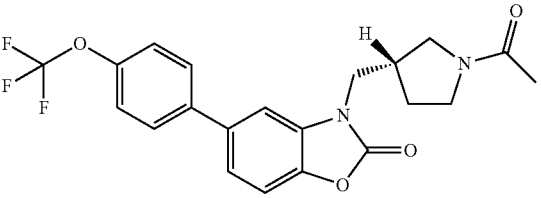
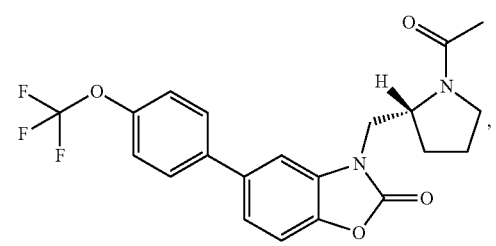
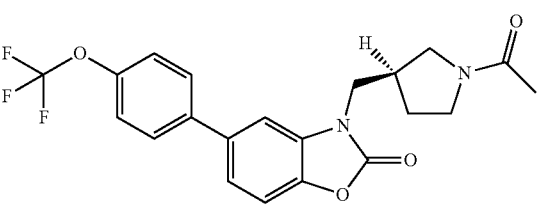
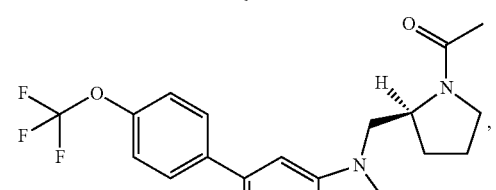
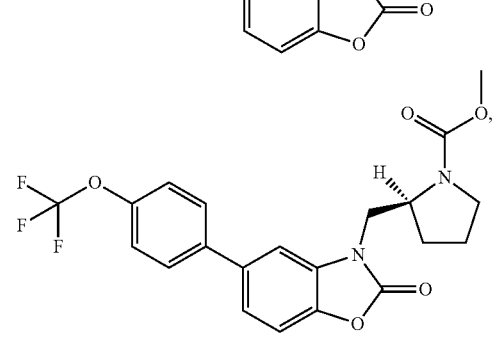

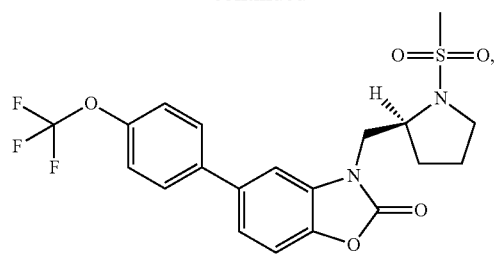
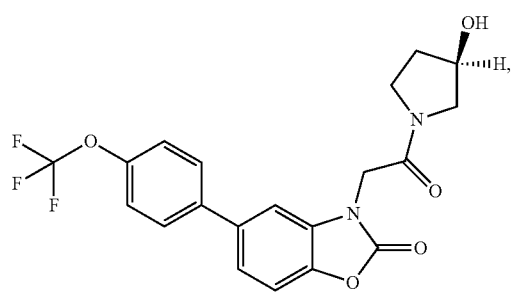
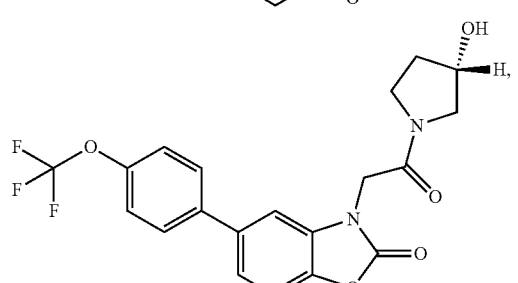
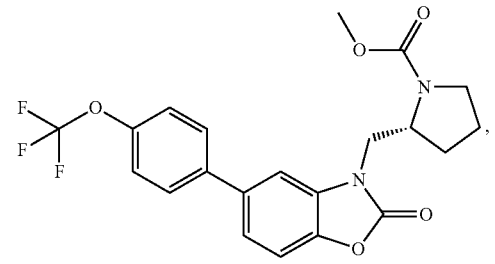
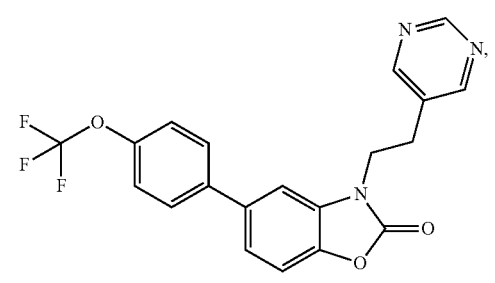
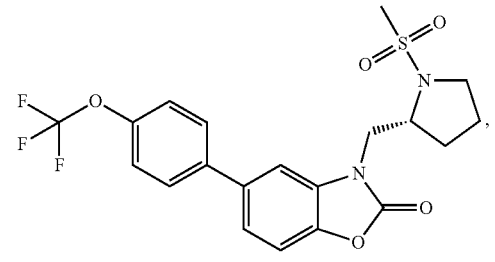
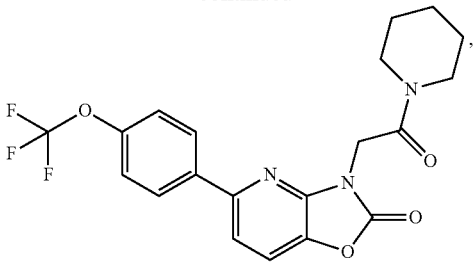
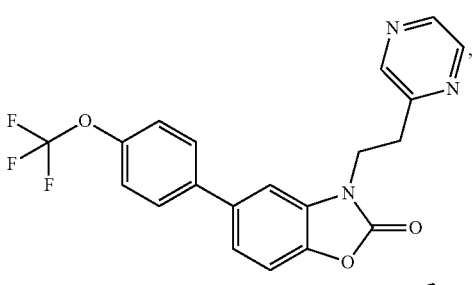
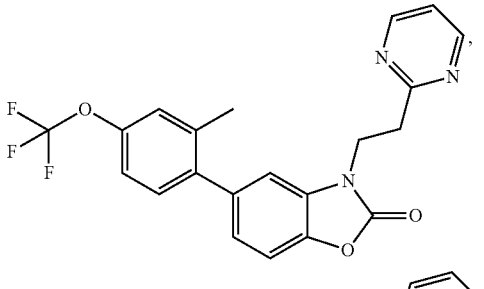
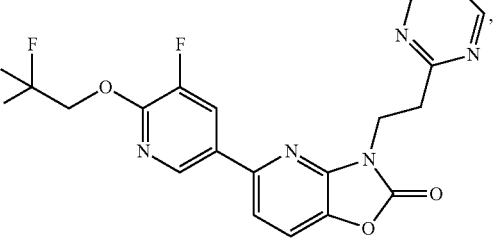
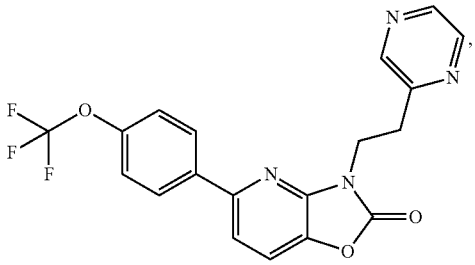
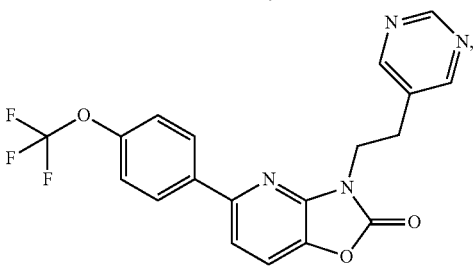

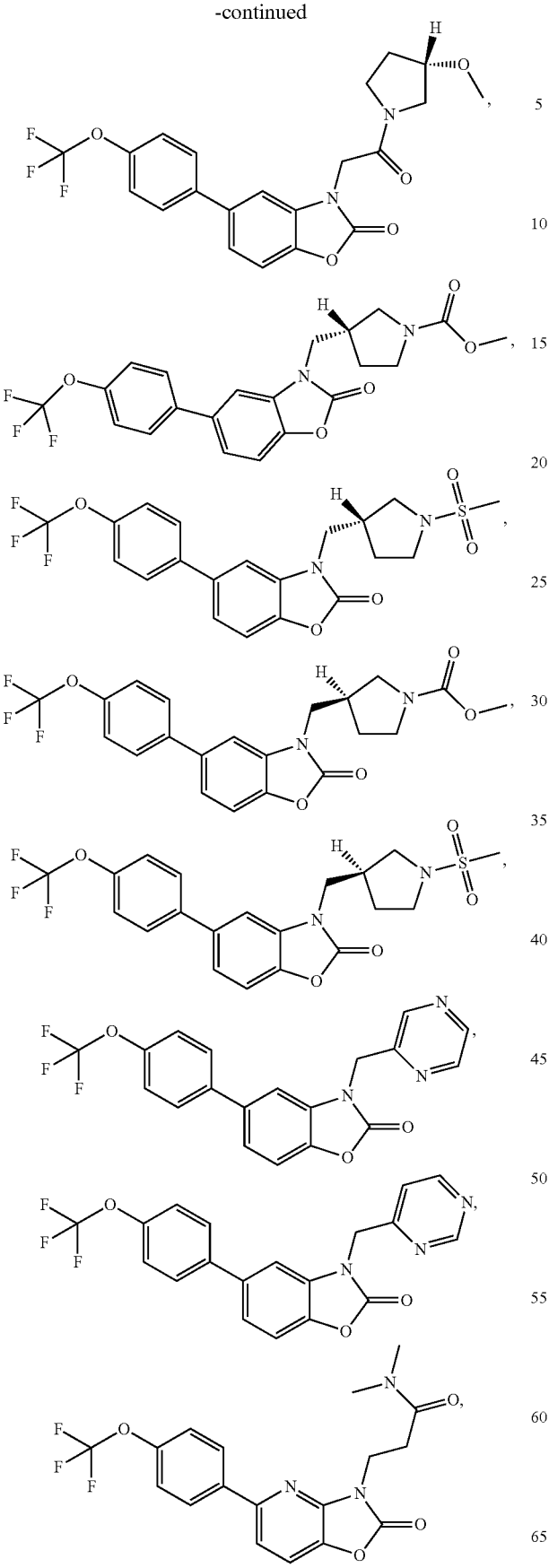
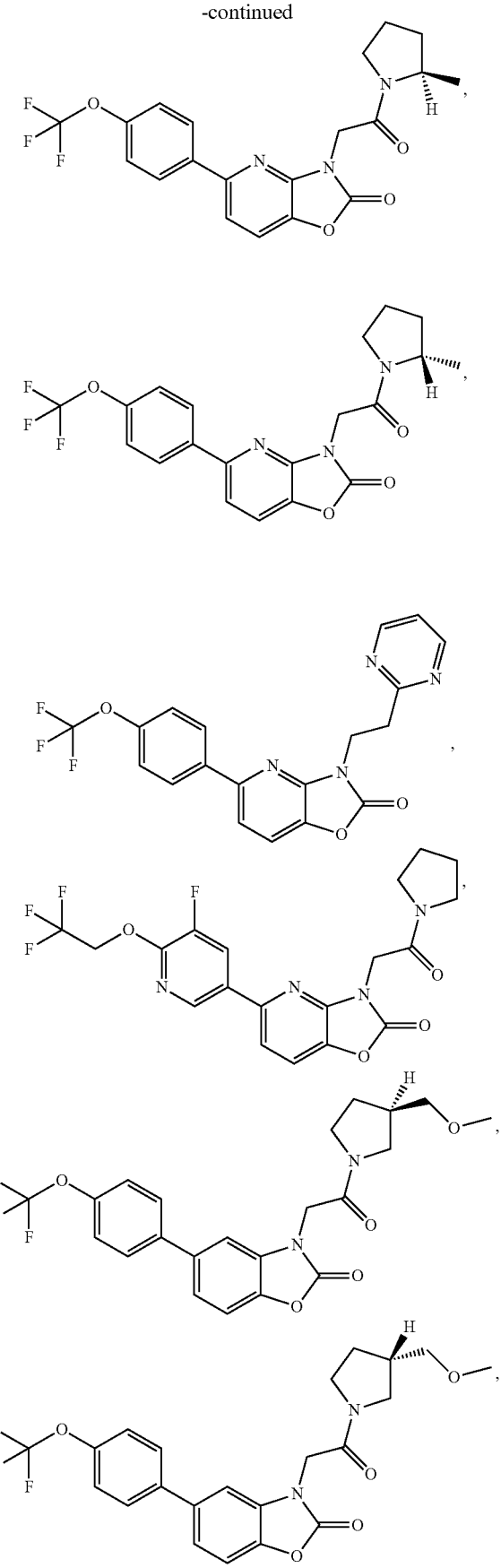

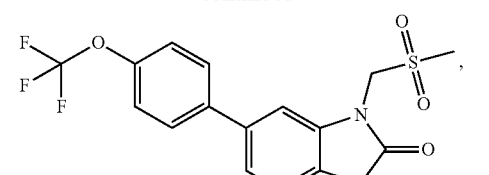
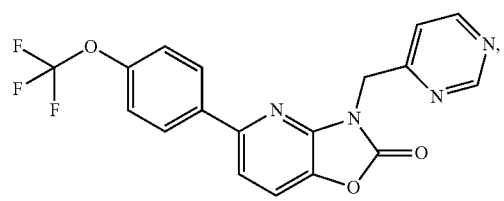
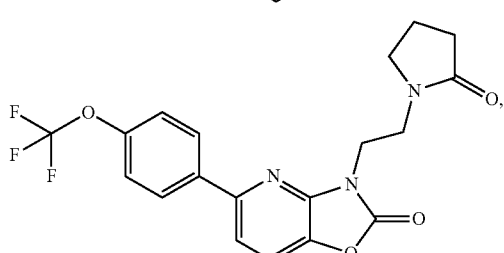
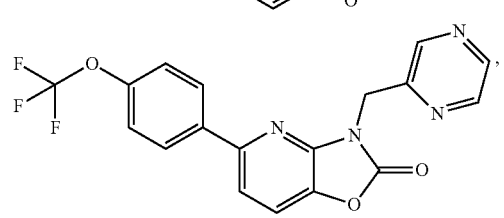
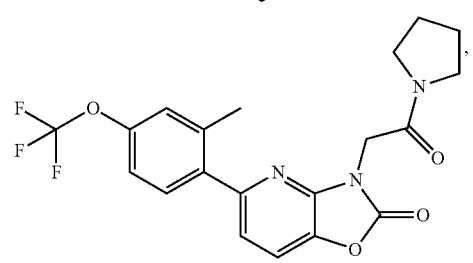
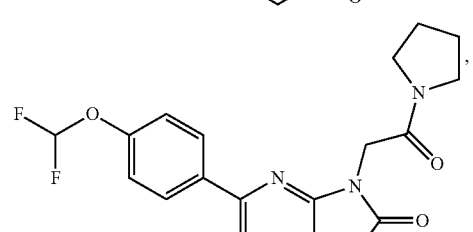
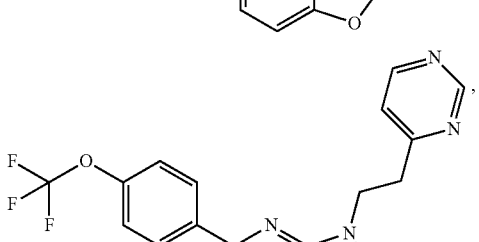
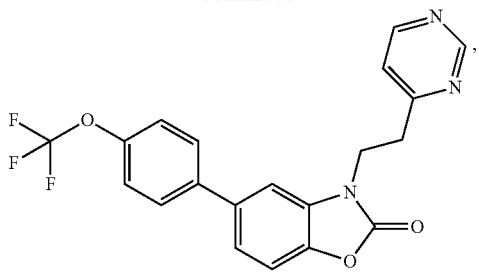
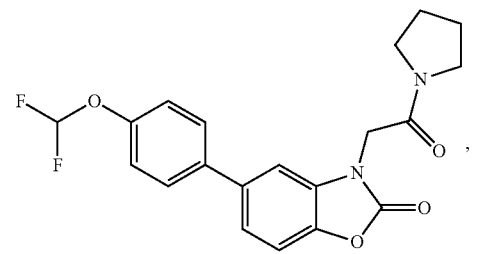
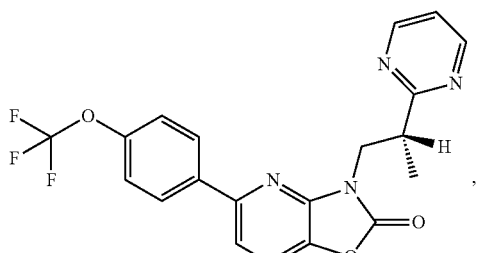
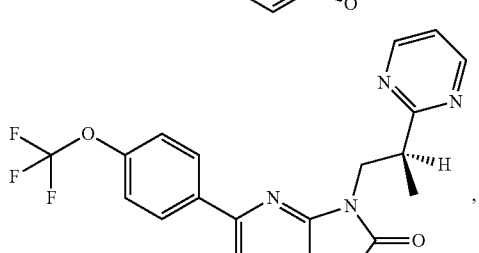
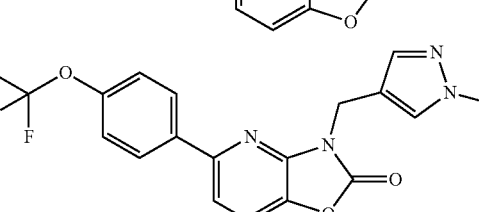
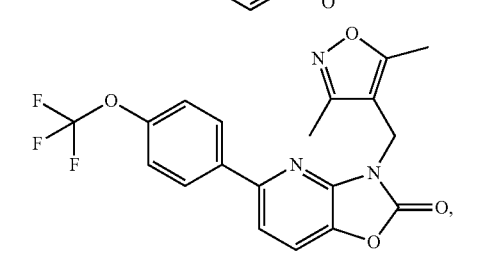
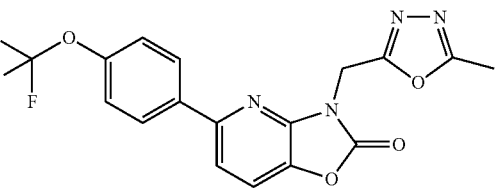

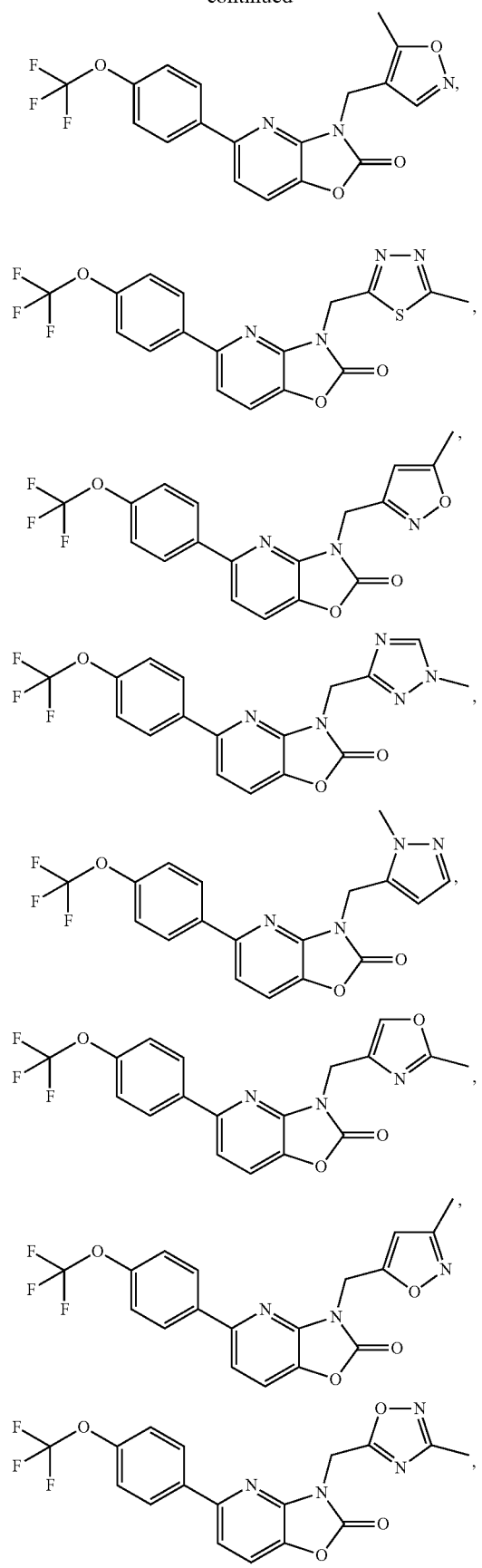
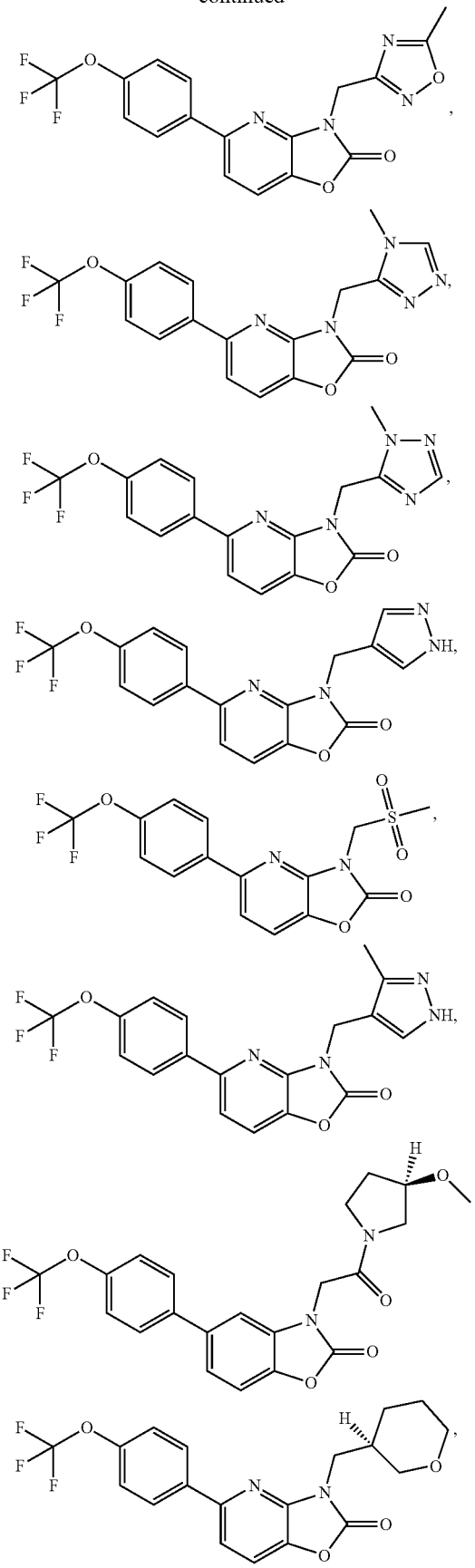

or a pharmaceutically acceptable salt thereof.

In any and all aspects, in certain embodiments, the compound of Formulae (I), (I-1), (I-2), (I-3), (I-4), (I-5), (I-6), (I-7), (I-a), (I-b), (I-c), or (I-d) is selected from:

51
-continued
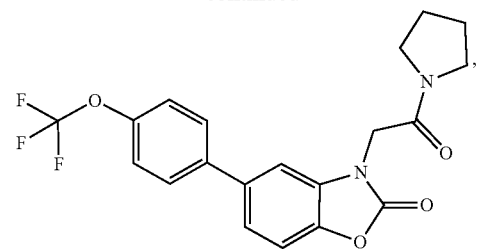
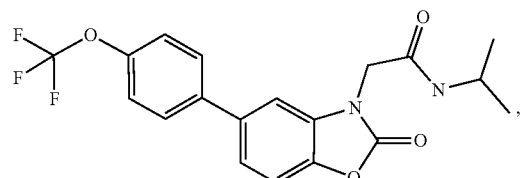
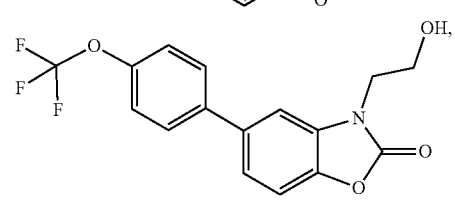
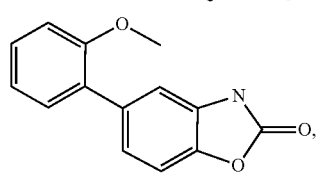
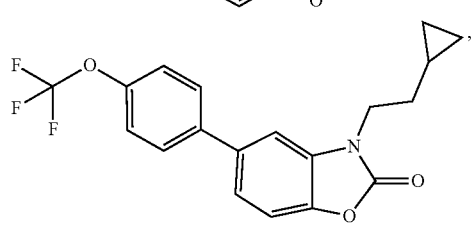
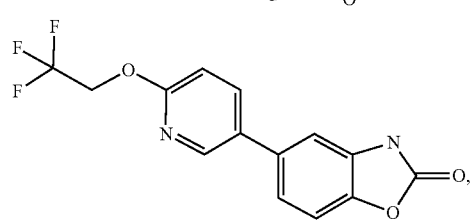
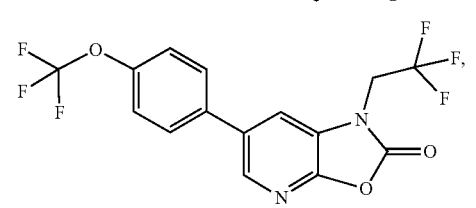
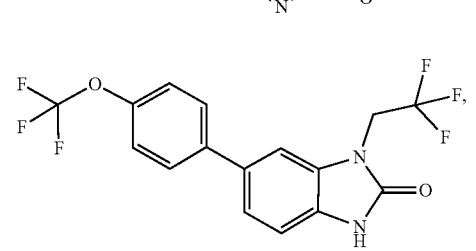
52
-continued
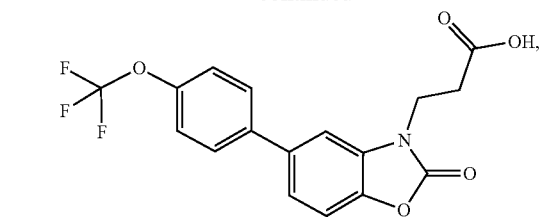
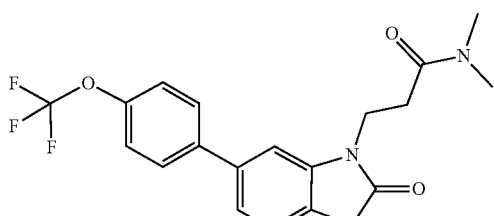
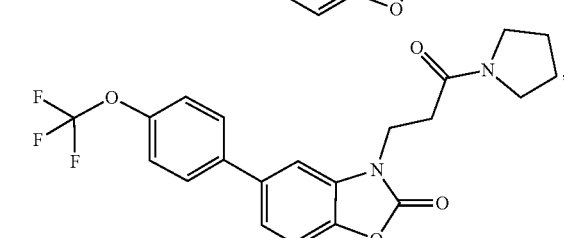
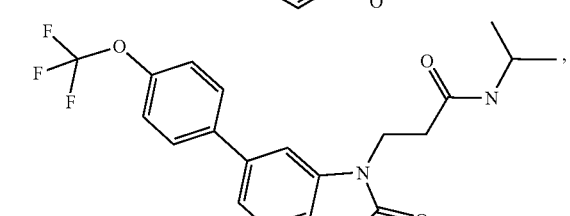
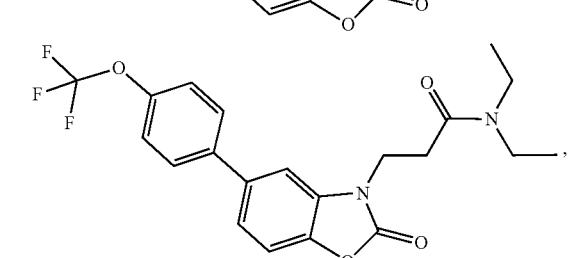
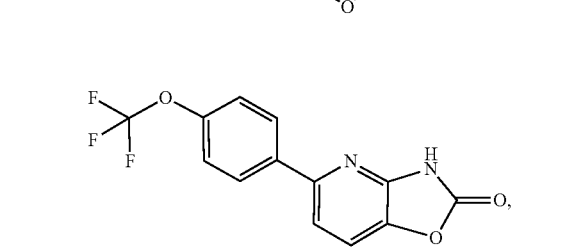
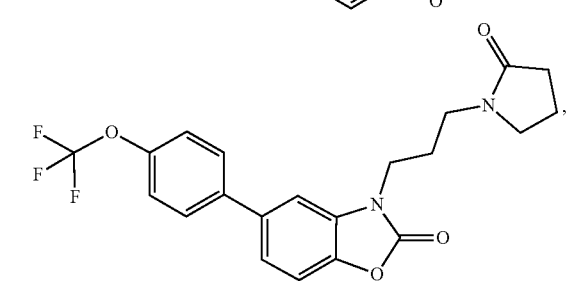

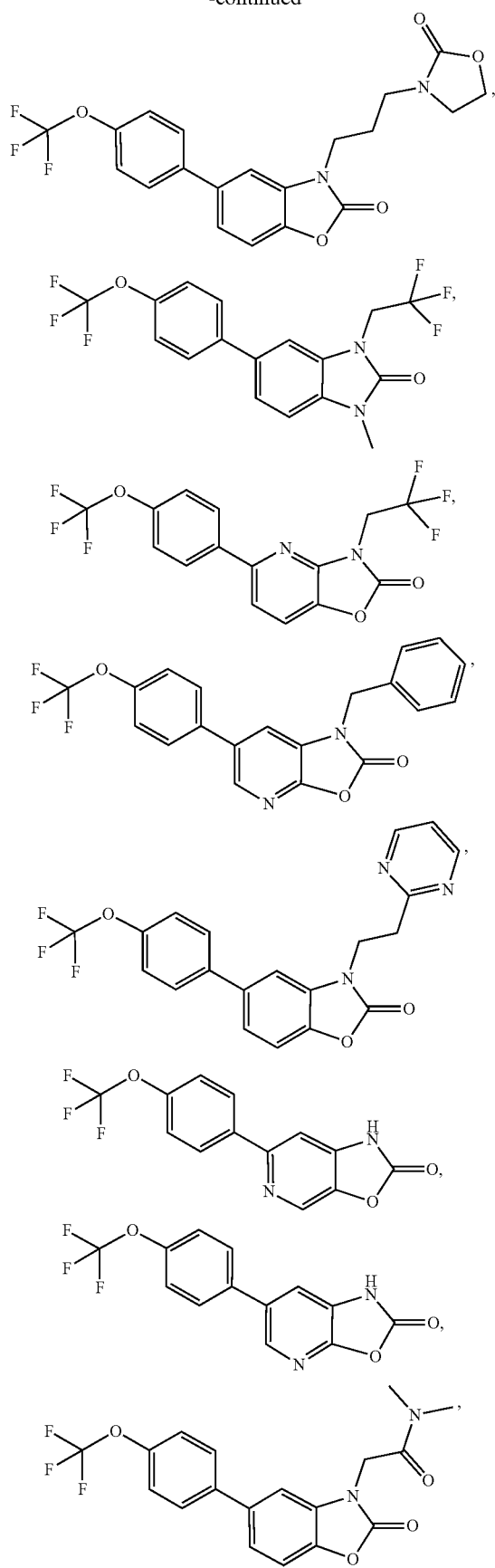
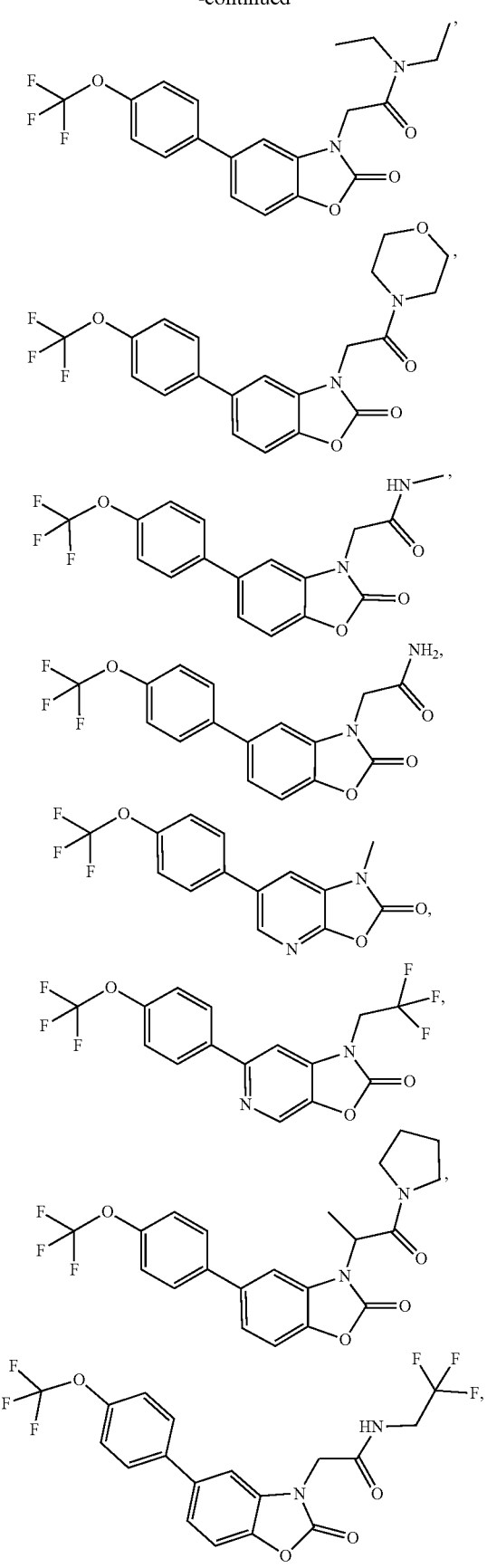

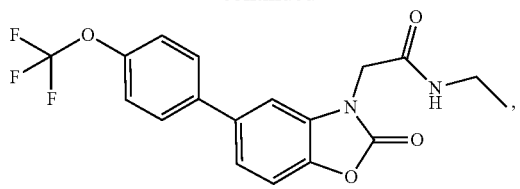
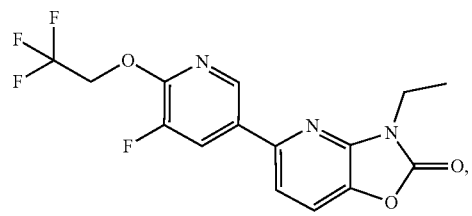
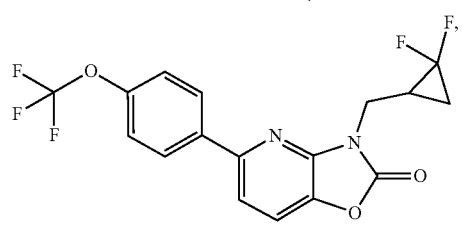
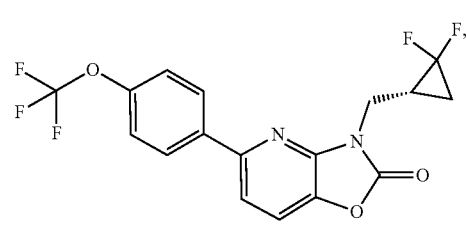
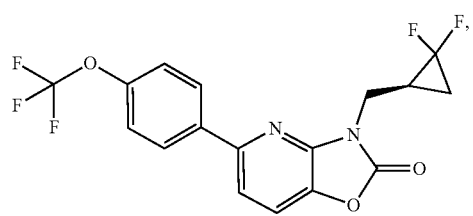
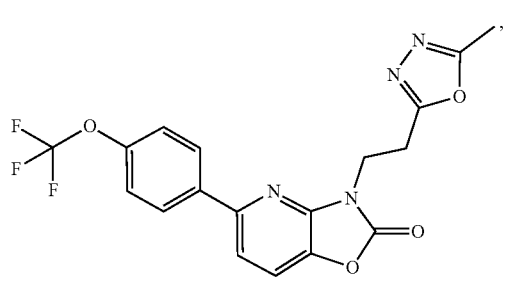
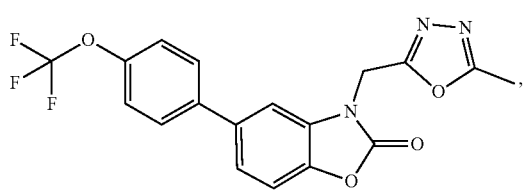
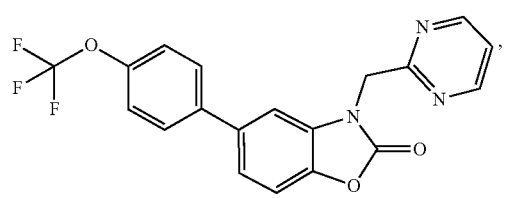
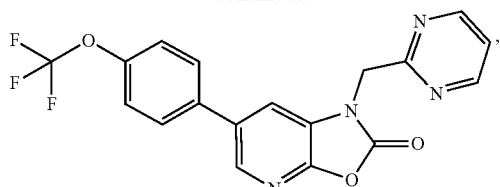
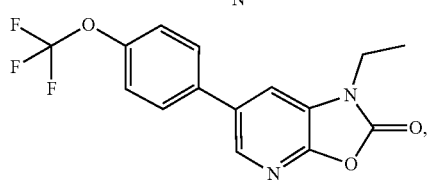
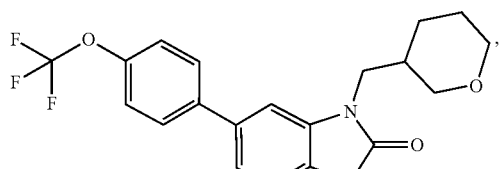
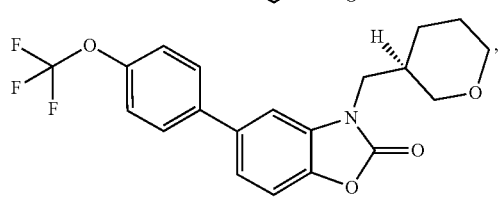
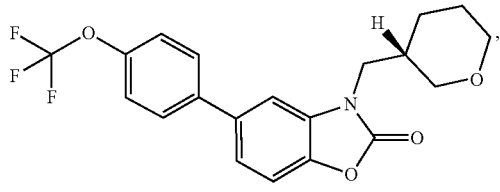
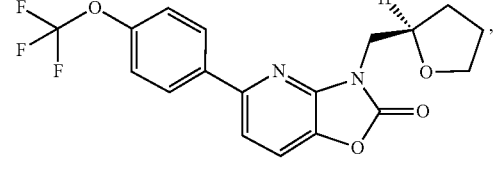
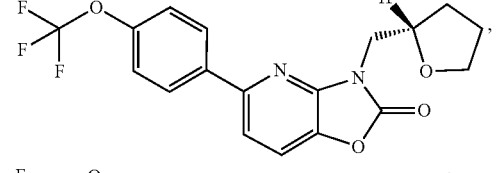
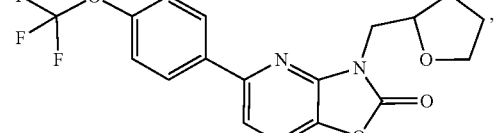
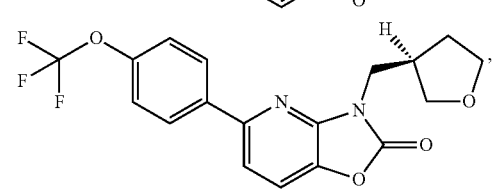

57
-continued
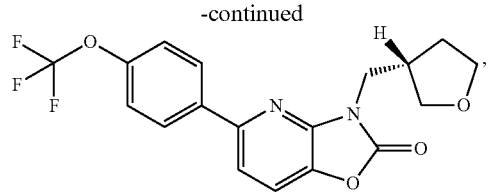
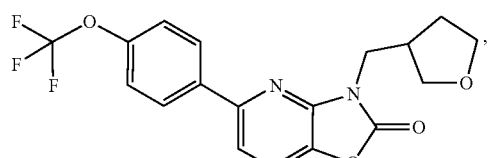
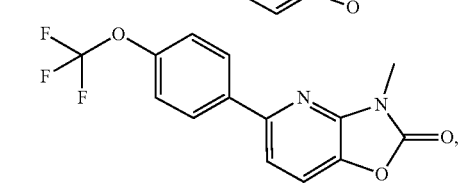
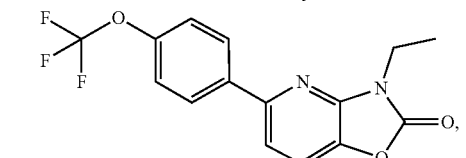
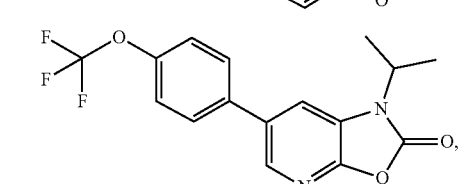
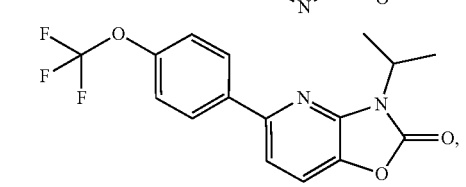
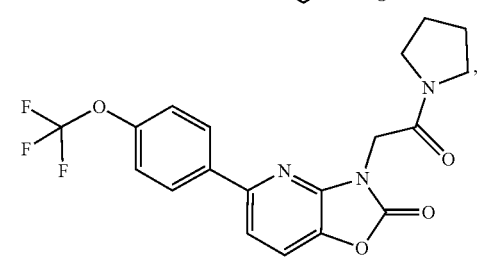
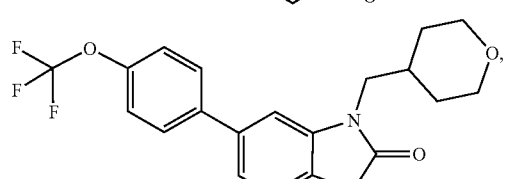
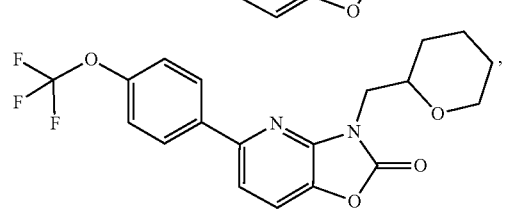
58
-continued
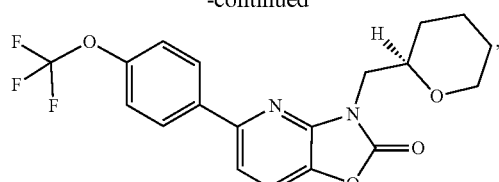
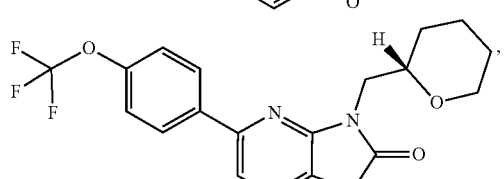
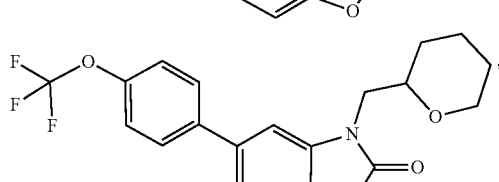
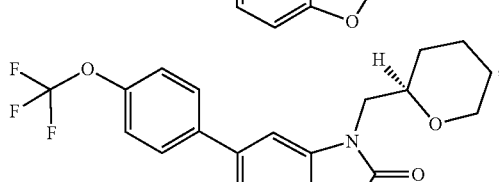
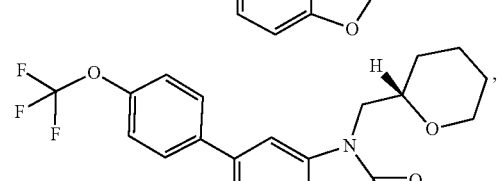
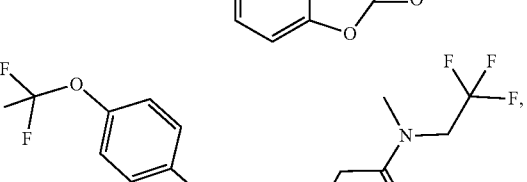
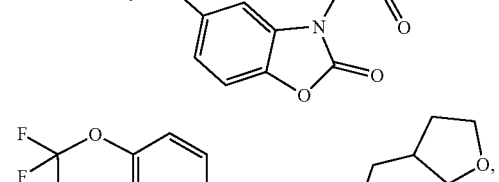
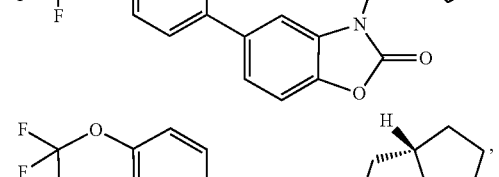
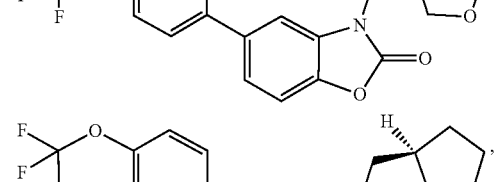
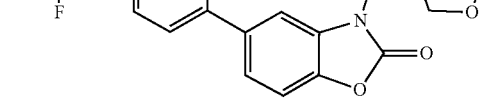

59
-continued
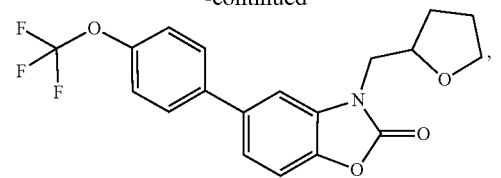,
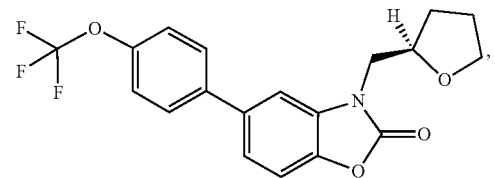,
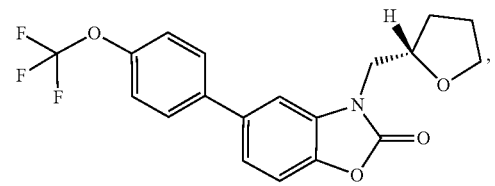,
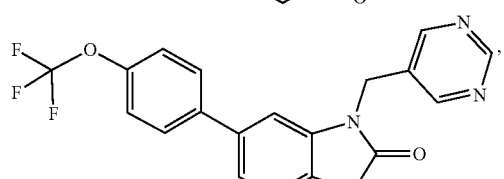,
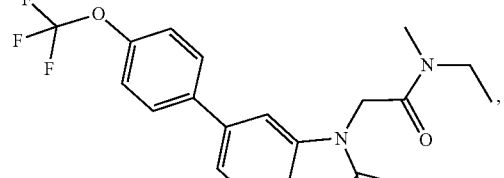,
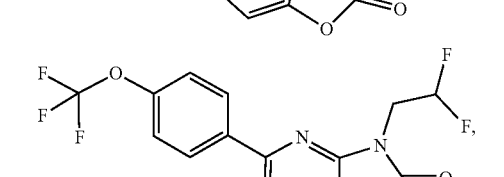,
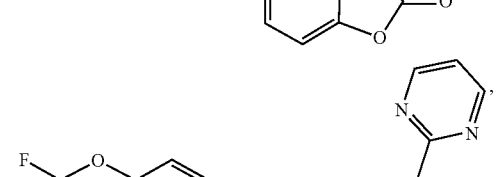,
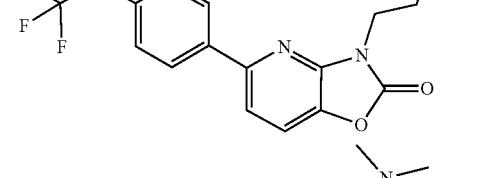,
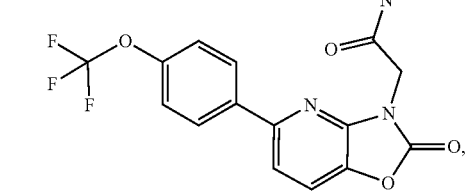,
60
-continued
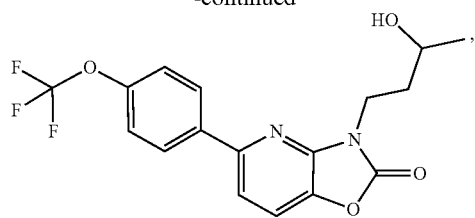,
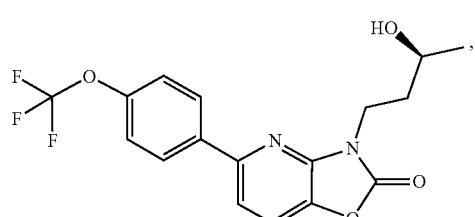,
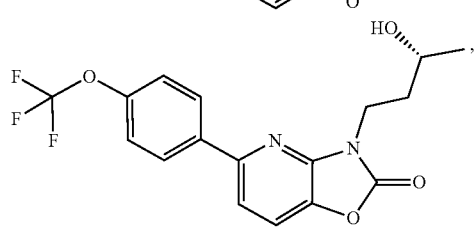,
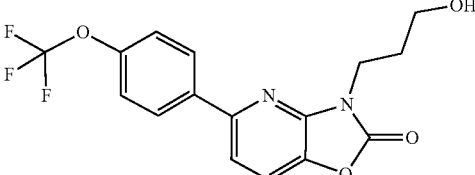,
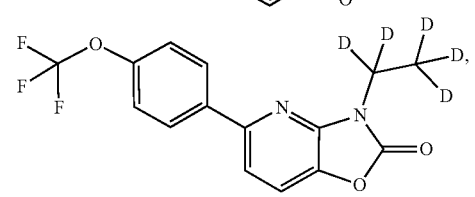,
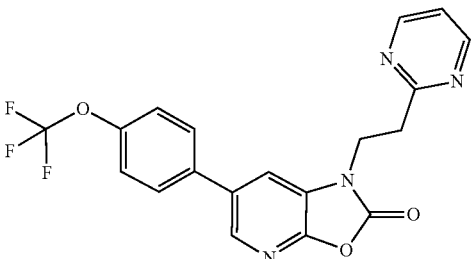,
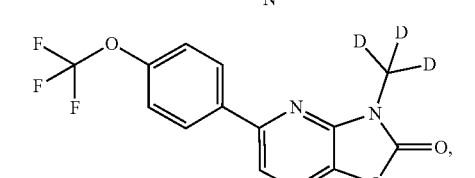,
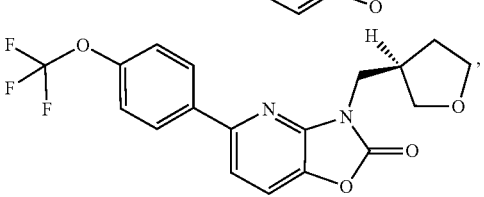,

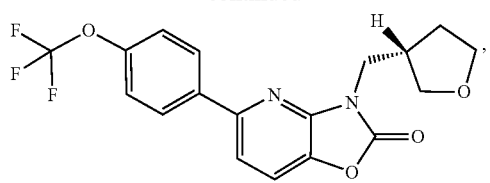
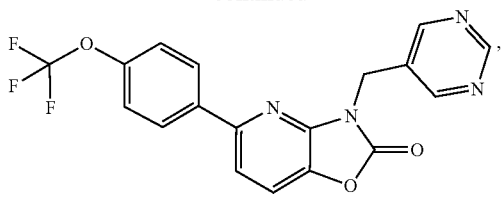
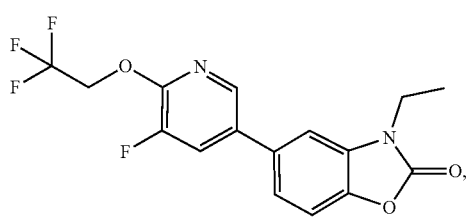
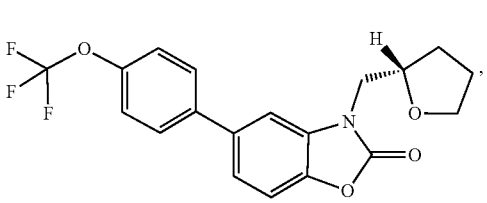
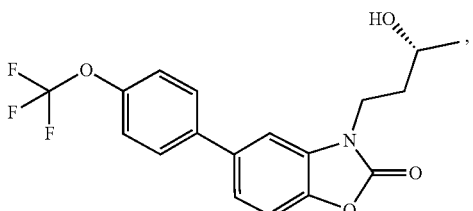
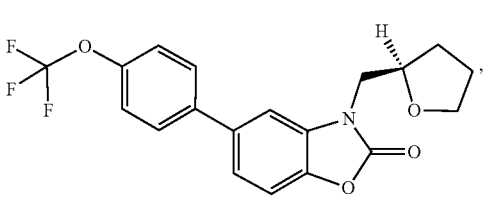
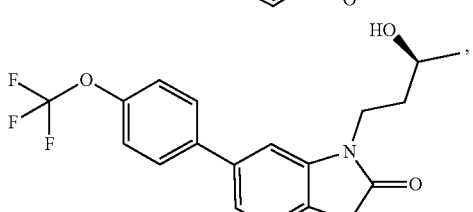
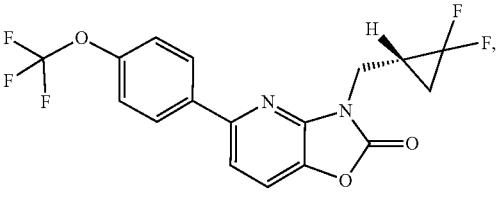
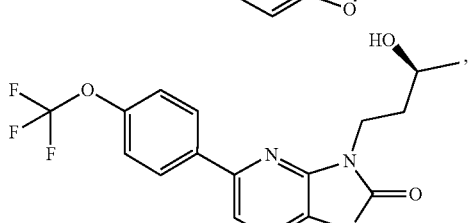
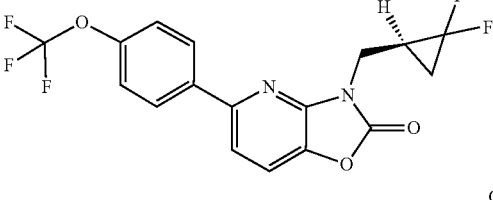
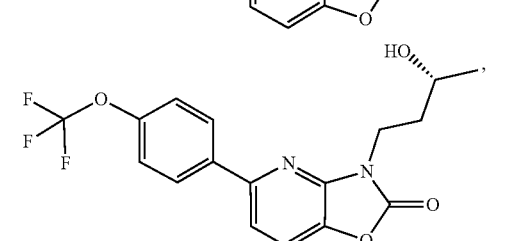
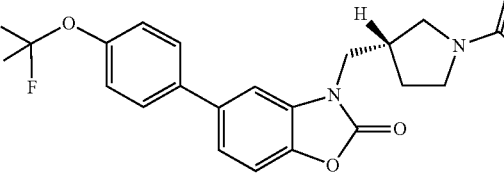
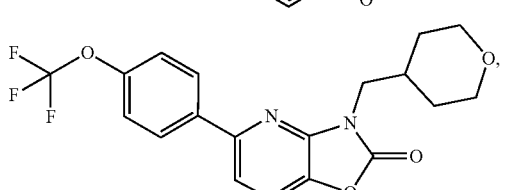
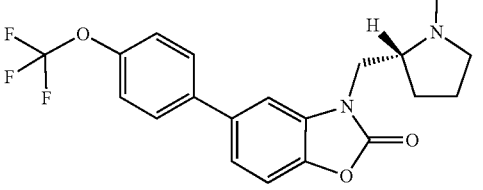
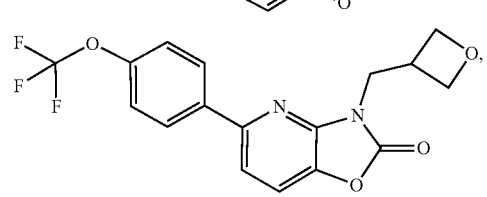
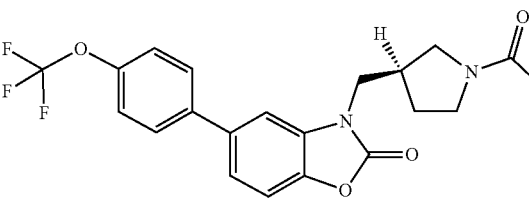

63
-continued
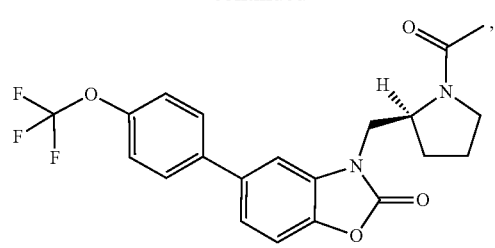
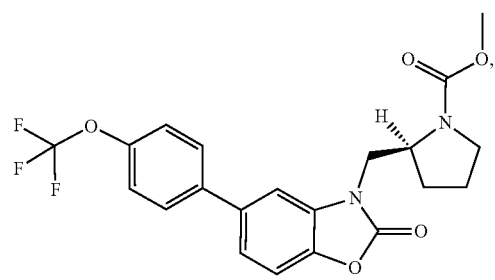
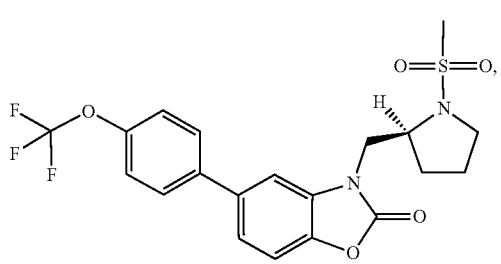
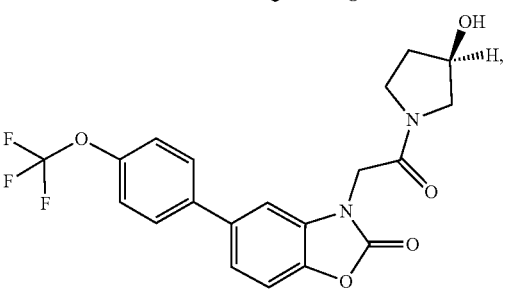
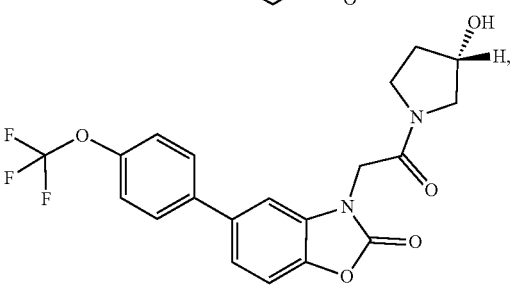
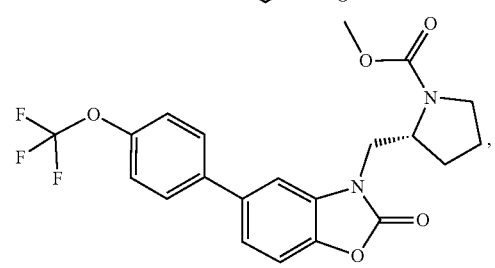
64
-continued
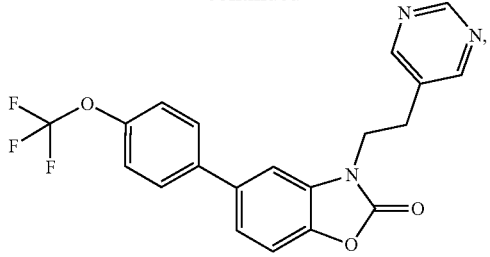
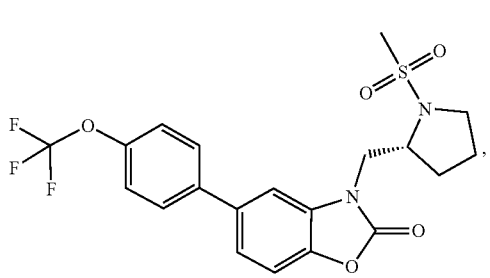
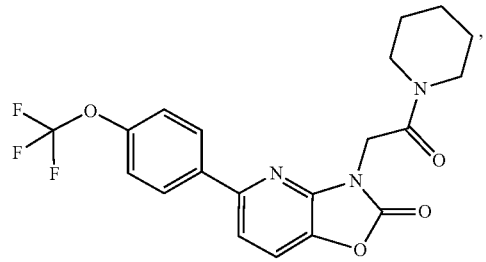
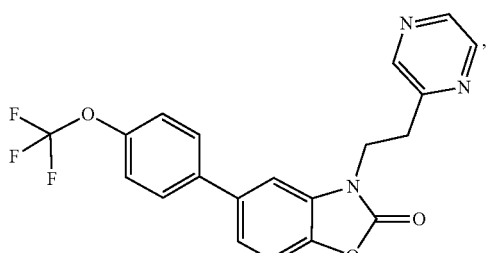
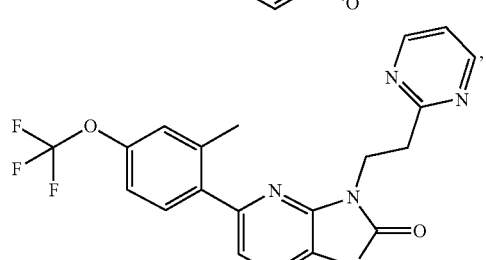
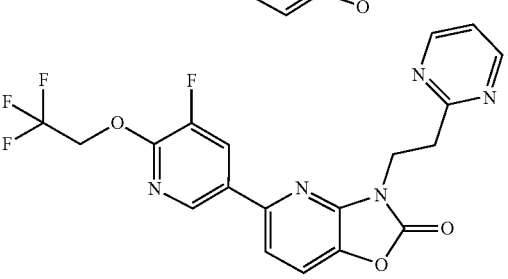

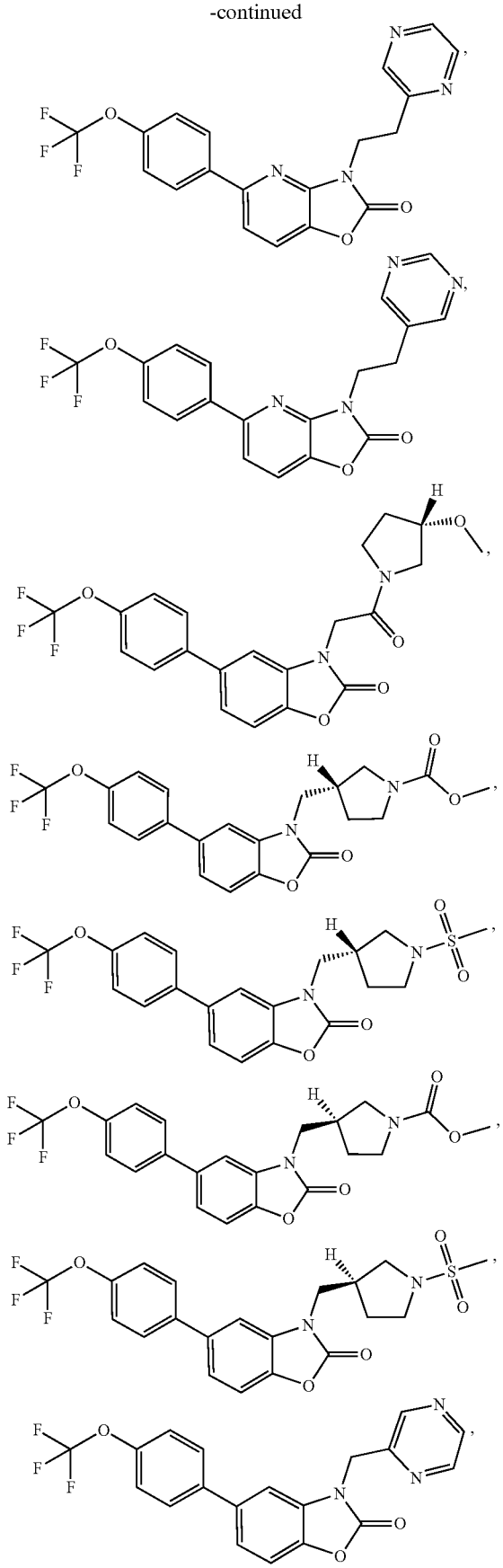
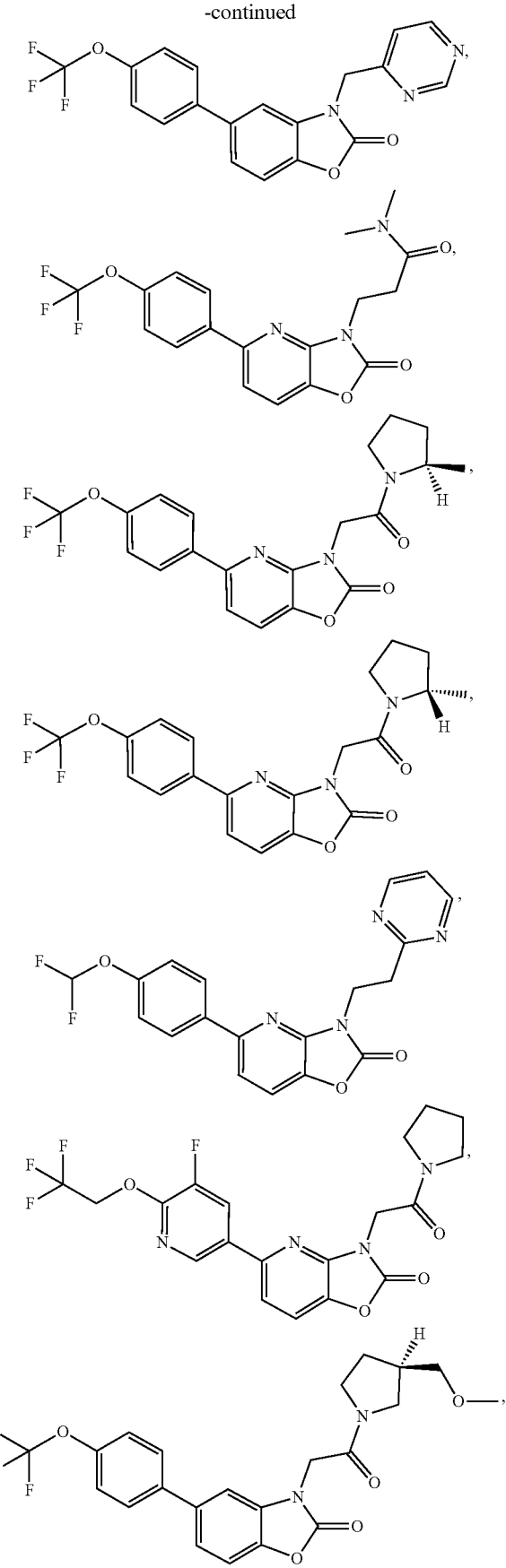

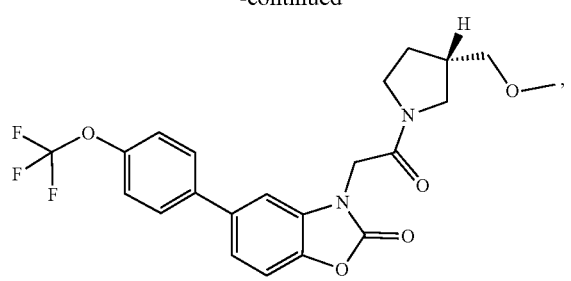
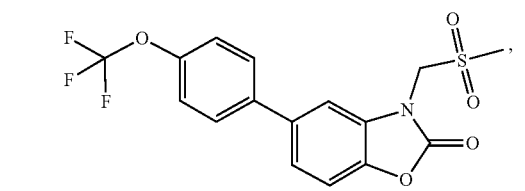
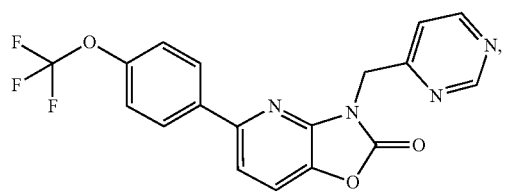
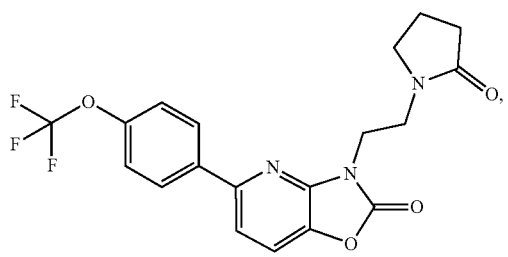
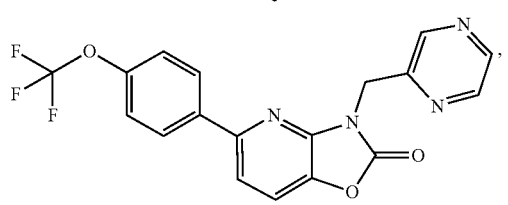
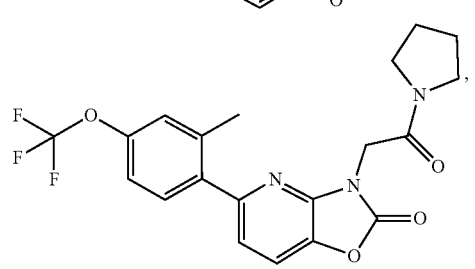
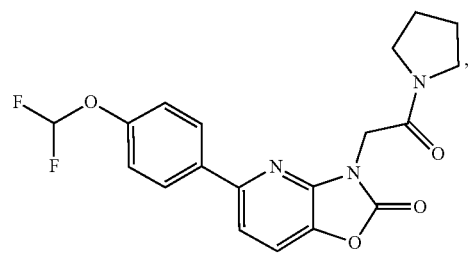
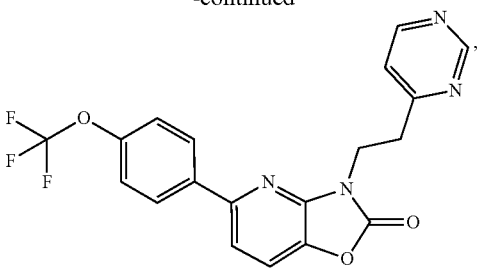
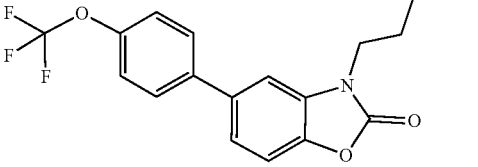
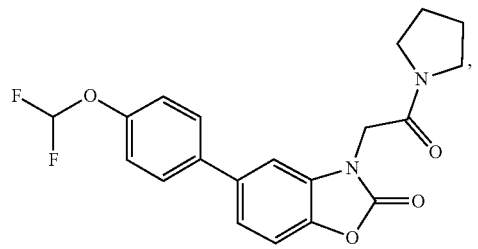
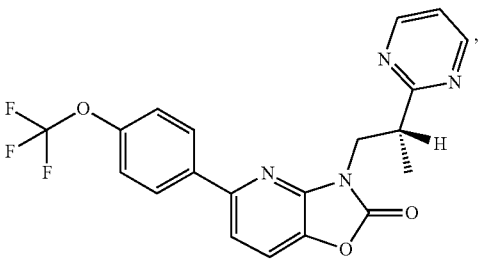
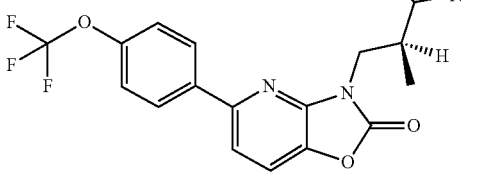
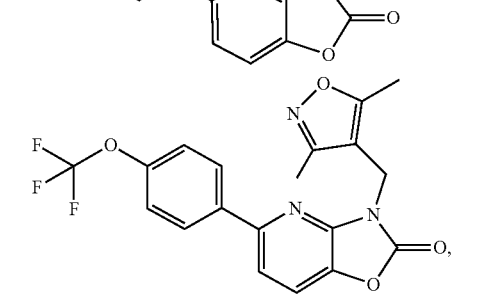

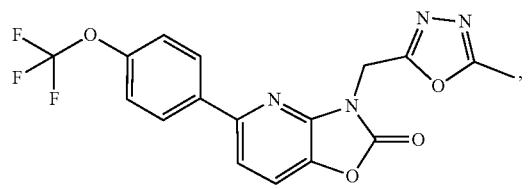
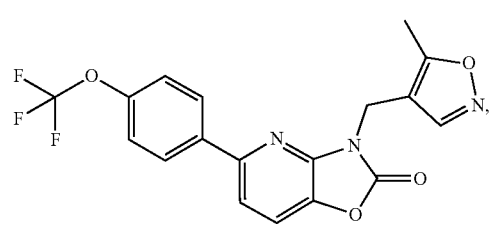
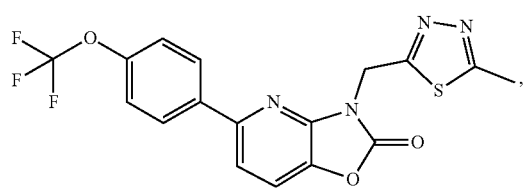
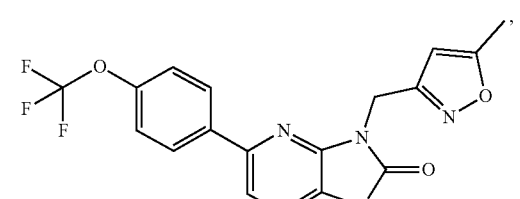
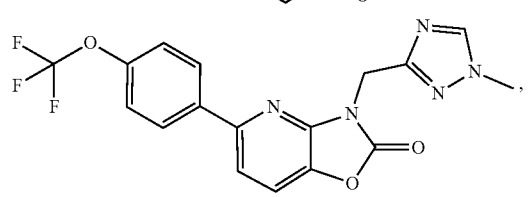
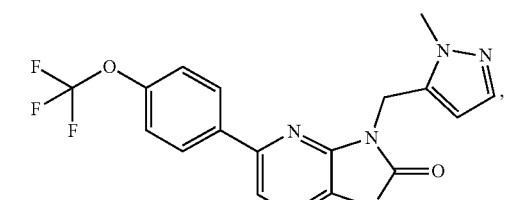
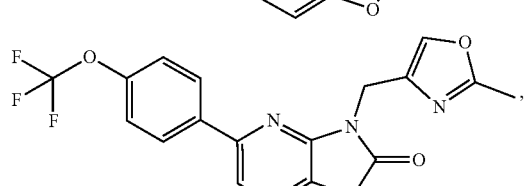
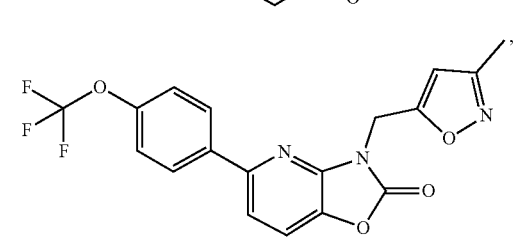
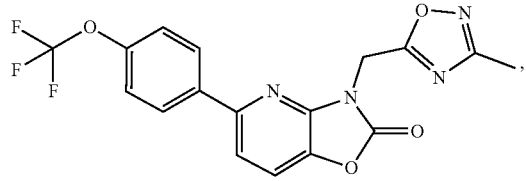
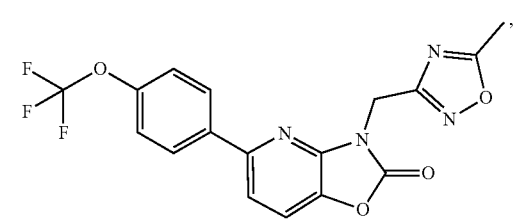
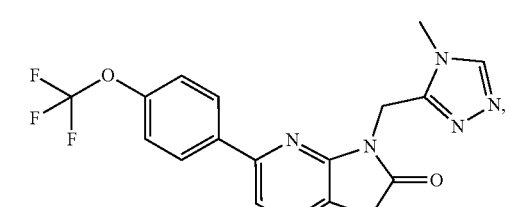
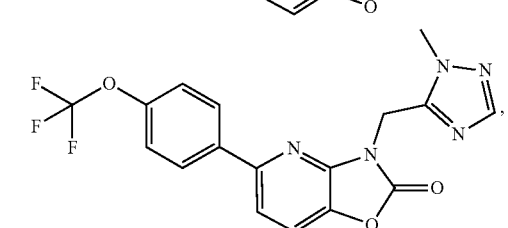
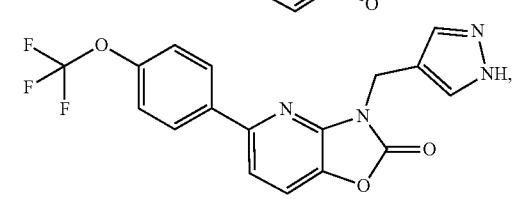
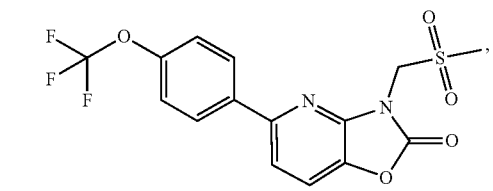
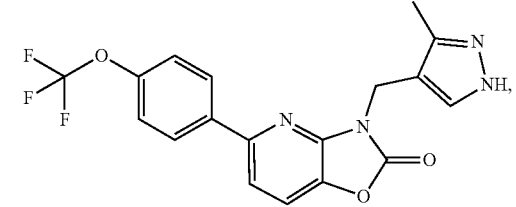
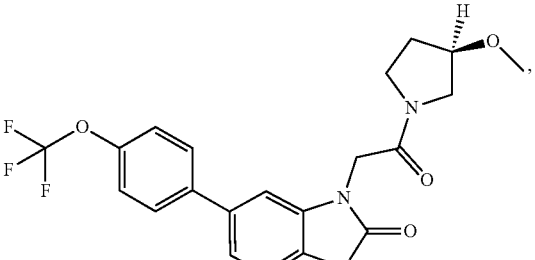

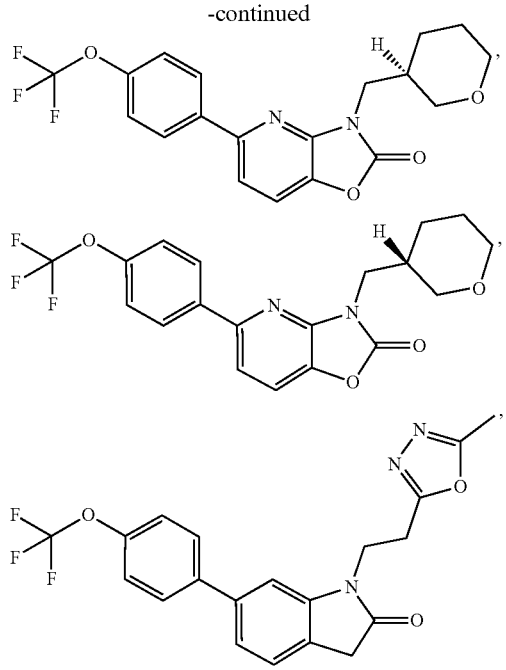

or a pharmaceutically acceptable salt thereof.

Methods of Treatment

Described herein are compounds and compositions thereof and their use to treat a disease, disorder, or condition relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. Compounds of the invention may also modulate all sodium ion channels, or may be specific to only one or a plurality of sodium ion channels, e.g., Nav 1.1, 1.2, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I), (I-1), (I-2), (I-3), (I-4), (I-5), (I-6), (I-7), (I-a), (I-b), (I-c), or (I-d); such as a compound of Formula (I) named herein.

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and actually turn blue. The return to consciousness is gradual and the person may be confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) prior to administration of a compound described herein (e.g., a compound of Formula (I), (I-1), (I-2), (I-3), (I-4), (I-5), (I-6), (I-7), (I-a), (I-b), (I-c), or (I-d)).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I):

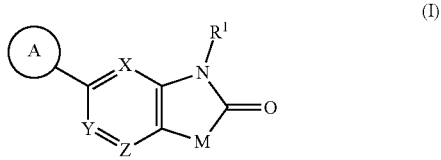

or a pharmaceutically acceptable salt thereof, wherein each of X, Y, and Z is independently N or CR'; M is O, C($R^{2a}$)($R^{2b}$), or N($R^{2c}$); A is aryl or heteroaryl (e.g., 6-membered aryl or heteroaryl), wherein aryl and heteroaryl are substituted by one or more $R^3$; R' is hydrogen, alkyl, —$OR^c$, or halogen; $R^1$ is hydrogen, alkyl, carbocyclyl, or heterocyclyl, wherein alkyl, carbocyclyl, and heterocyclyl are optionally substituted with one or more $R^4$; each of $R^{2a}$, $R^{2b}$, and $R^{2c}$ is independently hydrogen or alkyl, wherein alkyl is optionally substituted by one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, oxo, cyano, nitro, —$OR^c$, —N($R^d$)$_2$, —C(O)$R^c$, —C(O)$OR^c$, or —C(O)N($R^d$)$_2$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^d$ is independently hydrogen or alkyl, wherein each alkyl is optionally substituted by one or more $R^6$; or two $R^d$, taken together with the atoms to which they are attached, form a ring; each $R^6$ is independently alkyl, carbocyclyl, heterocyclyl, halo, cyano, nitro, or —OH; and each $R^7$ is independently alkyl, halo, or oxo.

A compound of the present invention (e.g., a compound of Formula (I), (I-1), (I-2), (I-3), (I-4), (I-5), (I-6), (I-7), (I-a), (I-b), (I-c), or (I-d)) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula (I), (I-1), (I-2), (I-3), (I-4), (I-5), (I-6), (I-7), (I-a), (I-b), (I-c), or (I-d)).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula (I), (I-1), (I-2), (I-3), (I-4), (I-5), (I-6), (I-7), (I-a), (I-b), (I-c), or (I-d)).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I):

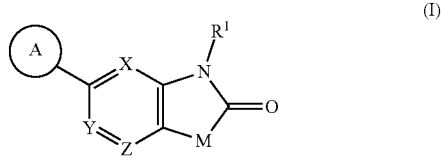

or a pharmaceutically acceptable salt thereof, wherein each of X, Y, and Z is independently N or CR'; M is O, C($R^{2a}$)($R^{2b}$), or N($R^{2c}$); A is aryl or heteroaryl (e.g., 6-membered aryl or heteroaryl), wherein aryl and heteroaryl are substituted by one or more $R^3$; R' is hydrogen, alkyl, —$OR^c$, or halogen; $R^1$ is hydrogen, alkyl, carbocyclyl, or heterocyclyl, wherein alkyl, carbocyclyl, and heterocyclyl are optionally substituted with one or more $R^4$; each of $R^{2a}$, $R^{2b}$, and $R^{2c}$ is independently hydrogen or alkyl, wherein alkyl is optionally substituted by one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^d$ is independently hydrogen or alkyl, wherein each alkyl is optionally substituted by one or more $R^6$; or two $R^d$, taken together with the atoms to which they are attached, form a ring; each $R^6$ is independently alkyl, carbocyclyl, heterocyclyl, halo, cyano, nitro, or —OH; and each $R^7$ is independently alkyl, halo, or oxo.

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula (I), (I-1), (I-2), (I-3), (I-4), (I-5), (I-6), (I-7), (I-a), (I-b), (I-c), or (I-d)).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound of Formula (I):

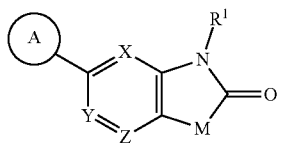

(I)

or a pharmaceutically acceptable salt thereof, wherein each of X, Y, and Z is independently N or CR'; M is O, $C(R^{2a})(R^{2b})$, or $N(R^{2c})$; A is aryl or heteroaryl (e.g., 6-membered aryl or heteroaryl), wherein aryl and heteroaryl are substituted by one or more $R^3$; R' is hydrogen, alkyl, —$OR^c$, or halogen; $R^1$ is hydrogen, alkyl, carbocyclyl, or heterocyclyl, wherein alkyl, carbocyclyl, and heterocyclyl are optionally substituted with one or more $R^4$; each of $R^{2a}$, $R^{2b}$, and $R^{2c}$ is independently hydrogen or alkyl, wherein alkyl is optionally substituted by one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$; each $R^d$ is independently hydrogen or alkyl, wherein each alkyl is optionally substituted by one or more $R^6$; or two $R^d$, taken together with the atoms to which they are attached, form a ring; each $R^6$ is independently alkyl, carbocyclyl, heterocyclyl, halo, cyano, nitro, or —OH; and each $R^7$ is independently alkyl, halo, or oxo.

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula (I), (I-1), (I-2), (I-3), (I-4), (I-5), (I-6), (I-7), (I-a), (I-b), (I-c), or (I-d)).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I):

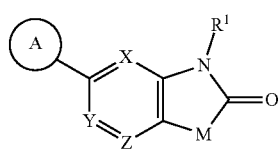

(I)

or a pharmaceutically acceptable salt thereof, wherein each of X, Y, and Z is independently N or CR'; M is O, $C(R^{2a})(R^{2b})$, or $N(R^{2c})$; A is aryl or heteroaryl (e.g., 6-membered aryl or heteroaryl), wherein aryl and heteroaryl are substituted by one or more $R^3$; R' is hydrogen, alkyl, —$OR^c$, or halogen; $R^1$ is hydrogen, alkyl, carbocyclyl, or heterocyclyl, wherein alkyl, carbocyclyl, and heterocyclyl are optionally substituted with one or more $R^4$; each of $R^{2a}$, $R^{2b}$, and $R^{2c}$ is independently hydrogen or alkyl, wherein alkyl is optionally substituted by one or more $R^4$; each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$; each of $R^4$ and $R^5$ is independently deuterium, alkyl, carbocyclyl, heterocyclyl, aryl, heteroaryl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, heterocyclyl, aryl, and heteroaryl is optionally substituted by one or more $R^7$; each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more R⁶; each $R^d$ is independently hydrogen or alkyl, wherein each alkyl is optionally substituted by one or more R⁶; or two $R^d$, taken together with the atoms to which they are attached, form a ring; each R⁶ is independently alkyl, carbocyclyl, heterocyclyl, halo, cyano, nitro, or —OH; and each R⁷ is independently alkyl, halo, or oxo.

Other Disorders

In some embodiments, a compound of the present invention (e.g., a compound of Formula (I), (I-1), (I-2), (I-3), (I-4), (I-5), (I-6), (I-7), (I-a), (I-b), (I-c), or (I-d)) may have appropriate pharmacokinetic properties such that they may active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy.

In one aspect, the present disclosure provides a method of treating a neurological disorder or a psychiatric disorder, wherein the method comprises administering to a subject in need thereof a compound of Formula (I):

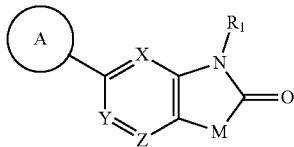

(I)

or a pharmaceutically acceptable salt thereof, wherein:
each of X, Y, and Z is independently N or CR';
M is O, C(R²ᵃ)(R²ᵇ) or N(R²ᶜ);
A is aryl or heteroaryl (e.g., 6-membered aryl or heteroaryl), wherein aryl and heteroaryl are substituted by one or more R³;
R' is hydrogen, alkyl, —ORᶜ, or halogen;
R¹ is hydrogen, alkyl, carbocyclyl, or heterocyclyl, wherein alkyl, carbocyclyl, and heterocyclyl are optionally substituted with one or more R⁴;
each of R²ᵃ, R²ᵇ, and R²ᶜ is independently hydrogen or alkyl, wherein alkyl is optionally substituted by one or more R⁴;
each R³ is independently alkyl, carbocyclyl, heterocyclyl, halo, cyano, nitro, or —ORᶜ, wherein alkyl, carbocyclyl, and heterocyclyl are optionally substituted with one or more R⁵;
each of R⁴ and R⁵ is independently deuterium, alkyl, carbocyclyl, heterocyclyl, aryl, heteroaryl, halo, oxo, cyano, nitro, —ORᶜ, —N(Rᵈ)₂, —C(O)Rᶜ, —C(O)ORᶜ, or —C(O)N(Rᵈ)₂, wherein alkyl, carbocyclyl, heterocyclyl, aryl, and heteroaryl is optionally substituted by one or more R⁷;
each Rᶜ is independently hydrogen, alkyl, carbocyclyl, heterocyclyl, aryl, or heteroaryl, wherein alkyl, carbocyclyl, heterocyclyl, aryl, and heteroaryl is optionally substituted by one or more R⁶;

each $R^d$ is independently hydrogen or alkyl, wherein each alkyl is optionally substituted by one or more R⁶;
or two $R^d$, taken together with the atoms to which they are attached, form a ring;
each R⁶ is independently alkyl, carbocyclyl, heterocyclyl, halo, cyano, nitro, or —OH;
and each R⁷ is independently alkyl, halo, or oxo.

In another aspect, the present disclosure provides a method of treating a neurological disorder or a psychiatric disorder, wherein the method comprises administering to a subject in need thereof a compound of Formula (I-1):

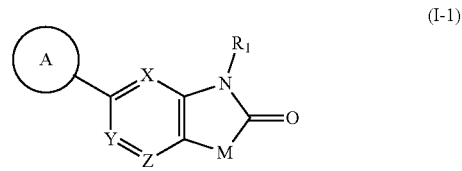

(I-1)

or a pharmaceutically acceptable salt thereof, wherein:
each of X, Y, and Z is independently N or CR';
M is O, C(R²ᵃ)(R²ᵇ) or N(R²ᶜ);
A is aryl or heteroaryl (e.g., 6-membered aryl or heteroaryl), wherein aryl and heteroaryl are substituted by one or more R³;
R' is hydrogen, alkyl, —ORᶜ, or halogen;
R¹ is hydrogen, alkyl, carbocyclyl, or heterocyclyl, wherein alkyl, carbocyclyl, and heterocyclyl are optionally substituted with one or more R⁴;
each of R²ᵃ, R²ᵇ, and R²ᶜ is independently hydrogen or alkyl, wherein alkyl is optionally substituted by one or more R⁴;
each R³ is independently alkyl, carbocyclyl, heterocyclyl, halo, cyano, nitro, or —ORᶜ, wherein alkyl, carbocyclyl, and heterocyclyl are optionally substituted with one or more R⁵;
each of R⁴ and R⁵ is independently deuterium, alkyl, carbocyclyl, heterocyclyl, aryl, heteroaryl, halo, oxo, cyano, nitro, —ORᶜ, —N(Rᵈ)₂, —C(O)Rᶜ, —C(O)ORᶜ, —S(O)₂—Rᵉ, —S(O)₂N(Rᵈ)₂, or —C(O)N(Rᵈ)₂, wherein alkyl, carbocyclyl, heterocyclyl, aryl, and heteroaryl is optionally substituted by one or more R⁷;
each Rᶜ is independently hydrogen, alkyl, carbocyclyl, heterocyclyl, aryl, or heteroaryl, wherein alkyl, carbocyclyl, heterocyclyl, aryl, or heteroaryl is optionally substituted by one or more R⁶;
each $R^d$ is independently hydrogen or alkyl, wherein each alkyl is optionally substituted by one or more R⁶;
or two $R^d$, taken together with the atoms to which they are attached, form a heterocyclyl optionally substituted with —OH, alkoxy, or alkyl optionally substituted with alkoxy;
each Rᵉ is alkyl;
each R⁶ is independently alkyl, carbocyclyl, heterocyclyl, halo, cyano, nitro, or —OH;
and each R⁷ is independently alkyl, halo, oxo, —C(O)Rᶜ, or —C(O)ORᶜ.

In some embodiments, the compound is not one of the following:

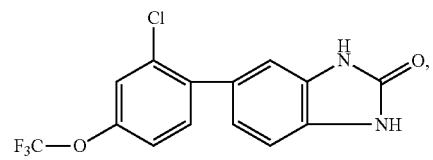

-continued

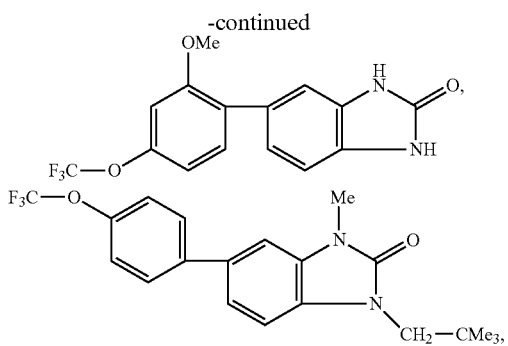

and a pharmaceutically acceptable salt thereof.

In some embodiments, the neurological disorder is epilepsy.

In some embodiments, the neurological disorder is an epileptic encephalopathy.

In some embodiments, the epileptic encephalopathy comprises Dravet syndrome, infantile spasms, or Lennox-Gastaut syndrome.

In some embodiments, each of X, Y, and Z is independently CR'(e.g., CH).

In some embodiments, X is N and each of Y and Z is independently CR'(e.g., CH).

In some embodiments, Z is N and each of X and Y is independently CR'(e.g., CH).

In some embodiments, M is O.

In some embodiments, M is $C(R^{2a})(R^{2b})$ (e.g., $CH_2$).

In some embodiments, M is $N(R^{2c})$ (e.g., NH, $NCH_3$).

In some embodiments, A is aryl (e.g., phenyl).

In some embodiments, A is phenyl substituted by 1 $R^3$ (e.g., wherein $R^3$ is in the para position).

In some embodiments, A is heteroaryl (e.g., pyridyl).

In some embodiments, A is pyridyl substituted by 1 $R^3$ (e.g., wherein $R^3$ is in the para position).

In some embodiments, $R^3$ is —$OR^c$.

In some embodiments, $R^c$ is alkyl substituted by one or more $R^6$.

In some embodiments, $R^6$ is halo (e.g., fluoro).

In some embodiments, $R^3$ is —$OCF_3$.

In some embodiments, $R^1$ is alkyl (e.g., substituted with 1-4 $R^4$).

In some embodiments, $R^4$ is deuterium, halo, —$OR^c$, oxo, carbocyclyl, heteroaryl, —$C(O)OR^c$, or —$C(O)N(R^d)_2$.

In some embodiments, $R^4$ is deuterium, fluoro, tetrahydrofuranyl, tetrahydropyranyl, pyrimidinyl, OH, C(O)N(CH$_3$)$_2$, C(O)N(CH$_3$)(CH$_2$CH$_3$), C(O)N(CH$_3$)(CH$_2$CF$_3$), or C(O)N— tetrahydropyrrolyl.

In some embodiments, $R^4$ is halo (e.g., fluoro).

In some embodiments, $R^1$ is —$CH_2CF_3$.

In some embodiments, the compound of Formula (I-1) is a compound of Formula (I-2):

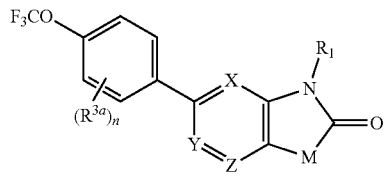

(I-2)

or a pharmaceutically acceptable salt thereof, wherein:

each of X, Y, and Z is independently N or CR';

M is O or $C(R^{2a})(R^{2b})$;

R' is hydrogen, alkyl, —$OR^c$, or halogen;

$R^1$ is hydrogen, alkyl, carbocyclyl, or heterocyclyl, wherein alkyl, carbocyclyl, and heterocyclyl are optionally substituted with one or more $R^4$;

each of $R^{2a}$ and $R^{2b}$ is independently hydrogen or alkyl, wherein alkyl is optionally substituted by one or more $R^4$;

each $R^{1a}$ is independently alkyl, carbocyclyl, heterocyclyl, halo, cyano, nitro, or —$OR^c$, wherein alkyl, carbocyclyl, and heterocyclyl are optionally substituted with one or more $R^5$;

each of $R^4$ and $R^5$ is independently deuterium, alkyl, carbocyclyl, heterocyclyl, aryl, heteroaryl, halo, cyano, nitro, —$C(O)N(R^d)_2$, —$C(O)R^c$, —$C(O)OR^c$, —$S(O)_2$—$R^e$, —$S(O)_2N(R^d)_2$, or —$OR^c$, wherein alkyl, carbocyclyl, heterocyclyl, aryl, and heteroaryl is optionally substituted by one or more $R^7$;

each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$;

each $R^d$ is independently hydrogen or alkyl optionally substituted with one or more halogen;

or two $R^d$, taken together with the atoms to which they are attached, form a heterocyclyl optionally substituted with —OH, alkoxy, or alkyl optionally substituted with alkoxy;

each $R^e$ is alkyl;

each $R^6$ is independently alkyl, carbocyclyl, heterocyclyl, halo, cyano, nitro, or —OH;

each $R^7$ is independently alkyl, oxo, halo, —$C(O)R^c$, or —$C(O)OR^c$; n is 0, 1, 2, 3, or 4.

In some embodiments, the compound of formula I-2 is a compound of formula I-3:

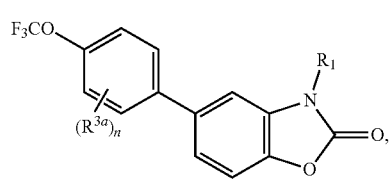

(I-3)

or a pharmaceutically acceptable salt thereof.

In some embodiments, the compound of formula I-2 is a compound of formula I-4:

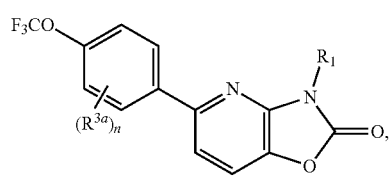

(I-4)

or a pharmaceutically acceptable salt thereof.

In some embodiments, the compound of formula I-2 is a compound of formula I-5:

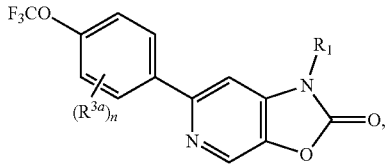

or a pharmaceutically acceptable salt thereof.

In some embodiments, the compound of formula I-2 is a compound of formula I-6:

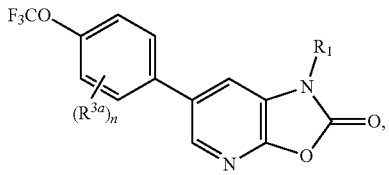

or a pharmaceutically acceptable salt thereof.

In some embodiments, each of X, Y, and Z is CR', wherein R' is hydrogen.

In some embodiments, M is O.

In some embodiments, M is $C(R^{2a})(R^{2b})$.

In some embodiments, $R^1$ is alkyl, wherein alkyl is optionally substituted with one or more $R^4$.

In some embodiments, each of $R^4$ and $R^5$ is independently deuterium, alkyl, carbocyclyl, heterocyclyl, aryl, heteroaryl, halo, cyano, nitro, or $-OR^c$, wherein alkyl, carbocyclyl, heterocyclyl, aryl, and heteroaryl is optionally substituted by one or more $R^7$.

In some embodiments, n is 0.

In some embodiments, the compound of Formula (I-1) is a compound of Formula (I-7):

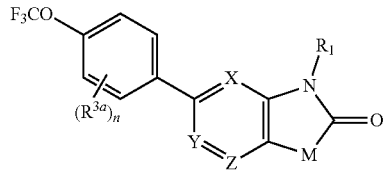

or a pharmaceutically acceptable salt thereof, wherein:
each of X, Y, and Z is independently N or CR';
M is $N(R^{2c})$;
R' is hydrogen, alkyl, $-OR^c$, or halogen;
$R^1$ is hydrogen, alkyl, carbocyclyl, or heterocyclyl, wherein alkyl, carbocyclyl, and heterocyclyl are optionally substituted with one or more $R^4$;
each of $R^{2c}$ is independently hydrogen or alkyl, wherein alkyl is optionally substituted by one or more $R^4$;
each $R^{1a}$ is independently alkyl, carbocyclyl, heterocyclyl, halo, cyano, nitro, or $-OR^c$, wherein alkyl, carbocyclyl, and heterocyclyl are optionally substituted with one or more $R^5$;
each of $R^4$ and $R^5$ is independently deuterium, alkyl, carbocyclyl, heterocyclyl, aryl, heteroaryl, halo, cyano, nitro, $-C(O)N(R^d)_2$, $-C(O)R^c$, $-C(O)OR^c$, $-S(O)_2-R^e$, $-S(O)_2N(R^d)_2$, or $-OR^c$, wherein alkyl, carbocyclyl, heterocyclyl, aryl, and heteroaryl is optionally substituted by one or more $R^7$;
each $R^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more $R^6$;
each $R^d$ is independently hydrogen or alkyl optionally substituted with one or more halogen;
or two $R^d$, taken together with the atoms to which they are attached, form a heterocyclyl optionally substituted with $-OH$, alkoxy, or alkyl optionally substituted with alkoxy;
each $R^e$ is alkyl;
each $R^6$ is independently alkyl, carbocyclyl, heterocyclyl, halo, cyano, nitro, or $-OH$;
each $R^7$ is independently alkyl, oxo, halo, $-C(O)R^c$, or $-C(O)OR^c$; and n is 0, 1, 2, 3, or 4.

In some embodiments, the compound is not one of the following:

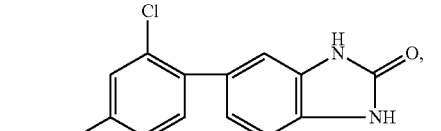

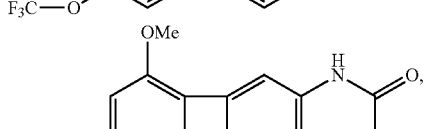

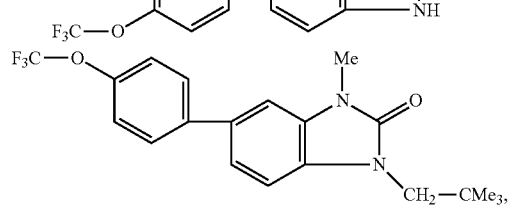

and a pharmaceutically acceptable salt thereof.

In some embodiments, each of X, Y, and Z is CR', wherein R' is hydrogen.

In some embodiments, $R^1$ is alkyl, wherein alkyl is optionally substituted with one or more $R^4$.

In some embodiments, each of $R^4$ and $R^5$ is independently deuterium, alkyl, carbocyclyl, heterocyclyl, aryl, heteroaryl, halo, cyano, nitro, or $-OR^c$, wherein alkyl, carbocyclyl, heterocyclyl, aryl, and heteroaryl is optionally substituted by one or more $R^7$.

In some embodiments, n is 0.

In one aspect, the present disclosure provides a method comprises administering a pharmaceutical composition disclosed herein.

In one aspect, the present disclosure provides a method of treating a neurological disorder or a psychiatric disorder, wherein the method comprises administering to a subject in need thereof a compound disclosed herein, or a pharmaceutically acceptable salt thereof or a pharmaceutical composition disclosed herein.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, the present disclosure provides a pharmaceutical composition comprising a disclosed compound, or pharmaceutically acceptable salt thereof, and a pharmaceutically acceptable carrier.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amioarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the Nav 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate C18 (2.1 mm×30 mm, 3 μm); A=$H_2O$ (0.04% TFA) and B=$CH_3CN$ (0.02% TFA); 50° C.; 1.2 mL/min; 10-80% B over 0.9 minutes, then 80% B for 0.6 minutes) and Method B (Chromolith Flash RP-18 endcapped C18 (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes).

LIST OF ABBREVIATIONS

DMF N,N-dimethylformamide
THF tetrahydrofuran
MeOH methanol
CDI 1,1'-Carbonyldiimidazole
DCM dichloromethane
EtOH ethanol
TsOH toluenesulfonic acid
DMSO dimethyl sulfoxide
MeI methyl iodide
EtI ethyl iodide
TFA trifluoroacetic acid
TFAA trifluoroacetic anhydride
LDA lithium diisopropylamide
DIBAH diisobutylaluminum hydride
$Et_3N$ trimethylamine
Pd(dppf)$Cl_2$ [1,1'-bis(diphenylphosphino)ferrocene]palladium(II) dichloride
AcN acetonitrile
Pd(t-$Bu_3P$)$_2$ bis(tri-tert-butylphosphine)palladium(0)
DIPEA N,N-diisopropylethylamine
DIEA N,N-diisopropylethylamine
HATU 1-[bis(dimethylamino)methylene]-1H-1,2,3-triazolo[4,5-b]pyridinium 3-oxide hexafluorophosphate PPh₃ triphenylphosphine
DIAD diisopropyl azodicarboxylate
DEAD diethyl azodicarboxylate
m-CPBA meta-chloroperoxybenzoic acid
AcN acetonitrile
AcOH acetic acid
BnOH benzyl alcohol
TDA 4,4'-thiodianiline
AcCl acetyl chloride
MsCl methanesulfonyl chloride Example 1: Synthesis of Compound 1

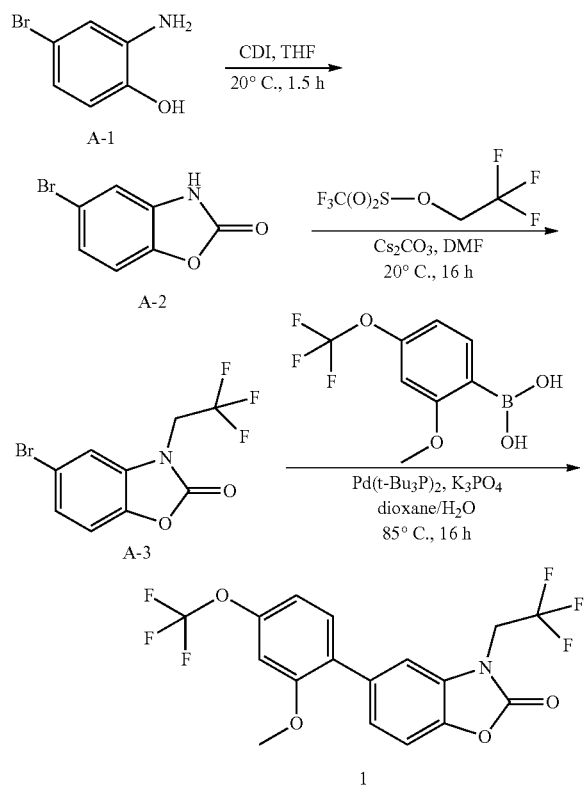

Synthesis of A-2:

To a solution of A-1 (5 g, 26.59 mmol, 1 eq) in THF (50 mL) was added CDI (5.17 g, 31.91 mmol, 1.2 eq), and the mixture was stirred at 20° C. for 1.5 hours. The mixture was poured into water (50 mL), acidized with 1 N HCl (40 mL), extracted with EtOAc (50 mL×2). The combined organic phase was washed with sat. Na₂CO₃ (40 mL) and brine (10 mL), dried over Na₂SO₄, filtered and concentrated to afford A-2 (6 g, crude) as a solid. ¹H NMR (DMSO-d₆ 400 MHz) $\delta_H$=7.43-7.00 (m, 3H)

Synthesis of A-3:

To a solution of A-2 (3 g, 14.02 mmol, 1 eq), Cs₂CO₃ (9.13 g, 28.04 mmol, 2 eq) in DMF (30 mL) was added 2,2,2-trifluoroethyl trifluoromethanesulfonate (4.88 g, 21.03 mmol, 1.5 eq), and the mixture was stirred at 20° C. for 16 hours. The mixture was diluted with H₂O (30 mL) and extracted with EtOAc (50 mL×2). The combined organic phase was washed with brine (20 mL), dried over Na₂SO₄, filtered and concentrated to give the crude product, which was purified by flash chromatography on silica gel (EtOAc in PE=0% to 25% to 60%) to afford A-3 (1 g, 3.38 mmol) as a solid. ¹H NMR (CDCl₃, 400 MHz) $\delta_H$=7.34 (dd, 1H), 7.22 (s, 1H), 7.14 (d, 1H), 4.40 (q, 2H)

Synthesis of Compound 1:

A mixture of A-3 (200 mg, 675.58 μmol, 1 eq), [2-methoxy-4-(trifluoromethoxy)phenyl]boronic acid (191.29 mg, 810.70 μmol, 1.2 eq), Pd(t-Bu₃P)₂ (51.79 mg, 101.34 μmol, 0.15 eq) and K₃PO₄ (286.81 mg, 1.35 mmol, 2 eq) in dioxane (5 mL) and H₂O (0.3 mL) was stirred at 85° C. for 16 hours.

The mixture was concentrated to give the crude product, which was purified by Prep-HPLC (Phenomenex Gemini (150 mm×25 mm, 10 μm); A=H₂O (0.04% NH₃H₂O) and B=CH₃CN); 55-85% B over 10 minutes) to afford Compound 1 (173.90 mg, 426.48 μmol) as a solid. ¹H NMR (DMSO-d₆ 400 MHz) $\delta_H$=7.54 (s, 1H), 7.47-7.38 (m, 2H), 7.28 (dd, 1H), 7.13 (s, 1H), 7.06 (d, 1H), 4.85 (d, 2H), 3.80 (s, 3H). LCMS $R_t$=1.41 min using Method A, MS ESI calcd. for C₁₇H₁₂F₆NO₄ [M+H]⁺ 408.1, found 407.9.

Example 2: Synthesis of Compound 2

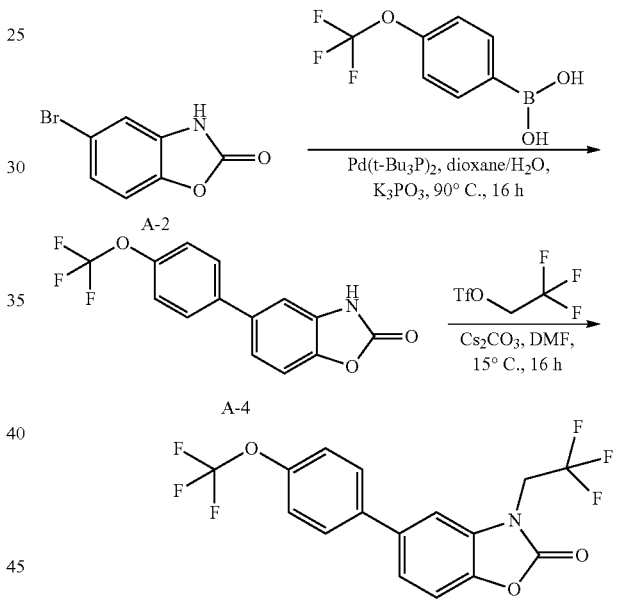

Synthesis of A-4:

A mixture of A-2 (500 mg, 2.34 mmol, 1.00 eq), [4-(trifluoromethoxy)phenyl]boronic acid (577.32 mg, 2.80 mmol, 1.20 eq), Pd(t-Bu₃P)₂ (238.79 mg, 467.25 μmol, 0.20 eq) and K₃PO₄ (991.82 mg, 4.67 mmol, 2.00 eq) in dioxane (8.00 mL) and H₂O (400.00 μL) was stirred at 80° C. for 16 hours. The mixture was then diluted with EtOAc (5 mL), filtered through silica gel, eluted with EtOAc (10 mL) and concentrated to give the crude product that was purified by flash chromatography on silica gel (PE:EtOAc=5:1 to 1:1) to afford A-4 (350.00 mg, 1.19 mmol) as a solid. ¹H NMR (DMSO-d₆ 400 MHz) $\delta_H$=11.79 (br s, 1H), 7.76 (d, 2H), 7.44 (d, 2H), 7.40-7.36 (m, 2H), 7.34-7.31 (m, 1H).

Synthesis of Compound 2:

To a solution of A-4 (50.00 mg, 169.37 μmol, 1.00 eq), Cs₂CO₃ (110.37 mg, 338.74 μmol, 2.00 eq) in DMF (2.00 mL) was added 2,2,2-trifluoroethyl trifluoromethanesulfonate (58.97 mg, 254.05 μmol, 1.50 eq), and the mixture was stirred at 15° C. for 16 hours. The mixture was then diluted with H₂O (20 mL) and extracted with EtOAc (20 mL×2). The combined organic phase was washed with brine (10 mL), dried over Na₂SO₄, filtered and concentrated to give the crude product that was purified by Prep-TLC (silica gel, PE:EtOAc=5:1) to afford Compound 2 (34.80 mg, 89.83 µmol) as a solid. ¹H NMR (CDCl₃, 400 MHz) δ$_H$=7.59-7.54 (m, 2H), 7.39-7.30 (m, 4H), 7.21 (s, 1H), 4.47 (q, 2H). LCMS R$_t$=1.41A min using Method A, MS ESI calcd. for C₁₆H₁₀F₆NO₃ [M+H]⁺ 378.0, found 377.9.

Example 3: Synthesis of Compound 3

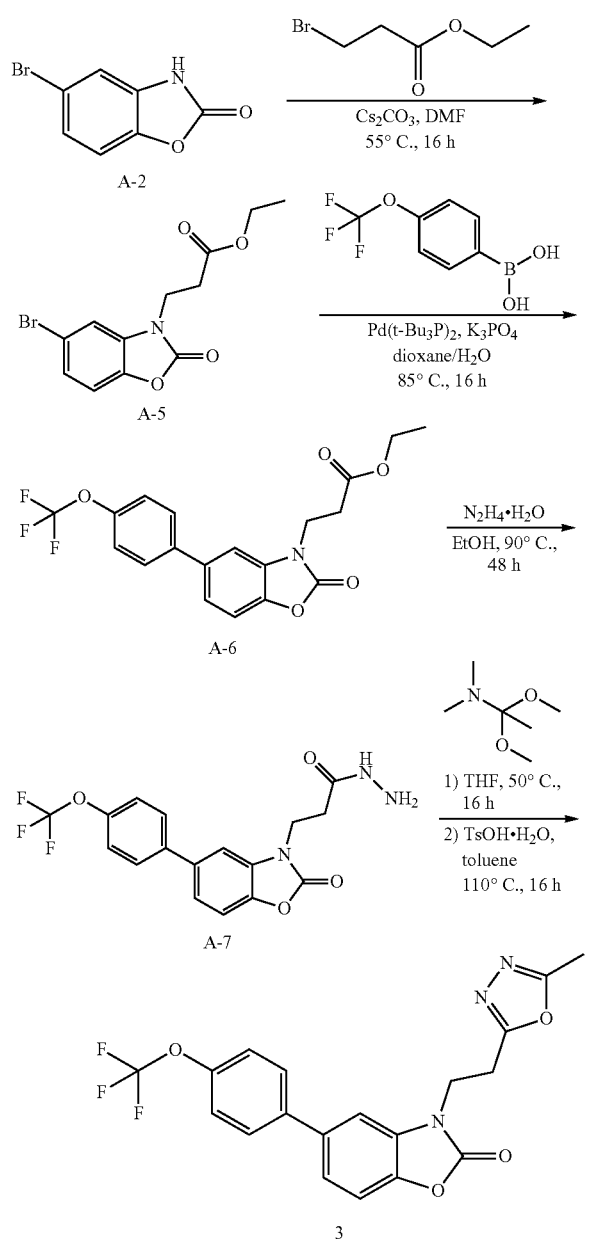

Synthesis of A-5:

To a solution of A-2 (3 g, 14.02 mmol, 1 eq) and Cs₂CO₃ (9.13 g, 28.04 mmol, 2 eq) in DMF (20 mL) was added ethyl 3-bromopropanoate (3.81 g, 21.03 mmol, 1.5 eq), and the mixture was stirred at 55° C. for 16 hours. The mixture was poured into water (20 mL), extracted with EtOAc (50 mL×2). The combined organic phase was washed with brine (20 mL), dried over Na₂SO₄, filtered and concentrated to give the crude product, which was purified by flash chromatography on silica gel (EtOAc in PE=10% to 20% to 50%) to afford A-5 (1 g, 2.81 mmol) as an oil. ¹H NMR (DMSO-d₆ 400 MHz) δ$_H$=7.66 (s, 1H), 7.30 (s, 2H), 4.08-3.99 (m, 4H), 2.78 (t, 2H), 1.12 (t, 3H). LCMS R$_t$=0.80 min using Method B, MS ESI calcd. for C₁₂H₁₃BrNO₄ [M+H+2]⁺ 316.0, found 315.7.

Synthesis of A-6:

A mixture of A-5 (800 mg, 2.55 mmol, 1 eq), [4-(trifluoromethoxy)phenyl]boronic acid (629.32 mg, 3.06 mmol, 1.2 eq), K₃PO₄ (1.08 g, 5.09 mmol, 2 eq) and Pd(t-Bu₃P)₂ (195.23 mg, 382.01 µmol, 0.15 eq) in dioxane (10 mL) and H₂O (2 mL) was stirred at 85° C. for 16 hours. The mixture was concentrated to give the crude product, which was purified by flash chromatography on silica gel (EtOAc in PE=0% to 20% to 30%) to afford A-6 (1 g, 2.53 mmol) as a solid. ¹H NMR (CDCl₃, 400 MHz) δ$_H$=7.58 (d, 2H), 7.31 (d, 2H), 7.29-7.26 (m, 3H), 4.19-4.15 (m, 2H), 4.14-4.09 (m, 2H), 2.85 (t, 2H), 1.20 (t, 3H).

Synthesis of A-7:

A mixture of A-6 (200 mg, 505.91 µmol, 1 eq) and N₂H₄·H₂O (129.21 mg, 2.53 mmol, 125.45 µmol, 5 eq) in EtOH (1 mL) was stirred at 90° C. for 48 hours. The mixture was concentrated to give the crude A-7 (150 mg, 393.39 µmol) as a solid. ¹H NMR (CDCl₃, 400 MHz) δ$_H$=7.80 (d, 2H), 7.54 (d, 2H), 7.51-7.49 (m, 1H), 7.49-7.45 (m, 2H), 4.43 (t, 2H), 2.92 (t, 2H).

Synthesis of Compound 3:

To a mixture of A-7 (120 mg, 314.71 µmol, 1 eq) in THF (3 mL) was added the 1,1-dimethoxy-N,N-dimethylethanamine (62.87 mg, 472.06 µmol, 69.02 µL, 1.5 eq) and the mixture was stirred at 50° C. for 16 hours. The mixture was concentrated to remove EtOH, and the residue was dissolved in toluene (3 mL), and TsOH.H₂O (54.19 mg, 314.71 µmol, 1 eq) was added. The mixture was stirred at 110° C. for 16 hours. The mixture was concentrated, and the residue was purified by Prep-HPLC (Waters Xbridge (150 mm×25 mm, 5 µm) A=H₂O (10 mM NH₄HCO₃) and B=CH₃CN); 38-68% B over 10 minutes) to afford Compound 3 (42.08 mg, 103.82 µmol) as a solid. ¹H NMR (DMSO-d₆+D₂O 400 MHz) δ$_H$=7.76 (d, 2H), 7.54 (s, 1H), 7.45-7.38 (m, 4H), 4.23 (t, 2H), 3.28 (t, 2H), 2.31 (s, 3H). LCMS R$_t$=1.25 min using Method A, MS ESI calcd. for C₁₉H₁₅F₃N₃O₄ [M+H]⁺ 406.1, found 406.0.

Example 4: Synthesis of Compound 4

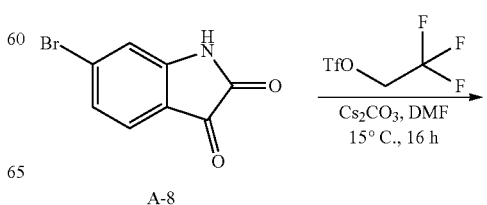

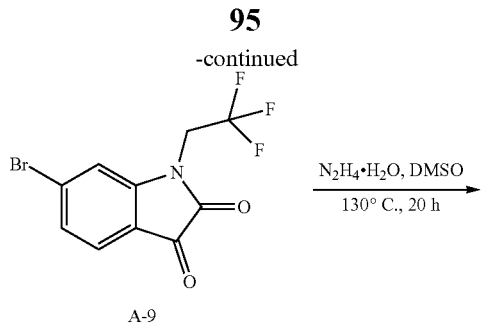

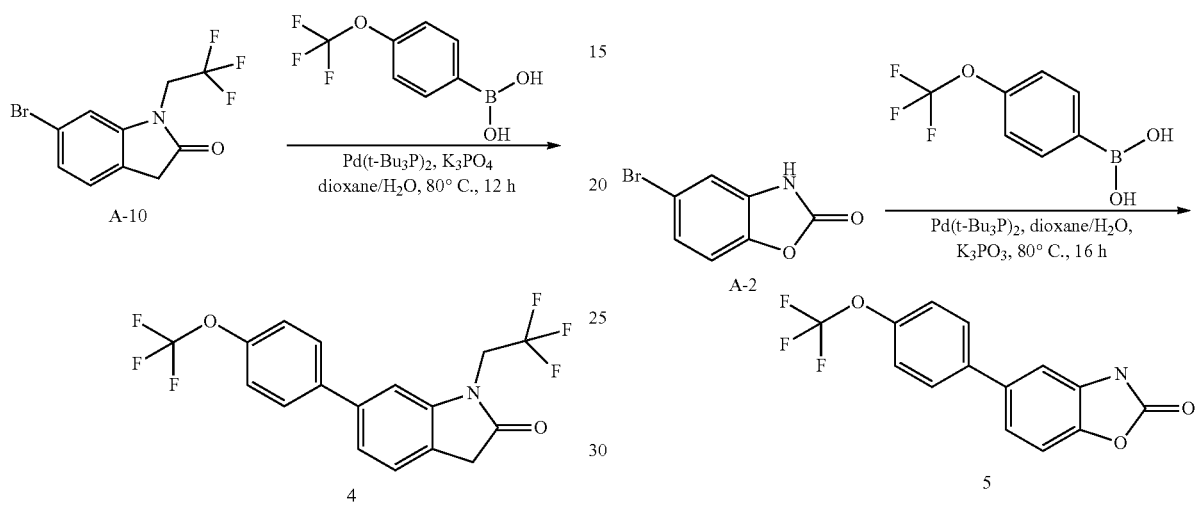

Synthesis of A-9:

To a solution of A-8 (3 g, 13.27 mmol, 1.00 eq) and Cs$_2$CO$_3$ (8.65 g, 26.55 mmol, 2.00 eq) in DMF (20 mL) was added 2,2,2-trifluoroethyl trifluoromethanesulfonate (4.62 g, 19.91 mmol, 1.5 eq), and the mixture was stirred at 15° C. for 16 hours. The mixture was diluted with H$_2$O (20 mL) and extracted with EtOAc (20 mL×2). The combined organic phase was washed with brine (10 mL), dried over Na$_2$SO$_4$, filtered, and concentrated to give the crude product, which was purified by flash chromatography on silica gel (PE:EtOAc=5:1 to 3:1) to afford A-9 (1.2 g, 3.90 mmol) as a solid. $^1$H NMR (DMSO-d$_6$ 400 MHz) $\delta_H$=7.69 (s, 1H), 7.55 (dd, 1H), 7.41 (dd, 1H), 4.66 (q, 2H).

Synthesis of A-10:

A mixture of A-9 (500 mg, 1.62 mmol, 1 eq) in N$_2$H$_4$·H$_2$O (5 mL) and DMSO (5 mL) was stirred at 130° C. for 20 hours. The mixture was diluted with H$_2$O (30 mL) and extracted with EtOAc (100 mL×2). The combined organic phase was washed with water (30 mL) and brine (30 mL), dried over Na$_2$SO$_4$, filtered and concentrated to give the crude product, which was purified by by flash chromatography on silica gel (EtOAc in PE=10% to 15% to 25%) to afford A-10 (70 mg, 238.04 µmol) as a solid. $^1$H NMR (CDCl$_3$, 400 MHz) $\delta_H$=7.25 (dd, 1H), 7.15 (d, 1H), 7.08 (s, 1H), 4.30 (q, 2H), 3.58 (s, 2H).

Synthesis of Compound 4:

A mixture of A-10 (70 mg, 238.04 µmol, 1 eq), [4-(trifluoromethoxy)phenyl]boronic acid (63.72 mg, 309.45 µmol, 1.3 eq), Pd(t-Bu$_3$P)$_2$ (24.33 mg, 47.61 µmol, 0.2 eq) and K$_3$PO$_4$ (101.06 mg, 476.08 µmol, 2 eq) in dioxane (5 mL) and H$_2$O (0.5 mL) was stirred at 80° C. for 12 hours in 20 mL sealed tube under N$_2$. The mixture was diluted with H$_2$O (20 mL) and extracted with EtOAc (50 mL×2). The combined organic phase was washed with water (20 mL×2) and brine (20 mL), dried over Na$_2$SO$_4$, filtered and concentrated to give the crude product, which was purified by Prep-TLC (silica gel, PE:EtOAc=4:1) to afford Compound 4 (22.07 mg, 58.56 µmol) as a solid. $^1$H NMR (DMSO-d$_6$ 400 MHz) $\delta_H$=7.81 (d, 2H), 7.53 (s, 1H), 7.48 (d, 2H), 7.42-7.35 (m, 2H), 4.71 (q, 2H), 3.75 (s, 2H). LCMS R$_t$=1.26 min using Method A, MS ESI calcd. for C$_{17}$H$_{12}$F$_6$NO$_2$ [M+H]$^+$ 376.1, found 375.8.

Example 5: Synthesis of Compound 5

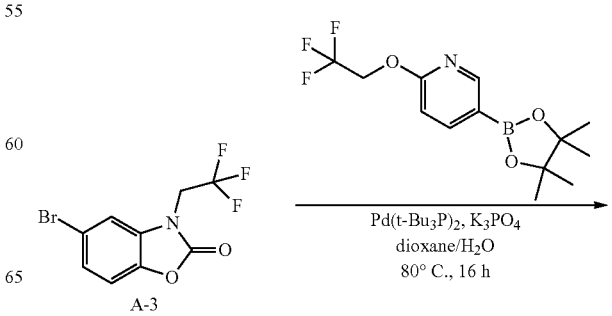

A mixture of A-2 (500 mg, 2.34 mmol, 1.00 eq), [4-(trifluoromethoxy)phenyl]boronic acid (577.32 mg, 2.80 mmol, 1.20 eq), Pd(t-Bu$_3$P)$_2$ (238.79 mg, 467.25 µmol, 0.20 eq) and K$_3$PO$_4$ (991.82 mg, 4.67 mmol, 2.00 eq) in dioxane (8.00 mL) and H$_2$O (400.00 µL) was stirred at 80° C. for 16 hours. The mixture was diluted with EtOAc (5 mL), filtered through silica gel, eluted with EtOAc (10 mL) and concentrated to give the crude product, which was purified by flash chromatography on silica gel (PE:EtOAc=5:1 to 1:1) and Prep-HPLC (Waters Xbridge (150 mm×25 mm, 5 µm) A=H$_2$O (10 mM NH$_4$HCO$_3$) and B=CH$_3$CN); 38-68% B over 10 minutes) to afford Compound 5 (23.72 mg, 78.54 µmol) as a solid. $^1$H NMR (DMSO-d$_6$ 400 MHz) $\delta_H$=11.79 (br s, 1H), 7.77 (d, 2H), 7.45 (d, 2H), 7.40-7.38 (m, 2H), 7.34-7.32 (m, 1H). LCMS R$_t$=1.14 min using Method A, MS ESI calcd. for C$_{14}$H$_9$F$_3$NO$_3$ [M+H]$^+$ 296.0, found 295.7.

Example 6: Synthesis of Compound 6

97

-continued

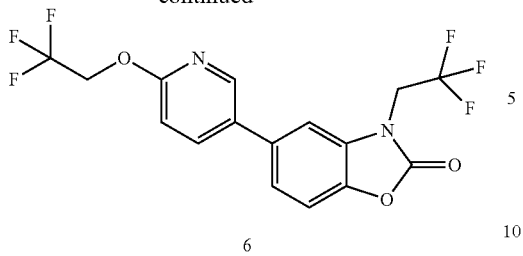

6

A mixture of A-3 (200 mg, 675.58 μmol, 1 eq), 5-(4,4,5,5-tetramethyl-1,3,2-dioxaborolan-2-yl)-2-(2,2,2-trifluoroethoxy)pyridine (819.04 mg, 1.35 mmol, 2 eq), Pd(t-Bu$_3$P)$_2$ (51.79 mg, 101.34 μmol, 0.15 eq) and K$_3$PO$_4$ (286.81 mg, 1.35 mmol, 2 eq) in dioxane (10 mL) was stirred at 80° C. for 16 hours. The mixture was concentrated to give the crude product, which was purified by Prep-HPLC (Phenomenex Gemini (150 mm×25 mm, 10 μm); A=H$_2$O (0.05% NH$_4$OH) and B=CH$_3$CN); 54-84% B over 9.5 minutes) and Prep-TLC (silica gel, PE:EtOAc=4:1) to afford Compound 6 (104.91 mg, 267.46 μmol) as a solid. $^1$H NMR (CDCl$_3$, 400 MHz) $\delta_H$=8.32 (d, 1H), 7.82 (dd, 1H), 7.38-7.30 (m, 2H), 7.17 (s, 1H), 6.98 (d, 1H), 4.83 (q, 2H), 4.47 (q, 2H). LCMS R$_f$=1.23 min using Method A, MS ESI calcd. for C$_{16}$H$_{11}$F$_6$N$_3$O$_3$ [M+H]$^+$ 393.1, found 392.8.

Example 7: Synthesis of Compound 7

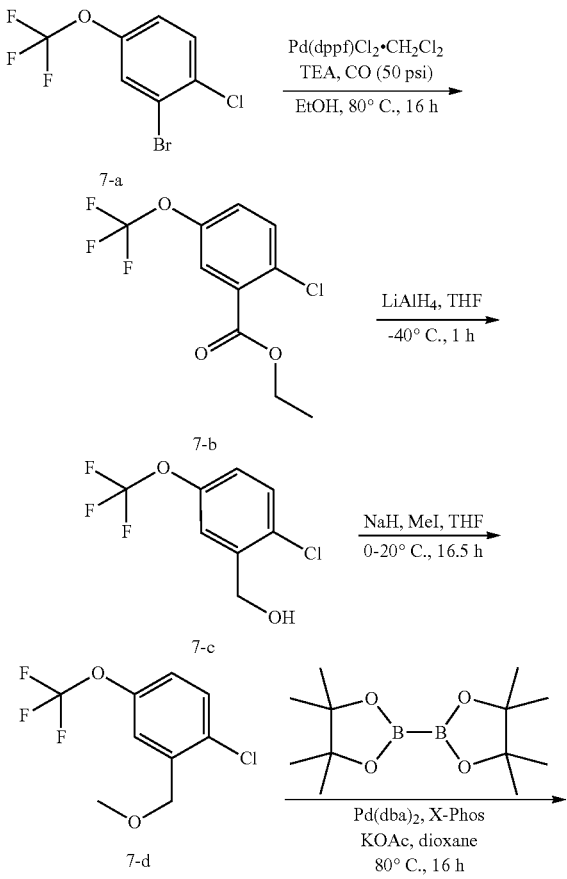

98

-continued

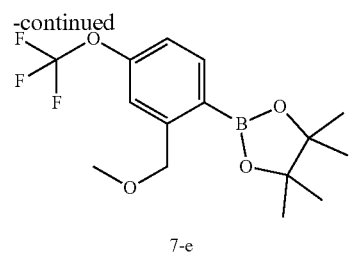

7-e

Synthesis of 7-b:

A mixture of 2-bromo-1-chloro-4-(trifluoromethoxy)benzene (5.00 g, 18.15 mmol), Pd(dppf)Cl$_2$.CH$_2$Cl$_2$ (1.48 g, 1.82 mmol) and Et$_3$N (5.51 g, 54.45 mmol) in EtOH (30 mL) was degassed, and refilled with CO. The reaction was stirred under CO (50 psi) for 16 hours at 80° C., at which point the desired product was observed by LCMS. The reaction mixture was diluted with EtOH (20 mL), and filtered through a Celite pad. The filtrate was concentrated. The residue was purified by flash chromatography on silica gel (EtOAc in PE=0%-5%) to afford compound 12-b (2.40 g, 8.93 mmol) as an oil. $^1$H NMR (400 MHz, CDCl$_3$) $\delta_H$=7.66-7.59 (m, 1H), 7.42 (d, 1H), 7.24-7.19 (m, 1H), 4.36 (q, 2H), 1.35 (t, 3H).

Synthesis of 7-c:

To a solution of 12-b (2.40 g, 8.93 mmol) in THF (30 mL) at −40° C. was added LiAlH$_4$ (406.67 mg, 10.72 mmol) slowly. The reaction was stirred at −40° C. for 1 hour. The reaction was quenched with sat.NH$_4$Cl (0.4 mL), diluted with EtOAc (30 mL). The solid formed was filtered through a Celite pad and eluted with EtOAc (30 mL). The filtrate was concentrated. The residue was purified by flash chromatography on silica gel (EtOAc in PE=0% to 10% to 20%) to afford compound 12-c (1.50 g, 6.62 mmol) as a solid. $^1$H NMR (400 MHz, CDCl$_3$) $\delta_H$=7.45-7.42 (m, 1H), 7.38 (d, 1H), 7.13-7.08 (m, 1H), 4.80 (d, 2H), 2.04 (t, 1H).

Synthesis of 7-d:

To a solution of compound 12-c (1.50 g, 6.62 mmol) in THF (20 mL) at 0° C. was added NaH (317.76 mg, 7.94 mmol, 60% purity) slowly. The mixture was stirred at 0° C. for 30 min. Then MeI (2.82 g, 19.86 mmol) was added. The reaction was stirred at 20° C. for 16 hours to give a mixture. The reaction mixture was quenched with sat.NH$_4$Cl (50 mL) and extracted with EtOAc (50 mL×3). The combined organic phase was washed with brine (50 mL), dried over Na$_2$SO$_4$, filtered and concentrated. The residue was purified by flash chromatography on silica gel (EtOAc in PE=0% to 5% to 10%) to afford compound 12-d (1.40 g, 5.82 mmol) as an oil. $^1$H NMR (CDCl$_3$ 400 MHz) $\delta_H$=7.43-7.32 (m, 2H), 7.09 (dd, 1H), 4.54 (s, 2H), 3.50 (s, 3H).

Synthesis of 7-e:

A mixture of 12-d (400.00 mg, 1.66 mmol), 4,4,5,5-tetramethyl-2-(4,4,5,5-tetramethyl-1,3,2-dioxaborolan-2-yl)-1,3,2-dioxaborolane (505.85 mg, 1.99 mmol), KOAc (325.82 mg, 3.32 mmol), X-Phos (197.84 mg, 415.00 μmol) and Pd$_2$(dba)$_3$ (152.01 mg, 166.00 umol) in dioxane (6 mL) was stirred under N$_2$ at 80° C. for 16 hours. The mixture was cooled to r.t., concentrated to give the crude product. The crude product was purified by silica gel column (PE:EA=1:0 to 50:1) to afford compound 12-e (300.00 mg, 903.29 μmol) as an oil. LCMS R$_f$=0.99 min using Method B, MS ESI calcd. for C$_{15}$H$_{21}$BF$_3$O$_4$[M+H]$^+$ 333.1, found 332.7.

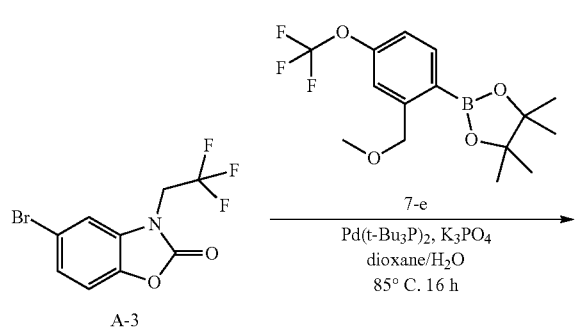

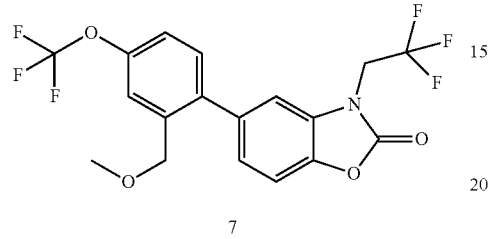

A mixture of A-3 (100 mg, 0.34 mmol), 2-[2-(methoxymethyl)-4-(trifluoromethoxy)phenyl]-4,4,5,5-tetramethyl-1,3,2-dioxaborolane (134.63 mg, 0.41 mmol), K$_3$PO$_4$ (110.17 mg, 0.52 mmol) and Pd(t-Bu$_3$P)$_2$ (19.92 mg, 0.0400 mmol) in 1,4-dioxane (2 mL) and water (0.2 mL) was stirred under N$_2$ at 85° C. for 16 hours. The mixture was diluted with EtOAc (20 mL), filtered through silica gel and eluted with EtOAc (10 mL), and the filtrate was concentrated to give the crude product, which was purified by Prep-HPLC (Waters Xbridge (150 mm×25 mm, 5 μm) A=H$_2$O (10 mM NH$_4$HCO$_3$) and B=CH$_3$CN); 53-83% B over 10 minutes) to afford Compound 7 (49.97 mg, 0.12 mmol) as a solid. $^1$H NMR (DMSO-d$_6$ 400 MHz) $\delta_H$=7.52-7.46 (m, 3H), 7.41 (s, 2H), 7.21 (dd, 1H), 4.85 (q, 2H), 4.36 (s, 2H), 3.25 (s, 3H). LCMS R$_t$=1.40 min using Method A, MS ESI calcd. for C$_{18}$H$_{14}$F$_6$NO$_4$ [M+H]$^+$ 422.0822, found 422.0892.

Example 8: Synthesis of Compound 8

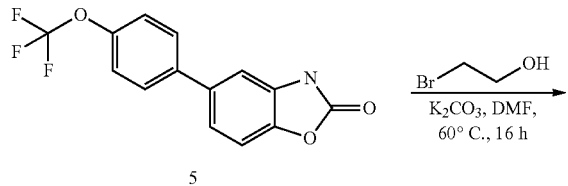

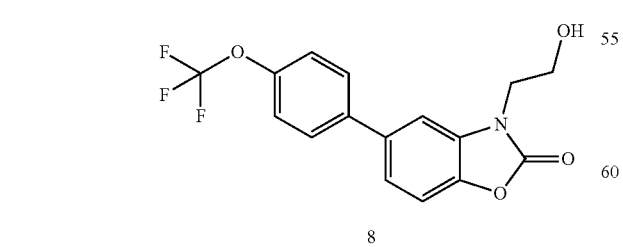

To a solution of Compound 5 (500 mg, 1.69 mmol, 1 eq) in anhydrous DMF (5 mL) was added K$_2$CO$_3$ (468.16 mg, 3.39 mmol, 2 eq) and 2-bromoethanol (423.30 mg, 3.39 mmol, 240.51 μL, 2 eq). The resulting mixture was stirred at 60° C. under N$_2$ for 16 hours. Saturated NH$_4$Cl aqueous (10 mL) and EtOAc (20 mL) was added to the reaction mixture and the mixture was stirred for 5 mins. The aqueous phase was extracted with EtOAc (20 mL×2) and the combined organic layers were washed with brine (20 mL×2), dried over anhydrous Na$_2$SO$_4$, filtered and concentrated to afford Compound 8 (250 mg, crude) as an oil. LCMS R$_t$=1.18 min using Method A, MS ESI calcd. for C$_{16}$H$_{13}$F$_3$NO$_4$ [M+H]$^+$ 340.1, found 339.9.

Example 9: Synthesis of Compound 9

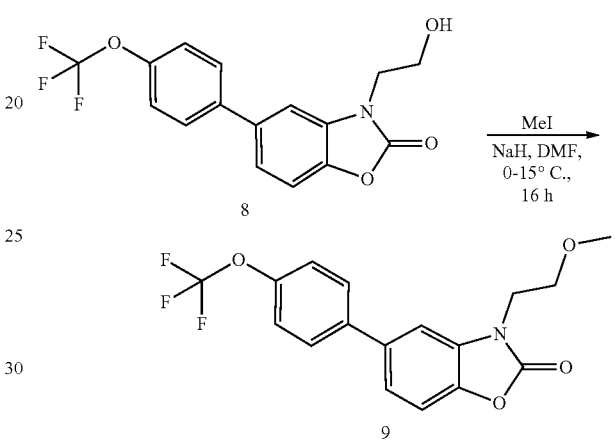

To a solution of Compound 8 (150 mg, 442.13 μmol, 1 eq) in DMF (2 mL) was added NaH (21.22 mg, 530.56 μmol, 60% purity, 1.2 eq) at 0° C., then MeI (313.78 mg, 2.21 mmol, 137.62 μL, μL, 5 eq) was added to the mixture at 0° C. The resulting mixture was stirred at 15° C. for 12 hours. Saturated NH$_4$Cl aqueous (10 mL) and EtOAc (10 mL) were added to the reaction suspension. The resulting mixture was stirred for 5 min. After separation, the organic layer was washed with brine (20 mL×2), dried over anhydrous Na$_2$SO$_4$, filtered and concentrated to give the crude product, which was purified by Prep-HPLC (Phenomenex Gemini C18 (150 mm×25 mm, 10 μm); A=H$_2$O (0.05% NH$_4$OH) and B=CH$_3$CN); 60-70% B over 8 minutes) to afford Compound 9 (51.05 mg, 144.50 μmol) as a solid. $^1$H NMR (DMSO-d$_6$ 400 MHz) $\delta_H$=7.75 (d, 2H), 7.71-7.63 (m, 2H), 7.44 (d, 2H), 7.23 (d, 1H), 4.46 (t, 2H), 3.95 (t, 2H), 3.90-3.83 (s, 3H). LCMS R$_t$=1.25 min using Method A, MS ESI calcd. for C$_{17}$H$_{15}$F$_3$NO$_4$ [M+H]$^+$ 354.1, found 353.9.

Example 10: Synthesis of Compound 10

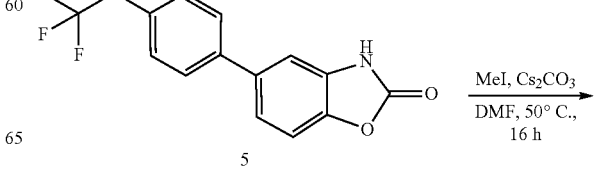

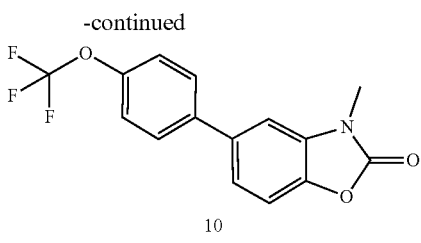

10

To a mixture of Compound 5 (150 mg, 508.11 μmol, 1 eq) and Cs$_2$CO$_3$ (331.10 mg, 1.02 mmol, 2 eq) in DMF (10 mL) was added MeI (360.60 mg, 2.54 mmol, 158.16 μL 5 eq) and the mixture was stirred at 50° C. for 16 hours. The mixture was diluted with sat.NH$_4$Cl (50 mL) and extracted with EtOAc (50 mL×2). The combined organic phase was washed with brine (20 mL), dried over Na$_2$SO$_4$, filtered and concentrated to give the crude product, which was purified by Prep-HPLC (Waters Xbridge (150 mm×25 mm, 5 μm) A=H$_2$O (10 mM NH$_4$HCO$_3$) and B=CH$_3$CN); 45-75% B over 10 minutes) to afford Compound 10 (49.15 mg, 156.52 μmol) as a solid. $^1$H NMR (DMSO-d$_6$+D$_2$O 400 MHz) $\delta_H$=7.77 (d, 2H), 7.51 (d, 1H), 7.43-7.37 (m, 4H), 3.36 (s, 3H). LCMS R$_t$=1.21 min using Method A, MS ESI calcd. for C$_{15}$H$_{11}$F$_3$NO$_3$ [M+H]$^+$ 310.1, found 309.9.

Example 11: Synthesis of Compound 11

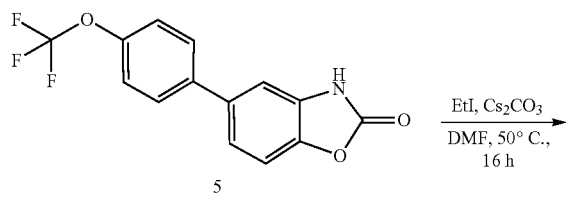

To a mixture of Compound 5 (150 mg, 508.11 μmol, 1 eq) and Cs$_2$CO$_3$ (331.10 mg, 1.02 mmol, 2 eq) in DMF (2 mL) was added the EtI (396.24 mg, 2.54 mmol, 203.20 μL, 5 eq) and the mixture was stirred at 50° C. for 16 hours. The mixture was diluted with sat.NH$_4$Cl (50 mL) and extracted with EtOAc (50 mL×2). The combined organic phase was washed with brine (20 mL), dried over Na$_2$SO$_4$, filtered and concentrated to give the crude product that was purified by Prep-HPLC (Waters Xbridge (150 mm×25 mm, 5 μm) A=H$_2$O (10 mM NH$_4$HCO$_3$) and B=CH$_3$CN); 48-78% B over 10 minutes) to afford Compound 11 (31.14 mg, 96.33 μmol) as a solid. $^1$H NMR (DMSO-d$_6$ 400 MHz) $\delta_H$=7.83 (d, 2H), 7.67 (s, 1H), 7.46 (d, 2H), 7.43 (d, 2H), 3.92 (q, 2H), 1.29 (t, 3H). LCMS R$_t$=1.24 min using Method A, MS ESI calcd. for C$_{16}$H$_{13}$F$_3$NO$_3$ [M+H]$^+$ 324.1, found 323.8.

Example 12: Synthesis of Compound 12

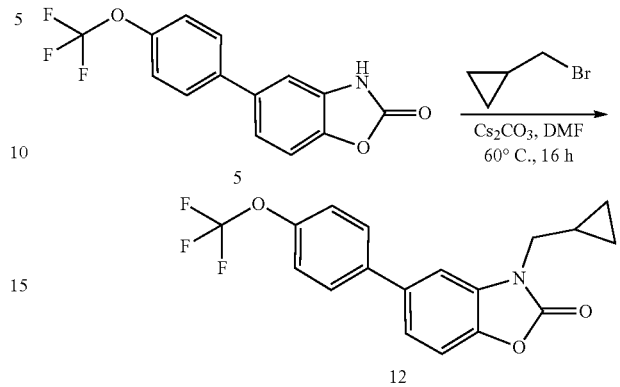

To a mixture of Compound 5 (150 mg, 508.11 μmol, 1 eq) and Cs$_2$CO$_3$ (331.10 mg, 1.02 mmol, 2 eq) in DMF (2 mL) was added bromomethylcyclopropane (137.19 mg, 1.02 mmol, 97.30 μL, 2 eq). The mixture was stirred at 60° C. under N$_2$ for 16 hours. Saturated NH$_4$Cl (10 mL) and EtOAc (20 mL) were added to the reaction mixture, and the aqueous phase was extracted with EtOAc (20 mL×2). The combined organic layers were washed with brine (20 mL×2), dried over anhydrous Na$_2$SO$_4$, filtered and concentrated to give the crude product, which was purified by Prep-HPLC (Phenomenex Gemini C18 (150 mm×25 mm, 10 μm); A=H$_2$O (0.04% NH$_3$H$_2$O) and B=CH$_3$CN); 70-80% B over 8 minutes) to afford Compound 12 (60.27 mg, 172.54 μmol) as a solid. $^1$H NMR (DMSO-d$_6$ 400 MHz) $\delta_H$=7.85-7.81 (m, 2H), 7.73 (s, 1H), 7.47 (d, 2H), 7.44 (d, 2H), 3.79 (d, 2H), 1.35-1.26 (m, 1H), 0.55-0.48 (m, 2H), 0.46-0.40 (m, 2H). LCMS R$_t$=1.44 min using Method A, MS ESI calcd. for C$_{18}$H$_{15}$F$_3$NO$_3$ [M+H]$^+$ 350.1, found 349.9.

Example 13: Synthesis of Compound 13

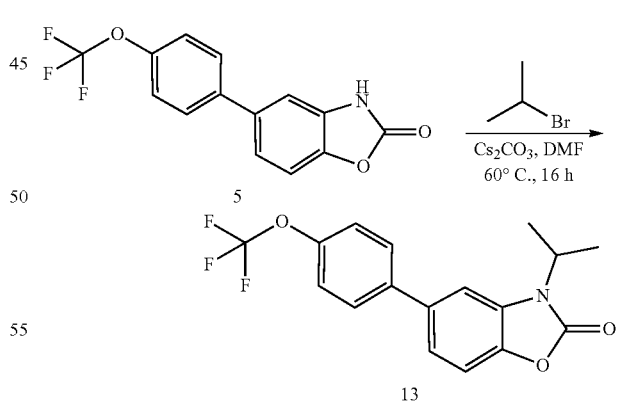

To a mixture of Compound 5 (150 mg, 508.11 μmol, 1 eq) and Cs$_2$CO$_3$ (331.10 mg, 1.02 mmol, 2 eq) in DMF (2 mL) was added 2-bromopropane (124.99 mg, 1.02 mmol, 95.41 μL, 2 eq). The mixture was stirred at 60° C. under N$_2$ for 16 hours. Saturated NH$_4$Cl (10 mL) and EtOAc (20 mL) were added, and the mixture was stirred for 5 min. The aqueous phase was then extracted with EtOAc (20 mL×2) and the combined organic layers were washed with brine (20 mL×2), dried over Na$_2$SO$_4$, filtered and concentrated to give the crude product, which was purified by Prep-HPLC (Phenomenex Gemini C18 (150 mm×25 mm, 10 μm); A=H$_2$O (0.05% NH$_4$OH) and B=CH$_3$CN); 68-78% B over 8 minutes) to afford Compound 13 (48.72 mg, 144.44 μmol) as a solid. $^1$H NMR (DMSO-d$_6$ 400 MHz) $\delta_H$=7.83 (d, 2H), 7.67 (s, 1H), 7.46 (d, 2H), 7.42 (s, 2H), 4.57 (q, 1H), 1.50 (d, 6H). LCMS R$_t$=1.40 min using Method A, MS ESI calcd. for C$_{17}$H$_{15}$F$_3$NO$_3$ [M+H]$^+$ 338.1, found 337.9.

Example 14: Synthesis of Compound 14

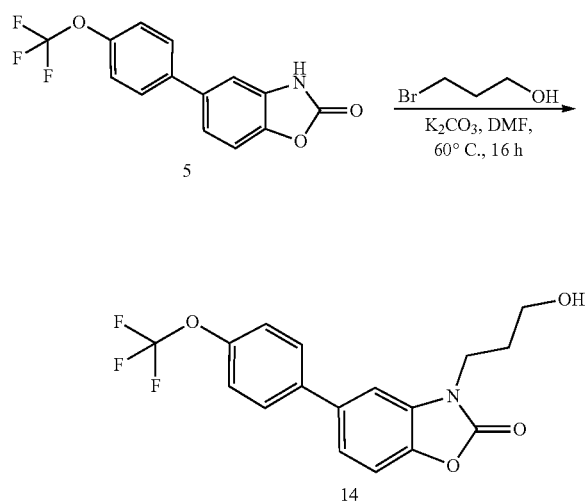

To a mixture of Compound 5 (200 mg, 677.48 μmol, 1 eq) and K$_2$CO$_3$ (187.26 mg, 1.35 mmol, 2 eq) in DMF (5 mL) was added 3-bromopropan-1-ol (188.33 mg, 1.35 mmol, 122.29 μL, 2 eq). The reaction mixture was heated to 60° C. and stirred for 16 hours. The mixture was diluted with H$_2$O (10 mL) and extracted with EtOAc (10 mL×2). The combined organic phase was washed with brine (10 mL), dried over Na$_2$SO$_4$, filtered and concentrated, and the residue was purified by Prep-HPLC (Phenomenex Gemini C18 (150 mm×25 mm, 10 μm); A=H$_2$O (0.05% NH$_4$OH) and B=CH$_3$CN); 45-75% B over 8 minutes) to afford Compound 14 (53.43 mg, 150.93 μmol) as a solid. $^1$H NMR (DMSO-d$_6$ 400 MHz) $\delta_H$=7.81 (d, 2H), 7.63 (s, 1H), 7.47 (d, 2H), 7.43 (d, 2H), 4.61 (t, 1H), 3.94 (t, 2H), 3.48 (q, 2H), 1.92-1.82 (m, 2H). LCMS R$_t$=0.83 min using Method B, MS ESI calcd. for C$_{17}$H$_{15}$F$_3$NO$_4$ [M+H]$^+$ 354.1, found 354.1.

Example 15: Synthesis of Compound 15

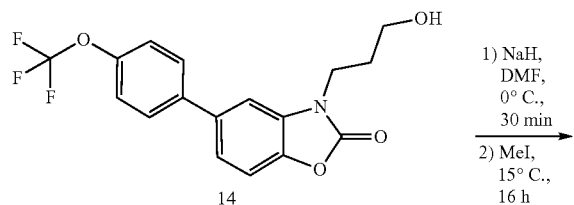

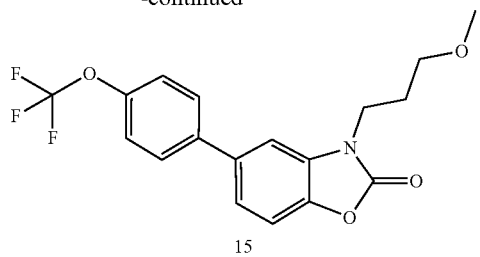

To a mixture of Compound 14 (150 mg, 424.58 μmol, 1 eq) in DMF (15 mL) was added NaH (20.38 mg, 509.49 μmol, 60% purity, 1.2 eq) at 0° C., and the mixture was stirred for 30 mins. MeI (301.32 mg, 2.12 mmol, 132.16 μL, 5 eq) was added, and the mixture was stirred at 15° C. for 16 hours. The mixture was diluted with sat. NH$_4$Cl (40 mL) and extracted with EtOAc (40 mL×2). The combined organic phase was washed with brine (20 mL), dried over Na$_2$SO$_4$, filtered and concentrated to give the crude product, which was purified by Prep-HPLC (Waters Xbridge (150 mm×25 mm, 5 μm) A=H$_2$O (10 mM NH$_4$HCO$_3$) and B=CH$_3$CN); 35-65% B over 10 minutes) afford Compound 15 (28.92 mg, 78.73 μmol) as a solid. $^1$H NMR (DMSO-d$_6$ 400 MHz) $\delta_H$=7.76 (d, 2H), 7.67-7.62 (m, 2H), 7.43 (d, 2H), 7.21 (d, 1H), 4.37-4.31 (m, 2H), 3.85 (s, 3H), 3.53 (t, 2H), 2.14-2.05 (m, 2H). LCMS R$_t$=1.15 min using Method A, MS ESI calcd. for C$_{18}$H$_{17}$F$_3$NO$_4$ [M+H]$^+$ 368.1, found 367.8.

Example 16: Synthesis of Compound 16

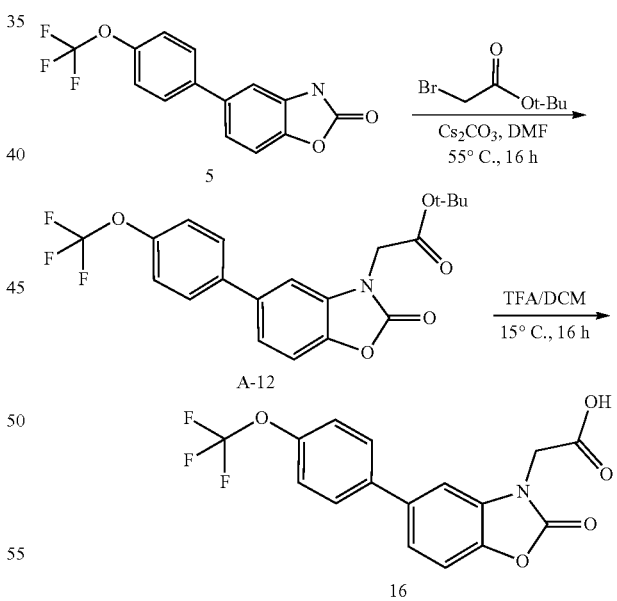

Synthesis of A-12:

To a mixture of Compound 5 (500 mg, 1.69 mmol, 1 eq) and Cs$_2$CO$_3$ (1.10 g, 3.39 mmol, 2 eq) in DMF (15 mL) was added tert-butyl 2-bromoacetate (495.54 mg, 2.54 mmol, 375.41 μL, 1.5 eq). The reaction mixture was stirred at 55° C. for 16 hours. The mixture was then diluted with H$_2$O (30 mL) and extracted with EtOAc (20 mL×2). The combined organic phase was washed with brine (20 mL), dried over Na$_2$SO$_4$, filtered and concentrated, and the residue purified by flash chromatography on silica gel (EtOAc in PE=0% to 10% to 30%) to afford A-12 (500 mg, 1.22 mmol) as a solid. ¹H NMR (DMSO-d₆ 400 MHz) $\delta_H$=7.79 (d, 2H), 7.73 (s, 1H), 7.50-7.45 (m, 4H), 4.72 (s, 2H), 1.43 (s, 9H).

Synthesis of Compound 16:

A mixture of A-12 (500 mg, 1.22 mmol, 1 eq) in DCM (20 mL) and TFA (10 mL) was stirred at 15° C. for 16 hours. The mixture was concentrated to give the crude product (520 mg), which was purified by Prep-HPLC (Boston Green ODS (150 mm×30 mm, 5 μm) A=H₂O (0.1% TFA) and B=CH₃CN); 35-65% B over 8 minutes) to afford Compound 16 (41.53 mg, 0.12 mmol) as a solid. ¹H NMR (DMSO-d₆ 400 MHz) $\delta_H$=13.68-13.15 (m, 1H), 7.80 (d, 2H), 7.75 (s, 1H), 7.55-7.38 (m, 4H), 4.70 (s, 2H). LCMS $R_t$=1.22 min using Method A, MSESI calcd. for $C_{16}H_9F_3NO_5$ [M−H]⁻ 352.0511, found 352.0569.

Example 17: Synthesis of Compound 17

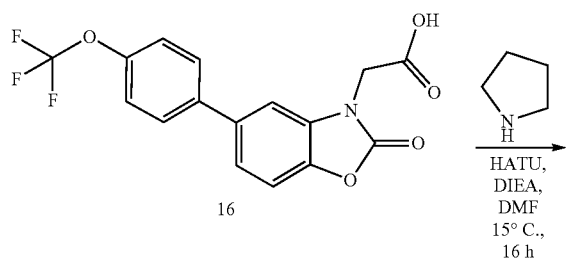

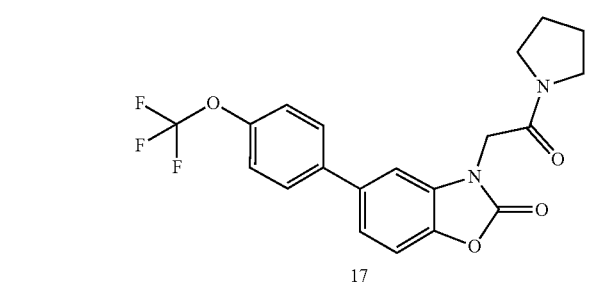

To the mixture of Compound 16 (100. mg, 0.28 mmol), HATU (161.4 mg, 0.42 mmol) and DIEA (73.04 mg, 0.57 mmol) in DMF (2 mL) was added pyrrolidine (24.16 mg, 0.34 mmol) and the mixture was stirred at 15° C. for 16 hours. The mixture was diluted with sat. NH₄Cl (10 mL), extracted with EtOAc (10 mL×2). The combined organic phase was washed with brine (10 mL), dried over Na₂SO₄, filtered and concentrated to give the crude product, which was purified by Prep-HPLC (Waters Xbridge (150 mm×25 mm, 5 μm) A=H₂O (10 mM NH₄HCO₃) and B=CH₃CN); 40-70% B over 10 minutes) to afford Compound 17 (19.77 mg, 0.05 mmol) as a solid. ¹H NMR (DMSO-d₆+D₂O 400 MHz) $\delta_H$=7.73 (d, 2H), 7.48 (s, 1H), 7.44-7.40 (m, 4H), 4.70 (s, 2H), 3.52 (t, 2H), 3.28 (t, 2H), 1.97-1.87 (m, 2H), 1.83-1.71 (m, 2H). LCMS $R_t$=1.26 min using Method A, MS ESI calcd. for $C_{20}H_{18}F_3N_2O_4$ [M+H]⁺ 407.1, found 407.0.

Example 18: Synthesis of Compound 18

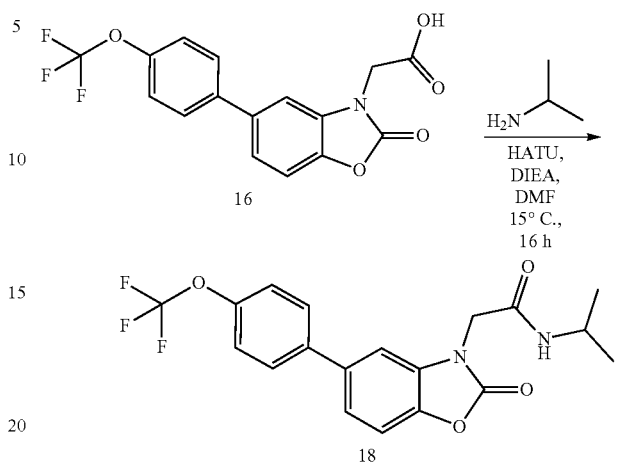

To the mixture of Compound 16 (100 mg, 0.28 mmol), HATU (161.36 mg, 0.42 mmol) and DIEA (73.04 mg, 0.57 mmol) in DMF (2 mL) was added propan-2-amine (20.08 mg, 0.34 mmol) and the mixture was stirred at 15° C. for 16 hours. The mixture was diluted with NH₄Cl (10 mL) and extracted with EtOAc (10 mL×2). The combined organic phase was washed with brine (10 mL), dried over Na₂SO₄, filtered and concentrated to give the crude product, which was purified by Prep-HPLC (Waters Xbridge (150 mm×25 mm, 5 μm) A=H₂O (10 mM NH₄HCO₃) and B=CH₃CN); 40-70% B over 10 minutes), to afford Compound 18 (17.87 mg, 0.05 mmol) as a solid. ¹H NMR (DMSO-d₆ 400 MHz) $\delta_H$=8.20 (d, 1H), 7.77 (d, 2H), 7.58 (s, 1H), 7.50-7.43 (m, 4H), 4.50 (s, 2H), 3.89-3.83 (m, 1H), 1.08 (d, 6H). LCMS $R_t$=1.25 min using Method A, MS ESI calcd. for $C_{19}H_{18}F_3N_2O_4$ [M+H]⁺ 395.1, found 395.0.

Example 19: Synthesis of Compound 19

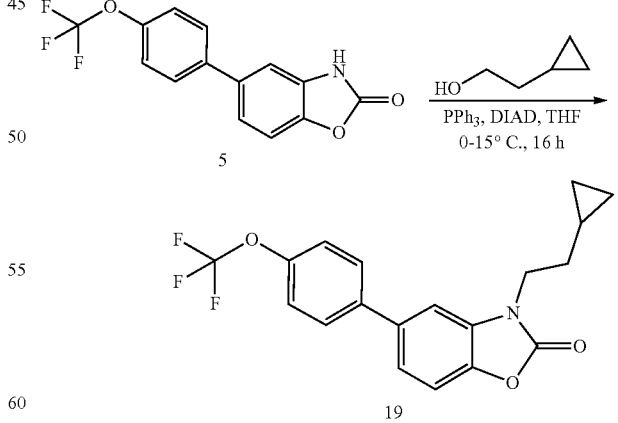

To a mixture of Compound 5 (100 mg, 0.34 mmol), 2-cyclopropylethanol (43.76 mg, 0.51 mmol) and PPh₃ (133.13 mg, 0.51 mmol) in THF (3 mL) under N₂ was added DIAD (102.64 mg, 0.51 mmol) drop-wise at 0° C. The reaction mixture was then stirred at 15° C. for 16 hours. The reaction mixture was concentrated, and the residue was purified by Prep-HPLC C (Phenomenex Gemini (150 mm×25 mm, 10 μm); A=H$_2$O (0.05% NH$_4$OH) and B=CH$_3$CN); 72-82% B over 8 minutes) to afford Compound 19 (57.45 mg, 0.16 mmol) as an oil. $^1$H NMR (MeOD-d$_4$ 400 MHz) δ$_H$=7.72 (d, 2H), 7.46 (d, 1H), 7.43-7.39 (m, 1H), 7.38-7.32 (m, 3H), 4.03 (t, 2H), 1.71 (q, 2H), 0.80-0.68 (m, 1H), 0.46-0.38 (m, 2H), 0.03 (q, 2H). LCMS R$_t$=1.12 min using Method A, MS ESI calcd. for C$_{19}$H$_{17}$F$_3$NO$_3$ [M+H]$^+$ 364.1, found 364.0.

Example 20: Synthesis of Compound 20

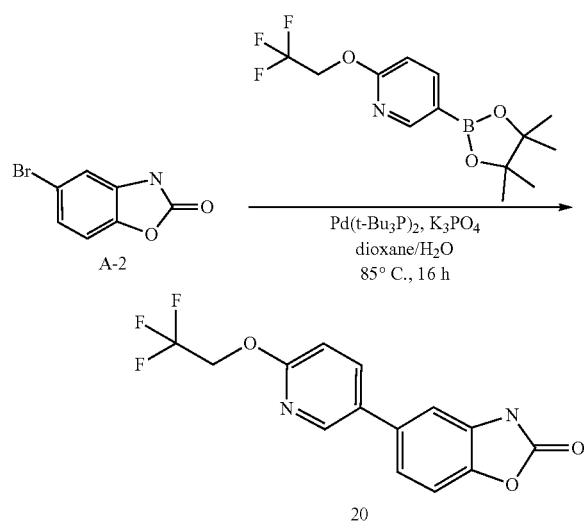

A mixture of A-2 (200 mg, 0.93 mmol), 5-(4,4,5,5-tetramethyl-1,3,2-dioxaborolan-2-yl)-2-(2,2,2-trifluoroethoxy)pyridine (566.47 mg, 1.87 mmol), Pd(t-BuP$_3$)$_2$ (95.51 mg, 0.19 mmol) and K$_3$PO$_4$ (257.92 mg, 1.87 mmol) in 1,4-dioxane (2 mL) and water (0.2 mL) was stirred at 85° C. for 16 hours. The mixture was diluted with EtOAc (10 mL), filtered through silica gel, eluted with EtOAc (10 mL) and the filtrate concentrated to give the crude product, which was purified by Prep-HPLC (Waters Xbridge (150 mm×25 mm, 5 μm) A=H$_2$O (10 mM NH$_4$HCO$_3$) and B=CH$_3$CN); 37-67% B over 10 minutes) to afford Compound 20 (48.55 mg, 0.16 mmol) as a solid. $^1$H NMR (DMSO-d$_6$ 400 MHz) δ=11.80 (br s, 1H), 8.48 (d, 1H), 8.10 (dd, 1H), 7.38 (s, 2H), 7.34 (s, 1H), 7.07 (d, 1H), 5.04 (q, 2H). LCMS R$_t$=1.20 min using Method A, MS ESI calcd. for C$_{14}$H$_{10}$F$_3$N$_3$O$_3$ [M+H]$^+$ 311.1, found 310.8.

Example 21: Synthesis of Compound 21

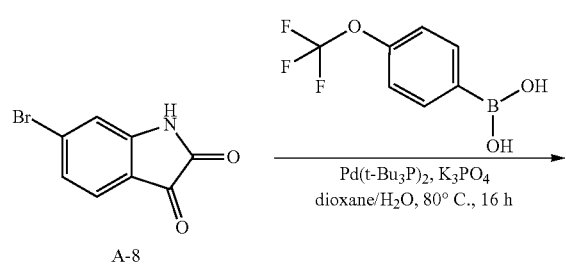

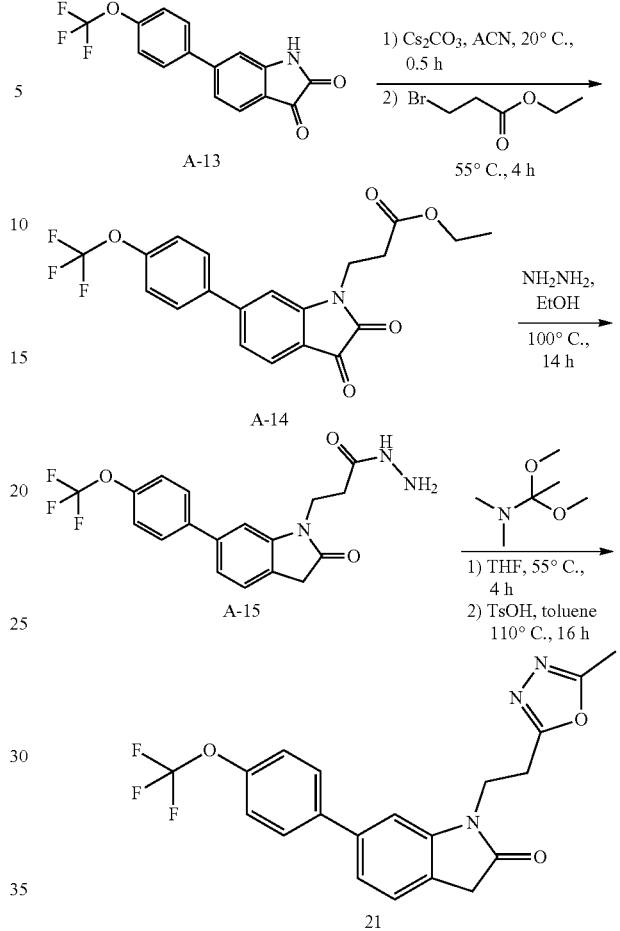

Synthesis of A-13:

A mixture of A-8 (4 g, 17.70 mmol, 1 eq), [4-(trifluoromethoxy)phenyl]boronic acid (4.37 g, 21.24 mmol, 1.2 eq), Pd(t-Bu$_3$P)$_2$ (633.09 mg, 1.24 mmol, 0.07 eq) and K$_3$PO$_4$ (9.39 g, 44.24 mmol, 2.5 eq) in dioxane (200 mL) and H$_2$O (40 mL) was stirred at 80° C. for 16 hours under N$_2$. The mixture was then concentrated to a residue, and the residue was diluted with H$_2$O (100 mL). The mixture was extracted with EtOAc (200 mL×2), and the combined organic phase was washed with water (50 mL×2) and brine (50 mL), dried over Na$_2$SO$_4$, filtered and concentrated to give a crude product that was purified by flash chromatography on silica gel (EtOAc in PE=20% to 30% to 50%) to afford A-13 (200 mg, 650.99 μmol). $^1$H NMR (DMSO-d$_6$ 400 MHz) δ$_H$=11.18 (br s, 1H), 7.85 (d, 2H), 7.61 (d, 1H), 7.51 (d, 2H), 7.37 (dd, 1H), 7.12 (d, 1H)

Synthesis of A-14:

A mixture of A-13 (200 mg, 650.99 μmol, 1 eq) and Cs$_2$CO$_3$ (424.21 mg, 1.30 mmol, 2 eq) in CH$_3$CN (20 mL) was stirred at 20° C. for 0.5 hour. To the mixture was added ethyl 3-bromopropanoate (235.69 mg, 1.30 mmol, 2 eq), then the mixture was stirred at 55° C. for 4 hours. The mixture was filtered through Celite, eluted with EtOAc (30 mL), and the filtrate was concentrated to give the crude product that was purified by flash chromatography on silica gel (EtOAc in PE=10% to 20% to 40%) to afford A-14 (130 mg, 319.14 μmol) as an oil. $^1$H NMR (CDCl$_3$, 400 MHz) δ$_H$=7.72-7.63 (m, 3H), 7.37 (d, 2H), 7.31 (dd, 1H), 7.22 (d, 1H), 4.13 (q, 2H), 4.10 (t, 2H), 2.80 (t, 2H), 1.22 (t, 3H).

Synthesis of A-15:

A mixture of A-14 (120 mg, 294.59 μmol, 1 eq) and hydrazine (944.03 mg, 29.46 mmol, 1.07 mL, 100 eq) in EtOH (3 mL) was stirred at 100° C. for 14 hours. After cooling, the mixture was concentrated to afford A-15 (110 mg, 259.82 μmol) as a solid. LCMS $R_t$=0.76 min using Method B, MS ESI calcd. for $C_{18}H_{17}F_3N_3O_3$ [M+H]+ 380.1, found 379.9.

Synthesis of Compound 21:

To a mixture of A-15 (110 mg, 289.98 μmol, 1 eq) in THF (4 mL) was added 1,1-dimethoxy-N,N-dimethylethanamine (77.24 mg, 579.97 μmol, 84.79 μL, 2 eq), then the mixture was stirred at 55° C. for 4 hours. The mixture was concentrated to a residue, followed by addition of toluene (4 mL) and TsOH.H₂O (11.03 mg, 58.00 μmol, 0.2 eq). The mixture was stirred at 110° C. for 16 hours. After cooling, the mixture was diluted with H₂O (10 mL), and the mixture was extracted with EtOAc (30 mL×2). The combined organic phase was washed with water (10 mL×2) and brine (10 mL), dried over Na₂SO₄, filtered and concentrated to give a crude product that was purified by Prep-TLC (silica gel, PE:EtOAc=1:1) to afford Compound 21 (50.22 mg, 124.51 μmol) as a solid. ¹H NMR (CDCl₃ 400 MHz) $δ_H$=7.57 (d, 2H), 7.36-7.28 (m, 3H), 7.22 (dd, 1H), 6.92 (s, 1H), 4.20 (t, 2H), 3.58 (s, 2H), 3.24 (t, 2H), 2.41 (s, 3H). LCMS $R_t$=1.17 min using Method A, MS ESI calcd. for $C_{20}H_{17}F_3N_3O_3$ [M+H]+ 404.1, found 403.9.

Example 22: Synthesis of Compound 22 product A-18 (2.3 g, crude). ¹H NMR (DMSO-d₆ 400 MHz) $δ_H$=12.82-11.26 (m, 1H), 8.04 (d, 1H), 7.71 (d, 1H).

Synthesis of A-19:

To a solution of A-18 (2.5 g, 11.63 mmol, 1 eq) and Cs₂CO₃ (7.58 g, 23.26 mmol, 2 eq) in DMF (20 mL) was added 2,2,2-trifluoroethyl trifluoromethanesulfonate (5.40 g, 23.26 mmol, 2 eq), and the mixture was stirred at 20° C. for 16 hours. The mixture was diluted with H₂O (10 mL) and extracted with EtOAc (40 mL×2). The combined organic phase was washed with brine (15 mL), dried over Na₂SO₄, filtered and concentrated to give the crude product, which was purified by flash chromatography on silica gel (EtOAc in PE=20% to 40% to 60%) to afford A-19 (700 mg, 2.36 mmol) as a solid. ¹H NMR (DMSO-d₆ 400 MHz) $δ_H$=8.16 (d, 1H), 8.13 (d, 1H), 4.90-4.82 (m, 2H).

Synthesis of Compound 22:

A mixture of A-19 (200 mg, 673.34 μmol, 1 eq), [4-(trifluoromethoxy)phenyl]boronic acid (207.99 mg, 1.01 mmol, 1.5 eq), Pd(t-Bu₃P)₂ (51.62 mg, 101.00 μmol, 0.15 eq) and K₃PO₄ (285.86 mg, 1.35 mmol, 2 eq) in dioxane (6 mL) and H₂O (0.6 mL) was stirred at 90° C. for 16 hours. The mixture was concentrated and the crude product was purified by Prep-HPLC (Phenomenex Gemini (150 mm×25 mm, 10 μm); A=H₂O (0.05% NH₄OH) and B=CH₃CN); 63-73% B over 8 minutes) to afford Compound 22 (35.08 mg, 90.81 μmol) as a solid. ¹H NMR (CDCl₃, 400 MHz) $δ_H$=8.29 (d, 1H), 7.60-7.54 (m, 2H), 7.47 (d, 1H), 7.37 (d, 2H), 4.50 (q, 2H). LCMS $R_t$=1.33 min using Method A, MS ESI calcd. for $C_{15}H_9F_6N_3O_3$ [M+H]+ 379.0, found 378.9.

Example 23: Synthesis of Compound 23

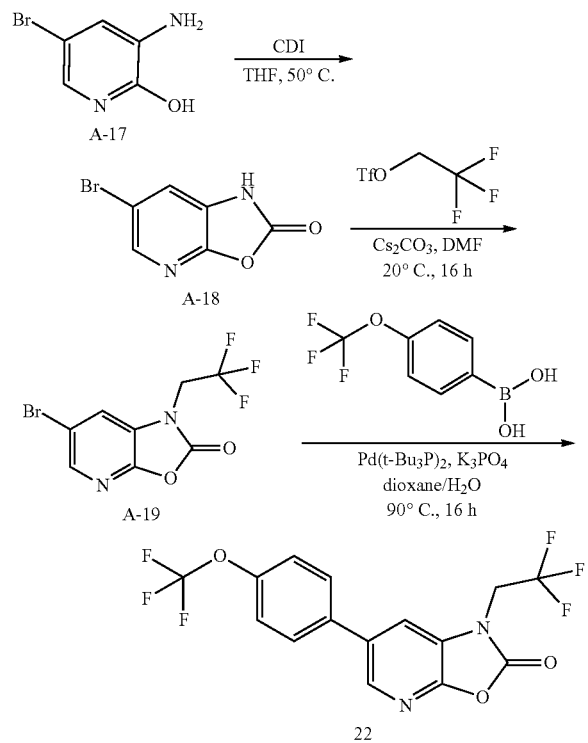

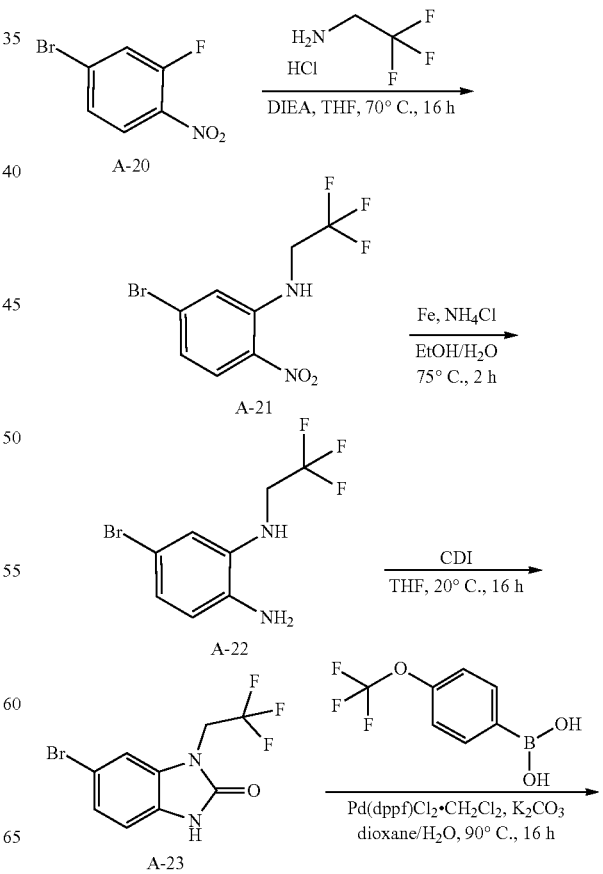

Synthesis of A-18:

A mixture of A-17 (2 g, 10.58 mmol, 1 eq) and CDI (2.06 g, 12.70 mmol, 1.2 eq) in THF (30 mL) was stirred at 50° C. for 2 hours. The mixture was then filtered through silica gel, and the filtrate was concentrated to provide the crude -continued

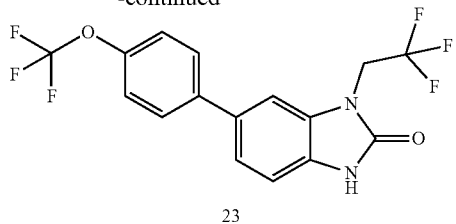

Synthesis of A-21:

A mixture of A-20 (5000 mg, 22.73 mmol), 2,2,2-trifluoroethanamine hydrochloride (4620 mg, 34.09 mmol) and DIEA (8811.82 mg, 68.18 mmol) in THF (30 mL) was stirred at 70° C. for 16 hours. After cooling to room temperature, the mixture was concentrated, then the mixture was diluted with $H_2O$ (100 mL) and extracted with EtOAc (100 mL×2). The combined organic phase was washed with brine (100 mL), dried over $Na_2SO_4$, filtered and concentrated to give the crude product that was purified by flash chromatography on silica gel (EtOAc in PE=0 to 30% to 100%) to give the product A-21 (6100 mg, 20.40 mmol). $^1H$ NMR (CDCl$_3$, 400 MHz) $\delta_H$=8.28 (br s, 1H), 8.09 (dd, 1H), 7.12 (s, 1H), 6.94 (dd, 1H), 4.08-3.86 (m, 2H)

Synthesis of A-22:

A mixture of A-21 (2 g, 6.69 mmol), Fe (3.74 g, 66.88 mmol) and $NH_4Cl$ (3.58 g, 66.88 mmol) in ethanol (20 mL) and water (20 mL) was stirred at 75° C. for 2 hours. After cooling to r.t, the mixture was filtrated through Celite, and eluted with EtOAc (50 mL×2). The filtration was concentrated and diluted with EtOAc (50 mL), washed with (30 mL×2) and brine (30 mL), dried over $Na_2SO_4$, filtered and concentrated to give the crude product of A-22 (1.7 g, 6.32 mmol). LCMS $R_t$=0.74 min using Method B, MS ESI calcd. for $C_8H_9BrF_3N_2$ [M+H]$^+$ 269.0, found 268.9.

Synthesis of A-23:

A mixture of A-22 (1000 mg, 3.72 mmol) and CDI (523.68 mg, 3.72 mmol) in THF (10 mL) was stirred at 20° C. for 16 hours. After cooling to r.t, the mixture was concentrated to give a residue that was purified by flash chromatography on silica gel (EtOAc in PE=0% to 50% to 100%) to afford A-23 (930 mg, 2.97 mmol) as a solid. $^1H$ NMR (CDCl$_3$, 400 MHz) $\delta_H$=9.76 (br s, 1H), 7.30-7.26 (m, 1H), 7.23 (s, 1H), 7.02 (d, 1H), 4.46 (q, 2H).

Synthesis of Compound 23:

A mixture of A-23 (400 mg, 1.36 mmol), [4-(trifluoromethoxy)phenyl]boronic acid (558.34 mg, 2.71 mmol), Pd(dppf)Cl$_2$.CH$_2$Cl$_2$ (221.42 mg, 0.27 mmol) and K$_2$CO$_3$ (374.73 mg, 2.71 mmol) in 1,4-dioxane (15 mL) and water (3 mL) was stirred at 90° C. for 16 hours. The mixture was concentrated to give a residue that was purified by Prep-HPLC (Phenomenex Gemini (150 mm×25 mm, 10 μm); A=H$_2$O (0.05% NH$_4$OH) and B=CH$_3$CN); 50-80% B over 10 minutes) to afford Compound 23 (44.78 mg, 0.12 mmol) as a solid. $^1H$ NMR (CDCl$_3$, 400 MHz) $\delta_H$=8.80 (br s, 1H), 7.58 (d, 2H), 7.36-7.28 (m, 3H), 7.25-7.16 (m, 2H), 4.53 (q, 2H). LCMS $R_t$=1.19 min using Method A, MS ESI calcd. for $C_{16}H_{11}F_6N_2O_2$ [M+H]$^+$ 377.1, found 377.0.

Example 24: Synthesis of Compound 24

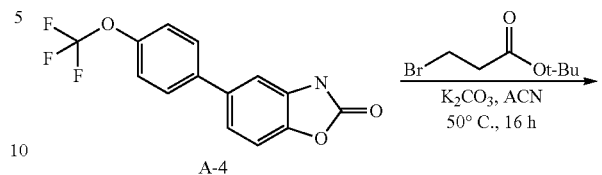

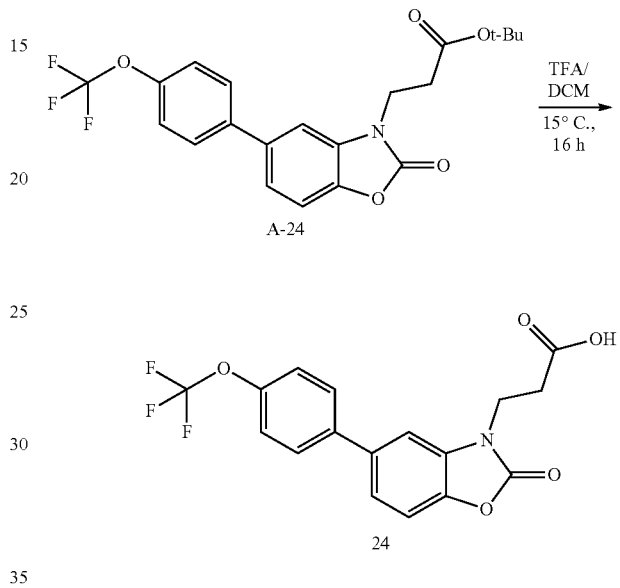

Synthesis of A-24:

To the mixture of the A-4 (1500 mg, 5.08 mmol) and K$_2$CO$_3$ (1402.39 mg, 10.16 mmol) in MeCN (5 mL) was added tert-butyl 3-bromopropanoate (1062.36 mg, 5.08 mmol), and the mixture was stirred at 50° C. for 16 hours. The mixture was cooled to r.t., diluted with sat.NH$_4$Cl (50 mL), extracted with EtOAc (50 mL×2), and the combined phase was washed over brine (20 mL), dried over Na$_2$SO$_4$ and concentrated to give the crude product. The crude product was purified by flash chromatography on silica gel (EtOAc in PE=5% to 10% to 20%) to afford A-24 (1300 mg, 3.07 mmol) as an oil. $^1H$ NMR (DMSO-d$_6$ 400 MHz) $\delta_H$=7.83 (d, 2H), 7.72 (s, 1H), 7.47 (d, 2H), 7.43 (s, 2H), 4.10 (t, 2H), 2.75 (t, 2H), 1.31 (s, 9H).

Synthesis of Compound 24:

A mixture of A-24 (700 mg, 1.65 mmol) in TFA (5 mL, 1.65 mmol) and DCM (10 mL) was stirred at 15° C. for 16 hours. The mixture was concentrated, diluted with H$_2$O (20 mL) and extracted with DCM (20 mL). The combined organic phase was washed with brine (10 mL), dried over Na$_2$SO$_4$, filtered and concentrated to give a residue that was purified by Prep-HPLC (Phenomenex Synergi (150 mm×30 mm, 4 inn); A=H$_2$O (0.1% TFA) and B=CH$_3$CN); 45-75% B over 8 minutes) to afford Compound 24 (34.06 mg, 0.09 mmol) as a solid. $^1H$ NMR (DMSO-d$_6$ 400 MHz) $\delta_H$=12.46 (br s, 1H), 7.82 (d, 2H), 7.72 (s, 1H), 7.47 (d, 2H), 7.43 (s, 2H), 4.09 (t, 2H), 2.76 (t, 2H). LCMS $R_t$=1.24 min using Method A, ESI calcd. for $C_{17}H_{13}F_3NO_5$ [M+H]$^+$ 368.0668, found 368.0683.

Example 25: Synthesis of Compound 25

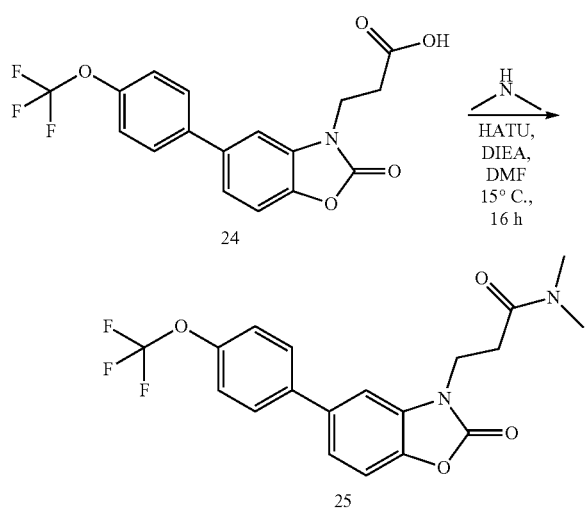

To the mixture of Compound 24 (150 mg, 0.41 mmol), HATU (232.79 mg, 0.61 mmol) and DIEA (105.37 mg, 0.82 mmol) in DMF (2 mL) was added N-methylmethanamine (22.09 mg, 0.49 mmol), and the mixture was stirred at 15° C. for 16 hours. The mixture was diluted with sat.NH$_4$Cl (10 mL), extracted with EtOAc (10 mL×2). The combined organic phase was washed with brine (10 mL), dried over Na$_2$SO$_4$, filtered and concentrated to give a residue that was purified by Prep-HPLC (Waters Xbridge (150 mm×25 mm, 5 μm) A=H$_2$O (10 mM NH$_4$HCO$_3$) and B=CH$_3$CN); 40-70% B over 10 minutes) to afford Compound 25 (77.68 mg, 0.20 mmol) as a solid. $^1$H NMR (DMSO-d$_6$ 400 MHz) $\delta_H$=7.83 (d, 2H), 7.73 (s, 1H), 7.47 (d, 2H), 7.44-7.39 (m, 2H), 4.07 (t, 2H), 2.92 (s, 3H), 2.83 (t, 2H), 2.80 (s, 3H). LCMS R$_t$=1.166 min using Method A, MS ESI calcd. for C$_{19}$H$_{18}$F$_3$N$_2$O$_4$ [M+H]$^+$ 395.1, found 395.0.

Example 26: Synthesis of Compound 26

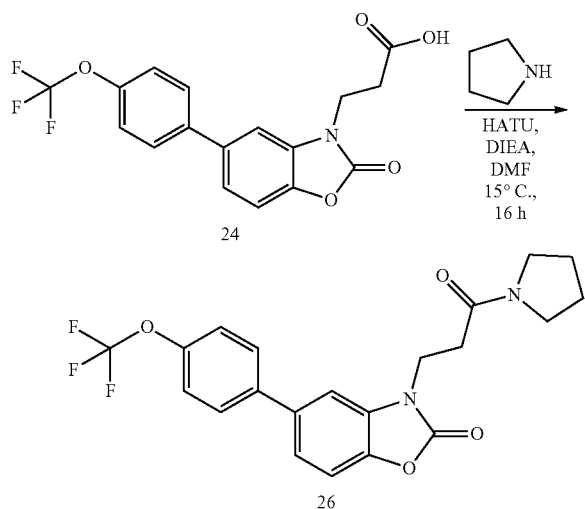

To the mixture of Compound 24 (150 mg, 0.4100 mmol), HATU (232.79 mg, 0.61 mmol) and DIEA (105.37 mg, 0.82 mmol) in DMF (2 mL) was added pyrrolidine (34.86 mg, 0.49 mmol) and the mixture was stirred at 15° C. for 16 hours. The mixture was diluted with sat.NH$_4$Cl (10 mL) and extracted with EtOAc (10 mL×2). The combined organic phase was washed with brine (10 mL), dried over Na$_2$SO$_4$, filtered and concentrated to give a residue that was purified by Prep-HPLC (Waters Xbridge (150 mm×25 mm, 5 μm) A=H$_2$O (10 mM NH$_4$HCO$_3$) and B=CH$_3$CN); 43-73% B over 10 minutes) to afford Compound 26 (72.24 mg, 0.17 mmol) as an oil. $^1$H NMR (DMSO-d$_6$+D$_2$O 400 MHz) $\delta_H$=7.77 (d, 2H), 7.58 (s, 1H), 7.46-7.33 (m, 4H), 4.07 (t, 2H), 3.30 (t, 2H), 3.17 (t, 2H), 2.73 (t, 2H), 1.82-1.73 (m, 2H), 1.71-1.62 (m, 2H). LCMS R$_t$=1.20 min ung Method A, MS ESI calcd. for C$_{21}$H$_{20}$F$_3$N$_2$O$_4$ [M+H]$^+$ 421.1, found 421.0.

Example 27: Synthesis of Compound 27

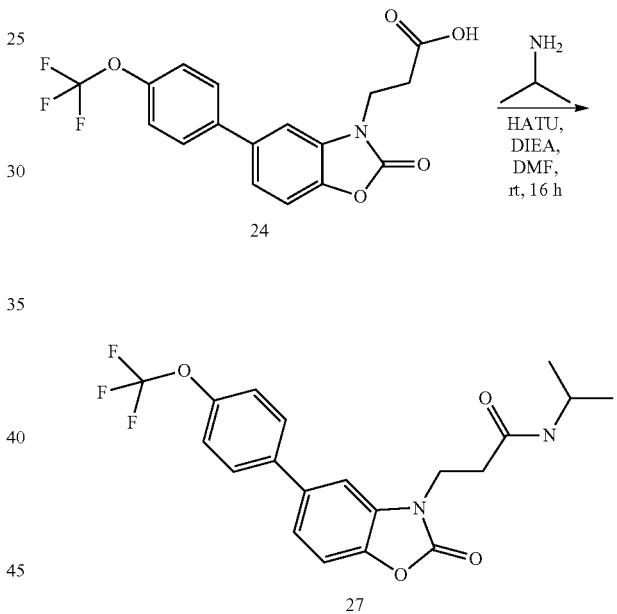

To a mixture of Compound 24 (150 mg, 0.41 mmol), HATU (232.94 mg, 0.61 mmol) and DIEA (105.53 mg, 0.82 mmol) in DMF (3 mL) was added propan-2-amine (28.97 mg, 0.49 mmol). The resulting mixture was stirred at 15° C. for 16 hours. To the stirred mixture was added saturated NH$_4$Cl aqueous (15 mL) and EtOAc (15 mL), and the organic layer was washed with brine (15 mL), dried over anhydrous Na$_2$SO$_4$, filtered and concentrated to give a crude product. The crude product was purified by Prep-HPLC (Xtimate C18 (250 mm×50 mm, 10 μm) A=H$_2$O (0.05% NH$_4$OH) and B=CH$_3$CN); 50-80% B over 8 minutes) to afford Compound 27 (78.39 mg, 0.19 mmol) as a solid. $^1$H NMR (CDCl$_3$, 400 MHz) $\delta_H$=7.62-7.56 (m, 2H), 7.36 (d, 1H), 7.33-7.27 (m, 3H), 7.26-7.23 (m, 1H), 5.43 (d, 1H), 4.21 (t, 2H), 4.04-3.93 (m, 1H), 2.66 (t, 2H), 1.01 (d, 6H). LCMS R$_t$=1.30 mins using Method A, MS ESI calcd. for C$_{20}$H$_{20}$F$_3$N$_2$O$_4$ [M+H]$^+$ 409.1, found 409.0.

Example 28: Synthesis of Compound 28

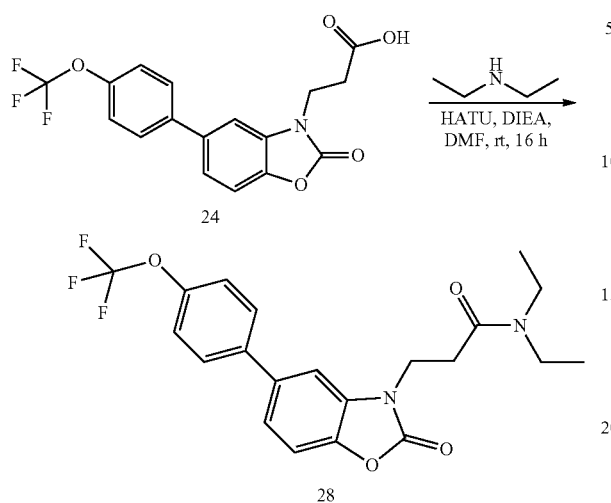

To a solution of Compound 24 (150 mg, 0.41 mmol), HATU (232.94 mg, 0.61 mmol) and DIEA (105.53 mg, 0.82 mmol) in DMF (3 mL) was added N-ethylethanamine (35.85 mg, 0.49 mmol). The resulting mixture was stirred at 15° C. for 16 hours. To the stirring mixture was added saturated NH$_4$Cl aqueous (15 mL) and EtOAc (15 mL). The organic layer was washed with brine (15 mL), dried over anhydrous Na$_2$SO$_4$, filtered and concentrated to give a crude product that was purified by Prep-HPLC Xtimate C18 (250 mm×50 mm, 10 μm) A=H$_2$O (0.05% NH$_4$OH) and B=CH$_3$CN); 58-88% B over 8 minutes) to afford Compound 28 (88.41 mg, 0.213 mmol) as an oil. $^1$H NMR (DMSO-d$_6$ 400 MHz) $\delta_H$=7.82 (d, 2H), 7.73 (s, 1H), 7.47 (d, 2H), 7.42 (s, 2H), 4.10 (t, 2H), 3.29-3.21 (m, 4H), 2.82 (t, 2H), 1.05 (t, 3H), 0.96 (t, 3H). LCMS R$_t$=1.35 mins using Method A, MS ESI calcd. for C$_{21}$H$_{22}$F$_3$N$_2$O$_4$ [M+H]$^+$ 423.1, found 423.0.

Example 29: Synthesis of Compound 29

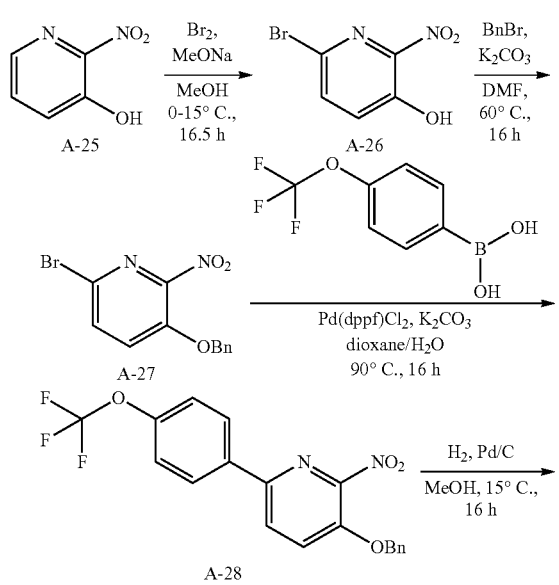

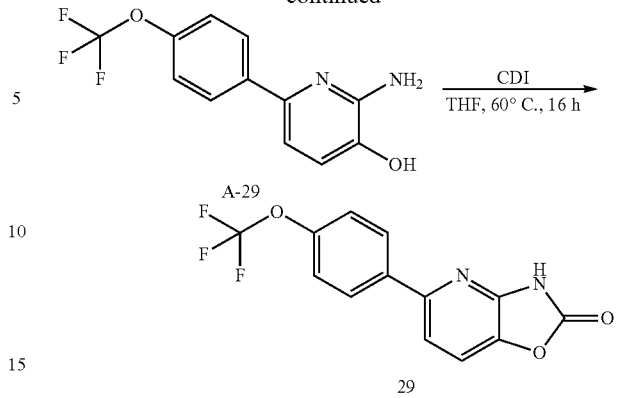

Synthesis of A-26:

To a solution of A-25 (10 g, 71.38 mmol) in methanol (200 mL) was added CH$_3$ONa (3.85 g, 71.38 mmol) slowly at 15° C. The resulting solution was stirred at 15° C. for 30 min. Then Br$_2$ (11.41 g, 71.38 mmol) was added to the solution dropwise 0° C. and the mixture was stirred at 15° C. for 16 hours. The reaction solution was quenched with glacial AcOH (1.25 mL) and concentrated to give the crude product of A-26 (22.00 g, crude) as a solid. The crude product was used in the next step without further purification. LCMS R$_t$=0.54 mins using Method B, MS ESI calcd. for C$_5$H$_4$BrN$_2$O$_3$ [M+H]$^+$ 218.9, found 219.1.

Synthesis of A-27:

To a mixture of A-26 (10 g, 45.66 mmol) and K$_2$CO$_3$ (6.31 g, 45.66 mmol) in DMF (150 mL) was added bromomethylbenzene (3.9 g, 22.83 mmol). The resulting mixture was stirred at 60° C. for 16 hours. The reaction mixture was cooled to room temperature. Water (300 mL) and EtOAc (200 mL) was added to the reaction mixture. The organic layer was washed with brine (100 mL×2), dried over Na$_2$SO$_4$, filtered and concentrated to give a crude product that was purified by flash chromatography on silica gel (PE:EtOAc=PE to 10:1 to 5:1 to 3:1) to afford A-27 (2.95 g, 9.54 mmol) as a solid. $^1$H NMR (DMSO-d$_6$ 400 MHz) $\delta_H$=8.05 (s, 2H), 7.44-7.34 (m, 5H), 5.39 (s, 2H).

Synthesis of A-28:

A mixture of A-27 (950 mg, 3.07 mmol), [4-(trifluoromethoxy)phenyl]boronic acid (759.45 mg, 3.69 mmol), Pd(t-Bu$_3$P)$_2$ (235.61 mg, 0.46 mmol) and K$_3$PO$_4$ (1304.9 mg, 6.15 mmol) in 1,4-dioxane (8 mL) and water (0.8 mL) was stirred under N$_2$ at 85° C. for 16 hours. The reaction mixture was cooled to room temperature and filtered through Celite. The filtrate was concentrated to give a crude product that was purified by flash chromatography on silica gel (PE:EtOAc=10:1 to 5:1 to 3:1) to afford A-28 (960 mg, 2.46 mmol) as a solid. $^1$H NMR (DMSO-d$_6$ 400 MHz) $\delta_H$=8.39 (d, 1H), 8.20-8.11 (m, 3H), 7.54-7.33 (m, 7H), 5.44 (s, 2H).

Synthesis of A-29:

A mixture of A-28 (150 mg, 0.38 mmol) and Pd/C (50 mg) in methanol (15 mL) was stirred under H$_2$ at 15° C. for 16 hours. The reaction mixture was filtered through Celite and the filtrate was concentrated to afford A-29 (100 mg, 0.37 mmol) as a solid. $^1$H NMR (DMSO-d$_6$ 400 MHz) $\delta_H$=7.98 (d, 2H), 7.34 (d, 2H), 7.00 (d, 1H), 6.90 (d, 1H), 5.58 (s, 2H).

Synthesis of Compound 29:

A mixture of 2-amino-6-[4-(trifluoromethoxy)phenyl]-pyridin-3-ol (100 mg, 0.37 mmol) and CDI (62.57 mg, 0.44 mmol) in THF (5 mL) was stirred at 60° C. for 16 hours. The reaction mixture was cooled to room temperature and concentrated to give a crude product that purified by Prep-HPLC Xtimate C18 (250 mm×50 mm, 10 μm) A=H$_2$O (0.05% NH$_4$OH) and B=CH$_3$CN); 30-60% B over 8 minutes) to afford Compound 29 (50.89 mg, 0.17 mmol) as a solid. $^1$H NMR (DMSO-d$_6$ 400 MHz) δ=12.55 (br s, 1H), 8.11 (d, 2H), 7.76-7.69 (m, 2H), 7.47 (br d, 2H). LCMS=R$_t$=1.23 min using Method A, MS ESI calcd. for C$_{13}$H$_8$F$_3$N$_3$O$_3$ [M+H]$^+$ 297.0, found 296.9.

Example 30: Synthesis of Compound 30

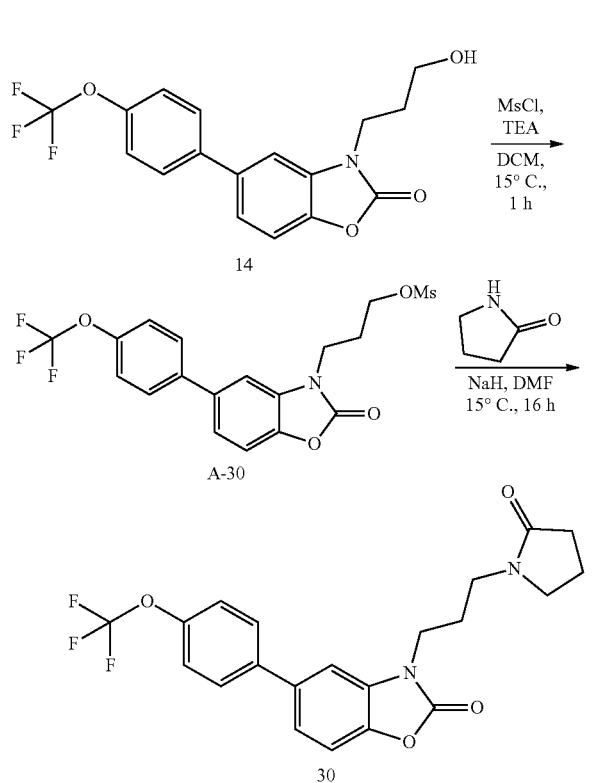

Synthesis of A-30:

To a solution of Compound 14 (320 mg, 0.91 mmol) in DCM (10 mL) at 0° C. was added methanesulfonyl chloride (0.08 mL, 1.09 mmol). The reaction mixture was stirred at 15° C. for 1 hour to give a solution The reaction was quenched with sat.NH$_4$Cl (30 mL), extracted with DCM (20 mL×3). The combined organic phase was washed with brine (20 mL), dried over Na$_2$SO$_4$, filtered and concentrated to give A-30 (420 mg, crude) as a solid. $^1$H NMR MeOD-d$_4$ 400 MHz) δ=7.75 (d, 2H), 7.49 (d, 1H), 7.44-7.40 (m, 1H), 7.38-7.30 (m, 3H), 4.34 (t, 2H), 4.08 (t, 2H), 3.05 (s, 3H), 2.31-2.22 (m, 2H).

Synthesis of Compound 30:

To the mixture of pyrrolidin-2-one (59.18 mg, 0.70 mmol) in DMF (3 mL) was added NaH (27.82 mg, 0.70 mmol) at 0° C. and the mixture was stirred for 30 mins. Then A-30 (200. mg, 0.46 mmol) was added, and the mixture was stirred at 15° C. for 16 hours. The mixture was quenched by sat.NH$_4$Cl (10 mL) and extracted with EtOAc (10 mL×2). The combined organic phase was washed with brine (10 mL), dried over Na$_2$SO$_4$, filtered and concentrated to give the crude product, which was purified by Prep-HPLC (Waters Xbridge (150 mm×25 mm, 5 μm) A=H$_2$O (10 mM NH$_4$HCO$_3$) and B=CH$_3$CN); 40-70% B over 10 minutes) to afford Compound 30 (12.42 mg, 0.03 mmol) as a solid. $^1$H NMR (CDCl$_3$, 400 MHz) δ$_H$=7.59 (d, 2H), 7.34-7.28 (m, 4H), 7.16 (s, 1H), 3.89 (t, 2H), 3.47-3.39 (m, 4H), 2.38 (t, 2H), 2.13-1.99 (m, 4H). LCMS R$_t$=1.16 min using Method A, MS ESI calcd. for C$_{21}$H$_{20}$F$_3$N$_2$O$_4$ [M+H]$^+$ 421.1, found 421.0.

Example 31: Synthesis of Compound 31

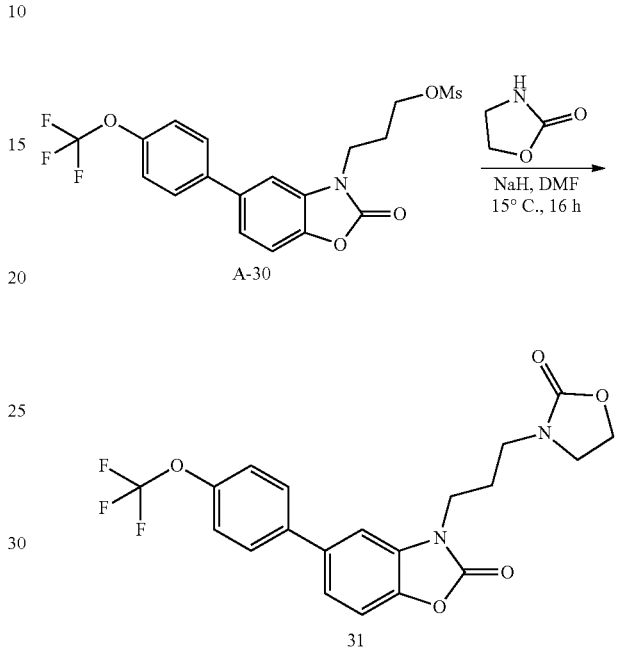

To the mixture of oxazolidin-2-one (60.56 mg, 0.70 mmol) in DMF (3 mL) was added the NaH (27.82 mg, 0.70 mmol) at 0° C. and the mixture was stirred for 30 mins. Then A-30 (200 mg, 0.46 mmol) was added and the mixture was stirred at 15° C. for 16 hours. The mixture was quenched by sat.NH$_4$Cl (10 mL), extracted with EtOAc (10 mL×2), and the combined organic phase was washed with brine (10 mL), dried over Na$_2$SO$_4$, filtered and concentrated to give a crude product. The crude product was purified by flash chromatography on silica gel (EtOAc in PE=10% to 20%) to afford Compound 31 (36.59 mg, 0.0843 mmol) as a solid. $^1$H NMR (DMSO-d$_6$ 400 MHz) δ$_H$=7.83 (d, 2H), 7.71 (s, 1H), 7.48 (d, 2H), 7.44 (d, 2H), 4.29-4.16 (m, 2H), 3.91 (t, 2H), 3.61-3.49 (m, 2H), 3.26 (t, 2H), 2.06-1.91 (m, 2H). LCMS R$_t$=1.15 min using Method A, MS ESI calcd. for C$_{20}$H$_{18}$F$_3$N$_2$O$_5$ [M+H]$^+$ 423.1, found 423.0.

Example 32: Synthesis of Compound 32

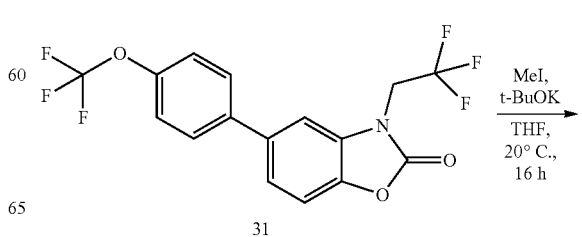

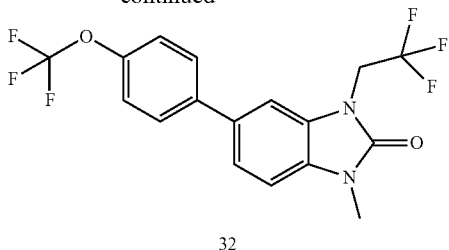

32

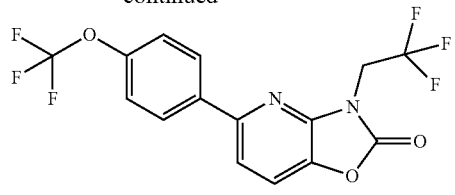

33

To a mixture of t-BuOK (47.71 mg, 0.43 mmol) and Compound 23 (80.00 mg, 0.21 mmol) in THF (10 mL) was added CH$_3$I (150.86 mg, 1.06 mmol). The mixture was stirred at 20° C. for 16 hours. After cooling to r.t, the mixture was concentrated to give the crude product, which was purified by Prep-HPLC (Phenomenex Gemini (150 mm×25 mm, 10 μm); A=H$_2$O (0.05% NH$_4$OH) and B=CH$_3$CN); 68-78% B over 8 minutes) afford Compound 32 (20.18 mg, 0.05 mmol) as a solid. $^1$H NMR (CDCl$_3$ 400 MHz) $\delta_H$=7.58 (d, 2H), 7.36 (dd, 1H), 7.31 (d, 2H), 7.23 (s, 1H), 7.09 (d, 1H), 4.53 (q, 2H), 3.49 (s, 3H). LCMS R$_t$=1.23 min using Method A, ESI calcd. for C$_{17}$H$_{13}$F$_6$N$_2$O$_2$ [M+H]$^+$ 391.0876, found 391.0818.

Example 33: Synthesis of Compound 33

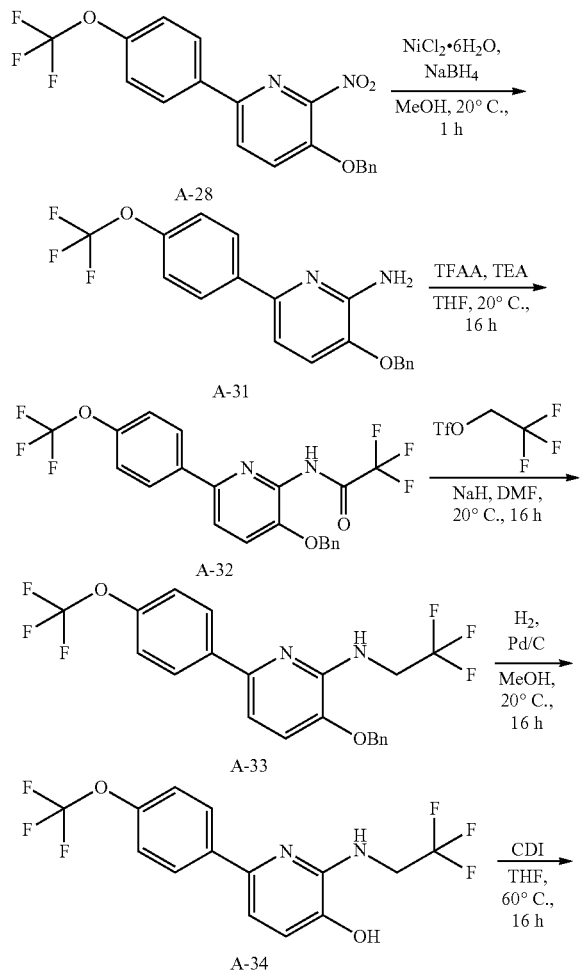

Synthesis of A-31:

To a solution of A-28 (660 mg, 1.69 mmol) in Methanol (5 mL) was added NiCl$_2$.6H$_2$O (1025.74 mg, 5.07 mmol). To the resulting mixture was added NaBH$_4$ (319.59 mg, 8.45 mmol) slowly and the mixture was stirred at 15° C. for 1 hour to give a suspension. Saturated NaHCO$_3$ aqueous (10 mL) and DCM (20 mL) was added to the reaction mixture and filtered through Celite. The filtrate was separated, and the organic layer was washed with brine (10 mL×2), dried over anhydrous Na$_2$SO$_4$, filtered through silica gel (300-400 mesh) and concentrated to give A-31 (220 mg, 0.61 mmol) as a solid. $^1$H NMR (DMSO-d$_6$ 400 MHz) $\delta_H$=8.02 (d, 2H), 7.52 (d, 2H), 7.43-7.30 (m, 5H), 7.21-7.16 (m, 1H), 7.12-7.07 (m, 1H), 5.87 (s, 2H), 5.19 (s, 2H). LCMS R$_t$=0.768 mins in 1.5 mins chromatography, MS ESI calcd. for C$_{19}$H$_{16}$F$_3$N$_2$O$_2$ [M+H]$^+$ 361.1, found 361.0.

Synthesis of A-32:

To a solution of A-31 (200 mg, 0.56 mmol) in THF (10 mL) was added TEA (168.51 mg, 1.67 mmol) and TFAA (233.15 mg, 1.11 mmol) slowly. The resulting mixture was stirred at 15° C. for 16 hours to give a solution. Saturated NaHCO$_3$ aqueous (10 mL) and EtOAc (20 mL) was added to the reaction mixture. After separation, the organic layer was washed with brine (10 mL×2), dried over anhydrous Na$_2$SO$_4$, filtered and concentrated to give A-32 (180 mg, 0.37 mmol) as a solid. LCMS R$_t$=0.97 min using Method B, MS ESI calcd. for C$_{21}$H$_{15}$F$_6$N$_3$O$_3$ [M+H]$^+$ 457.1, found 456.9.

Synthesis of A-33:

To a solution of A-32 (180 mg, 0.39 mmol) in DMF (5 mL) was added NaH (78.89 mg, 1.97 mmol). The resulting mixture was stirred at 15° C. for 10 mins. To the mixture was added 1,1,1-trifluoro-2-(trifluoromethylsulfonyl)ethane (255.72 mg, 1.18 mmol). The reaction mixture was stirred at 15° C. for 16 hours. Saturated NH$_4$Cl aqueous (25 mL) and EtOAc (30 mL) were added to the reaction mixture. After separation, the organic layer was washed with brine (20 mL×2), dried over anhydrous Na$_2$SO$_4$, filtered and concentrated to give a crude product that was purified by flash chromatography on silica gel (EtOAc in PE=0% to 10% to 20%) to afford A-33 (100 mg, 0.22 mmol) as a solid. $^1$H NMR (DMSO-d$_6$ 400 MHz) $\delta_H$=8.08 (d, 2H), 7.53 (d, 2H), 7.44-7.38 (m, 4H), 7.37-7.32 (m, 1H), 7.30-7.20 (m, 2H), 6.74 (t, 1H), 5.23 (s, 2H), 4.34-4.20 (m, 2H). LCMS R$_t$=1.03 min using Method B, MS ESI calcd. for C$_{21}$H$_{17}$F$_6$N$_2$O$_2$ [M+H]$^+$ 443.1, found 443.4.

Synthesis of A-34:

To a solution of A-33 (100 mg, 0.23 mmol) in methanol (5 mL) was added Pd/C (50 mg, 0.2300 mmol). The resulting mixture was stirred at 15° C. under H$_2$ balloon (15 psi) for 3 hours to give a suspension. The reaction mixture was filtered through Celite, and the filtrate was concentrated to give A-34 (86 mg, 0.22 mmol) as a solid. $^1$H NMR (DMSO-d$_6$ 400 MHz) $\delta_H$=8.03 (d, 2H), 7.37 (d, 2H), 7.12 (d, 1H), 6.97 (d, 1H), 6.51 (t, 1H), 4.29-4.19 (m, 2H). LCMS $R_t$=0.89 min using Method B, MS ESI calcd. for $C_{14}H_{11}F_6N_2O_2$ [M+H]$^+$ 353.1, found 353.3.

Synthesis of Compound 33:

To a solution of A-34 (86 mg, 0.24 mmol) in THF (4 mL) was added CDI (41.28 mg, 0.29 mmol) and the resulting mixture was stirred at 55° C. under N$_2$ for 16 hours to give a colorless solution. The reaction solution was cooled to room temperature and concentrated to give a crude product that was purified by Prep-HPLC (Waters Xbridge (150 mm×25 mm, 5 μm) A=H$_2$O (10 mM NH$_4$HCO$_3$) and B=CH$_3$CN); 45-75% B over 10 minutes) to afford Compound 33 (35.88 mg, 0.09 mmol) as a solid. $^1$H NMR (DMSO-d$_6$ 400 MHz) $\delta_H$=8.20 (d, 2H), 7.94-7.85 (m, 2H), 7.50 (d, 2H), 4.79 (q, 2H). LCMS $R_t$=1.41 min using Method A, MS ESI calcd. for $C_{13}H_9F_6N_3O_3$ [M+H]$^+$ 379.0, found 378.9.

Example 34. Synthesis of Compound 34

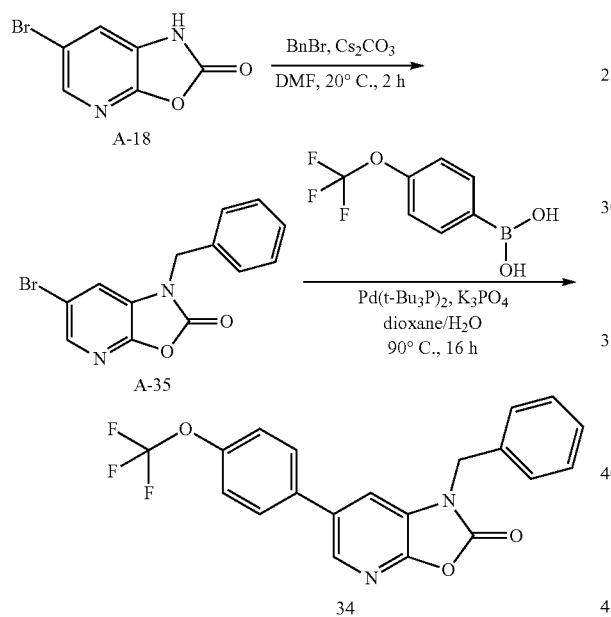

Synthesis of A-35:

To a solution of A-18 (300 mg, 1.4 mmol) in DMF (7 mL) was added Cs$_2$CO$_3$ (909.77 mg, 2.79 mmol) and BnBr (286.38 mg, 1.67 mmol), and the mixture was stirred at 20° C. for 2 hours. The mixture was poured into water (15 mL) and extracted with EtOAc (30 mL×2). The combined organic phase was washed with brine (10 mL), dried over Na$_2$SO$_4$, filtered and concentrated to give the crude product that was purified by flash chromatography on silica gel (EtOAc in PE=20% to 40% to 60%) to afford A-35 (370 mg, 0.93 mmol) as a solid. $^1$H NMR (DMSO-d$_6$ 400 MHz) $\delta_H$=8.12 (d, 1H), 7.96 (d, 1H), 7.45-7.40 (m, 2H), 7.40-7.31 (m, 3H), 5.04 (s, 2H). LCMS $R_t$=0.81 min using Method B, MS ESI calcd. for $C_{13}H_{10}BrN_2O_2$ [M+H+2]$^+$ 307.0, found 306.7.

Synthesis of Compound 34:

A mixture of A-35 (300 mg, 0.98 mmol), [4-(trifluoromethoxy)phenyl]boronic acid (242.96 mg, 1.18 mmol), Pd(t-Bu$_3$P)$_2$ (100.48 mg, 0.20 mmol) and K$_3$PO$_4$ (416.87 mg, 1.97 mmol) in 1,4-dioxane (10 mL) and water (2 mL) was stirred at 90° C. for 16 hours. After cooling to r.t., the mixture was concentrated to give the crude product, which was purified by by flash chromatography on silica gel (EtOAc in PE=15% to 40% to 70%) and Prep-HPLC (Waters Xbridge (150 mm×25 mm, 5 μm) A=H$_2$O (10 mM NH$_4$HCO$_3$) and B=CH$_3$CN); 57-87% B over 8 minutes) to afford Compound 34 (43.43 mg, 0.11 mmol) as a solid. 1H NMR (DMSO-d$_6$ 400 MHz) $\delta_H$=8.32 (d, 1H), 8.03 (d, 1H), 7.81 (d, 2H), 7.52-7.45 (m, 4H), 7.40-7.29 (m, 3H), 5.12 (s, 2H). LCMS $R_t$=1.40 min using Method A, MS ESI calcd. for $C_{20}H_{14}F_3N_3O_3$ [M+H]$^+$ 387.1, found 387.0.

Example 35. Synthesis of Compound 35

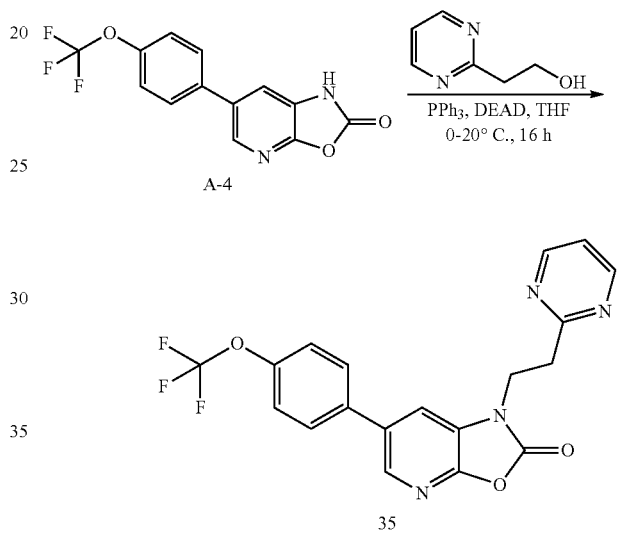

To a mixture of A-4 (100 mg, 0.34 mmol), 2-pyrimidin-2-ylethanol (75.69 mg, 0.61 mmol) and PPh$_3$ (159.75 mg, 0.61 mmol) in THF (3 mL) under N$_2$ was added DEAD (106.19 mg, 0.61 mmol) drop-wise at 0° C. The reaction mixture was then stirred at 20° C. for 16 hours. The mixture was concentrated to give the crude product that was purified by Prep-HPLC (Phenomenex Gemini (150 mm×25 mm, 10 μm); A=H$_2$O (0.05% NH$_4$OH) and B=CH$_3$CN); 60-70% B over 8 minutes) to afford Compound 35 (65.01 mg, 0.1575 mmol) as an oil. $^1$H NMR (DMSO-d$_6$+D$_2$O 400 MHz) $\delta_H$=8.69 (d, 2H), 7.77 (d, 2H), 7.52 (s, 1H), 7.46 (d, 2H), 7.40 (d, 2H), 7.33 (t, 1H), 4.33 (t, 2H), 3.33 (t, 2H). LCMS $R_t$=1.26 min in using Method A, MS ESI calcd. for $C_{20}H_{15}F_3N_3O_3$ [M+H]$^+$ 402.1, found 402.0.

Example 36. Synthesis of Compound 36

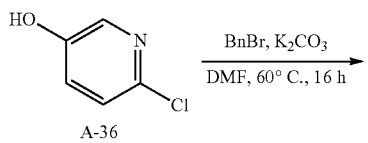

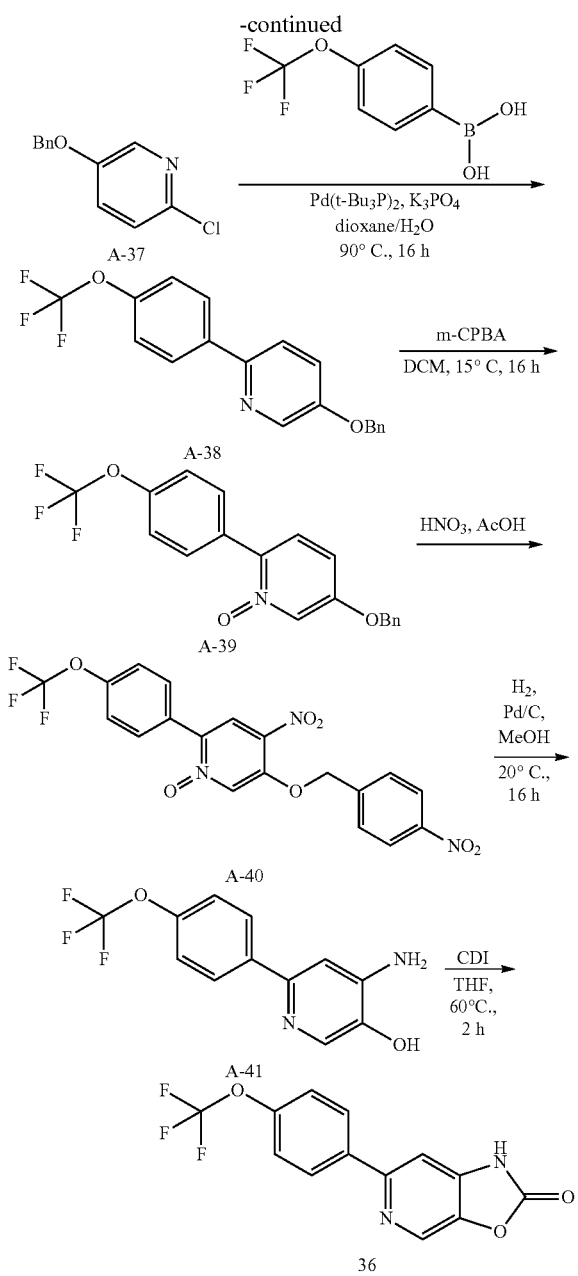

Synthesis of A-37:

To a mixture of A-36 (5 g, 38.6 mmol) and $K_2CO_3$ (10.65 g, 77.2 mmol) in DMF (40 mL) was added bromomethylbenzene (5.04 mL, 42.46 mmol). The reaction mixture was heated to 60° C. for 16 hours. After cooling, the mixture was diluted with $H_2O$ (150 mL), and the mixture was extracted with EtOAc (100 mL×2). The combined organic phase was washed with brine (80 mL), dried over $Na_2SO_4$, filtered and concentrated to afford A-37 (8000 mg, 36.42 mmol), which was used directly in next step. 1H NMR ($CDCl_3$, 400 MHz) $\delta_H$=8.14 (d, 1H), 7.44-7.34 (m, 5H), 7.26-7.21 (m, 2H), 5.11 (s, 2H).

Synthesis of A-38:

A mixture of A-37 (3 g, 13.66 mmol), [4-(trifluoromethoxy)phenyl]-boronic acid (3.09 g, 15.02 mmol), Pd(t-Bu$_3$P)$_2$ (1.0 g, 2.05 mmol) and $K_3PO_4$ (5.79 g, 27.31 mmol) in 1,4-dioxane (15 mL) and water (1.5 mL) under $N_2$ was heated to 90° C. and stirred for 16 hours. After cooling, the reaction mixture was diluted with EtOAc (20 mL), filtered through a Celite pad, eluted with EtOAc (20 mL) and concentrated. The residue was purified by flash chromatography on silica gel (EtOAc in PE=0% to 10% to 20%) to afford A-38 (4000 mg, 11.58 mmol) as a solid. $^1$H NMR (DMSO-$d_6$ 400 MHz) $\delta_H$=8.46 (d, 1H), 8.13 (d, 2H), 7.96 (d, 1H), 7.57 (dd, 1H), 7.52-7.32 (m, 7H), 5.25 (s, 2H).

Synthesis of A-39:

To a solution of A-38 (4 g, 11.58 mmol) in DCM (100 mL) was added m-CPBA (4.69 g, 23.17 mmol). The reaction mixture was stirred at 15° C. for 16 hours. The reaction was quenched with sat.NaHCO$_3$ (200 mL), extracted with DCM (150 mL×3). The combined organic phase was washed with sat.NaHCO$_3$ (100 mL), dried over Na$_2$SO$_4$, filtered and concentrated. The residue was purified by flash chromatography on silica gel (EtOAc in PE=0% to 20% to 40%) to afford A-39 (2000 mg, 5.54 mmol) as a solid. $^1$H NMR (DMSO-$d_6$ 400 MHz) $\delta_H$=8.27 (d, 1H), 7.92 (d, 2H), 7.61 (d, 1H), 7.49-7.36 (m, 7H), 7.21 (dd, 1H), 5.24 (s, 2H).

Synthesis of A-40:

To a mixture of A-39 (2 g, 5.54 mmol) in AcOH (20 mL) at 0° C. was added fuming HNO$_3$ (20 mL) dropwise. The reaction mixture was then heated to 90° C. and stirred for 16 hours. The reaction mixture was concentrated, and the residue was treated with sat.NaHCO$_3$ (100 mL) and extracted with EtOAc (100 mL×2). The combined organic phase was washed with brine (50 mL), dried over Na$_2$SO$_4$, filtered and concentrated. The residue was purified by flash chromatography on silica gel (EtOAc in PE=0% to 30% to 50%) to afford A-40 (250 mg, 0.55 mmol) as a solid. $^1$H NMR (DMSO-$d_6$ 400 MHz) $\delta_H$=8.76 (s, 1H), 8.43-8.31 (m, 3H), 7.94 (d, 2H), 7.77 (d, 2H), 7.52 (d, 2H), 5.60 (s, 2H).

Synthesis of A-41:

A mixture of A-40 (200 mg, 0.44 mmol) and wet Pd/C (200 mg) in methanol (10 mL) was degassed and refilled with H$_2$. The reaction mixture was stirred under H$_2$ (50 psi) at 20° C. for 16 hours. The reaction mixture was diluted with MeOH (10 mL), filtered through a Celite pad and eluted with MeOH (10 mL). The filtrate was concentrated to give A-41 (160 mg, crude). LCMS R$_t$=0.67 min using Method B, MS ESI calcd. for $C_{12}H_{10}F_3N_2O_2$ [M+H]$^+$ 271.1, found 270.9.

Synthesis of Compound 36:

To a solution of A-41 (160 mg, 0.59 mmol) in THF (5 mL) was added CDI (143.89 mg, 0.89 mmol). The reaction mixture was heated to 60° C. and stirred for 2 hours. The reaction mixture was concentrated, and the residue was purified by Prep-HPLC (Phenomenex Gemini (150 mm×25 mm, 10 µm); A=H$_2$O (0.05% NH$_4$OH) and B=CH$_3$CN); 25-55% B over 8 minutes) to afford Compound 36 (25.54 mg, 0.09 mmol) as a solid. $^1$H NMR (DMSO-$d_6$ 400 MHz) $\delta_H$=12.35 (br s, 1H), 8.56 (s, 1H), 8.17 (d, 2H), 7.72 (s, 1H), 7.46 (d, 2H). LCMS R$_t$=1.05 min using Method A, MS ESI calcd. for $C_{13}H_8F_3N_3O_3$ [M+H]$^+$ 297.0, found 296.9.

Example 37. Synthesis of Compound 37

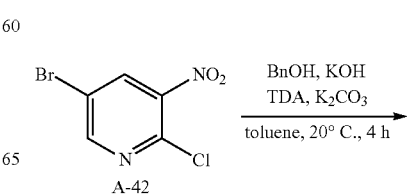

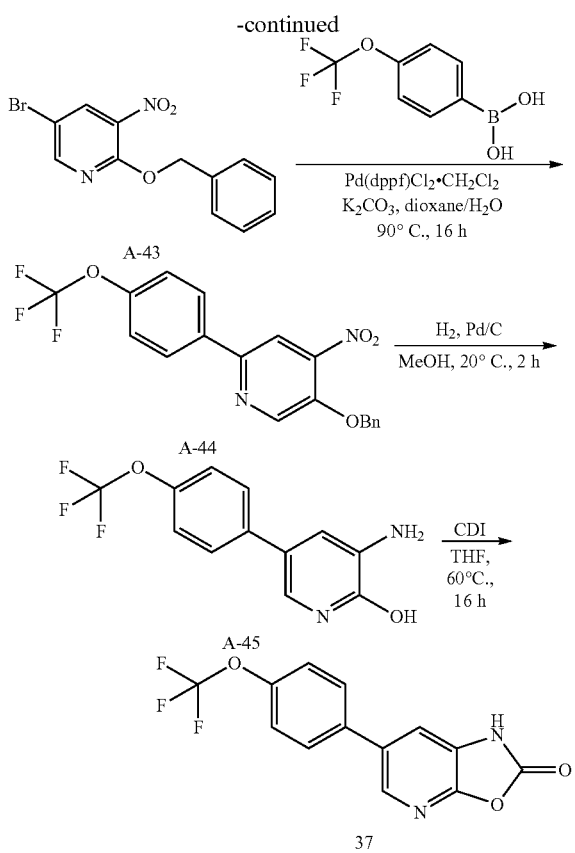

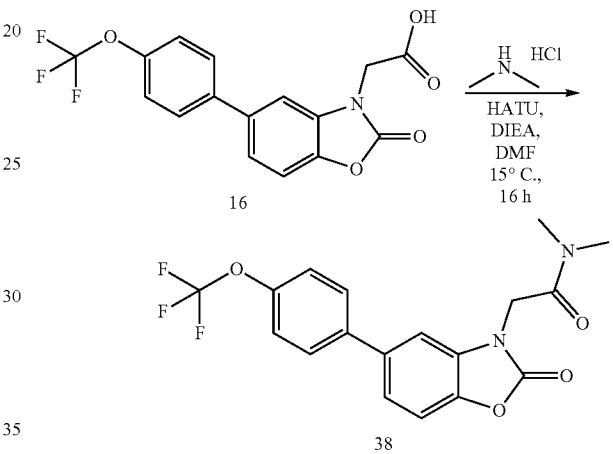

mg, 0.93 mmol) as a solid, which was used directly without any further purification. LCMS $R_t$=0.73 min using Method B, MS ESI calcd. for $C_{12}H_{10}F_3N_2O_2$ [M+H]$^+$ 271.0, found 270.9.

Synthesis of Compound 37:

A mixture of A-45 (300 mg, 1.11 mmol) and CDI (360.05 mg, 2.22 mmol) in THF (10 mL) was stirred at 60° C. for 16 hours. The mixture was filtered through silica gel and concentrated, and the residue was dissolved in MeOH (~3 mL). The filtrate was concentrated to afford Compound 37 (47.80 mg, 0.16 mmol) as a solid. $^1$H NMR (DMSO-d$_6$ 400 MHz) $\delta_H$=8.26 (d, 1H), 7.84 (d, 2H), 7.75 (d, 1H), 7.49 (d, 2H). LCMS $R_t$=1.08 min using Method A, MS ESI calcd. for $C_{13}H_8F_3N_3O_3$ [M+H]$^+$ 297.0, found 296.9.

Example 38. Synthesis of Compound 38

Synthesis of A-43:

To a solution of A-42 (2 g, 8.42 mmol) in Toluene (20 mL) was added phenylmethanol (1 g, 9.27 mmol), tris[2-(2-methoxyethoxy)ethyl]amine (272.43 mg, 0.84 mmol), KOH (471.7 mg, 8.42 mmol) and K$_2$CO$_3$ (1162.4 mg, 8.42 mmol), and the mixture was stirred at for 4 hours. The mixture was filtered through Celite and eluted with EtOAc (30 mL×3). The filtrate was concentrated to give the crude product that was filtered through silica gel (~20 g), The filtrate was concentrated to give the impure product, which was triturated from i-Pr$_2$O (10 mL) to afford A-43 (2200 mg, 7.12 mmol) as a solid. $^1$H NMR (CDCl$_3$, 400 MHz) $\delta_H$=8.45 (d, 1H), 8.41 (d, 1H), 7.49 (d, 2H), 7.44-7.30 (m, 3H), 5.58 (s, 2H).

Synthesis of A-44:

A mixture of A-43 (1 g, 3.23 mmol), [4-(trifluoromethoxy)phenyl]-boronic acid (1 g, 4.85 mmol), K$_2$CO$_3$ (892.86 mg, 6.47 mmol) and Pd(dppf)Cl$_2$.CH$_2$Cl$_2$ (396.25 mg, 0.49 mmol) in 1,4-dioxane (10 mL) and water (1 mL) was stirred at 90° C. for 16 hours. After cooling to r.t., the mixture was diluted with PE (10 mL), filtered through silica gel (~20 g) and eluted. The filtrate was concentrated to give the crude product that was purified by flash chromatography on silica gel (EtOAc in PE=10% to 15% to 20%) to afford A-44 (900 mg, 2.30 mmol) as a solid. $^1$H NMR (CDCl$_3$, 400 MHz) $\delta_H$=8.60 (d, 1H), 8.47 (d, 1H), 7.59 (d, 2H), 7.54 (d, 2H), 7.45-7.32 (m, 5H), 5.65 (s, 2H).

Synthesis of A-45:

A mixture of A-44 (400 mg, 1.02 mmol) and Pd/C (100 mg) in Methanol (10 mL) was stirred at 20° C. under H$_2$ balloon (15 psi) for 2 hours. The mixture was filtered through Celite and eluted with MeOH (10 mL×2). The filtrate was concentrated to give the crude product A-45 (250

To a solution of Compound 16 (80 mg, 0.23 mmol) in DMF (3 mL) was added HATU (155 mg, 0.41 mmol), DIPEA (87.81 mg, 0.68 mmol) and N-methylmethanamine hydrochloride (22.16 mg, 0.27 mmol). The resulting mixture was stirred at 15° C. for 16 hours. Saturated NH$_4$Cl aqueous (20 mL) and EtOAc (20 mL) were added to the reaction solution. After separation, the organic layer was washed with brine (20 mL×2), dried over anhydrous Na$_2$SO$_4$, filtered and concentrated to give a residue that was purified by Prep-HPLC (Waters Xbridge (150 mm×25 mm, 5 μm) A=H$_2$O (10 mM NH$_4$HCO$_3$) and B=CH$_3$CN); 37-67% B over 10 minutes) to afford Compound 38 (26.69 mg, 0.07 mmol) as a solid. $^1$H NMR (DMSO-d$_6$ 400 MHz) $\delta_H$=7.77 (d, 2H), 7.61 (s, 1H), 7.49-7.44 (m, 4H), 4.85 (s, 2H), 3.10 (s, 3H), 2.86 (s, 3H). LCMS $R_t$=1.18 min using Method A, MS ESI calcd. for $C_{18}H_{16}F_3N_2O_4$ [M+H]$^+$ 381.1, found 381.0.

Example 39. Synthesis of Compound 39

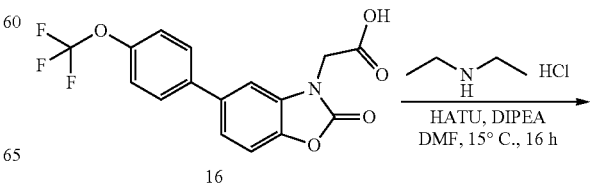

-continued

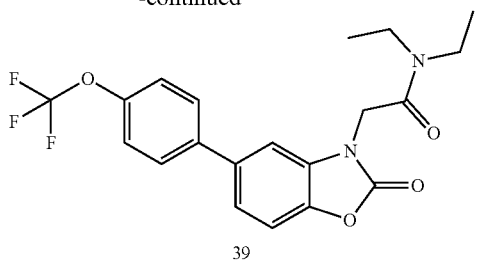

39

To a mixture of Compound 16 (90 mg, 0.25 mmol), HATU (145.31 mg, 0.38 mmol) and DIPEA (65.85 mg, 0.51 mmol) in DMF (2 mL) was added the N-ethylethanamine (33.79 mg, 0.31 mmol) and the mixture was stirred at 15° C. for 16 hours. The mixture was diluted with sat.NH$_4$Cl (10 mL), extracted with EtOAc (10 mL×2). The combined organic phase was washed with brine (10 mL), dried over Na$_2$SO$_4$, filtered and concentrated to a residue that was purified by Prep-HPLC (Waters Xbridge (150 mm×25 mm, 5 μm) A=H$_2$O (10 mM NH$_4$HCO$_3$) and B=CH$_3$CN); 45-75% B over 10 minutes) to afford Compound 39 (41.81 mg, 0.1024 mmol) as a solid. $^1$H NMR (DMSO-d$_6$+D$_2$O 400 MHz) $\delta_H$=7.73 (d, 2H), 7.48-7.39 (m, 5H), 4.79 (s, 2H), 3.39 (q, 2H), 3.26 (q, 2H), 1.20 (t, 3H), 1.00 (t, 3H). LCMS R$_t$=1.25 min using Method A, MS ESI calcd. for C$_{20}$H$_{20}$F$_3$N$_2$O$_4$ [M+H]$^+$ 409.1, found 409.0.

Example 40. Synthesis of Compound 40

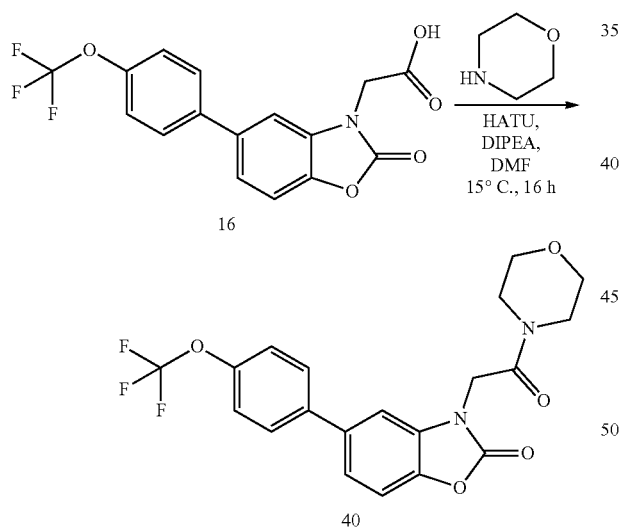

To a solution of Compound 16 (80 mg, 0.23 mmol) in DMF (3 mL) was added HATU (155 mg, 0.41 mmol), DIPEA (87.81 mg, 0.68 mmol) and morpholine (23.68 mg, 0.27 mmol). The resulting mixture was stirred at 15° C. for 16 hours. Saturated NH$_4$Cl aqueous (20 mL) and EtOAc (20 mL) were added to the reaction solution. After separation, the organic layer was washed with brine (20 mL×2), dried over anhydrous Na$_2$SO$_4$, filtered and concentrated to give the crude product that was purified by Prep-HPLC (Waters Xbridge (150 mm×25 mm, 5 μm) A=H$_2$O (10 mM NH$_4$HCO$_3$) and B=CH$_3$CN); 37-67% B over 10 minutes) to afford Compound 40 (8.33 mg, 0.02 mmol) as a solid. $^1$H NMR (DMSO-d$_6$ 400 MHz) $\delta$=7.76 (d, 2H), 7.60 (d, 1H), 7.51-7.41 (m, 4H), 4.91 (s, 2H), 3.72-3.66 (m, 2H), 3.60-3.54 (m, 4H), 3.47-3.41 (m, 2H). LCMS R$_t$=1.17 min using Method A, MS ESI calcd. for C$_{20}$H$_{18}$F$_3$N$_2$O$_5$ [M+H]$^+$ 423.1, found 423.0.

Example 41. Synthesis of Compound 41

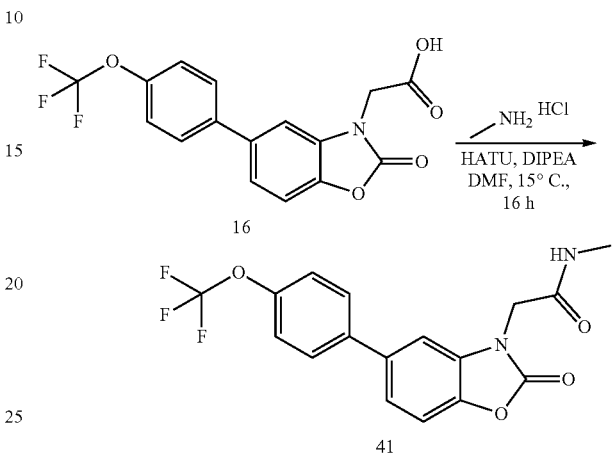

To a mixture of Compound 16 (90 mg, 0.25 mmol), HATU (145.31 mg, 0.38 mmol) and DIPEA (65.85 mg, 0.51 mmol) in DMF (2 mL) was added methanamine hydrochloride (20.64 mg, 0.31 mmol), and the mixture was stirred at 15° C. for 16 hours. The mixture was diluted with sat.NH$_4$Cl (10 mL), extracted with EtOAc (10 mL×2). The combined organic phase was washed with brine (10 mL), dried over Na$_2$SO$_4$, filtered and concentrated to give a residue that purified by Prep-HPLC (Waters Xbridge (150 mm×25 mm, 5 μm) A=H$_2$O (10 mM NH$_4$HCO$_3$) and B=CH$_3$CN); 8-38% B over 9 minutes) to afford Compound 41 (27.35 mg, 0.0747 mmol) as a solid. $^1$H NMR (CDCl$_3$, 400 MHz) $\delta_H$=7.56 (d, 2H), 7.37-7.29 (m, 4H), 7.22 (d, 1H), 5.97 (br s, 1H), 4.50 (s, 2H), 2.87 (d, 3H). LCMS R$_t$=1.14 min using Method A, MS ESI calcd. for C$_{17}$H$_{14}$F$_3$N$_2$O$_4$ [M+H]$^+$ 367.1, found 367.0.

Example 42. Synthesis of Compound 42

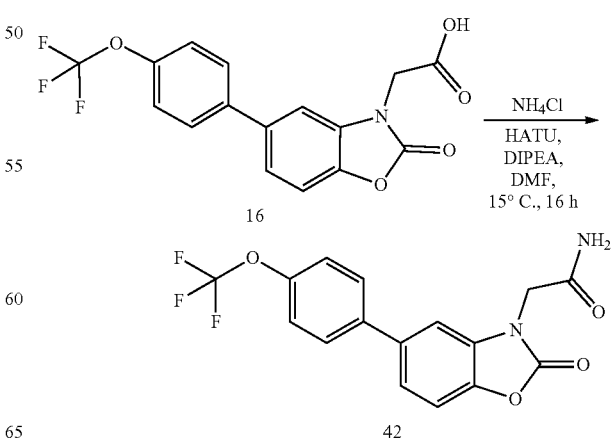

To a solution of Compound 16 (80 mg, 0.23 mmol) in DMF (3 mL) was added HATU (155 mg, 0.41 mmol), DIPEA (146.34 mg, 1.13 mmol) and ammonia hydrochloride (60.57 mg, 1.13 mmol). The resulting mixture was stirred at 15° C. for 16 hours. Saturated NH$_4$Cl aqueous (20 mL) and EtOAc (20 mL) were added to the reaction solution. After separation, the organic layer was washed with brine (20 mL×2), dried over anhydrous Na$_2$SO$_4$, filtered and concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN); 34-54% B over 10 minutes) to afford Compound 42 (22.9 mg, 0.07 mmol) as a solid. 1H NMR (DMSO-d$_6$ 400 MHz) δ$_H$=7.85-7.75 (m, 3H), 7.61 (s, 1H), 7.50-7.43 (m, 4H), 7.36 (s, 1H), 4.52 (s, 2H). LCMS R$_t$=1.11 min using Method A, MS ESI calcd. for C$_{16}$H$_{12}$F$_3$N$_2$O$_4$ [M+H]$^+$ 353.1, found 352.9.

Example 43. Synthesis of Compound 43

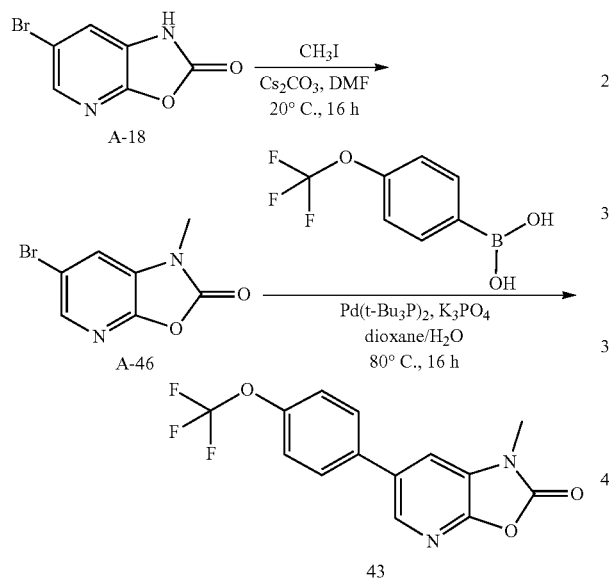

Synthesis of A-46:

To a mixture of A-18 (300 mg, 1.4 mmol) and Cs$_2$CO$_3$ (681.91 mg, 2.09 mmol) in DMF (5 mL) was added CH$_3$I (0.13 mL, 2.09 mmol). The mixture was stirred at 20° C. for 16 hours. The reaction was diluted with water (20 mL), and the mixture was extracted with EtOAc (20 mL×2). The combined organic phase was washed with brine (10 mL), dried over Na$_2$SO$_4$, filtered and concentrated to give the crude product, which was purified by flash chromatography on silica gel (EtOAc in PE=0% to 30% to 100%) to afford A-46 (110 mg, 0.33 mmol) as a solid. $^1$H NMR (CDCl$_3$ 400 MHz) δ$_H$=8.12 (d, 1H), 7.38 (d, 1H), 3.43 (s, 3H). LCMS R$_t$=0.63 min using Method B, MS ESI calcd. for C$_7$H$_6$BrN$_2$O$_2$ [M+H]$^+$ 229.0, found 228.8.

Synthesis of Compound 43:

A mixture of A-46 (110 mg, 0.48 mmol), [4-(trifluoromethoxy)phenyl]boronic acid (118.69 mg, 0.58 mmol), Pd(t-Bu$_3$P)$_2$ (49.09 mg, 0.10 mmol) and K$_3$PO$_4$ (203.93 mg, 0.96 mmol) in 1,4-dioxane (3 mL) and water (0.5 mL) was stirred at 80° C. for 16 hours under N$_2$. The mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product that was purified by Prep-HPLC (Phenomenex Gemini (150 mm×25 mm, 10 μm); A=H$_2$O (0.05% NH$_4$OH) and B=CH$_3$CN); 55-66% B over 8 minutes) to afford Compound 43 (17.91 mg, 0.06 mmol) as a solid. $^1$H NMR (CDCl$_3$, 400 MHz) δ$_H$=8.22 (d, 1H), 7.58 (d, 2H), 7.40-7.30 (m, 3H), 3.50 (s, 3H). LCMS R$_t$=1.17 min using Method A, MS ESI calcd. for C$_{14}$H$_{10}$F$_3$N$_3$O$_3$ [M+H]$^+$ 311.1, found 310.9.

Example 44. Synthesis of Compound 44

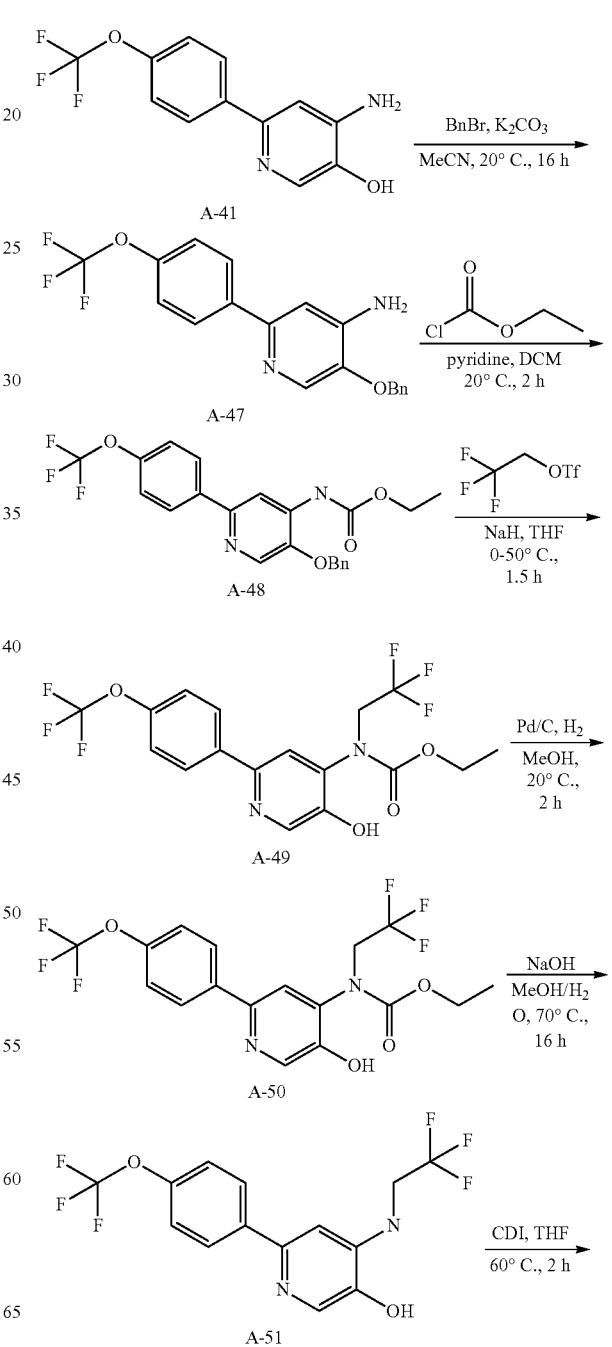

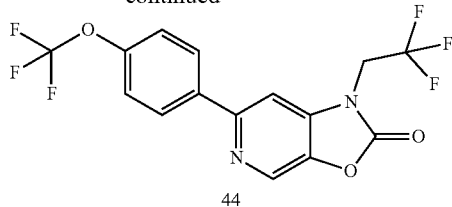

Synthesis of A-47:

To a mixture of A-47 (400 mg, 1.48 mmol) and K$_2$CO$_3$ (613.79 mg, 4.44 mmol) in MeCN (15 mL) was added bromomethylbenzene (329.14 mg, 1.92 mmol). The reaction mixture was stirred at 20° C. for 16 hours. The reaction mixture was diluted with EtOAc (10 mL), filtered through a Celite pad and eluted with EtOAc (10 mL). The residue was purified by by flash chromatography on silica gel (EtOAc in PE=0% to 20% to 40%) to afford A-47 (150 mg, 0.4163 mmol) as a solid. 1H NMR (CDCl$_3$, 400 MHz) $\delta_H$=8.13 (s, 1H), 7.90 (d, 2H), 7.48-7.35 (m, 5H), 7.29-7.24 (m, 2H), 7.02 (s, 1H), 5.19 (s, 2H), 4.37 (s, 2H).

Synthesis of A-48:

To a mixture of A-47 (180 mg, 0.5 mmol) and pyridine (118.54 mg, 1.5 mmol) in DCM (5 mL) was added ethyl carbonochloridate (65.05 mg, 0.6 mmol). The reaction mixture was stirred at 20° C. for 2 hours. The reaction mixture was quenched with sat.NaHCO$_3$ (20 mL), extracted with EtOAc (20 mL×3). The combined organic phase was washed with brine (20 mL), dried over Na$_2$SO$_4$, filtered and concentrated. The residue was purified by by flash chromatography on silica gel (EtOAc in PE=0% to 20% to 40%) to afford A-48 (170 mg, 0.39 mmol) as a solid. $^1$H NMR (DMSO-d$_6$ 400 MHz) $\delta_H$=9.04 (s, 1H), 8.42-8.38 (m, 2H), 8.02 (d, 2H), 7.57 (d, 2H), 7.46-7.32 (m, 5H), 5.33 (s, 2H), 4.20 (q, 2H), 1.27 (t, 3H).

Synthesis of A-49:

To a solution of A-49 (170 mg, 0.39 mmol) in THF (5 mL) at 0° C. was added NaH (78.63 mg, 1.97 mmol). The reaction mixture was stirred at 0° C. for 20 min. Then 2,2,2-trifluoroethyl trifluoromethanesulfonate (456.27 mg, 1.97 mmol) was added. The reaction mixture was stirred at 50° C. for 1 hour. The reaction was quenched with sat.NH$_4$Cl (20 mL), extracted with EtOAc (20 mL×3). The combined organic phase was washed with brine (20 mL), dried over Na$_2$SO$_4$, filtered and concentrated. The residue was purified by flash chromatography on silica gel (EtOAc in PE=0% to 10% to 30%) to afford A-49 (180 mg, 0.3499 mmol) as a solid. $^1$H NMR (DMSO-d$_6$ 400 MHz) $\delta_H$=8.64 (s, 1H), 8.17 (d, 2H), 8.03 (s, 1H), 7.50-7.31 (m, 7H), 5.35 (s, 2H), 4.62-4.46 (m, 2H), 4.12-3.99 (m, 2H), 1.13-0.94 (m, 3H).

Synthesis of A-50:

A mixture of A-50 (180 mg, 0.35 mmol) and 10% wed Pd/C (200 mg, 0.19 mmol) in Methanol (10 mL) under N$_2$ was degassed and refilled with H$_2$. The reaction mixture was stirred under H$_2$ (15 psi, balloon) at 20° C. for 2 hours. The reaction mixture was diluted with EtOAc (10 mL), and filtered through a Celite pad to remove Pd/C, eluted with EtOAc (10 mL). The filtrate was concentrated to afford A-50 (120 mg, 0.28 mmol) as a oil. $^1$H NMR (DMSO-d$_6$ 400 MHz) $\delta$=8.32 (s, 1H), 8.09 (d, 2H), 7.83 (s, 1H), 7.42 (d, 2H), 4.52-4.40 (m, 2H), 4.11 (q, 2H), 1.20-1.05 (m, 3H).

Synthesis of A-51:

To a mixture of A-50 (120 mg, 0.28 mmol) in methanol (10 mL) and water (2 mL) was added NaOH (113.13 mg, 2.83 mmol). The reaction mixture was stirred at 70° C. for 16 hours. The mixture was acidified with 2M HCl to pH=5-6, then concentrated to give the residue, which was treated with THF (20 mL) and filtered. The filtrate was concentrated to afford A-51 (120 mg, 0.34 mmol, crude) as a solid. $^1$H NMR (DMSO-d$_6$ 400 MHz) $\delta_H$=8.19 (s, 1H), 8.09 (d, 2H), 7.90 (s, 1H), 7.39 (d, 2H), 7.31 (s, 1H), 6.21 (t, 1H), 4.22-4.10 (m, 2H).

Synthesis of Compound 44:

A mixture of A-51 (120 mg, 0.34 mmol) and di(imidazol-1-yl)methanone (82.86 mg, 0.51 mmol) in THF (5 mL) was heated to 60° C. and stirred at 60° C. for 2 hours to give a solution. The reaction mixture was concentrated. The residue was purified by flash chromatography on silica gel (EtOAc in PE=0% to 20% to 40%) to afford Compound 44 (82.61 mg, 0.21 mmol) as a solid. $^1$H NMR (DMSO-d$_6$ 400 MHz) $\delta_H$=8.69 (s, 1H), 8.21 (s, 1H), 8.18 (d, 2H), 7.53 (d, 2H), 4.91 (q, 2H). LCMS R$_t$=1.27 min using Method A, MS ESI calcd. for C$_{15}$H$_9$F$_6$N$_3$O$_3$ [M+H]$^+$ 379.1, found 378.9.

Example 45. Synthesis of Compound 45

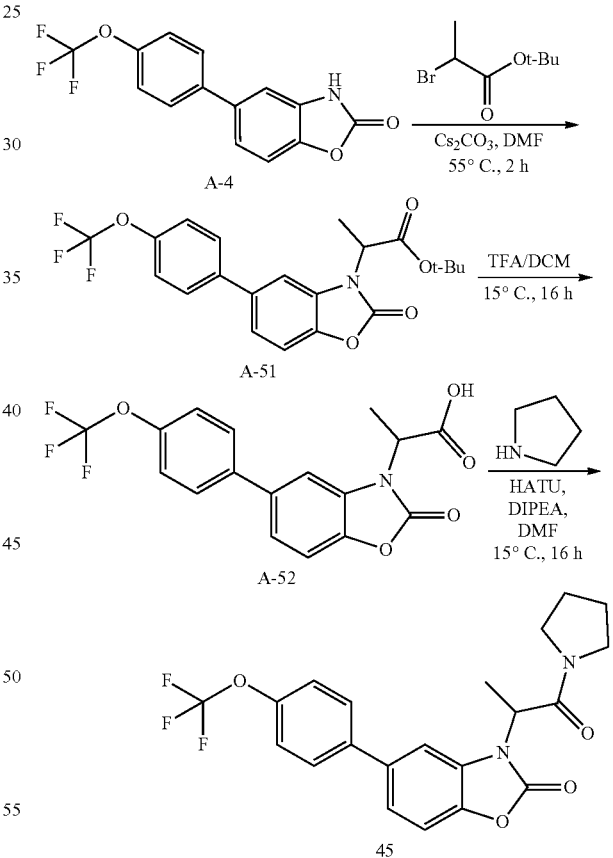

Synthesis of A-51:

To a solution of A-4 (200 mg, 0.68 mmol) in DMF (4 mL) was added tert-butyl 2-bromopropanoate (169.98 mg, 0.81 mmol) and Cs$_2$CO$_3$ (441.45 mg, 1.35 mmol). The resulting mixture was stirred at 55° C. for 2 hours. Saturated NH$_4$Cl aqueous (20 mL) and EtOAc (20 mL) were added to the reaction mixture. After separation, the organic layer was washed with brine (20 mL×2), dried over anhydrous Na$_2$SO$_4$, filtered and concentrated to give the crude product that was purified by flash chromatography on silica gel (EtOAc in PE=0% to 10% to 20%) to afford A-51 (235 mg, 0.55 mmol) as an oil. 1H NMR (CDCl₃, 400 MHz) δ$_H$=7.53 (d, 2H), 7.33-7.28 (m, 4H), 7.13 (s, 1H), 5.05 (q, 1H), 1.75 (d, 3H), 1.44 (s, 9H)

Synthesis of A-52:

To a solution A-51 (235 mg, 0.56 mmol) in DCM (4 mL) was added TFA (2 mL, 26.93 mmol). The resulting solution was stirred at 15° C. for 16 hours. The reaction solution was concentrated to give the crude product A-52 (200 mg, 0.54 mmol) as a solid. ¹H NMR (DMSO-d₆ 400 MHz) δ$_H$=7.80 (d, 2H), 7.66 (s, 1H), 7.50-7.44 (m, 4H), 5.23 (q, 1H), 1.70 (d, 3H)

Synthesis of Compound 45:

To a solution of A-52 (200 mg, 0.54 mmol) in DMF (4 mL) was added HATU (372.69 mg, 0.98 mmol), DIPEA (211.13 mg, 1.63 mmol) and pyrrolidine (46.47 mg, 0.65 mmol). The resulting mixture was stirred at 15° C. for 16 hours. Saturated NH₄Cl aqueous (20 mL) and EtOAc (20 mL) were added to the reaction solution. After separation, the organic layer was washed with brine (20 mL×2), dried over anhydrous Na₂SO₄, filtered and concentrated to give the crude product. The crude product was purified by Prep-HPLC (Waters Xbridge (150 mm×25 mm, 5 μm) A=H₂O (10 mM NH₄HCO₃) and B=CH₃CN); 43-73% B over 10 minutes) to afford Compound 45 (77.94 mg, 0.19 mmol) as a solid. ¹H NMR (CDCl₃ DMSO-d₆ 400 MHz) δ=7.72 (d, 2H), 7.57 (d, 1H), 7.51-7.40 (m, 4H), 5.27 (q, 1H), 3.63-3.56 (m, 1H), 3.40-3.34 (m, 1H), 3.30-3.21 (m, 2H), 1.89-1.66 (m, 4H), 1.59 (d, 3H). LCMS R$_f$=1.27 min using Method A, MS ESI calcd. for C₂₁H₂₀F₃N₂O₄ [M+H]⁺ 421.1, found 421.0.

Example 46. Synthesis of Compound 46

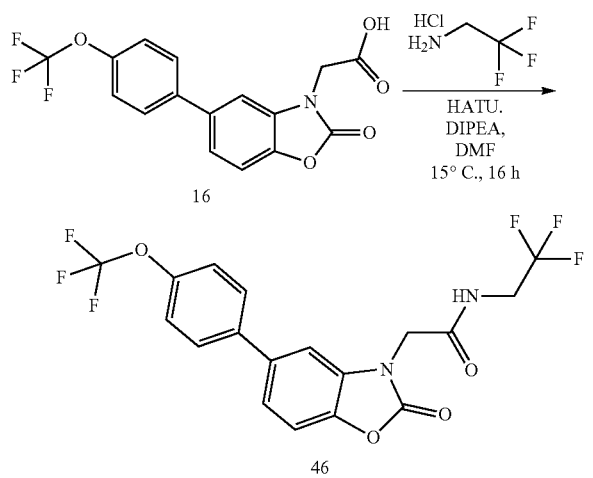

To a solution of Compound 16 (140 mg, 0.40 mmol) in DMF (4 mL) was added HATU (226.04 mg, 0.59 mmol), DIPEA (153.66 mg, 1.19 mmol) and 2,2,2-trifluoroethanamine hydrochloride (107.42 mg, 0.79 mmol). The resulting mixture was stirred at 15° C. for 16 hours. Saturated NH₄Cl aqueous (20 mL) and EtOAc (20 mL) was added to the reaction solution. After separation, the organic layer was washed with brine (20 mL×2), dried over anhydrous Na₂SO₄, filtered and concentrated to give the crude product, which was purified by Prep-HPLC (Boston Green ODS (150 mm×30 mm, 5 μm) A=H₂O (0.1% TFA) and B=CH₃CN); 42-72% B over 10 minutes) to afford Compound 46 (54.91 mg, 0.12 mmol) as a solid. ¹H NMR (DMSO-d₆ 400 MHz) δ$_H$=9.02 (t, 1H), 7.77 (d, 2H), 7.60 (s, 1H), 7.50-7.43 (m, 4H), 4.67 (s, 2H), 4.02-3.92 (m, 2H). LCMS R$_f$=1.21 min using Method A, MS ESI calcd. for C₁₈H₁₃F₆N₂O₄ [M+H]⁺ 435.1, found 435.0.

Example 47. Synthesis of Compound 47

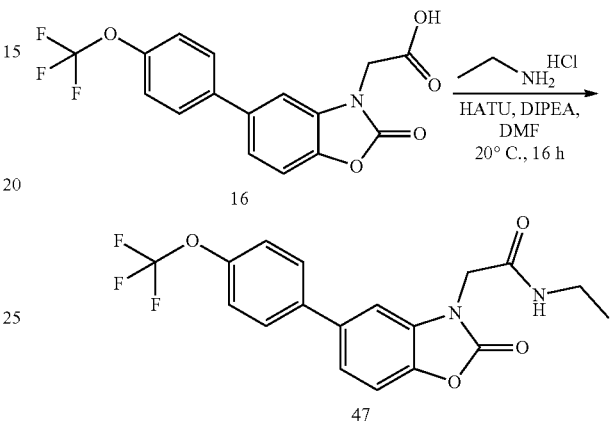

To the mixture of Compound 16 (180 mg, 0.51 mmol), HATU (290.62 mg, 0.76 mmol) and DIPEA (131.71 mg, 1.02 mmol) in DMF (2 mL) was added ethanamine hydrochloride (49.86 mg, 0.61 mmol) and the mixture was stirred at 20° C. for 16 hours. The mixture was diluted with sat. NH₄Cl (30 mL), extracted with EtOAc (30 mL×2). The combined organic phase was washed with brine (20 mL), dried over Na₂SO₄, filtered and concentrated to give the crude product, which was purified by Prep-HPLC (Phenomenex Gemini (150 mm×25 mm, 10 μm); A=H₂O (0.05% NH₄OH) and B=CH₃CN); 50-80% B over 8 minutes) to afford Compound 47 (18.7 mg, 0.05 mmol) as a solid. ¹H NMR (DMSO-d₆ 400 MHz) δ$_H$=8.29 (t, 1H), 7.78 (d, 2H), 7.59 (s, 1H), 7.49-7.44 (m, 4H), 4.52 (s, 2H), 3.16-3.07 (m, 2H), 1.03 (t, 3H). LCMS R$_f$=1.17 min using Method A, MS ESI calcd. for C₁₈H₁₆F₃N₂O₄ [M+H]⁺ 381.1, found 381.0.

Example 48. Synthesis of Compound 48

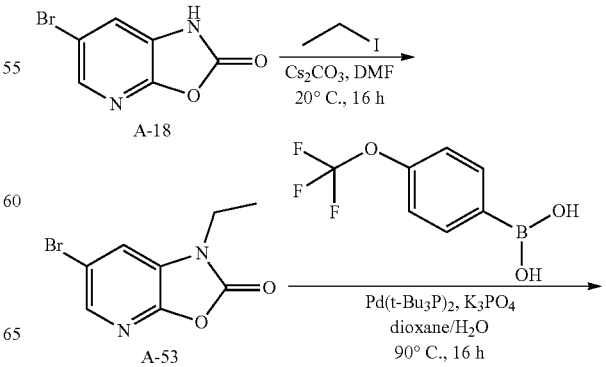

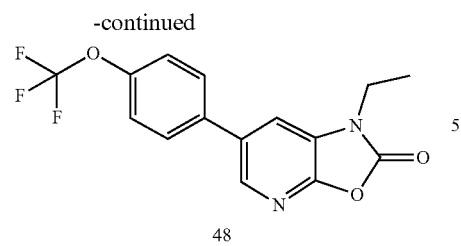

48

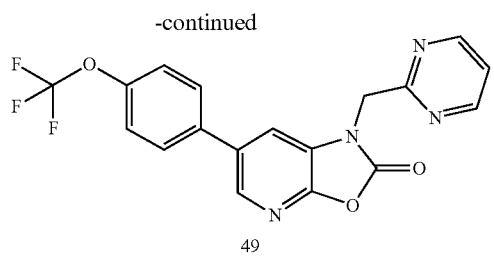

49

Synthesis of A-53:

To the mixture of A-18 (300 mg, 1.4 mmol) and $Cs_2CO_3$ (909.21 mg, 2.79 mmol) in DMF (5 mL) was added iodoethane (435.27 mg, 2.79 mmol) and the mixture was stirred at 20° C. for 16 hours. The mixture was diluted with $H_2O$ (10 mL), extracted with EtOAc (10 mL×2). The combined organic phase was washed with brine (10 mL), dried over $Na_2SO_4$, filtered and the filtrate was concentrated to give the crude product. The crude product was purified by flash chromatography on silica gel (EtOAc in PE=10% to 30%) to afford A-53 (160 mg, 0.66 mmol) as a solid. $^1H$ NMR (DMSO-$d_6$ 400M Hz) $\delta_H$=8.13-8.05 (m, 2H), 3.85 (q, 2H), 1.26 (t, 3H)

Synthesis of Compound 48:

A mixture of A-53 (90 mg, 0.37 mmol), [4-(trifluoromethoxy)phenyl]boronic acid (90.75 mg, 0.44 mmol), $Pd(t-Bu_3P)_2$ (28.15 mg, 0.06 mmol), and $K_3PO_4$ (155.93 mg, 0.73 mmol) in 1,4-dioxane (2 mL) and water (0.2 mL) was stirred under $N_2$ at 90° C. for 16 hours. The mixture was cooled to r.t., diluted with EtOAc (10 mL), filtered with silica gel, eluted with EtOAc (15 mL) and the filtrate was concentrated to give the crude product. The crude product was purified by Prep-HPLC (Waters Xbridge (150 mm×25 mm, 5 μm) A=$H_2O$ (10 mM $NH_4HCO_3$) and B=$CH_3CN$); 35-65% B over 10 minutes) to afford Compound 48 (81.71 mg, 0.25 mmol) as a solid. $^1H$ NMR (DMSO-$d_6$ 400M Hz) $\delta_H$=8.31 (d, 1H), 8.10 (d, 1H), 7.88 (d, 2H), 7.51 (d, 2H), 3.92 (q, 2H), 1.31 (t, 3H). LCMS $R_t$=1.20 min using Method A, MS ESI calcd. for $C_{15}H_{12}F_3N_3O_3$ [M+H]$^+$ 325.1, found 324.9.

Example 49. Synthesis of Compound 49

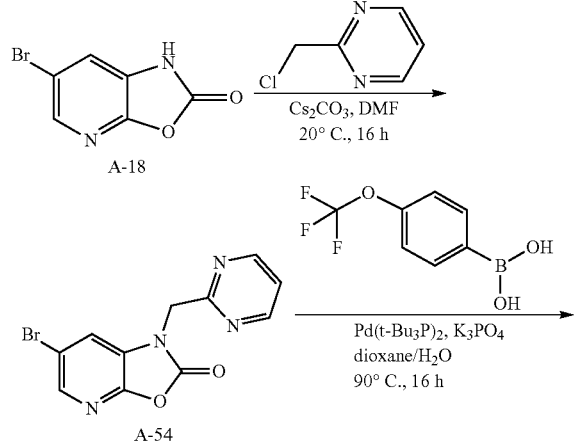

Synthesis of A-54:

To the mixture of A-18 (300 mg, 1.4 mmol) and $Cs_2CO_3$ (909.21 mg, 2.79 mmol) in DMF (3 mL) was added the 2-(chloromethyl)pyrimidine (358.77 mg, 2.79 mmol) and the mixture was stirred at 20° C. for 16 hours. The mixture was diluted with $H_2O$ (10 mL), and the mixture was extracted with EtOAc (10 mL×2). The combined organic phase was washed with brine (10 mL), dried over $Na_2SO_4$, filtered and concentrated to give the crude product, which was purified by flash chromatography on silica gel (EtOAc in PE=20% to 50%) to afford A-54 (170 mg, 0.55 mmol) as a solid. $^1H$ NMR (DMSO-$d_6$ 400 MHz) $\delta_H$=8.79 (d, 2H), 8.16 (d, 1H), 8.08 (d, 1H), 7.47 (t, 1H), 5.32 (s, 2H).

Synthesis of Compound 49:

A mixture of A-54 (90 mg, 0.29 mmol), [4-(trifluoromethoxy)phenyl]boronic acid (71.95 mg, 0.35 mmol), $Pd(t-Bu_3P)_2$ (22.32 mg, 0.04 mmol), and $K_3PO_4$ (123.62 mg, 0.58 mmol) in 1,4-dioxane (2 mL) and water (0.2 mL) was stirred under $N_2$ at 90° C. for 16 hours. The mixture was cooled to r.t., diluted with EtOAc (10 ml), filtered with silica gel, eluted with EtOAc (15 mL) and the filtrate was concentrated to give the crude product, which was purified by Prep-HPLC (Waters Xbridge (150 mm×25 mm, 5 μm) A=$H_2O$ (10 mM $NH_4HCO_3$) and B=$CH_3CN$); 43-73% B over 10 minutes) to afford Compound 49 (69.86 mg, 0.18 mmol) as a solid. $^1H$ NMR (DMSO-$d_6$ 400 MHz) $\delta$1-1=8.79 (d, 2H), 8.36 (d, 1H), 8.11 (d, 1H), 7.81 (d, 2H), 7.51-7.44 (m, 3H), 5.39 (s, 2H). LCMS $R_t$=1.15 min using Method A, MS ESI calcd. for $C_{18}H_{12}F_3N_4O_3$ [M+H]$^+$ 389.1, found 389.0.

Example 50. Synthesis of Compound 50

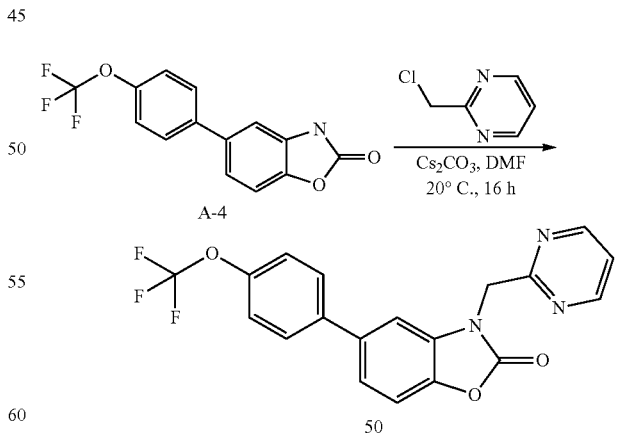

To the mixture of A-4 (200 mg, 0.68 mmol) and $Cs_2CO_3$ (441.45 mg, 1.35 mmol) in DMF (3 mL) was added 2-(chloromethyl)pyrimidine (174.19 mg, 1.35 mmol) and the mixture was stirred at 20° C. for 16 hours. The mixture was diluted with $H_2O$ (20 mL), and the mixture was extracted with EtOAc (20 mL×2). The combined organic phase was washed with brine (10 mL), dried over Na$_2$SO$_4$, filtered and the filtrate was concentrated to give the crude product, which was purified by Prep-HPLC (Phenomenex Gemini (150 mm×25 mm, 10 μm); A=H$_2$O (0.05% NH$_4$OH) and B=CH$_3$CN) 50-80% B over 8 minutes) to afford Compound 50 (67.92 mg, 0.18 mmol) as a solid. $^1$H NMR (DMSO-d$_6$ 400 MHz) δ$_H$=8.78 (d, 2H), 7.75 (d, 2H), 7.63 (d, 1H), 7.51-7.42 (m, 5H), 5.37 (s, 2H). LCMS R$_t$=1.22 min using Method A, MS ESI calcd. for C$_{19}$H$_{13}$F$_3$N$_3$O$_3$ [M+H]$^+$ 388.1, found 388.0.

Example 51. Synthesis of Compound 51

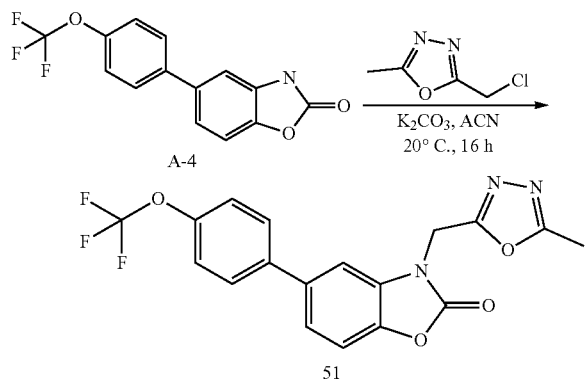

To the mixture of A-4 (200 mg, 0.68 mmol) and 2-(chloromethyl)-5-methyl-1,3,4-oxadiazole (179.6 mg, 1.35 mmol) in ACN (3 mL) was added K$_2$CO$_3$ (187.27 mg, 1.35 mmol) and the mixture was stirred at 20° C. for 16 hours. The mixture was diluted with H$_2$O (20 mL), and the mixture was extracted with EtOAc (20 mL×2). The combined organic phase was washed with brine (10 mL), dried over Na$_2$SO$_4$, filtered and the filtrate was concentrated to give the crude product, which was purified by Prep-HPLC (Phenomenex Gemini (150 mm×25 mm, 10 μm); A=H$_2$O (0.05% NH$_4$OH) and B=CH$_3$CN); 58-68% B over 8 minutes) to afford Compound 51 (52.03 mg, 0.13 mmol) as a solid. $^1$H NMR (MeOD-d$_4$ 400 MHz) δ$_H$=7.70 (d, 2H), 7.52 (d, 1H), 7.48-7.44 (m, 1H), 7.40-7.34 (m, 3H), 5.40 (s, 2H), 2.52 (s, 3H). LCMS R$_t$=1.18 min using Method A, MS ESI calcd. for C$_{18}$H$_{13}$F$_3$N$_3$O$_4$ [M+H]$^+$ 392.1, found 391.9.

Example 52. Synthesis of Compound 52

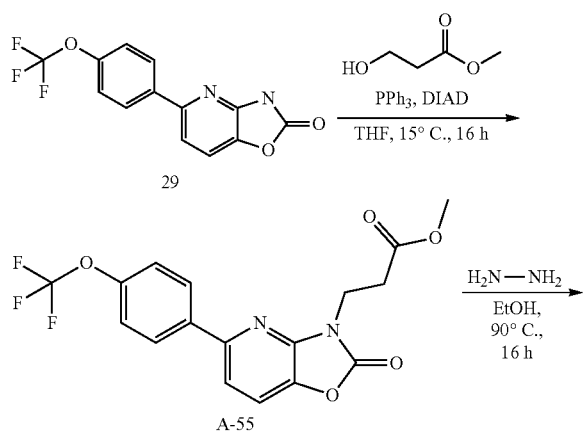

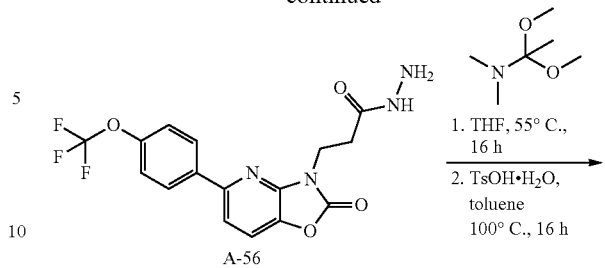

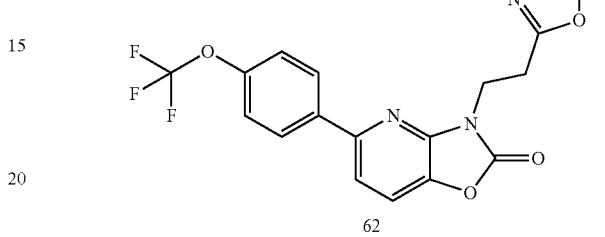

To a solution of 5-[4-(trifluoromethoxy)phenyl]-3H-oxazolo[4,5-b]pyridin-2-one (100 mg, 0.34 mmol) in THF (4 mL) was added methyl 3-hydroxypropanoate (105.44 mg, 1.01 mmol), PPh$_3$ (177.1 mg, 0.68 mmol) and then DIAD (136.54 mg, 0.68 mmol). The resulting mixture was stirred at 15° C. under N$_2$ for 16 hours to give a light yellow solution. The reaction solution was concentrated to give the crude product. The crude product was purified by silica gel column (PE:EtOAc=0% to 10% to 20%) to give the product of methyl 3-[2-oxo-5-[4-(trifluoromethoxy)phenyl]oxazolo[4,5-b]pyridin-3-yl]propanoate (100 mg, 0.2616 mmol, 77% yield) as a solid. $^1$H NMR (CDCl$_3$, 400 MHz) δ=8.01 (d, 2H), 7.48 (d, 2H), 7.32 (d, 2H), 4.33 (t, 2H), 3.69 (s, 3H), 2.98 (t, 2H).

To a solution of methyl 3-[2-oxo-5-[4-(trifluoromethoxy)phenyl]oxazolo[4,5-b]pyridin-3-yl]propanoate (100 mg, 0.26 mmol) in Ethanol (5 mL) was added hydrazine (25.15 mg, 0.78 mmol). The resulting solution was stirred at 90° C. under N$_2$ for 16 hours to give a yellow solution. The reaction solution was cooled to room temperature and concentrated to give the crude product (100 mg, 0.1892 mmol) as a solid. The crude product was used to next step directly. LCMS R$_t$=0.752 min in 1.5 min chromatography, MS ESI calcd. for C$_{16}$H$_{14}$F$_3$N$_4$O$_4$ [M+H]$^+$ 383.1, found 383.0.

To a solution of 3-[2-oxo-5-[4-(trifluoromethoxy)phenyl]oxazolo[4,5-b]pyridin-3-yl]propanehydrazide (100 mg, 0.19 mmol) in THF (5 mL) was added 1,1-dimethoxy-N,N-dimethyl-ethanamine (37.8 mg, 0.28 mmol). The resulting mixture was stirred at 55° C. under N$_2$ for 16 hours to give a yellow solution. The solution was concentrated to give a residue. Then the residue was re-dissolved in Toluene (5 mL) and TsOH.H$_2$O (5.4 mg, 0.03 mmol) was added. The resulting mixture was stirred at 100° C. for 16 hours to give a brown solution. The reaction mixture was cooled to room temperature and concentrated to give the crude product. The crude product was purified by Prep-TLC (PE:EtOAc=1:1) to give the product (54.07 mg, 0.1322 mmol, 70% yield) as a solid. $^1$H NMR (CDCl$_3$, 400 MHz) δ=7.95 (d, 2H), 7.48 (s, 2H), 7.32 (d, 2H), 4.44 (t, 2H), 3.44 (t, 2H), 2.39 (s, 3H). LCMS R$_t$=1.197 min in 2.0 min chromatography, MS ESI calcd. for C$_{18}$H$_{14}$F$_3$N$_4$O$_4$ [M+H]$^+$ 407.1, found 407.0.

Example 53. Synthesis of Compounds 54 and 55

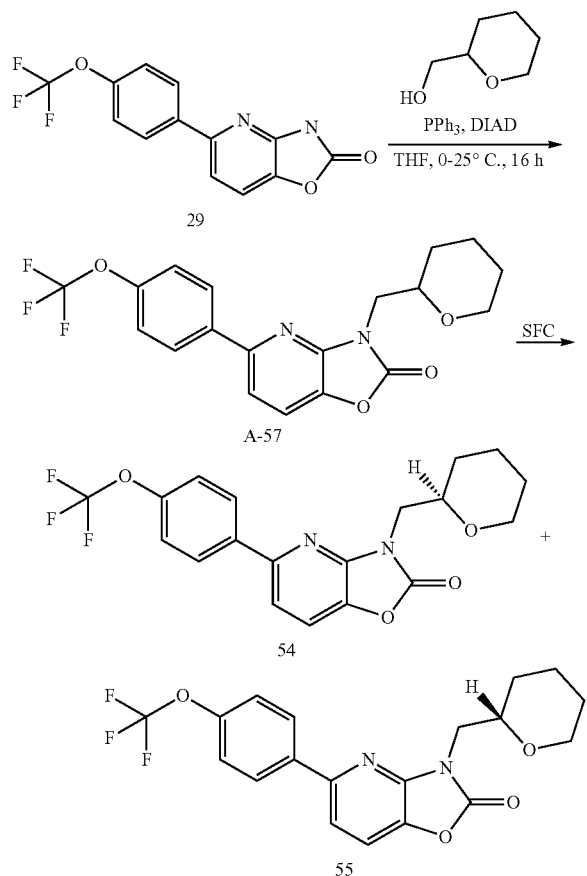

To a mixture of Compound 29 (100 mg, 0.34 mmol), tetrahydropyran-2-ylmethanol (117.65 mg, 1.01 mmol) and PPh$_3$ (177.1 mg, 0.68 mmol) in THF (3 mL) was added DIAD (136.54 mg, 0.68 mmol) at 0° C. The mixture was allowed to warm to 25° C. and stirred for 16 hours under N$_2$. The mixture was concentrated and purified by flash chromatography on silica gel (EtOAC in PE=0 to 30%) to give Compound 94, which was further purified by SFC (Chiralcel IC (250 mm×30 mm, 10 μm); A=CO$_2$ and B=EtOH (0.1% NH$_3$.H$_2$O); 38° C.; 60 mL/min; 20% B over 9 minutes; multiple injections) to afford Enantiomer 1, randomly assigned as Compound 54 (R$_t$=6.5 min) and Enantiomer 2, randomly assigned as Compound 55 (R$_t$=7.2 min). Compound 54 (36.04 mg, 0.09 mmol)$^1$H NMR (CDCl$_3$, 400 MHz), δ$_H$=7.93 (d, 2H), 7.39 (d, 2H), 7.25 (d, 2H), 4.10-4.01 (m, 1H), 3.92-3.79 (m, 3H), 3.30 (dt, 1H), 1.85-1.77 (m, 1H), 1.68-1.60 (m, 1H), 1.58-1.51 (m, 1H), 1.48-1.32 (m, 3H). LCMS R$_t$=1.37 min using Method A, MS ESI calcd. for C$_{19}$H$_{18}$F$_3$N$_2$O$_4$ [M+H]$^+$ 395.1, found 395.0. Compound 55 (31.94 mg, 0.0810 mmol)$^1$H NMR (CDCl$_3$+D$_2$O 400 MHz) δ$_H$=8.00 (d, 2H), 7.47 (s, 2H), 7.32 (d, 2H), 4.18-4.09 (m, 1H), 4.00-3.87 (m, 3H), 3.38 (dt, 1H), 1.95-1.85 (m, 1H), 1.75-1.68 (m, 1H), 1.67-1.59 (m, 1H), 1.56-1.38 (m, 3H). LCMS R$_t$=1.34 min using Method A, MS ESI calcd. for C$_{19}$H$_{18}$F$_3$N$_2$O$_4$ [M+H]$^+$ 395.1, found 395.0.

Example 54. Synthesis of Compound 56

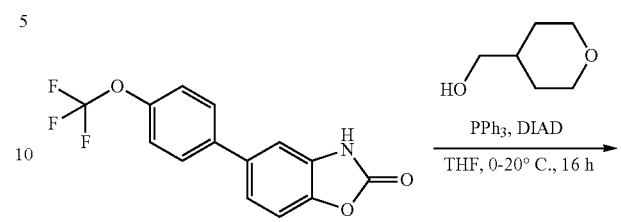

To the mixture of Compound 5 (200 mg, 0.68 mmol), tetrahydropyran-4-ylmethanol (141.65 mg, 1.22 mmol) and PPh$_3$ (319.86 mg, 1.22 mmol) in THF (5 mL) was added the DIAD (246.59 mg, 1.22 mmol) at 0° C. and the mixture was stirred under N$_2$ at 20° C. for 16 hours. The mixture was diluted with H$_2$O (20 mL), and extracted with EtOAc (20 mL×2). The combined organic phase was washed with brine (10 mL), dried over Na$_2$SO$_4$, filtered and concentrated to give the crude product, which purified by Prep-HPLC (Waters Xbridge (150 mm×25 mm, 5 μm) A=H$_2$O (10 mM NH$_4$HCO$_3$) and B=CH$_3$CN); 56-86% B over 10 minutes) to afford Compound 56 (78.49 mg, 0.20 mmol) as a solid. $^1$H NMR (DMSO-d$_6$+D$_2$O 400 MHz) δ$_H$=7.75 (d, 2H), 7.52 (s, 1H), 7.44-7.36 (m, 4H), 3.83-3.69 (m, 4H), 3.22 (br t, 2H), 2.13-1.95 (m, 1H), 1.54-1.43 (m, 2H), 1.32-1.22 (m, 2H). LCMS R$_t$=1.29 min using Method A, MS ESI calcd. for C$_{20}$H$_{19}$F$_3$NO$_4$ [M+H]$^+$ 394.1, found 394.1.

Example 55. Synthesis of Compounds 57, 58, and 59

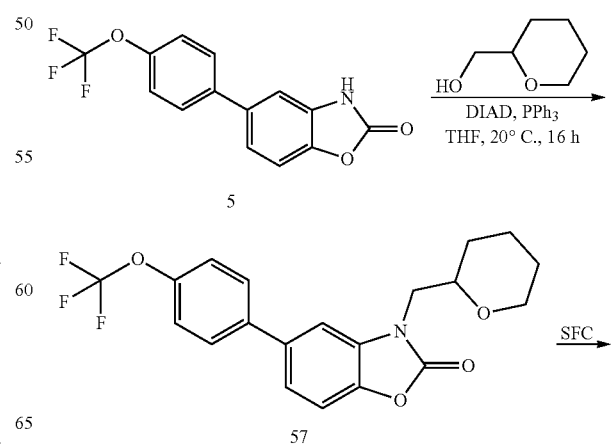

-continued

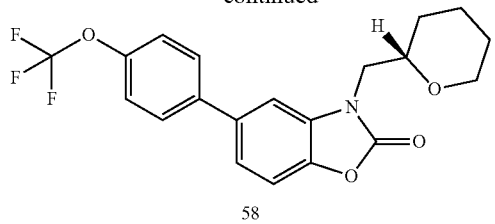

58

59

To a mixture of Compound 5 (150 mg, 0.51 mmol), DIAD (184.94 mg, 0.91 mmol) and tetrahydropyran-2-ylmethanol (106.24 mg, 0.91 mmol) in THF (5 mL) was added PPh$_3$ (239.89 mg, 0.91 mmol). The mixture was stirred at 20° C. for 16 hours under N$_2$. The mixture was concentrated, the residue was diluted with sat.NH$_4$Cl (20 mL), extracted with EtOAc (20 mL×2). The combined organic phase was washed with brine (10 mL), dried over Na$_2$SO$_4$ and filtered. The filtrate was concentrated to give a residue, which was purified by Prep-HPLC Xtimate C18 (250 mm×50 mm, 10 μm) A=H$_2$O (10 mM NH$_4$HCO$_3$) and B═CH$_3$CN); 50-80% B over 10 minutes) to afford Compound 57 as a solid. $^1$H NMR (CD$_3$CN-d$_3$ 400 MHz) $\delta_H$=7.71 (d, 2H), 7.44-7.34 (m, 4H), 7.32-7.26 (m, 1H), 3.92-3.79 (m, 3H), 3.77-3.68 (m, 1H), 3.38-3.30 (m, 1H), 1.87-1.75 (m, 1H), 1.75-1.64 (m, 1H), 1.59-1.43 (m, 3H), 1.42-1.28 (m, 1H). LCMS R$_t$=1.349 min using Method A, MS ESI calcd. for C$_{20}$H$_{19}$F$_3$NO$_4$ [M+H]$^+$ 394.1, found 394.0. Compound 57 was purified by SFC (Chiralcel OJ (250 mm×30 mm, 5 μm); A=CO$_2$ and B=MeOH (0.1% NH$_3$H$_2$O); 38° C.; 50 mL/min; 25% B over 9 minutes; multiple injections) to afford Enantiomer 1, randomly assigned as Compound 58 (R$_t$=7.05 min) and Enantiomer 2, randomly assigned as Compound 59 (R$_t$=7.95 min). Compound 58 (7.55 mg, 0.019 mmol)$^1$H NMR (CD$_3$CN-d$_3$ 400 MHz) $\delta_H$=7.71 (d, 2H), 7.45-7.34 (m, 4H), 7.31-7.26 (m, 1H), 3.94-3.80 (m, 3H), 3.76-3.67 (m, 1H), 3.38-3.28 (m, 1H), 1.87-1.79 (m, 1H), 1.69 (d, 1H), 1.55-1.43 (m, 3H), 1.38-1.29 (m, 1H). LCMS R$_t$=1.36 min using Method A, MS ESI calcd. for C$_{20}$H$_{19}$F$_3$NO$_4$ [M+H]$^+$ 394.1, found 394.1. Compound 59 (10.33 mg, 0.025 mmol)$^1$H NMR (CD$_3$CN-d$_3$ 400 MHz) $\delta_H$=7.71 (d, 2H), 7.43-7.35 (m, 4H), 7.31-7.26 (m, 1H), 3.89-3.80 (m, 3H), 3.76-3.69 (m, 1H), 3.39-3.29 (m, 1H), 1.87-1.81 (m, 1H), 1.70 (d, 1H), 1.55-1.44 (m, 3H), 1.40-1.31 (m, 1H). LCMS R$_t$=1.36 min using Method A, MS ESI calcd. for C$_{20}$H$_{19}$F$_3$NO$_4$ [M+H]$^+$ 394.1, found 394.0.

Example 56. Synthesis of Compound 60, 61, and 62

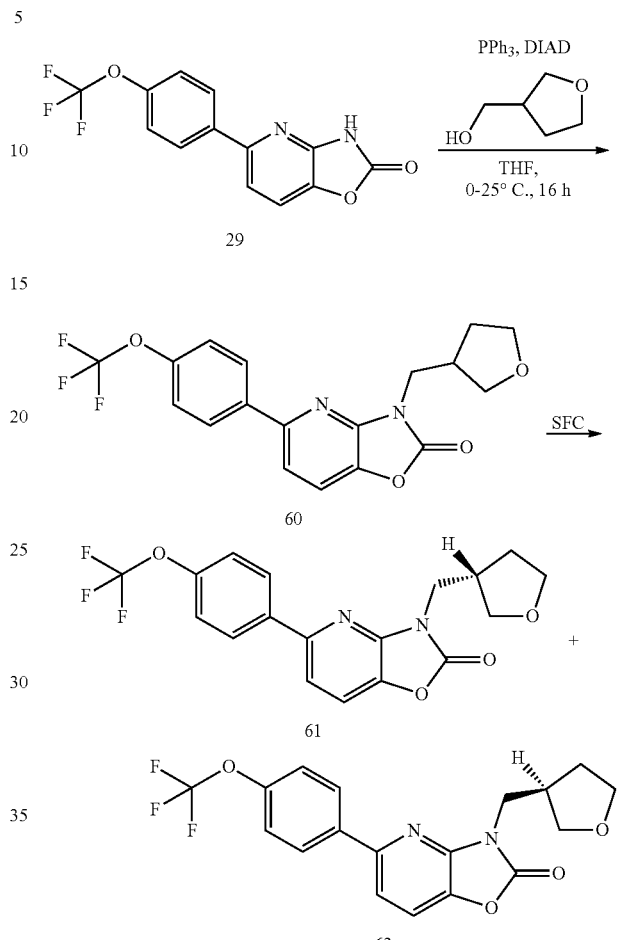

To a mixture of Compound 29 (100 mg, 0.34 mmol), tetrahydrofuran-3-ylmethanol (103.44 mg, 1.01 mmol) and PPh$_3$ (177.1 mg, 0.68 mmol) in THF (3 mL) was added DIAD (136.54 mg, 0.68 mmol) at 0° C. The mixture was allowed to warm to 25° C. and stirred for 16 hours under N$_2$. The mixture was concentrated to give Compound 60, which was purified by flash chromatography on silica gel (EtOAC in PE=0 to 30%) and SFC (ChiralCel OJ-H (150×4.6 mm, 5 μm); A=CO$_2$ and B=iPrOH (0.05% DEA); 40° C.; 2.5 mL/min; from 5% to 40% of B in 5.5 min and hold 40%, for 3 min, then 5% of B for 1.5 min) to afford Enantiomer 1, randomly assigned as Compound 61 (R$_t$=3.615 min) and Enantiomer 2, randomly assigned as Compound 62 (R$_t$=3.483 min). Compound 61 (22.50 mg, 0.060 mmol). 1H NMR (CDCl$_3$, 400 MHz) $\delta$=8.00 (d, 2H), 7.49 (s, 2H), 7.33 (d, 2H), 4.10-3.97 (m, 3H), 3.91-3.74 (m, 3H), 3.04-2.94 (m, 1H), 2.15-2.05 (m, 1H), 1.90-1.80 (m, 1H). LCMS R$_t$=1.28 min using Method A, MS ESI calcd. for C$_{18}$H$_{16}$F$_3$N$_2$O$_4$ [M+H]$^+$ 381.1, found 381.0. Compound 62 (15.4 mg, 0.04 mmol). $^1$H NMR (CDCl$_3$, 400 MHz), $\delta_H$=8.00 (d, 2H), 7.49 (s, 2H), 7.33 (d, 2H), 4.10-3.97 (m, 3H), 3.93-3.74 (m, 3H), 3.06-2.94 (m, 1H), 2.15-2.04 (m, 1H), 1.91-1.79 (m, 1H). LCMS R$_t$=1.26 min using Method A, MS ESI calcd. for C$_{18}$H$_{16}$F$_3$N$_2$O$_4$ [M+H]$^+$ 381.1, found 381.0.

Example 57. Synthesis of Compounds 63, 64, and 65

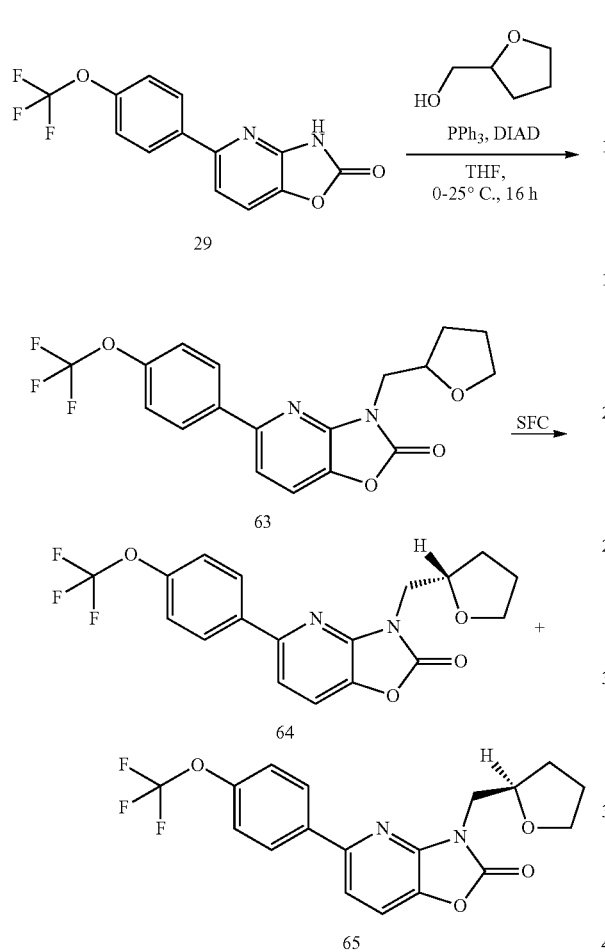

To a mixture of tetrahydrofuran-2-ylmethanol (103.44 mg, 1.01 mmol), Compound 29 (100 mg, 0.34 mmol) and PPh$_3$ (177.1 mg, 0.68 mmol) in THF (3 mL) was added DIAD (136.54 mg, 0.68 mmol) at 0° C. The mixture was allowed to warm to 25° C. and stirred for 16 hours under N$_2$. The mixture was concentrated to give Compound 63, which was purified by flash chromatography on silica gel (EtOAc in PE=0 to 30%) and SFC (Chiralcel IC (250 mm×30 mm, 10 μm); A=CO$_2$ and B=EtOH (0.1% NH$_3$H$_2$O); 38° C.; 60 mL/min; 25% B over 9 minutes; multiple injections) to afford Enantiomer 1, randomly assigned as Compound 64 (R$_t$=5.8 min) and Enantiomer 2, randomly assigned as Compound 65 (R$_t$=7.2 min). Compound 64 (41.18 mg, 0.11 mmol) $^1$H NMR (CDCl$_3$, 400 MHz), δ$_H$=8.00 (d, 2H), 7.47 (s, 2H), 7.32 (d, 2H), 4.60-4.51 (m, 1H), 4.15-4.07 (m, 1H), 4.02-3.91 (m, 2H), 3.85-3.77 (m, 1H), 2.16-1.90 (m, 3H), 1.86-1.77 (m, 1H). LCMS R$_t$=1.29 min using Method A, MS ESI calcd. for C$_{18}$H$_{16}$F$_3$N$_2$O$_4$ [M+H]$^+$ 381.1, found 381.0. Compound 65 (42.61 mg, 0.11 mmol) $^1$H NMR (CDCl$_3$, 400 MHz), δ$_H$=8.03-7.96 (m, 2H), 7.47 (s, 2H), 7.32 (d, 2H), 4.60-4.51 (m, 1H), 4.15-4.06 (m, 1H), 4.02-3.90 (m, 2H), 3.86-3.76 (m, 1H), 2.16-1.90 (m, 3H), 1.86-1.74 (m, 1H). LCMS R$_t$=1.29 min using Method A, MS ESI calcd. for C$_{18}$H$_{16}$F$_3$N$_2$O$_4$ [M+H]$^+$ 381.1, found 381.0.

Example 58. Synthesis of Compounds 66 and 67

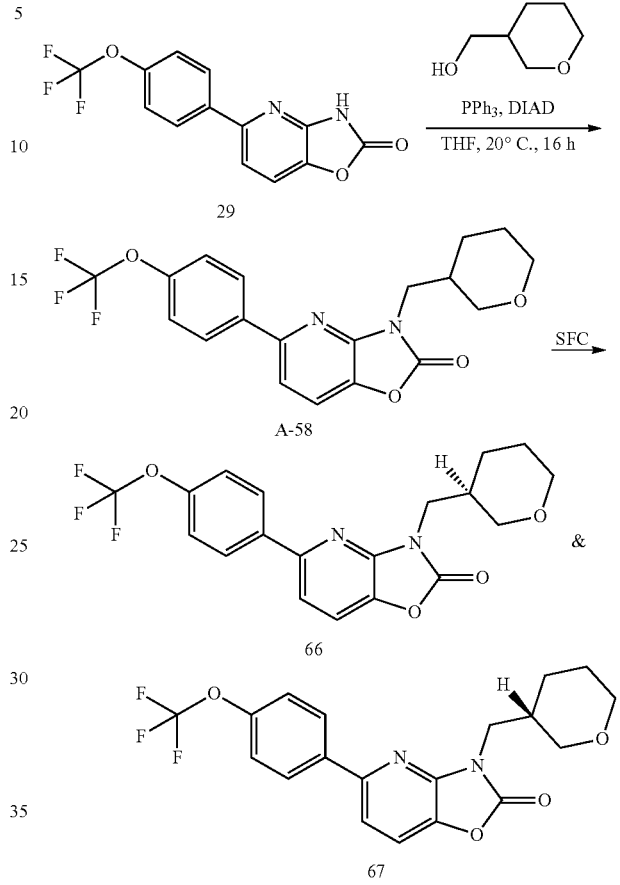

To a solution of Compound 29 (100 mg, 0.34 mmol) in THF (4 mL) was added tetrahydropyran-3-ylmethanol (117.65 mg, 1.01 mmol), PPh$_3$ (177.1 mg, 0.68 mmol) and then DIAD (136.54 mg, 0.68 mmol). The resulting mixture was stirred at 20° C. under N$_2$ for 16 hours. The reaction solution was concentrated to give the crude product, which was purified by flash chromatography on silica gel (EtOAc in PE=0% to 10% to 20%) and Prep-TLC (silica gel, PE:EtOAc=4:1) to afford A-58 (50 mg) as a solid. A-58 was purified by SFC (Chiralcel AD (250 mm×30 mm, 5 μm); A=CO$_2$ and B=EtOH (0.1% NH$_3$H$_2$O); 38° C.; 50 mL/min; 30% B over 11 minutes; multiple injections) to afford Enantiomer 1, randomly assigned as Compound 66 (R$_t$=6.8 min) and Enantiomer 2, randomly assigned as Compound 67 (R$_t$=9.2 min). Compound 66 (14.37 mg, 0.04 mmol) $^1$H NMR (CDCl$_3$ 400 MHz) δ$_H$=8.00 (d, 2H), 7.48 (s, 2H), 7.33 (d, 2H), 4.01-3.80 (m, 4H), 3.56-3.35 (m, 2H), 2.43-2.30 (m, 1H), 1.96-1.85 (m, 1H), 1.82-1.72 (m, 1H), 1.69-1.59 (m, 1H), 1.49-1.37 (m, 1H). LCMS R$_t$=1.32 min using Method A, MS ESI calcd. for C$_{19}$H$_{18}$F$_3$N$_2$O$_4$ [M+H]$^+$ 395.1, found 395.0. Compound 67 (15.66 mg, 0.04 mmol) $^1$H NMR (CDCl$_3$, 400 MHz) δ$_H$=8.00 (d, 2H), 7.48 (s, 2H), 7.33 (d, 2H), 4.00-3.81 (m, 4H), 3.55-3.46 (m, 1H), 3.41 (dd, 1H), 2.43-2.31 (m, 1H), 1.96-1.86 (m, 1H), 1.82-1.72 (m, 1H), 1.69-1.59 (m, 1H), 1.49-1.37 (m, 1H). LCMS R$_t$=1.33 min using Method A, MS ESI calcd. for C$_{19}$H$_{18}$F$_3$N$_2$O$_4$ [M+H]$^+$ 395.1, found 395.1.

Example 59. Synthesis of Compounds 68, 69, and 70

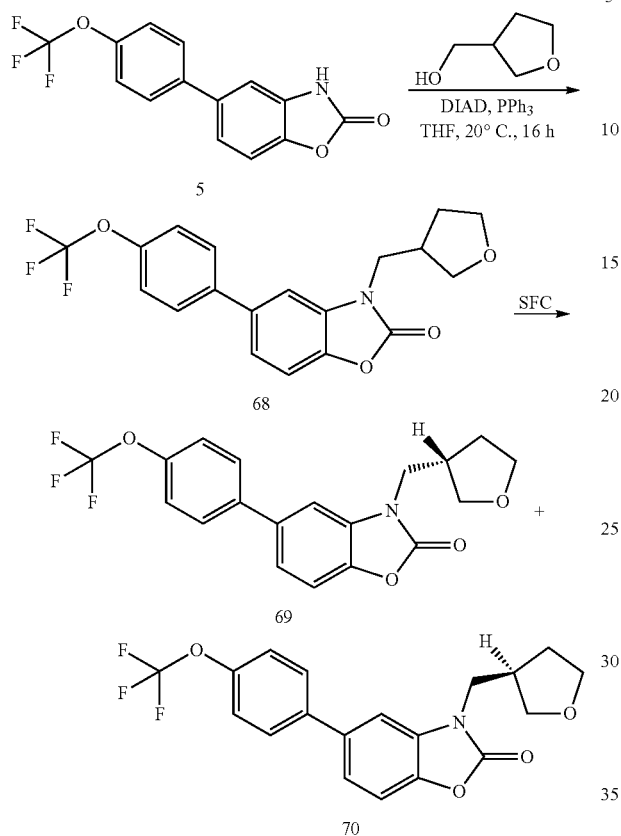

Example 60. Synthesis of Compound 71

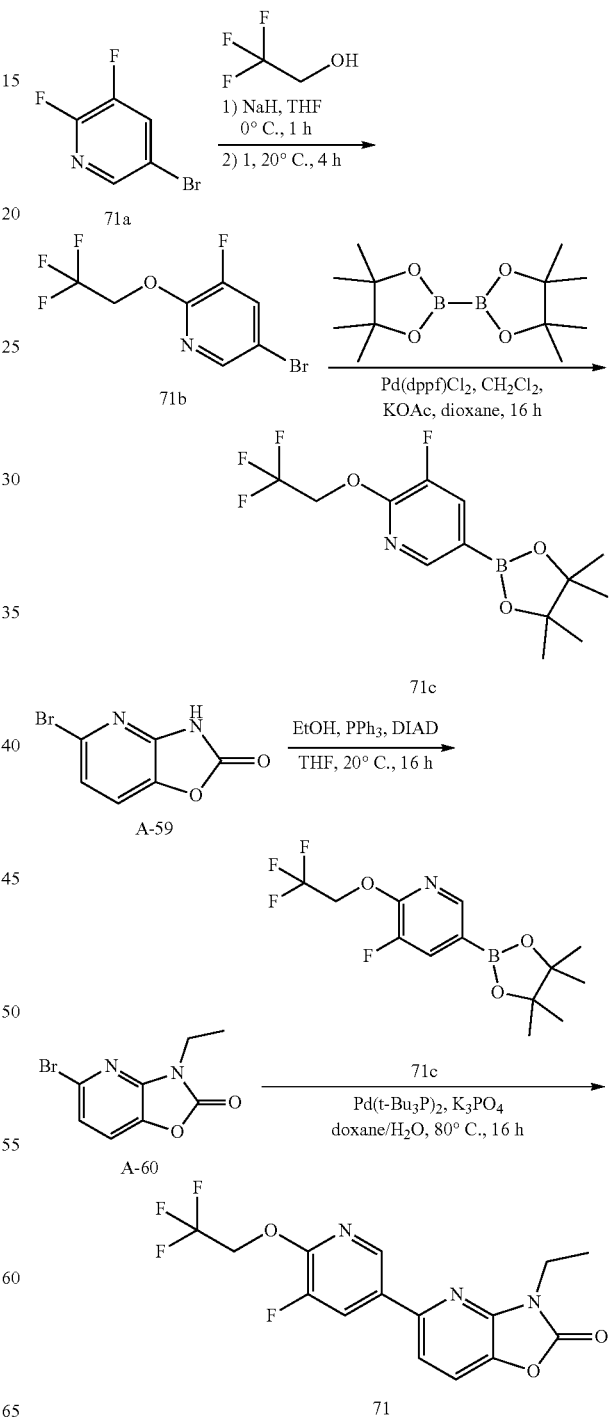

To the mixture of Compound 5 (200 mg, 0.68 mmol), tetrahydrofuran-3-ylmethanol (124.54 mg, 1.22 mmol) and PPh$_3$ (319.86 mg, 1.22 mmol) in THF (5 mL) was added DIAD (246.59 mg, 1.22 mmol). The mixture was stirred under N$_2$ at 20° C. for 16 hours. The mixture was diluted with sat.NH$_4$Cl (20 mL) and extracted with EtOAc (20 mL×2). The combined organic phase was washed with brine (10 mL), dried over Na$_2$SO$_4$, filtered and the filtrate was concentrated to give the crude product, which was purified by Prep-HPLC (Phenomenex Gemini (150 mm×25 mm, 10 μm); A=H$_2$O (0.05% NH$_4$OH) and B=CH$_3$CN); 55-85% B over 8 minutes) to afford Compound 68 (48.85 mg, 0.13 mmol) as a solid. $^1$H NMR (DMSO-d$_6$ 400 MHz) δ$_H$=7.82 (d, 2H), 7.72 (s, 1H), 7.47 (d, 2H), 7.44 (d, 2H), 3.89 (d, 2H), 3.85-3.79 (m, 1H), 3.71 (dd, 1H), 3.63 (q, 1H), 3.52 (dd, 1H), 2.87-2.75 (m, 1H), 2.04-1.90 (m, 1H), 1.76-1.62 (m, 1H). LCMS R$_t$=1.244 min using Method A, MS ESI calcd. for C$_{19}$H$_{17}$F$_3$NO$_4$ [M+H]$^+$ 380.1, found 380.2. The product was purified by SFC (Chiralcel AD (250 mm×30 mm, 5 μm); A=CO$_2$ and B=MeOH (0.1% NH$_3$H$_2$O); 38° C.; 50 mL/min; 30% B over 12 minutes; multiple injections) to afford Enantiomer 1, randomly assigned as Compound 69 (R$_t$=6.5 min) and Enantiomer 2, randomly assigned as Compound 70 (R$_t$=10.5 min). Compound 69 (12.76 mg, 0.03 mmol) $^1$H NMR (DMSO-d$_6$ 400 MHz) δ$_H$=7.85-7.79 (m, 2H), 7.72 (s, 1H), 7.52-7.39 (m, 4H), 3.89 (d, 2H), 3.82 (dt, 1H), 3.71 (dd, 1H), 3.63 (q, 1H), 3.51 (dd, 1H), 2.87-2.75 (m, 1H), 2.02-1.91 (m, 1H), 1.72-1.61 (m, 1H). LCMS R$_t$=1.25 min using Method A, MS ESI calcd. for C$_{19}$H$_{17}$F$_3$NO$_4$ [M+H]$^+$ 380.1, found 380.0. Compound 70 (12.37 mg, 0.03 mmol) $^1$H NMR (DMSO-d$_6$ 400 MHz) δ$_H$=7.86-7.79 (m, 2H), 7.73 (s, 1H), 7.52-7.41 (m, 4H), 3.89 (d, 2H), 3.82 (dt,), 3.72 (dd, 1H), 3.64 (q, 1H), 3.52 (dd, 1H), 2.88-2.75 (m, 1H), 2.02-1.90 (m, 1H), 1.73-1.60 (m, 1H). LCMS R$_t$=1.26 min using Method A, MS ESI calcd. for C$_{19}$H$_{17}$F$_3$NO$_4$ [M+H]$^+$ 380.1, found 379.9.

Synthesis of Compound 71b:

To a suspension of NaH (453.66 mg, 11.34 mmol) in THF (50 mL) was added 2,2,2-trifluoroethanol (1.13 g, 11.34 mmol) at 0° C., and the mixture was stirred at 20° C. for 1 hour. Then to the mixture was added 71a (2 g, 10.31 mmol), and the mixture was stirred at 20° C. for another 4 hours. The mixture was quenched with sat.NH$_4$Cl (50 mL), and the mixture was extracted with EtOAc (100 mL×2). The combined organic phase was washed with brine (50 mL), dried over Na$_2$SO$_4$, filtered and concentrated to afford Compound 71b (1500 mg, 5.47 mmol) as an oil. $^1$H NMR (CDCl$_3$, 400 MHz) $\delta_H$=8.00 (d, 1H), 7.58 (dd, 1H), 4.81 (q, 2H).

Synthesis of Compound 71c:

A mixture of Compound 71b (1500 mg, 5.47 mmol), 4,4,5,5-tetramethyl-2-(4,4,5,5-tetramethyl-1,3,2-dioxaborolan-2-yl)-1,3,2-dioxaborolane (2780.26 mg, 10.95 mmol), Pd(dppf)Cl$_2$.CH$_2$Cl$_2$ (447.05 mg, 0.55 mmol) and KOAc (1074.49 mg, 10.95 mmol) in 1,4-dioxane (100 mL) was stirred at 90° C. for 16 hours. After cooling to r.t., the mixture was concentrated to a residue that was diluted with H$_2$O (50 mL) and extracted with EtOAc (50 mL×2). The combined organic phase was washed with brine (50 mL), dried over Na$_2$SO$_4$, filtered and concentrated to give the crude product, which was purified by flash chromatography on silica gel (EtOAc in PE=0 to 5% to 30%) column to afford Compound 71c (3800 mg, 11.835 mmol) as a solid. $^1$H NMR (CDCl$_3$, 400 MHz) O$_H$=8.26 (s, 1H), 7.72 (dd, 1H), 4.87 (q, 2H), 1.35 (s, 12H)

Synthesis of A-60:

To a solution of A-59 (240 mg, 1.12 mmol) in THF (4 mL) was added ethanol (154.28 mg, 3.35 mmol), PPh$_3$ (585.58 mg, 2.23 mmol) and then DIAD (451.45 mg, 2.23 mmol). The resulting mixture was stirred at 20° C. under N$_2$ for 16 hours. The reaction solution was concentrated to give the crude product that was purified by flash chromatography on silica gel (EtOAc in PE=0% to 10% to 20%) to afford A-60 (180 mg, 0.74 mmol) as a solid. $^1$H NMR (CDCl$_3$, 400 MHz) $\delta_H$=7.33-7.20 (m, 2H), 4.01 (q, 2H), 1.44 (t, 3H).

Synthesis of Compound 71:

A mixture of A-59 (100 mg, 0.41 mmol), Compound 71c (198.15 mg, 0.62 mmol), K$_3$PO$_4$ (174.69 mg, 0.82 mmol) and Pd(t-Bu$_3$P)$_2$ (31.54 mg, 0.06 mmol) in 1,4-dioxane (5 mL) and water (0.50 mL) was stirred at 80° C. under N$_2$ for 16 hours. The reaction mixture was cooled to room temperature, filtered through Celite and eluted with EtOAc (10 mL×2). The filtrate was concentrated to give the crude product, which was purified by flash chromatography on silica gel (EtOAc in PE=0% to 10% to 20%) to afford Compound 71 (125.91 mg, 0.35 mmol) as a solid. $^1$H NMR (CDCl$_3$, 400 MHz) $\delta_H$=8.50 (d, 1H), 8.08 (dd, 1H), 7.51-7.41 (m, 2H), 4.91 (q, 2H), 4.07 (q, 2H), 1.49 (t, 3H). LCMS R$_t$=1.26 min using Method A, MS ESI calcd. for C$_{15}$H$_{12}$F$_4$N$_3$O$_3$ [M+H]$^+$ 358.1, found 358.0.

Example 61. Synthesis of Compounds 72, 73, and 74

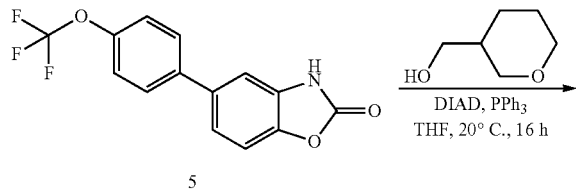

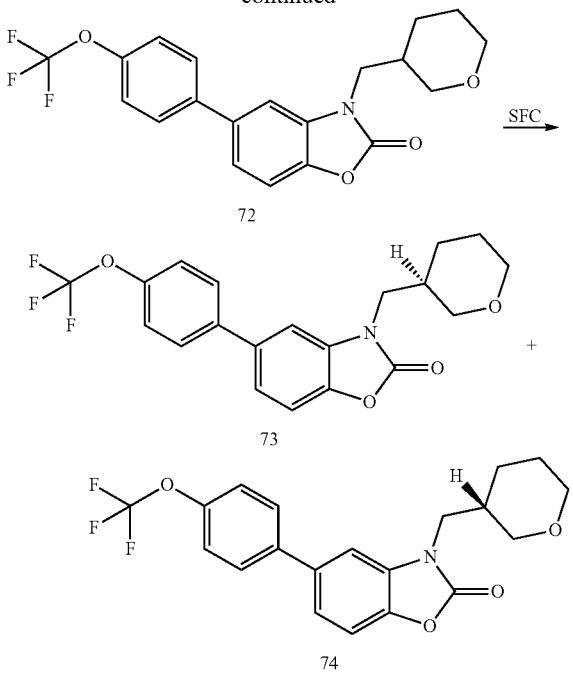

To the mixture of Compound 5 (150 mg, 0.51 mmol), DIAD (184.94 mg, 0.91 mmol) and tetrahydropyran-3-ylmethanol (106.24 mg, 0.91 mmol) in THF (5 mL) was added PPh$_3$ (239.89 mg, 0.91 mmol). The mixture was stirred at 20° C. for 16 hours under N$_2$. The mixture was concentrated, and the residue was diluted with sat.NH$_4$Cl (20 mL), and extracted with EtOAc (20 mL×2). The combined organic phase was washed with brine (10 mL), dried over Na$_2$SO$_4$ and filtered, and the filtrate was concentrated to give a residue that was purified by Prep-HPLC (Xtimate C18 (250 mm×50 mm, 10 μm) A=H$_2$O (10 mM % NH$_3$HCO$_3$) and B=CH$_3$CN); 55-85% B over 11.3 minutes) to afford Compound 72 (52.87 mg, 0.13 mmol) as an oil. $^1$H NMR (CD$_3$CN 400 MHz) $\delta_H$=7.73 (d, 2H), 7.42-7.35 (m, 4H), 7.33-7.27 (m, 1H), 3.83-3.69 (m, 4H), 3.43 (dt, 1H), 3.34-3.26 (m, 1H), 2.24-2.15 (m, 1H), 1.89-1.80 (m, 1H), 1.73-1.64 (m, 1H), 1.58-1.46 (m, 1H), 1.46-1.34 (m, 1H). LCMS R$_t$=1.293 min using Method A, MS ESI calcd. for C$_{20}$H$_{19}$F$_3$NO$_4$ [M+H]$^+$ 394.1, found 394.1. Compound 72 was purified by SFC (Chiralcel O$_{J-3}$ 150×4.6 mm I.D., 3 um Mobile phase: A: CO$_2$ B:ethanol (0.05% DEA)) to give Compound 73 (11.22 mg, 0.0285 mmol) (Peak1, R$_t$=3.171 min in SFC, compound 73) as a solid and Compound 74 (8.6 mg, 0.0219 mmol) (Peak2, R$_t$=3.378 min in SFC) as a solid. Stereochemistry of compound 73 and 74 was randomly assigned.

Compound 73

$^1$H NMR (CD$_3$CN-d$_3$ 400 MHz) $\delta_H$=7.73 (d, 2H), 7.43-7.36 (m, 4H), 7.33-7.28 (m, 1H), 3.82-3.70 (m, 4H), 3.48-3.40 (m, 1H), 3.30 (dd, 1H), 2.24-2.17 (m, 1H), 1.90-1.78 (m, 1H), 1.72-1.64 (m, 1H), 1.57-1.48 (m, 1H), 1.44-1.35 (m, 1H). LCMS R$_t$=1.30 min, MS ESI calcd. for C$_{20}$H$_{19}$F$_3$NO$_4$ [M+H]$^+$ 394.1, found 394.2.

Compound 74

$^1$H NMR CD$_3$CN-d$_3$ 400 MHz δ=7.78-7.69 (m, 2H), 7.47-7.33 (m, 4H), 7.33-7.26 (m, 1H), 3.82-3.69 (m, 4H), 3.48-3.40 (m, 1H), 3.30 (dd, 1H), 2.25-2.16 (m, 1H), 1.90-1.80 (m, 1H), 1.72-1.64 (m, 1H), 1.56-1.46 (m, 1H), 1.45-

1.38 (m, 1H). LCMS $R_t$=1.334 min in 2.0 min chromatography, MS ESI calcd. for $C_{20}H_{19}F_3NO_4$ [M+H]$^+$ 394.1, found 394.1.

Example 62. Synthesis of Compound 75

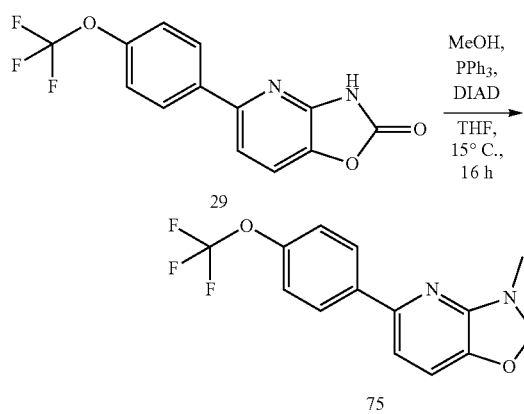

To a solution of Compound 29 (100 mg, 0.34 mmol) in THF (5 mL) was added MeOH (32.41 mg, 1.01 mmol), PPh$_3$ (177.1 mg, 0.68 mmol) and then DIAD (136.54 mg, 0.68 mmol). The resulting mixture was stirred at 15° C. under N$_2$ for 16 hours to give a solution. The solution was concentrated to give the crude product, which was purified by flash chromatography on silica gel (EtOAc in PE=0% to 10% to 20%) to afford Compound 75 (45.57 mg, 0.15 mmol) as a solid. $^1$H NMR (CDCl$_3$, 400 MHz) $\delta_H$=8.02 (d, 2H), 7.48 (s, 2H), 7.33 (d, 2H), 3.55 (s, 3H). LCMS $R_t$=1.26 min using Method A, MS ESI calcd. for $C_{14}H_{10}F_3N_3O_3$ [M+H]$^+$ 311.1, found 310.9.

Example 63. Synthesis of Compound 76

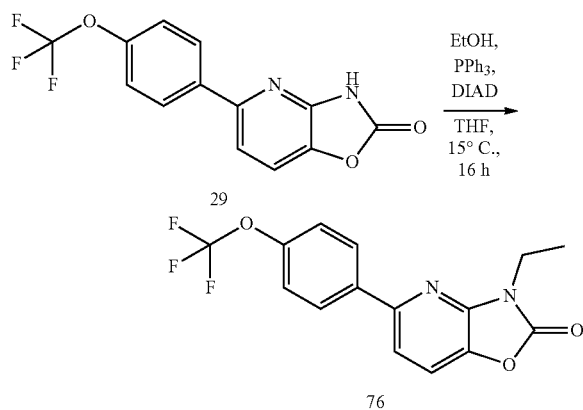

To a solution of Compound 29 (100 mg, 0.34 mmol) in THF (5 mL) was added EtOH (46.69 mg, 1.01 mmol), PPh$_3$ (177.1 mg, 0.68 mmol) and then DIAD (136.54 mg, 0.68 mmol). The resulting mixture was stirred at 15° C. under N$_2$ for 16 hrs. The solution was then concentrated to give the crude product, which was purified by flash chromatography on silica gel (EtOAc in PE=0 to 20% to 50%) to afford Compound 76 (86.45 mg, 0.27 mmol) as a solid. $^1$H NMR (DMSO-d$_6$ 400 MHz) $\delta_H$=8.18 (d, 2H), 7.84-7.74 (m, 2H), 7.49 (d, 2H), 3.94 (q, 2H), 1.37 (t, 3H). LCMS $R_t$=1.32 min using Method A, MS ESI calcd. for $C_{15}H_{12}F_3N_3O_3$ [M+H]$^+$ 325.1, found 324.9.

Example 64. Synthesis of Compound 77

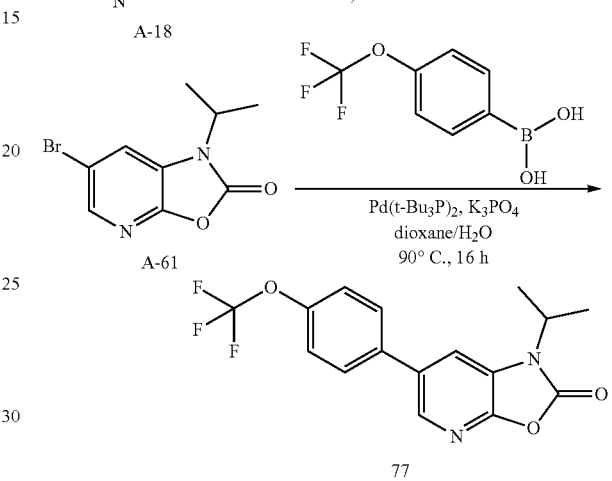

Synthesis of A-61:

To a mixture of A-18 (400 mg, 1.86 mmol) and Cs$_2$CO$_3$ (1212.28 mg, 3.72 mmol) in DMF (5 mL) was added 2-bromopropane (457.64 mg, 3.72 mmol). The mixture was stirred at 50° C. for 16 hours. The mixture was diluted with H$_2$O (50 mL) and extracted with EtOAc (50 mL×2). The combined organic phase was washed with brine (50 mL), dried over Na$_2$SO$_4$, filtered and concentrated to give the crude product that was purified by flash chromatography on silica gel (EtOAc in PE=0 to 20% to 50%) to afford A-60 (200 mg, 0.70 mmol) as a solid, $^1$H NMR (CDCl$_3$, 400 MHz) $\delta_H$=8.10 (d, 1H), 7.47 (d, 1H), 4.57 (spt, 1H), 1.56-1.50 (m, 6H). LCMS $R_t$=0.73 min using Method B, MS ESI calcd. for $C_9H_{10}BrN_2O_2$ [M+H]$^+$ 257.0, found 256.7.

Synthesis of Compound 77:

A mixture of A-60 (200 mg, 0.78 mmol), [4-(trifluoromethoxy)phenyl]boronic acid (192.25 mg, 0.93 mmol), Pd(t-Bu$_3$P)$_2$ (79.52 mg, 0.16 mmol) and K$_3$PO$_4$ (330.33 mg, 1.56 mmol) in 1,4-dioxane (5 mL) and water (1 mL) was stirred at 90° C. for 16 hours. After cooling, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by Prep-HPLC (Phenomenex Gemini (150 mm×25 mm, 10 μm); A=H$_2$O (0.05% NH$_4$OH) and B=CH$_3$CN); 55-85% B over 8 minutes) to give Compound 77 (24.22 mg, 0.07 mmol) as a solid. $^1$H NMR (CDCl$_3$, 400 MHz) $\delta_H$=8.19 (d, 1H), 7.57 (d, 2H), 7.46 (d, 1H), 7.36 (d, 2H), 4.63 (spt, 1H), 1.60 (d, 6H). LCMS $R_t$=1.23 min using Method A, MS ESI calcd. for $C_{16}H_{14}F_3N_3O_3$ [M+H]$^+$ 339.1, found 338.9.

Example 65. Synthesis of Compound 78

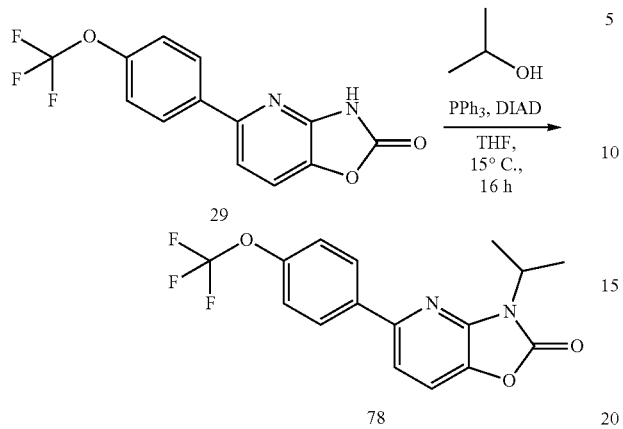

To a solution of Compound 29 (100 mg, 0.34 mmol) in THF (5 mL) was added propan-2-ol (60.87 mg, 1.01 mmol), PPh$_3$ (177.1 mg, 0.68 mmol) and DIAD (136.54 mg, 0.68 mmol). The resulting mixture was stirred at 15° C. under N$_2$ for 16 hours. The reaction solution was concentrated to give the crude product, which was purified by flash chromatography on silica gel (EtOAc in PE=0% to 10% to 20%) to afford Compound 78 (49.62 mg, 0.15 mmol) as a solid. $^1$H NMR (DMSO-d$_6$ 400 MHz) $\delta_H$=8.17 (d, 2H), 7.82-7.73 (m, 2H), 7.49 (d, 2H), 4.62 (spt, 1H), 1.58 (d, 6H). LCMS R$_t$=1.34 min using Method A, MS ESI calcd. for C$_{16}$H$_{14}$F$_3$N$_3$O$_3$ [M+H]$^+$ 339.1, found 338.9.

Example 66. Synthesis of Compound 79

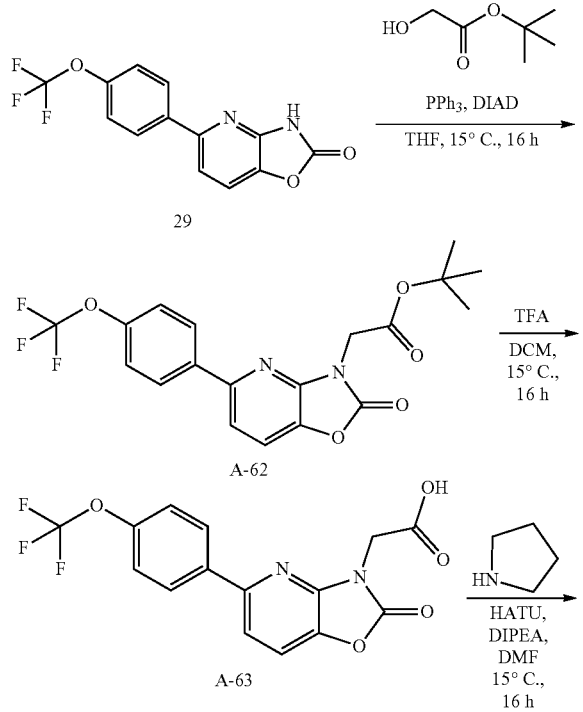

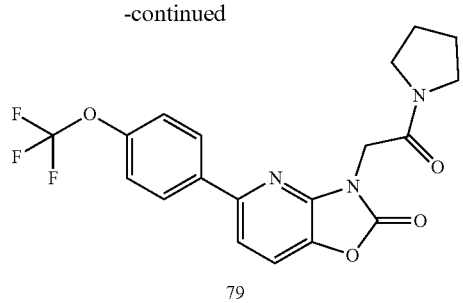

Synthesis of A-62:

To a solution of Compound 29 (200 mg, 0.68 mmol) in THF (5 mL) was added tert-butyl 2-hydroxyacetate (267.71 mg, 2.03 mmol), PPh$_3$ (354.21 mg, 1.35 mmol) and DIAD (273.07 mg, 1.35 mmol). The resulting mixture was stirred at 15° C. under N$_2$ for 16 hours. The reaction solution was concentrated, and the residue was purified by flash chromatography on silica gel (EtOAc in PE=0% to 10% to 20%) to afford A-61 (270 mg, 0.66 mmol) as a solid. $^1$H NMR (CDCl$_3$, 400 MHz) $\delta_H$=7.97 (d, 2H), 7.49 (s, 2H), 7.30 (d, 2H), 4.62 (s, 2H), 1.49 (s, 9H).

Synthesis of A-63:

To a solution of A-61 (270 mg, 0.66 mmol) in DCM (4 mL) was added TFA (2 mL, 26.93 mmol). The resulting mixture was stirred at 15° C. for 16 hours. The reaction solution was concentrated to afford A-62 (220 mg, 0.62 mmol) as a solid. $^1$H NMR (DMSO-d$_6$ 400 MHz) $\delta_H$=8.17 (d, 2H), 7.91-7.86 (m, 1H), 7.85-7.80 (m, 1H), 7.48 (d, 2H), 4.67 (s, 2H).

Synthesis of Compound 79:

To a solution of A-62 (110 mg, 0.31 mmol) in DMF (3 mL) was added HATU (177.11 mg, 0.47 mmol), DIPEA (120.4 mg, 0.93 mmol) and pyrrolidine (26.5 mg, 0.37 mmol). The resulting mixture was stirred at 15° C. for 16 hours. Saturated NH$_4$Cl aqueous (20 mL) and EtOAc (20 mL) was added to the reaction solution. After separation, the organic layer was washed with brine (20 mL×2), dried over anhydrous Na$_2$SO$_4$, filtered and concentrated, and the residue was purified by Prep-HPLC (Waters Xbridge (150 mm×25 mm, 5 μm) A=H$_2$O (10 mM NH$_4$HCO$_3$) and B=CH$_3$CN); 49-69% B over 8 minutes) to afford Compound 79 (21.73 mg, 0.05 mmol) as a solid. $^1$H NMR (CDCl$_3$, 400 MHz) $\delta_H$=7.94 (d, 2H), 7.47 (q, 2H), 7.29 (d, 2H), 4.70 (s, 2H), 3.61 (t, 2H), 3.54 (t, 2H), 2.09 (quin, 2H), 1.92 (quin, 2H). LCMS R$_t$=1.21 min using Method A, MS ESI calcd. for C$_{19}$H$_{17}$F$_3$N$_3$O$_4$ [M+H]$^+$ 408.1, found 407.9.

Example 67. Synthesis of Compound 80

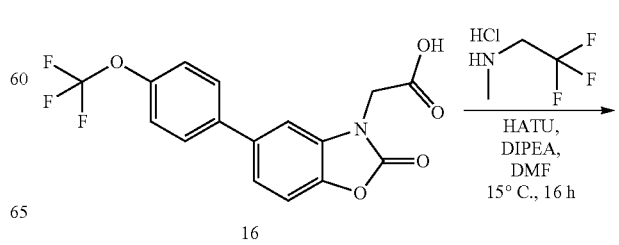

-continued

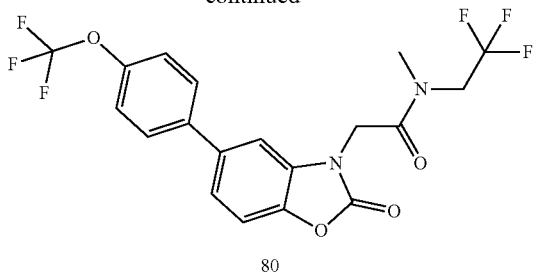

80

Synthesis of Compound 80:

To a solution of Compound 16 (100 mg, 0.28 mmol) in DMF (3 mL) was added HATU (161.46 mg, 0.42 mmol), DIPEA (109.76 mg, 0.85 mmol) and 2,2,2-trifluoro-N-methyl-ethanamine hydrochloride (50.8 mg, 0.34 mmol). The resulting mixture was stirred at 15° C. for 16 hours. Saturated NH$_4$Cl aqueous (20 mL) and EtOAc (20 mL) were added to the reaction solution. After separation, the organic layer was washed with brine (20 mL×2), dried over anhydrous Na$_2$SO$_4$, filtered and concentrated to give the crude product, which was purified by Prep-HPLC (Waters Xbridge (150 mm×25 mm, 5 μm) A=H$_2$O (10 mM NH$_4$HCO$_3$) and B=CH$_3$CN); 55-75% B over 10.5 minutes) to afford Compound 80 (55.77 mg, 0.12 mmol) as a solid $^1$H NMR (CDCl$_3$, 400 MHz) δ$_H$=7.74 (m, 2H), 7.65-7.40 (m, 5H), 5.00 (s, 1.6H), 4.91 (s, 0.4H), 4.47 (m, 0.4H), 4.19 (m, 1.6H), 3.25 (s, 2.4H), 2.96 (s, 0.6H). Note that rotamers were observed in the $^1$H NMR spectrum of this compound. LCMS R$_t$=1.25 min using Method A, MS ESI calcd. for C$_{19}$H$_{15}$F$_6$N$_2$O$_4$ [M+H]$^+$ 449.0931, found 449.0990.

Example 68. Synthesis of Compound 84

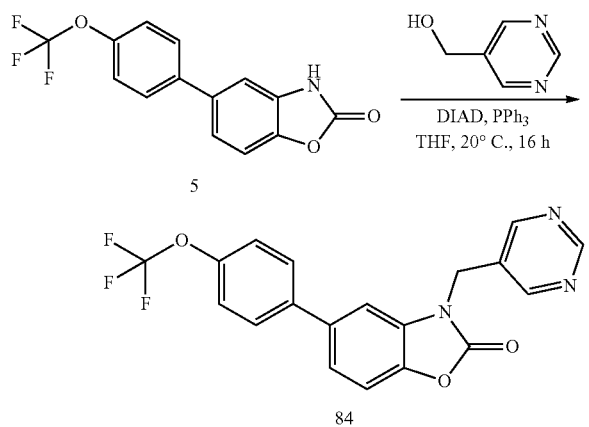

84

To the mixture of Compound 5 (150 mg, 0.51 mmol), DIAD (184.94 mg, 0.91 mmol) and pyrimidin-5-ylmethanol (100.71 mg, 0.91 mmol) in THF (5 mL) was added PPh$_3$ (239.89 mg, 0.91 mmol) and the mixture was stirred at 20° C. for 16 hours under N$_2$. The mixture was concentrated, the residue was diluted with NH$_4$Cl (20 mL) extracted with EtOAc (20 mL×2). The combined organic phase was washed with brine (10 mL), dried over Na$_2$SO$_4$, filtered, and concentrated to give a residue that was purified by Prep-HPLC (Waters Xbridge (150 mm×25 mm, 5 μm) A=H$_2$O (10 mM NH$_4$HCO$_3$) and B=CH$_3$CN); 40-70% B over 10 minutes) to afford Compound 84 as a solid. $^1$H NMR (DMSO-d$_6$ 400 MHz) δ$_H$=9.14 (s, 1H), 8.92 (s, 2H), 7.81-7.74 (m, 3H), 7.51-7.44 (m, 4H), 5.19 (s, 2H). LCMS R$_t$=1.19 min using Method A, MS ESI calcd. for C$_{19}$H$_{13}$F$_3$N$_3$O$_3$ [M+H]$^+$ 388.1, found 388.0.

Example 69. Synthesis of Compound 85

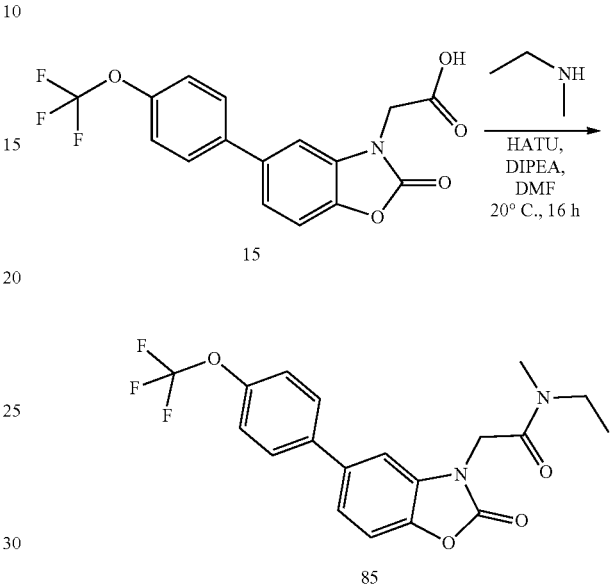

85

To the a mixture of Compound 15 (100 mg, 0.28 mmol), HATU (161.46 mg, 0.42 mmol) and DIPEA (73.17 mg, 0.57 mmol) in DMF (2 mL) was added N-methylethanamine (20.08 mg, 0.34 mmol) and the mixture was stirred at 20° C. for 16 hours. The mixture was diluted with sat. NH$_4$Cl (10 mL), extracted with EtOAc (10 mL×2), and the combined organic phase was washed with brine (10 mL), dried over Na$_2$SO$_4$, and filtered. The filtrate was concentrated to give a residue that was purified by Prep-HPLC Xtimate C18 (250 mm×50 mm, 10 μm) A=H$_2$O (10 mM NH$_3$HCO$_3$) and B=CH$_3$CN); 50-70% B over 7 minutes) to afford Compound 85 (25.86 mg 0.0656 mmol) as a solid. $^1$H NMR (DMSO-d$_6$+D$_2$O 400 MHz) δ$_H$=7.72 (d, 2H), 7.52-7.35 (m, 5H), 4.79 (d, 2H), 3.40 (d, 0.9H), 3.28 (d, 1H), 3.03 (s, 1.7H), 2.79 (s, 1.3H), 1.18 (t, 1.3H), 0.98 (t, 1.7H). Note that rotamers were observed in the $^1$H NMR spectrum of this compound. LCMS R$_t$=1.21 min using Method A, MS ESI calcd. for C$_{19}$H$_{18}$F$_3$N$_2$O$_4$ [M+H]$^+$ 395.1, found 395.0.

Example 70. Synthesis of Compound 86

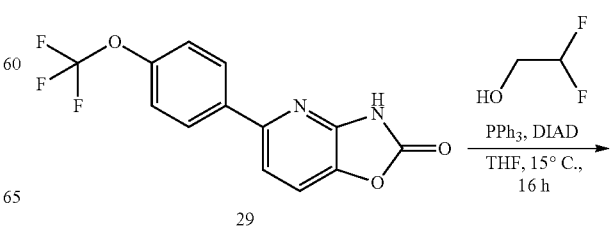

29

-continued

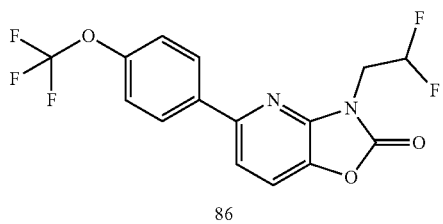

86

To a solution of Compound 29 (100 mg, 0.34 mmol) in THF (5 mL) was added 2,2-difluoroethanol (83.1 mg, 1.01 mmol), PPh$_3$ (177.1 mg, 0.68 mmol) and DIAD (136.54 mg, 0.68 mmol). The resulting mixture was stirred at 15° C. under N$_2$ for 16 hours. The reaction solution was concentrated to give a residue that was purified by flash chromatography on silica gel (EtOAc in PE=0% to 10% to 20%) to afford Compound 86 (77.26 mg, 0.21 mmol) as a solid. $^1$H NMR (CDCl$_3$, 400 MHz) $\delta_H$=8.03-7.97 (m, 2H), 7.53 (d, 2H), 7.33 (d, 2H), 6.30 (tt, 1H), 4.37 (dt, 2H). LCMS R$_t$=1.25 min using Method A, MS ESI calcd. for C$_{15}$H$_{10}$F$_5$N$_3$O$_3$ [M+H]$^+$ 361.1, found 361.0.

Example 71. Synthesis of Compound 87

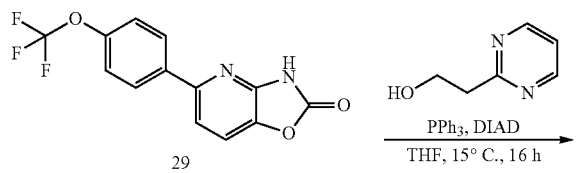

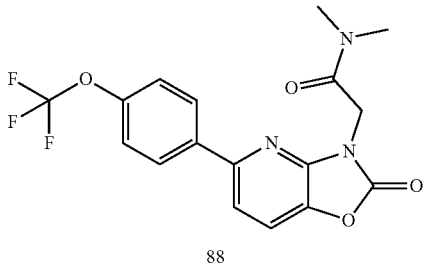

87

To a solution of Compound 29 (100 mg, 0.34 mmol) in THF (4 mL) was added 2-pyrimidin-2-ylethanol (125.73 mg, 1.01 mmol), PPh$_3$ (177.1 mg, 0.68 mmol) and DIAD (136.54 mg, 0.68 mmol). The resulting mixture was stirred at 15° C. under N$_2$ for 16 hours. The reaction solution was concentrated to give a residue that was purified by flash chromatography on silica gel (EtOAc in PE=0% to 10% to 20%) to afford Compound 87 (84.69 mg, 0.21 mmol) as a solid. $^1$H NMR (CDCl$_3$, 400 MHz) $\delta_H$=8.62 (d, 2H), 7.95 (d, 2H), 7.44 (s, 2H), 7.30 (d, 2H), 7.10 (t, 1H), 4.53 (t, 2H), 3.56 (t, 2H). LCMS R$_t$=1.20 min using Method A, MS ESI calcd. for C$_{19}$H$_{14}$F$_3$N$_4$O$_3$ [M+H]$^+$ 403.1, found 403.1.

Example 72. Synthesis of Compound 88

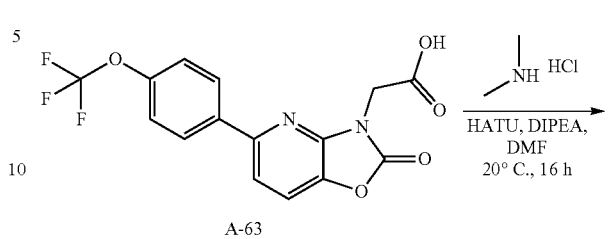

A-63

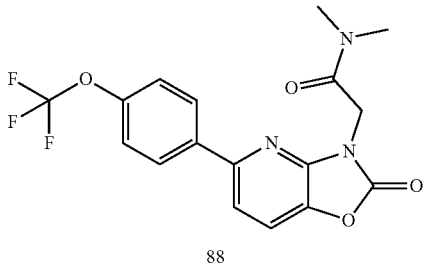

88

To a solution of A-62 (110 mg, 0.31 mmol) in DMF (3 mL) was added HATU (177.11 mg, 0.47 mmol), DIPEA (120.4 mg, 0.93 mmol), and then N-methylmethanamine hydrochloride (30.38 mg, 0.37 mmol). The resulting mixture was stirred at 20° C. for 16 hours. Saturated NH$_4$Cl aqueous (20 mL) and EtOAc (20 mL) was added to the reaction solution. After separation, the organic layer was washed with brine (20 mL×2), dried over anhydrous Na$_2$SO$_4$, filtered and concentrated to give a residue that was purified by Prep-HPLC (Waters Xbridge (150 mm×25 mm, 5 μm) A=H$_2$O (10 mM NH$_4$HCO$_3$) and B=CH$_3$CN); 47-67% B over 8 minutes) to afford Compound 88 (34.39 mg, 0.09 mmol) as a solid. $^1$H NMR (DMSO-d$_6$ 400 MHz) $\delta_H$=8.15 (d, 2H), 7.87 (d, 1H), 7.79 (d, 1H), 7.47 (d, 2H), 4.86 (s, 2H), 3.14 (s, 3H), 2.86 (s, 3H). LCMS R$_t$=1.16 min using Method A, MS ESI calcd. for C$_{17}$H$_{15}$F$_3$N$_3$O$_4$ [M+H]$^+$ 382.1, found 382.0.

Example 73. Synthesis of Compounds 89, 99, and 100

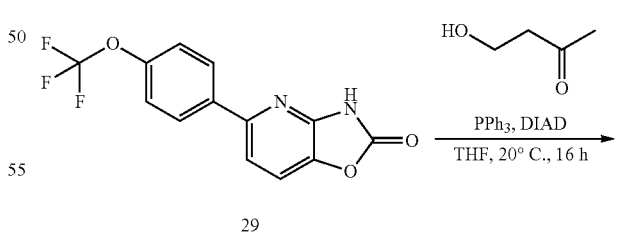

29

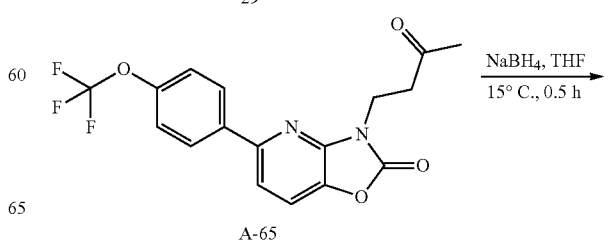

A-65

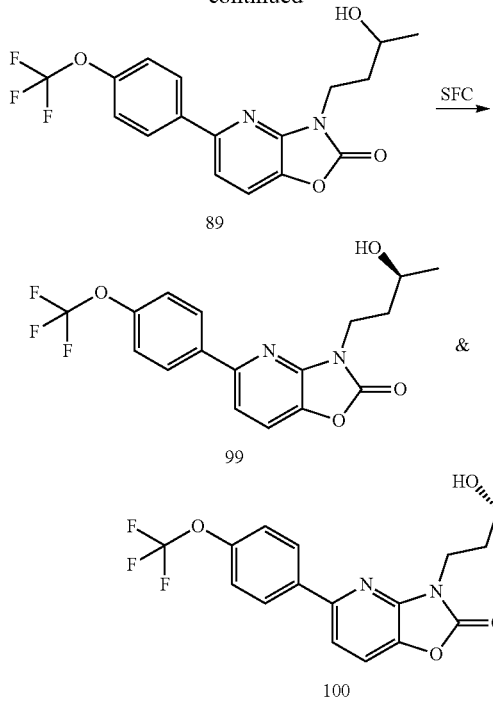

89

99

100

To a solution of 5-[4-(trifluoromethoxy)phenyl]-3H-oxazolo[4,5-b]pyridin-2-one (200 mg, 0.68 mmol) in THF (5 mL) was added PPh$_3$ (354.21 mg, 1.35 mmol), 4-hydroxybutan-2-one (178.48 mg, 2.03 mmol) and then DIAD (273.07 mg, 1.35 mmol). The resulting solution was stirred at 20° C. under N$_2$ for 16 hours to give a solution. The reaction solution was concentrated to give the crude product. The crude product was purified by flash chromatography on silica gel (EtOAc in PE=0% to 10% to 20%) to give the product (200 mg, 0.5231 mmol) as a solid. $^1$H NMR (CDCl$_3$ 400 MHz) S=8.00 (d, 2H), 7.47 (d, 2H), 7.32 (d, 2H), 4.28 (t, 2H), 3.11 (t, 2H), 2.23 (s, 3H). LCMS R$_t$=0.881 min in 1.5 min chromatography, MS ESI calcd. for C$_{17}$H$_{14}$F$_3$N$_2$O$_4$ [M+H]$^+$ 367.1, found 367.0.

To a solution of 3-(3-oxobutyl)-5-[4-(trifluoromethoxy)phenyl]oxazolo[4,5-b]pyridin-2-one (200 mg, 0.55 mmol) in THF (20 mL) was added NaBH$_4$ (41.31 mg, 1.09 mmol). The resulting mixture was stirred at 15° C. for 0.5 h to give a suspension. Saturated NH$_4$Cl aqueous (20 mL) and EtOAc (30 mL) was added to the reaction suspension. After separated, the organic layer was washed with brine (20 mL×2), dried over anhydrous Na$_2$SO$_4$, filtered and concentrated to give the crude product. The crude product was purified by flash chromatography on silica gel (EtOAc in PE=0% to 10% to 20%) to give the product.

The product was purified by SFC (AD (250 mm×30 mm, 5 μm; A=CO$_2$ and B=EtOH (0.1% NH$_3$H$_2$O); 38° C.; 50 mL/min; 20% B; 10 min run; 15 injections, R$_t$ of peak 1=8.0 min, R$_t$ of Peak 2=8.6 min) to give Compound 99 (3.02 mg, 0.0079 mmol) (Peak 1, Rt=3.250 min in SFC) as a solid and Compound 100 (10.09 mg, 0.0274 mmol) (Peak 2: Rt=3.381 min in SFC) as a solid. The stereochemistry of compound 99 and compound 100 was randomly assigned Compound 99

$^1$H NMR (CDCl$_3$, 400 MHz) δ=7.96 (d, 2H), 7.56-7.48 (m, 2H), 7.34 (d, 2H), 4.29-4.11 (m, 2H), 3.86-3.70 (m, 1H), 3.67-3.56 (m, 1H), 2.10-1.99 (m, 1H), 1.90-1.76 (m, 1H), 1.25 (d, 3H). LCMS R$_t$=1.201 min in 2.0 min chromatography, MS ESI calcd. for C$_{17}$H$_{16}$F$_3$N$_2$O$_4$ [M+H]$^+$ 369.1, found 369.0.

Compound 100

$^1$H NMR (CDCl$_3$, 400 MHz) δ=7.95 (d, 2H), 7.55-7.46 (m, 2H), 7.33 (d, 2H), 4.28-4.10 (m, 2H), 3.81-3.69 (m, 1H), 3.63-3.52 (m, 1H), 2.09-1.97 (m, 1H), 1.88-1.75 (m, 1H), 1.24 (d, 3H). LCMS R$_t$=1.226 min in 2.0 min chromatography, MS ESI calcd. for C$_{17}$H$_{16}$F$_3$N$_2$O$_4$ [M+H]$^+$ 369.1, found 369.0.

Example 74. Synthesis of Compound 90

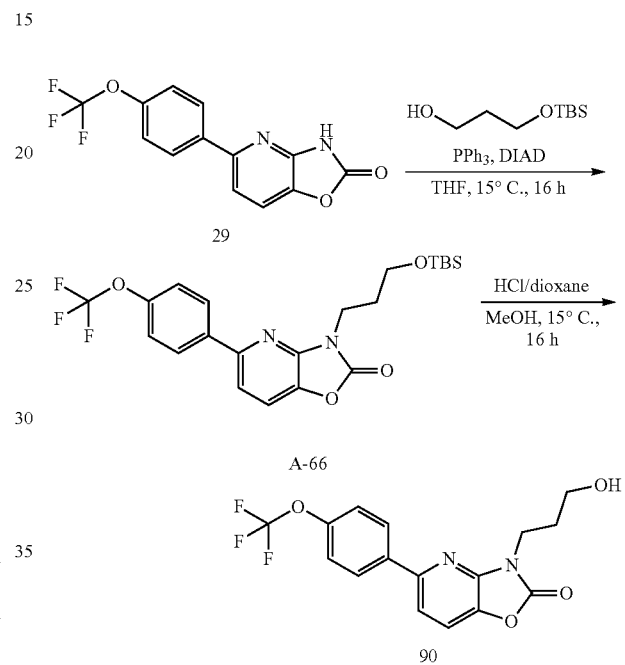

29

A-66

90

Synthesis of A-66:

To a solution of Compound 29 (150 mg, 0.51 mmol) in THF (4 mL) was added 3-[tert-butyl(dimethyl)silyl]oxypropan-1-ol (289.2 mg, 1.52 mmol), PPh$_3$ (265.65 mg, 1.01 mmol) and DIAD (204.8 mg, 1.01 mmol). The resulting mixture was stirred at 15° C. under N$_2$ for 16 hours. The reaction solution was concentrated to give a residue that was purified by flash chromatography on silica gel (EtOAc in PE=0% to 10% to 20%) to afford A-66 (180 mg, 0.38 mmol) as a solid. $^1$H NMR (CDCl$_3$, 400 MHz) δ$_H$=8.02 (d, 2H), 7.49-7.43 (m, 2H), 7.31 (d, 2H), 4.13 (t, 2H), 3.77 (t, 2H), 2.17-2.08 (m, 2H), 0.89 (s, 9H), 0.04 (s, 6H).

Synthesis of Compound 90:

To a solution of A-66 (40 mg, 0.09 mmol) in methanol (2 mL) was added HCl/dioxane (2 mL, 0.09 mmol). The resulting solution was stirred at 15° C. for 16 hours. The reaction was concentrated to give a residue that was purified by Prep-TLC (silica gel, PE:EtOAc=1:1) to afford Compound 90 (21.59 mg, 0.06 mmol) as a solid. $^1$H NMR (DMSO-d$_6$ 400 MHz) δ$_H$=8.17 (d, 2H), 7.83-7.74 (m, 2H), 7.49 (d, 2H), 4.58 (t, 1H), 3.96 (t, 2H), 3.52 (q, 2H), 1.97 (quin, 2H). LCMS R$_t$=1.16 min using Method A, MS ESI calcd. for C$_{16}$H$_{14}$F$_3$N$_2$O$_4$ [M+H]$^+$ 355.1, found 355.0.

Example 75. Synthesis of Compound 91

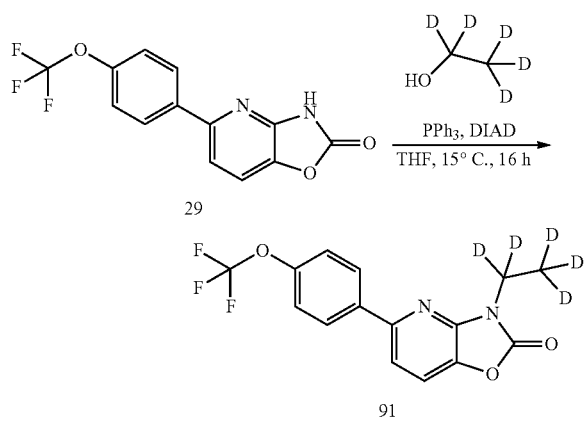

To a solution of Compound 29 (100 mg, 0.34 mmol) in THF (4 mL) was added 1,1,1,2,2-pentadeuterio-2-deuteriooxy-ethane (52.78 mg, 1.01 mmol), PPh₃ (177.1 mg, 0.68 mmol) and then DIAD (136.54 mg, 0.68 mmol). The resulting mixture was stirred at 15° C. under N₂ for 16 hours. The reaction solution was concentrated to give a residue that was purified by flash chromatography on silica gel (EtOAc in PE=0% to 10% to 20%) to afford Compound 91 (49.41 mg, 0.15 mmol) as a solid. ¹H NMR (DMSO-d₆ 400 MHz) $\delta_H$=8.18 (d, 2H), 7.84-7.74 (m, 2H), 7.49 (d, 2H). LCMS $R_t$=1.29 min using Method A, MS ESI calcd. for $C_{15}H_7D_5F_3N_3O_3$ [M+H]⁺ 330.1108, found 330.1104.

Example 76. Synthesis of Compound 92

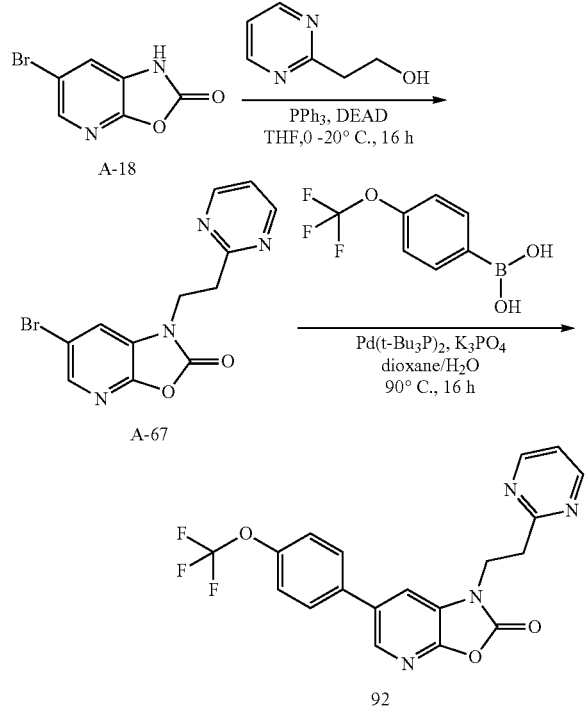

Synthesis of A-67:

To a mixture of A-18 (173.22 mg, 1.4 mmol) and PPh₃ (439.18 mg, 1.67 mmol) in THF (3 mL) under N₂ was added DEAD (291.6 mg, 1.67 mmol) drop-wise at 0° C. The reaction mixture was then stirred at 20° C. for 16 hours. The mixture was concentrated to give a residue that was purified by flash chromatography on silica gel (EtOAc in PE=0 to 50% to 100%) to afford A-67 (250 mg, 0.26 mmol) as a solid. LCMS $R_t$=0.67 min using Method B, MS ESI calcd. for $C_{12}H_{10}BrN_4O_2$ [M+H+2]⁺ 323.0, found 322.9.

Synthesis of Compound 92:

A mixture of A-67 (250 mg, 0.78 mmol), K₃PO₄ (330.55 mg, 1.56 mmol), [4-(trifluoromethoxy)phenyl]boronic acid (192.38 mg, 0.93 mmol) and Pd(t-Bu₃P)₂ (79.57 mg, 0.16 mmol) in 1,4-dioxane (5 mL) and water (1 mL) was stirred at 90° C. for 16 hours under N₂. After cooling, the mixture was filtered through silica gel and eluted with EtOAc (20 mL×2). The filtrate was concentrated and diluted with EtOAc (30 mL), washed with water (10 mL×2) and brine (10 mL), dried over Na₂SO₄, filtered and concentrated to give a residue that was purified by Prep-HPLC (Phenomenex Gemini (150 mm×25 mm, 10 μm); A=H₂O (0.05% NH₄OH) and B=CH₃CN); 53-63% B over 8 minutes) to afford Compound 92 (50.95 mg, 0.12 mmol) as a solid. ¹H NMR (CDCl₃, 400 MHz) $\delta_H$=8.65 (d, 2H), 8.17 (d, 1H), 7.54 (d, 2H), 7.40 (d, 1H), 7.35 (d, 2H), 7.17 (t, 1H), 4.44 (t, 2H), 3.50 (t, 2H). LCMS $R_t$=1.15 min using Method A, MS ESI calcd. for $C_{19}H_{14}F_3N_4O_3$ [M+H]⁺ 403.1, found 403.0.

Example 77. Synthesis of Compound 93

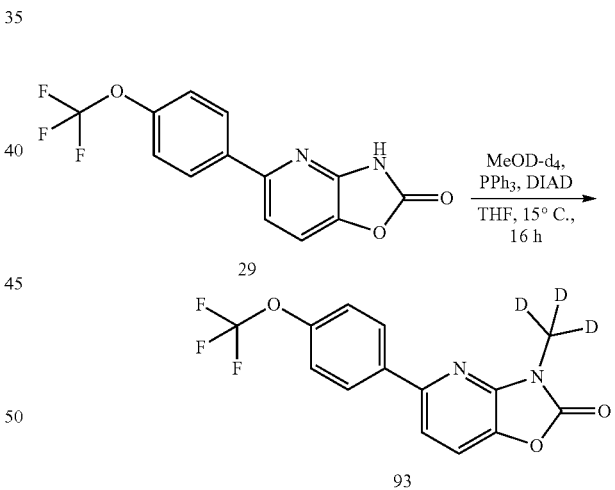

To a solution of Compound 29 (100 mg, 0.34 mmol) in THF (4 mL) was added trideuterio(deuteriooxy)-methane (36.53 mg, 1.01 mmol), PPh₃ (177.1 mg, 0.68 mmol) and then DIAD (136.54 mg, 0.68 mmol). The resulting mixture was stirred at 15° C. under N₂ for 16 hours. The reaction solution was concentrated to give a residue that was purified by flash chromatography on silica gel (EtOAc in PE=0% to 10% to 20%) to afford Compound 93 (68.88 mg, 0.22 mmol) as a solid. ¹H NMR (DMSO-d₆ 400 MHz) $\delta_H$=8.19 (d, 2H), 7.84-7.74 (m, 2H), 7.49 (d, 2H). LCMS $R_t$=1.23 min using Method A, MS ESI calcd. for $C_{14}H_7D_3F_3N_3O_3$ [M+H]⁺ 314.0826, found 314.0815.

Example 78. Synthesis of Compound 96

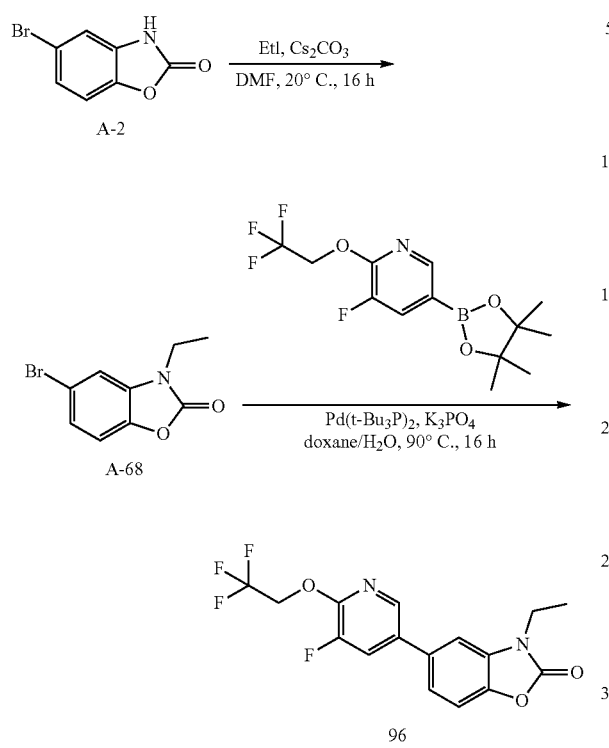

To the mixture of 5-bromo-3H-1,3-benzoxazol-2-one (300 mg, 1.4 mmol) and Cs$_2$CO$_3$ (913.37 mg, 2.8 mmol) in DMF (5 mL) was added iodoethane (437.26 mg, 2.8 mmol) and the mixture was stirred at 20° C. for 16 hours. The mixture was diluted with H$_2$O (20 mL), and the mixture was extracted with EtOAc (20 mL×2). The combined organic phase was washed with brine (10 mL), dried over Na$_2$SO$_4$, filtered and the filtrate was concentrated to give the crude product. The crude product was purified by flash chromatography on silica gel (EtOAc in PE=20% to 50%) to give the product of 5-bromo-3-ethyl-1,3-benzoxazol-2-one (220 mg, 0.908 mmol, 645% yield) as a solid. $^1$H NMR (CDCl$_3$, 400 MHz) δ=7.24 (dd, 1H), 7.13 (d, 1H), 7.08 (d, 1H), 3.87 (q, 2H), 1.39 (t, 3H).

A mixture of 5-bromo-3-ethyl-1,3-benzoxazol-2-one (200 mg, 0.83 mmol), 3-fluoro-5-(4,4,5,5-tetramethyl-1,3,2-dioxaborolan-2-yl)-2-(2,2,2-trifluoroethoxy)pyridine (397.92 mg, 1.24 mmol), K$_3$PO$_4$ (350.81 mg, 1.65 mmol), and Pd(t-Bu$_3$P)$_2$ (63.33 mg, 0.12 mmol) in 1,4-Dioxane (3 mL) and Water (0.3 mL) was stirred at 90° C. for 16 hours under N$_2$ to give a mixture. The mixture was cooled to r.t., diluted with EtOAc (20 mL), filtered through silica gel and eluted with EtOAc (20 mL). The filtrate was concentrated to give the crude product. The crude product was purified by Prep-HPLC (column: Waters Xbridge 150*25 5 u; mobile phase: [water (10 mM NH$_4$HCO$_3$)-ACN]; B %: 51%-81%, 7 min) to give the product (134.4 mg, 0.3712 mmol, 45% yield) as a solid. $^1$H NMR DMSO-d$_6$ 400 MHz δ=8.41 (d, 1H), 8.25 (dd, 1H), 7.74 (d, 1H), 7.54-7.41 (m, 2H), 5.14 (q, 2H), 3.91 (q, 2H), 1.30 (t, 3H). LCMS R$_t$=1.254 min in 2.0 min chromatography, MS ESI calcd. for C$_{16}$H$_{13}$F$_4$N$_3$O$_3$ [M+H]$^+$ 357.1, found 357.0.

Example 79. Synthesis of Compound 97 and Compound 98

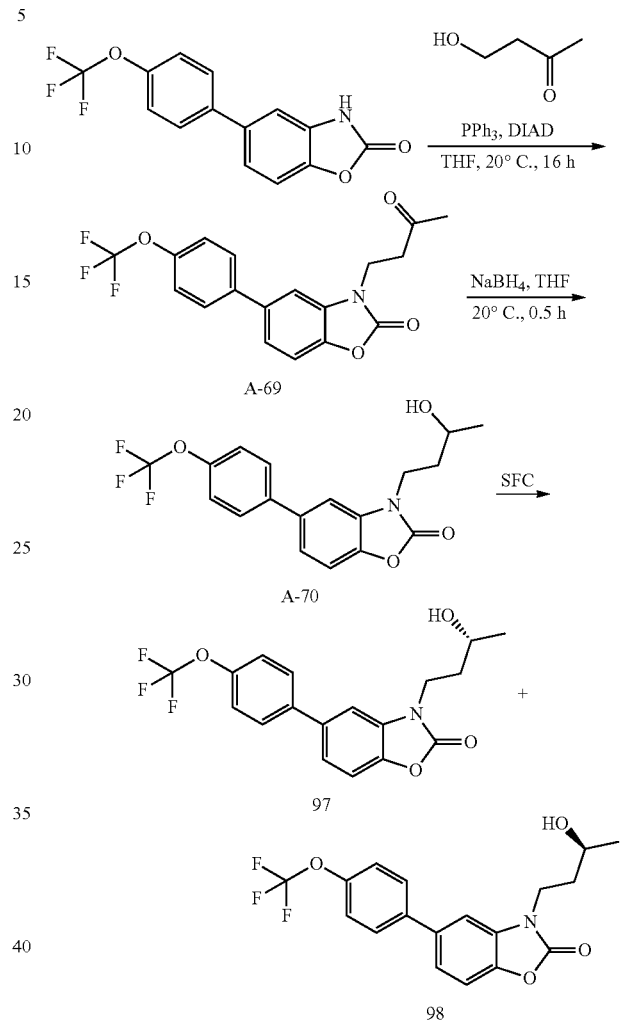

To a solution of 5-[4-(trifluoromethoxy)phenyl]-3H-1,3-benzoxazol-2-one (400 mg, 1.35 mmol) in THF (5 mL) was added PPh$_3$ (710.79 mg, 2.71 mmol), and 4-hydroxybutan-2-one (358.16 mg, 4.06 mmol), then DIAD (547.98 mg, 2.71 mmol). The resulting solution was stirred at 20° C. under N$_2$ for 16 hours to give a solution. The mixture was diluted with H$_2$O (20 mL), and the mixture was extracted with EtOAc (20 mL×2). The combined organic phase was washed with brine (10 mL), dried over Na$_2$SO$_4$, filtered and concentrated to give the crude product. The crude product was purified by Prep-HPLC (column: Waters Xbridge 150*25 5 u, mobile phase: water (10 mM NH$_4$HCO$_3$)-CAN, B %: 55%-75%, 7 min) to give the product (150 mg, 0.410 mmol, 30% yield) as a solid. $^1$H NMR DMSO-d$_6$ 400 MHz δ=7.82 (d, 2H), 7.69 (s, 1H), 7.47 (d, 2H), 7.42 (s, 2H), 4.04 (t, 2H), 3.00 (t, 2H), 2.13 (s, 3H).

To a solution of 3-(3-oxobutyl)-5-[4-(trifluoromethoxy)phenyl]-1,3-benzoxazol-2-one (150 mg, 0.41 mmol) in methanol (2 mL) was added NaBH$_4$ (31.07 mg, 0.82 mmol). The resulting mixture was stirred at 20° C. for 0.5 h to give a suspension. Saturated NH$_4$Cl aqueous (10 mL) and EtOAc (10 mL) was added to the reaction suspension. After separation, the organic layer was washed with brine (5 mL×2), dried over anhydrous Na$_2$SO$_4$, filtered and concentrated to give the product (120 mg).

The product was purified by SFC (AD (250 mm×30 mm, 5 μm), A=CO$_2$ and B=EtOH (0.1% NH$_3$H$_2$O); 38° C.; 50 mL/min; 20% B; 9 min run; 12 injections, R$_t$ of peak 1=6.7 min, R$_t$ of Peak 2=7.8 min) to give compound 97 (29.78 mg, 0.0811 mmol) (Peak1, R$_t$=3.090 min in SFC) as oil and compound 98 (31.57 mg, 0.086 mmol) (Peak2, R$_t$=3.301 min in SFC) as oil.

Compound 97

$^1$H NMR DMSO-d$_6$ 400 MHz δ=7.81 (d, 2H), 7.60 (s, 1H), 7.47 (d, 2H), 7.42 (s, 2H), 4.63 (d, 1H), 3.98-3.89 (m, 2H), 3.71-3.64 (m, 1H), 1.85-1.66 (m, 2H), 1.10 (d, 3H). LCMS R$_t$=1.228 min in 2.0 min chromatography, MS ESI calcd. for C$_{18}$H$_{17}$F$_3$NO$_4$ [M+H]$^+$ 368.1, found 368.0.

Compound 98

$^1$H NMR DMSO-d$_6$ 400 MHz δ=7.81 (d, 2H), 7.60 (s, 1H), 7.47 (d, 2H), 7.42 (s, 2H), 4.64 (d, 1H), 3.97-3.91 (m, 2H), 3.70-3.64 (m, 1H), 1.84-1.67 (m, 2H), 1.10 (d, 3H). LCMS R$_t$=1.230 min in 2.0 min chromatography, MS ESI calcd. for C$_{18}$H$_{17}$F$_3$NO$_4$ [M+H]$^+$ 368.1, found 368.0.

Example 80. Synthesis of Compound 101

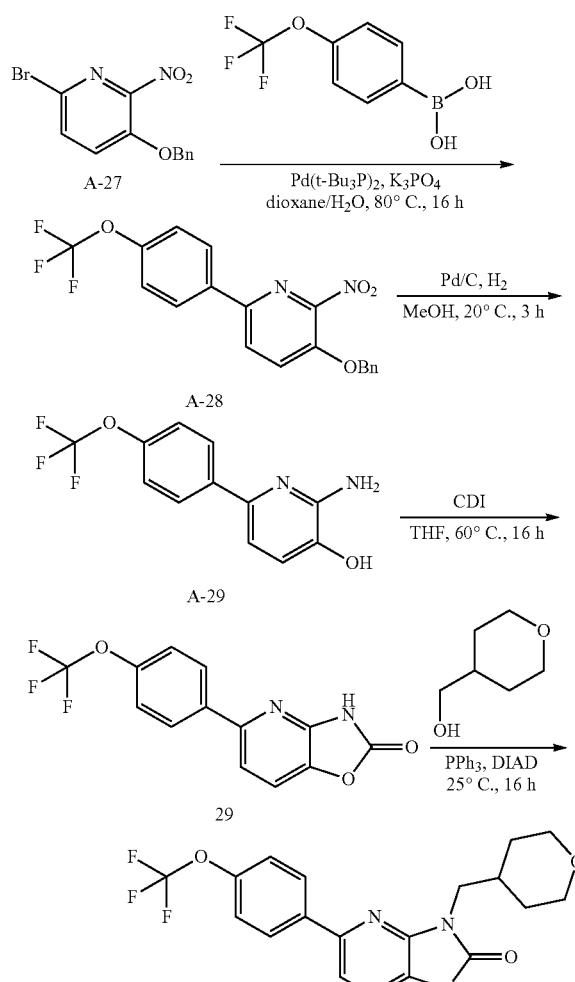

A mixture of 3-benzyloxy-6-bromo-2-nitro-pyridine (1.9 g, 6.15 mmol), [4-(trifluoromethoxy)phenyl]boronic acid (1.52 g, 7.38 mmol), K$_3$PO$_4$ (2.61 g, 12.29 mmol) and Pd(t-Bu$_3$P)$_2$ (471.17 mg, 0.92 mmol) in 1,4-Dioxane (20 mL) and Water (2 mL) was stirred at 80° C. under N$_2$ for 16 hours to give a suspension. The reaction mixture was cooled to room temperature and filtered through Celite. The filtrate was concentrated to give the crude product. The crude product was purified by flash chromatography on silica gel (EtOAc in PE=0% to 10% to 20%) to give the product (1000 mg, 2.56 mmol, 42% yield) as a solid. $^1$H NMR (DMSO-d$_6$ 400 MHz) δ$_H$=8.36 (d, 1H), 8.17-8.07 (m, 3H), 7.53-7.31 (m, 7H), 5.42 (s, 2H).

To a solution of 3-benzyloxy-2-nitro-6-[4-(trifluoromethoxy)phenyl]pyridine (1 g, 2.56 mmol) in Methanol (50 mL) was added Pd/C (200 mg, 1.89 mmol). The resulting mixture was stirred at 20° C. under molecular hydrogen (512.36 mg, 253.64 mmol) (15 psi) for 3 hours to give a black suspension. The reaction mixture was filtered through Celite. The filtrate was concentrated to give the crude product (690 mg, 2.55 mmol,) as a solid. $^1$H NMR (DMSO-d$_6$ 400 MHz) δ11=7.98 (d, 2H), 7.35 (d, 2H), 7.01 (d, 1H), 6.91 (d, 1H), 5.59 (s, 2H).

To a solution of 2-amino-6-[4-(trifluoromethoxy)phenyl]pyridin-3-ol (690 mg, 2.55 mmol) in THF (30 mL) was added di(imidazol-1-yl)methanone (496.87 mg, 3.06 mmol). The resulting mixture was stirred at 60° C. for 16 hours to give a solution. The reaction mixture was cooled to room temperature and concentrated to give the crude product. The crude product was purified by flash chromatography on silica gel (EtOAc in PE=20% to 40% to 50%) to give the product of 5-[4-(trifluoromethoxy)phenyl]-3H-oxazolo[4,5-b]pyridin-2-one (700 mg, 2.3633 mmol, 92.548% yield) as a solid. $^1$H NMR DMSO-d$_6$ 400 MHz δ$_H$=12.55 (br s, 1H), 8.10 (d, 2H), 7.78-7.66 (m, 2H), 7.46 (d, 2H).

To a solution of 5-[4-(trifluoromethoxy)phenyl]-3H-oxazolo[4,5-b]pyridin-2-one (100 mg, 0.34 mmol) in THF (5 mL) was added tetrahydropyran-4-ylmethanol (117.65 mg, 1.01 mmol), PPh$_3$ (177.1 mg, 0.68 mmol) and then DIAD (136.54 mg, 0.68 mmol). The resulting mixture was stirred at 25° C. under N$_2$ for 16 hours to give a solution. The reaction solution was concentrated to give the crude product. The crude product was purified by flash chromatography on silica gel (EtOAc in PE=0% to 10% to 20%) to give the product (42.79 mg, 0.11 mmol,) as a solid. $^1$H NMR (CDCl$_3$, 400 MHz) δ$_H$=8.00 (d, 2H), 7.48 (s, 2H), 7.33 (d, 2H), 4.00 (dd, 2H), 3.92 (d, 2H), 3.40 (t, 2H), 2.35-2.23 (m, 1H), 1.71-1.63 (m, 2H), 1.56-1.48 (m, 2H). LCMS R$_t$=1.28 min in 2.0 min chromatography, MS ESI calcd. for C$_{19}$H$_{18}$F$_3$N$_2$O$_4$ [M+H]$^+$ 395.1, found 395.0.

Example 81. Synthesis of Compound 102

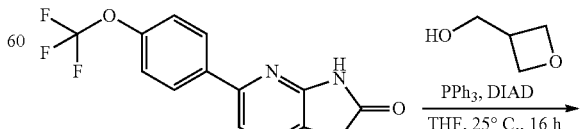

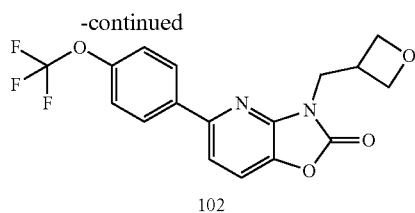

102

To a solution of 5-[4-(trifluoromethoxy)phenyl]-3H-oxazolo[4,5-b]pyridin-2-one (100 mg, 0.34 mmol) in THF (5 mL) was added oxetan-3-ylmethanol (89.24 mg, 1.01 mmol), PPh₃ (177.1 mg, 0.68 mmol) and then DIAD (136.54 mg, 0.68 mmol). The resulting mixture was stirred at 25° C. under N₂ for 16 hours to give a solution. The reaction solution was concentrated to give the crude product. The crude product was purified by flash chromatography on silica gel (EtOAc in PE=0% to 10% to 20%) to give the product (84.3 mg, 0.23 mmol, 68% yield) as a solid. ¹H NMR (CDCl₃, 400 MHz) $\delta_H$=7.99 (d, 2H), 7.49 (s, 2H), 7.33 (d, 2H), 4.90-4.84 (m, 2H), 4.71 (t, 2H), 4.34 (d, 2H), 3.66-3.54 (m, 1H). LCMS $R_t$=1.22 min in 2.0 min chromatography, MS ESI calcd. for $C_{17}H_{14}F_3N_2O_4$ [M+H]⁺ 367.1, found 367.0.

Example 82. Synthesis of Compound 103

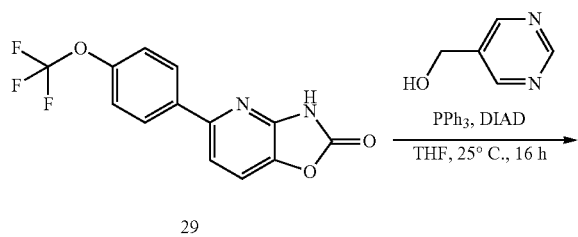

103

To a solution of 5-[4-(trifluoromethoxy)phenyl]-3H-oxazolo[4,5-b]pyridin-2-one (100 mg, 0.34 mmol) in THF (5 mL) was added pyrimidin-5-ylmethanol (111.52 mg, 1.01 mmol), PPh₃ (177.1 mg, 0.68 mmol) and then DIAD (136.54 mg, 0.68 mmol). The resulting mixture was stirred at 25° C. under N₂ for 16 hours to give a solution. The reaction solution was concentrated to give the crude product. The crude product was purified by flash chromatography on silica gel (EtOAc in PE=0% to 10% to 20%) to give the product (98.9 mg, 0.25 mmol, 75% yield) as a solid. ¹H NMR DMSO-d₆ 400 MHz $\delta_H$=9.14 (s, 1H), 8.96 (s, 2H), 8.16 (d, 2H), 7.85-7.78 (m, 2H), 7.48 (d, 2H), 5.17 (s, 2H). LCMS $R_t$=1.17 min in 2.0 min chromatography, MS ESI calcd. for $C_{18}H_{12}F_3N_4O_3$ [M+H]⁺ 389.1, found 389.0.

Example 83. Synthesis of Compound 104

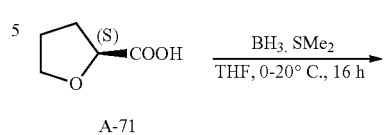

A-71

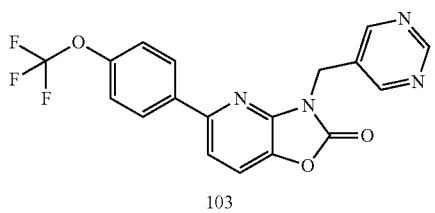

104

To a solution of (2S)-tetrahydrofuran-2-carboxylic acid (2 g, 17.22 mmol) in THF (3 mL) was added the BH₃.SMe₂ (2.58 mL, 25.84 mmol) at 0° C., then the mixture was stirred at 20° C. for 16 hours to give a colorless solution. 2N NaOH (10 mL) was added to the mixture slowly at 0° C. Then the mixture was extracted with EtOAc (20 mL×2). The combined organic phase was washed with brine (10 mL), dried over Na₂SO₄, filtered and concentrated to give the crude product (400 mg, 3.92 mmol, 23% yield) as colorless oil. ¹H NMR CDCl₃, 400 MHz $\delta_H$=4.06-3.99 (m, 1H), 3.92-3.84 (m, 1H), 3.83-3.75 (m, 1H), 3.73-3.62 (m, 1H), 3.57-3.45 (m, 1H), 2.13-2.05 (m, 1H), 1.98-1.87 (m, 3H), 1.70-1.59 (m, 1H).

To the mixture of 5-[4-(trifluoromethoxy)phenyl]-3H-1,3-benzoxazol-2-one (100.00 mg, 0.34 mmol), [(2S)-tetrahydrofuran-2-yl]methanol (103.79 mg, 1.02 mmol) and PPh₃ (177.70 mg, 0.68 mmol) in THF (5.00 mL) was added the DIAD (136.99 mg, 0.68 mmol) at 0° C. and the mixture was stirred under N₂ at 20° C. for 16 hours to give a mixture. The mixture was diluted with H₂O (20 mL), extracted with EtOAc (20 mL×2). The combined organic phase was washed with brine (10 mL), dried over Na₂SO₄, filtered and the filtrate was concentrated to give the crude product. The crude product was purified by Prep-HPLC (Waters Xbridge (150 mm×25 mm, 5 □m), A=H₂O (10 mM NH₄HCO₃) and B=CH₃CN; 60-90% B over 6.6 minutes) to give the product (40.86 mg, 0.11 mmol, 32% yield) as oil.

Note: the Specific rotation was +19.79 (c=1, CHCl₃, 27.5° C.). ¹H NMR DMSO-d₆ 400 MHz $\delta_H$=7.80 (d, 2H), 7.66 (s, 1H), 7.47 (d, 2H), 7.43 (s, 2H), 4.30-4.20 (m, 1H), 3.97-3.87 (m, 2H), 3.78-3.70 (m, 1H), 3.66-3.59 (m, 1H), 2.08-1.75 (m, 3H), 1.71-1.59 (m, 1H). LCMS $R_t$=1.48 min in 2.0 min chromatography, MS ESI calcd. for $C_{19}H_{17}F_3NO_4$ [M+H]⁺ 380.1, found 380.1.

Example 84. Synthesis of Compound 105

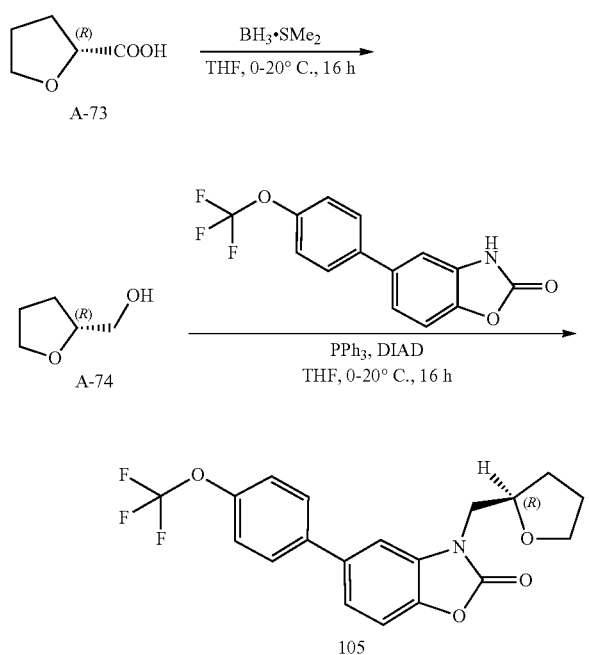

Example 85. Synthesis of Compounds 53, 106, and 107

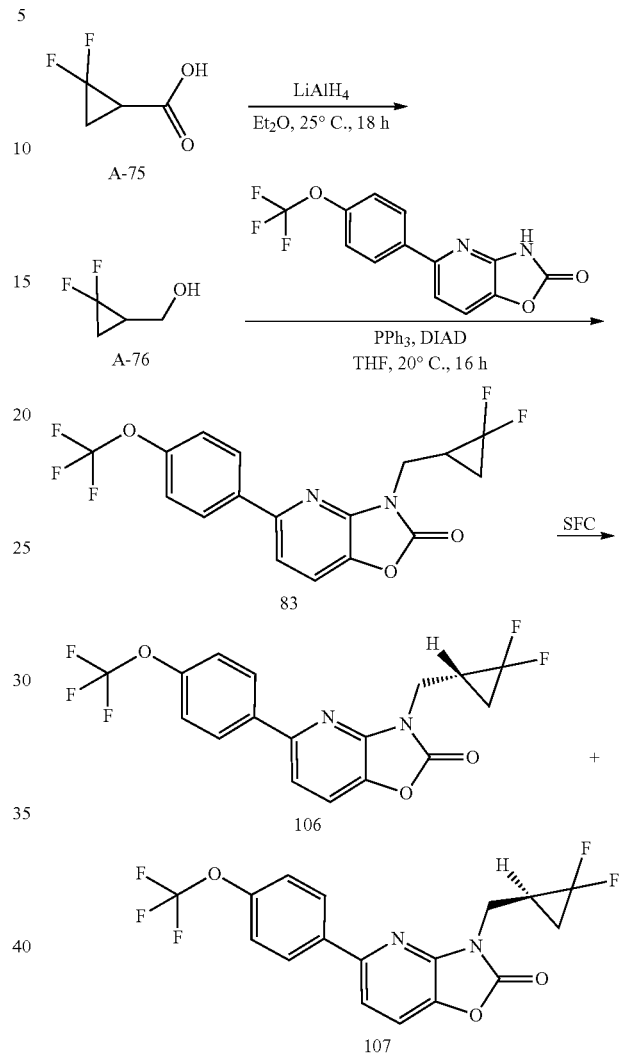

To a solution of (2R)-tetrahydrofuran-2-carboxylic acid (2 g, 17.22 mmol) in THF (20 mL) was added the BH$_3$.SMe$_2$ (2.58 mL, 25.84 mmol) at 0° C., then the mixture was stirred at 20° C. for 16 hours to give the colorless solution. 2N NaOH (10 mL) was added to the mixture slowly at 0° C. Then the mixture was extracted with EtOAc (20 mL×2). The combined organic phase was washed with brine (10 mL), dried over Na$_2$SO$_4$, filtered and concentrated to give the crude product (450.00 mg, 4.41 mmol, 26% yield) as colorless oil. $^1$H NMR (CDCl$_3$, 400 MHz) $\delta_H$=4.07-3.97 (m, 1H), 3.94-3.85 (m, 1H), 3.84-3.76 (m, 1H), 3.72-3.63 (m, 1H), 3.55-3.46 (m, 1H), 2.02-1.87 (m, 4H), 1.72-1.65 (m, 1H).

To the mixture of 5-[4-(trifluoromethoxy)phenyl]-3H-1,3-benzoxazol-2-one (150.00 mg, 0.51 mmol), [(2R)-tetrahydrofuran-2-yl]methanol (155.68 mg, 1.52 mmol) and PPh$_3$ (266.55 mg, 1.02 mmol) in THF (5 mL) was added the DIAD (205.49 mg, 1.02 mmol) at 0° C. and the mixture was stirred under N$_2$ at 20° C. for 16 hours to give the mixture. The mixture was diluted with H$_2$O (20 mL), and the mixture was extracted with EtOAc (20 mL×2). The combined organic phase was washed with brine (10 mL), dried over Na$_2$SO$_4$, filtered and the filtrate was concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 56-86% B over 6 minutes) to give the product (28.34 mg, 0.07 mmol, 15% yield) as oil.

Note: the Specific rotation was −14.51 (c=1, CHCl$_3$, 27.7° C.). $^1$H NMR DMSO-d$_6$ 400 MHz $\delta_H$=7.80 (d, 2H), 7.66 (s, 1H), 7.47 (d, 2H), 7.43 (s, 2H), 4.29-4.21 (m, 1H), 3.98-3.87 (m, 2H), 3.79-3.71 (m, 1H), 3.67-3.58 (m, 1H), 2.08-1.74 (m, 3H), 1.70-1.60 (m, 1H). LCMS R$_t$=1.35 min in 2.0 min chromatography, MS ESI calcd. for C$_{19}$H$_{17}$F$_3$NO$_4$ [M+H]$^+$ 380.1, found 379.8.

To a solution of 2,2-difluorocyclopropanecarboxylic acid (1 g, 8.19 mmol) in Ether (30 mL) was added LiAlH$_4$ (466.33 mg, 12.29 mmol) slowly at 0° C. over 10 mins. After the addition, the resulting colorless suspension was allowed to warm to 25° C., and stirred for a further 18 hours to give a suspension. The reaction mixture was then cooled in an ice-bath, and then 2M NaOH (1 mL) was added in a dropwise manner to quench the reaction, followed by H$_2$O (1 mL). The mixture was filtered, and rinsed with Et$_2$O (10 mL×2). The filtrate was concentrated to give a residue. Then the residue was re-dissolved in DCM (20 mL), dried over anhydrous MgSO$_4$ and filtered. The filtrate was concentrated at 5-10° C. to give the crude product (800 mg, 7.40 mmol, 90% yield) as oil. $^1$H NMR (CDCl$_3$, 400 MHz) δ=3.82-3.74 (m, 1H), 3.71-3.63 (m, 1H), 1.98-1.76 (m, 1H), 1.53-1.41 (m, 1H), 1.22-1.11 (m, 1H).

To a solution of (2,2-difluorocyclopropyl)methanol (232 mg, 2.15 mmol) and 5-[4-(trifluoromethoxy)phenyl]-3H-oxazolo[4,5-b]pyridin-2-one (200 mg, 0.68 mmol) in THF (4 mL) was added PPh$_3$ (354.21 mg, 1.35 mmol) and DIAD (273.07 mg, 1.35 mmol). The resulting mixture was stirred at 20° C. under N₂ for 16 hours to give a solution. The reaction solution was concentrated to give the crude product. The crude product was purified by flash chromatography on silica gel (EtOAc in PE=0% to 10% to 20%) to give compound 53 (150 mg) as a solid.

Compound 53

¹H NMR (CDCl₃+D₂O 400 MHz) $\delta_H$=8.00 (d, 2H), 7.51 (s, 2H), 7.33 (d, 2H), 4.31-4.22 (m, 1H), 4.09-4.00 (m, 1H), 2.35-2.21 (m, 1H), 1.61 (m, 2H). LCMS $R_t$=1.31 min using Method A, MS ESI calcd. for $C_{17}H_{12}F_5N_3O_3$ [M+H]⁺ 387.1, found 387.0.

The product was purified by SFC (Column: OJ (250 mm×30 mm, 5 μm); A=CO₂ and B=Neu-ETOH; 35° C.; 50 mL/min; 20% B; 10 min run; 13 injections, $R_t$ of Peak 1=7.7 min, $R_t$ of Peak 2=8.5 min) to give the compound 106 (24.52 mg, 0.06 mmol) (Peak 1, $R_t$=2.749 min in SFC) as a solid and compound 107 (Peak 2, $R_t$=2.959 min in SFC) (~80 mg, ee %=80%).

The impure compound 107 was purified again by SFC (Column: OJ (250 mm×30 mm, 5 μm); A=CO₂ and B=0.1% NH₃H₂O ETOH; 35° C.; 50 mL/min; 25% B; 9 min run; 8 injections, $R_t$ of Peak 1=7.17 min, $R_t$ of Peak 2=7.8 min) to give the product of 3-[[(1S)-2,2-difluorocyclopropyl]methyl]-5-[4-(trifluoromethoxy)phenyl]oxazolo[4,5-b]pyridin-2-one (39.28 mg, 0.10 mmol, 14.95% yield, 99.29% purity) (Peak 2, $R_t$=2.959 min in SFC) as a solid.

Compound 106:

¹H NMR CDCl₃+D₂O 400 MHz δ=8.00 (d, 2H), 7.51 (s, 2H), 7.33 (d, 2H), 4.26 (dd, 1H), 4.04 (dd, 1H), 2.36-2.20 (m, 1H), 1.62-1.46 (m, 2H). LCMS $R_t$=1.27 min in 2.0 min chromatography, MS ESI calcd. for $C_{17}H_{12}F_5N_3O_3$ [M+H]⁺ 387.1, found 387.0.

Compound 107:

¹H NMR CDCl₃+D₂O 400 MHz δ=8.00 (d, 2H), 7.51 (s, 2H), 7.33 (d, 2H), 4.26 (dd, 1H), 4.04 (dd, 1H), 2.36-2.19 (m, 1H), 1.62-1.46 (m, 2H). LCMS $R_t$=1.32 min in 2.0 min chromatography, MS ESI calcd. for $C_{17}H_{12}F_5N_3O_3$ [M+H]⁺ 387.1, found 387.0.

Example 86. Synthesis of Compound 108

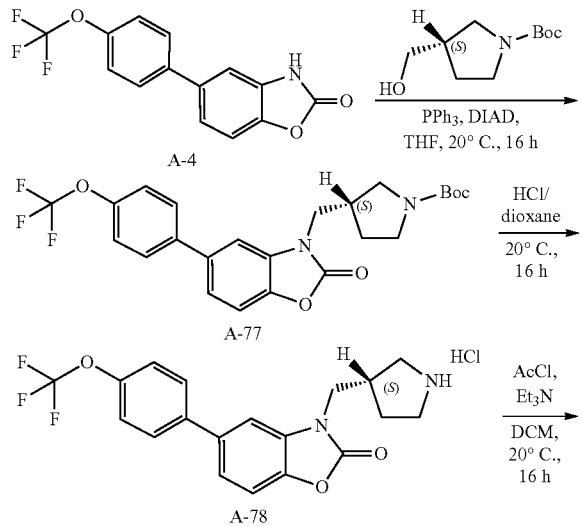

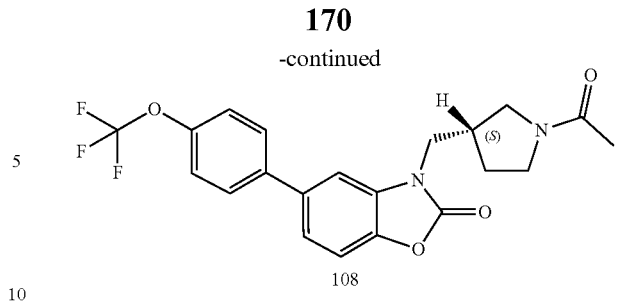

A mixture of 5-[4-(trifluoromethoxy)phenyl]-3H-1,3-benzoxazol-2-one (300 mg, 1.02 mmol), tert-butyl (3S)-3-(hydroxymethyl)pyrrolidine-1-carboxylate (409.05 mg, 2.03 mmol), PPh₃ (533.09 mg, 2.03 mmol) and DIAD (410.98 mg, 2.03 mmol) in THF (20 mL) was stirred at 20° C. under N₂ for 16 hours. The mixture was concentrated and purified by flash chromatography on silica gel (EtOAc in PE=10% to 25%) to afford the product (430 mg, 0.90 mmol, 88% yield) as an oil. LCMS $R_t$=0.95 min in 1.5 min chromatography, MS ESI calcd. for $C_{24}H_{25}F_3N_2O_5Na$ [M+Na]⁺ 501.2, found 501.2.

A mixture of tert-butyl(3S)-3-[[2-oxo-5-[4-(trifluoromethoxy)phenyl]-1,3-benzoxazol-3-yl]methyl]pyrrolidine-1-carboxylate (430 mg, 0.90 mmol) in 4 M HCl/dioxane (10 mL, 0.90 mmol) was stirred at 20° C. for 16 hours. The mixture was concentrated to afford the crude product (400 mg, 0.96 mmol) as oil. LCMS $R_t$=0.75 min in 1.5 min chromatography, MS ESI calcd. for $C_{19}H_{18}F_3N_3O_3$ [M+H]⁺ 379.1, found 379.0.

A mixture of 3-[[(3S)-pyrrolidin-3-yl]methyl]-5-[4-(trifluoromethoxy)phenyl]-1,3-benzoxazol-2-one hydrochloride (100 mg, 0.24 mmol), acetyl chloride (37.85 mg, 0.48 mmol) and Et₃N (0.17 mL, 1.21 mmol) in CH₂Cl₂ (20 mL) was stirred at 20° C. for 16 h. The reaction mixture was concentrated and purified by prep-HPLC (Waters Xbridge (150 mm×25 mm, 5 μm), A=H₂O (10 mM NH₄HCO₃) and B=CH₃CN; 45-75% B over 6 minutes) to give the product (35.75 mg, 0.09 mmol, 35% yield, 100%) as a solid. ¹H NMR (MeOD-d₄ 400 MHz) $\delta_H$=7.74 (d, 2H), 7.51 (dd, 1H), 7.46-7.40 (m, 1H), 7.39-7.32 (m, 3H), 3.99 (dd, 2H), 3.75-3.33 (m, 4H), 2.97-2.78 (m, 1H), 2.23-2.08 (m, 1H), 2.06-2.01 (m, 3H), 1.98-1.75 (m, 1H). LCMS $R_t$=1.19 min in 2.0 min chromatography, MS ESI calcd. for $C_{21}H_{20}F_3N_2O_4$ [M+H]⁺ 421.1, found 421.1.

Example 87. Synthesis of Compound 109

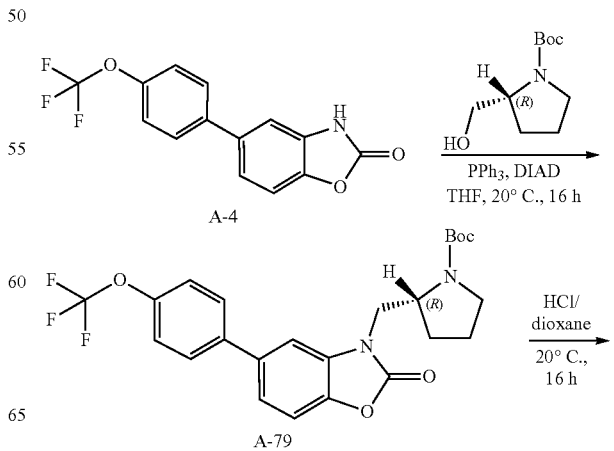

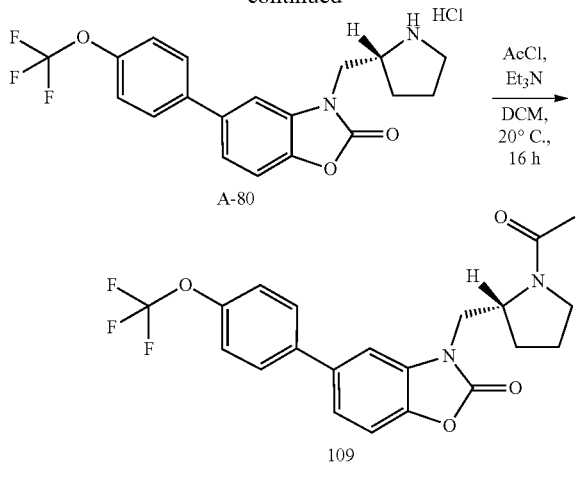

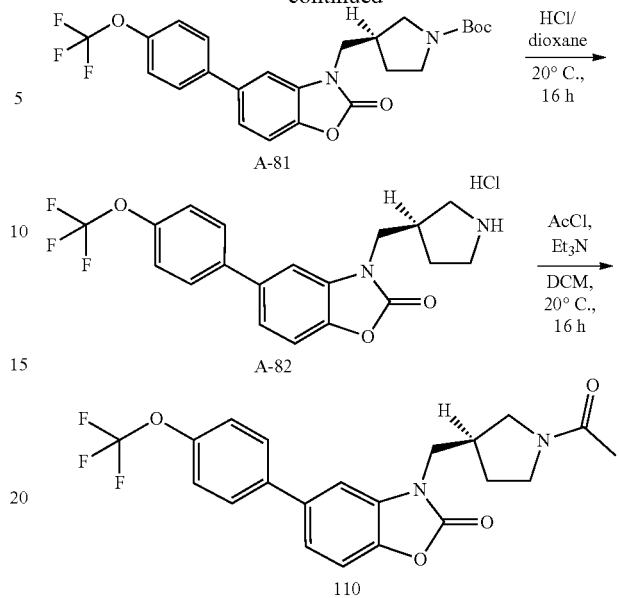

A mixture of 5-[4-(trifluoromethoxy)phenyl]-3H-1,3-benzoxazol-2-one (300 mg, 1.02 mmol), tert-butyl (2R)-2-(hydroxymethyl)pyrrolidine-1-carboxylate (409.05 mg, 2.03 mmol), PPh$_3$ (533.09 mg, 2.03 mmol) and DIAD (410.98 mg, 2.03 mmol) in THF (20 mL) was stirred at 20° C. under N$_2$ for 16 hours. The mixture was concentrated and purified by flash chromatography on silica gel (EtOAc in PE=10% to 25%) to afford the product (330 mg, 0.69 mmol, 68% yield) as an oil. LCMS R$_t$=1.16 min in 1.5 min chromatography, MS ESI calcd. for C$_{24}$H$_{25}$F$_3$N$_2$O$_5$Na [M+Na]$^+$ 501.2, found 501.2.

A mixture of tert-butyl(2R)-2-[[2-oxo-5-[4-(trifluoromethoxy)phenyl]-1,3-benzoxazol-3-yl]methyl]pyrrolidine-1-carboxylate (330 mg, 0.69 mmol) in 4M HCl/dioxane (10 mL, 0.69 mmol) was stirred at 20° C. for 16 hours. The mixture was concentrated to give the product (280 mg, 0.67 mmol, 98% yield) as a solid. LCMS R$_t$=0.76 min in 1.5 min chromatography, MS ESI calcd. for C$_{19}$H$_{18}$F$_3$N$_3$O$_3$ [M+H]$^+$ 379.1, found 379.0.

A mixture of 3-[[(2R)-pyrrolidin-2-yl]methyl]-5-[4-(trifluoromethoxy)phenyl]-1,3-benzoxazol-2-one hydrochloride (100 mg, 0.24 mmol), acetyl chloride (37.85 mg, 0.48 mmol) and Et$_3$N (0.17 mL, 1.21 mmol) in DCM (25 mL) was stirred at 20° C. for 16 hours. The mixture was concentrated and purified by Prep-HPLC (Waters Xbridge (150 mm×25 mm, 5 μm), A=H$_2$O (10 mM NH$_4$HCO$_3$) and B=CH$_3$CN; 47-77% B over 6 minutes) to give the product (47.32 mg, 0.11 mmol, 46% yield) as a solid. $^1$H NMR (MeOD, 400 MHz) δ$_H$=7.79-7.66 (m, 3H), 7.45-7.30 (m, 4H), 4.57-4.47 (m, 1H), 4.08-3.93 (m, 2H), 3.65-3.56 (m, 1H), 3.54-3.45 (m, 1H), 2.18-1.94 (m, 7H). LCMS R$_t$=1.23 min in 2.0 min chromatography, MS ESI calcd. for C$_{21}$H$_{20}$F$_3$N$_2$O$_4$ [M+H]$^+$ 421.1, found 421.1.

Example 88. Synthesis of Compound 110

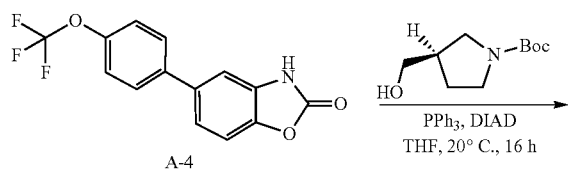

A mixture of 5-[4-(trifluoromethoxy)phenyl]-3H-1,3-benzoxazol-2-one (300 mg, 1.02 mmol), tert-butyl (3R)-3-(hydroxymethyl)pyrrolidine-1-carboxylate (409.05 mg, 2.03 mmol), PPh$_3$ (533.09 mg, 2.03 mmol) and DIAD (410.98 mg, 2.03 mmol) in THF (20 mL) was stirred at 20° C. under N$_2$ for 16 hours. The reaction was diluted with sat.NH$_4$Cl (20 mL), and the mixture was extracted with EtOAc (10 mL×2). The combined organic phase was washed with brine (10 mL), dried over Na$_2$SO$_4$, filtered and concentrated to give the crude product. The crude product was purified by flash chromatography on silica gel (EtOAc in PE=10% to 25%) to give the impure product (600 mg, 1.25 mmol) as oil. LCMS R$_t$=0.96 min in 1.5 min chromatography, MS ESI calcd. for C$_{24}$H$_{25}$F$_3$N$_2$O$_5$Na [M+Na]$^+$ 501.2, found 501.1.

A mixture of tert-butyl (3R)-3-[[2-oxo-5-[4-(trifluoromethoxy)phenyl]-1,3-benzoxazol-3-yl]methyl]pyrrolidine-1-carboxylate (600 mg, 1.25 mmol) in 4M HCl/dioxane (10 mL) was stirred at 20° C. for 16 hours. The mixture was concentrated to give the crude product (600 mg, 1.45 mmol) as oil. The product was used directly without any further purification. LCMS R$_t$=0.75 min in 1.5 min chromatography, MS ESI calcd. for C$_{19}$H$_{18}$F$_3$N$_3$O$_3$ [M+H]$^+$ 379.1, found 379.0.

A mixture of 3-[[(3R)-pyrrolidin-3-yl]methyl]-5-[4-(trifluoromethoxy)phenyl]-1,3-benzoxazol-2-one hydrochloride (100 mg, 0.24 mmol), acetyl chloride (37.85 mg, 0.48 mmol) and Et$_3$N (0.17 mL, 1.21 mmol) in DCM (20 mL) was stirred at 20° C. for 16 hours to give a mixture. From LCMS, desired MS was observed, and no starting material was remained. The reaction was diluted with sat.NH$_4$Cl (20 mL), and the mixture was extracted with DCM (15 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm 5 μm), A=H$_2$O (10 mM NH$_4$HCO$_3$) and B=CH$_3$CN, 45%-55% B over 8 minutes) to give the impure product. The impure product was purified by Prep-TLC (silica gel, PE:EtOAc=1: 1) to give the product (11.95 mg, 0.03 mmol, 12% yield) as a solid. $^1$H NMR DMSO-d$_6$ 400 MHz δ$_H$=7.74 (d, 2H), 7.53-7.48 (m, 1H), 7.45-7.40 (m, 1H), 7.39-7.31 (m, 3H), 3.98 (dd, 2H), 3.73-3.32 (m, 4H), 2.97-2.79 (m, 1H), 2.19-2.07 (m, 1H), 2.05-2.00 (m, 3H), 1.96-1.77 (m, 1H). LCMS $R_t$=1.22 min in 2 min chromatography, MS ESI calcd. for $C_{21}H_{20}F_3N_2O_4$ [M+H]$^+$ 421.1, found 421.1.

Example 89. Synthesis of Compound 111

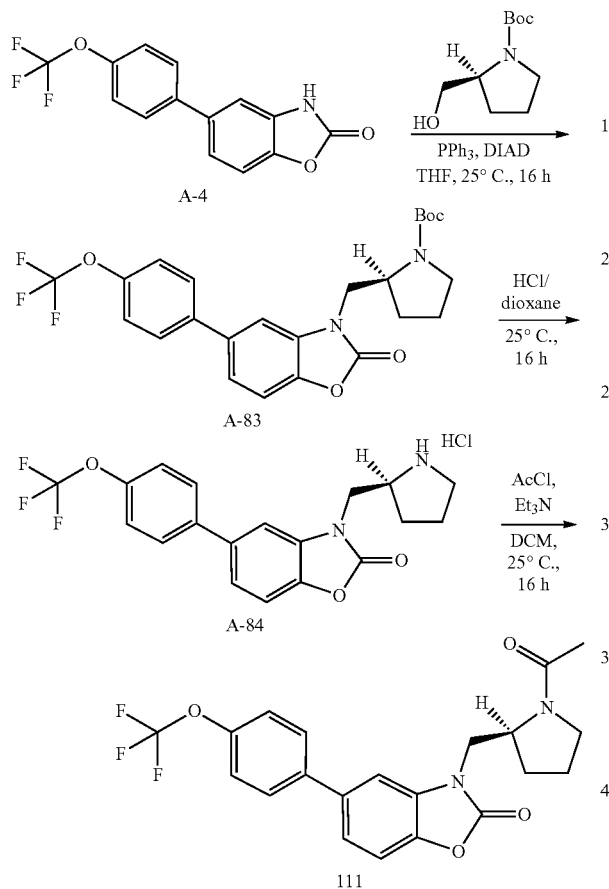

A mixture of 5-[4-(trifluoromethoxy)phenyl]-3H-1,3-benzoxazol-2-one (300 mg, 1.02 mmol), tert-butyl (2S)-2-(hydroxymethyl)pyrrolidine-1-carboxylate (409.05 mg, 2.03 mmol), PPh$_3$ (533.09 mg, 2.03 mmol) and DIAD (410.98 mg, 2.03 mmol) in THF (20 mL) was stirred at 25° C. under N$_2$ for 16 hours. The reaction was quenched with sat.NH$_4$Cl (20 mL), and the mixture was extracted with EtOAc (10 mL×2). The combined organic phase was washed with brine (10 mL), dried over Na$_2$SO$_4$, filtered and concentrated to give the crude product. The crude product was purified by flash chromatography on silica gel (EtOAc in PE=10% to 25%) to afford the crude product (400 mg, 0.84 mmol, 83% yield) as oil. $^1$H NMR (CDCl$_3$, 400 MHz) $\delta_H$=7.62-7.39 (m, 3H), 7.22-6.98 (m, 4H), 4.25-4.15 (m, 1H), 3.98-3.79 (m, 2H), 3.43-3.18 (m, 2H), 1.95-1.77 (m, 4H), 1.30 (s, 9H).

A mixture of tert-butyl(2S)-2-[[2-oxo-5-[4-(trifluoromethoxy)phenyl]-1,3-benzoxazol-3-yl]methyl]pyrrolidine-1-carboxylate (400 mg, 0.84 mmol) in 4 M HCl/dioxane (10 mL) was stirred at 25° C. for 16 hours. The mixture was concentrated to afford the crude product (300 mg, 0.68 mmol, 82% yield) as oil. LCMS $R_t$=0.75 min in 1.5 min chromatography, MS ESI calcd. for $C_{19}H_{18}F_3N_3O_3$ [M+H]$^+$ 379.1, found 379.0.

A mixture of 3-[[(2S)-pyrrolidin-2-yl]methyl]-5-[4-(trifluoromethoxy)phenyl]-1,3-benzoxazol-2-one hydrochloride (100 mg, 0.24 mmol), acetyl chloride (37.85 mg, 0.48 mmol) and Et$_3$N (0.17 mL, 1.21 mmol) in CH$_2$Cl$_2$ (20 mL) was stirred at 25° C. for 16 hours to give a solution. The reaction was quenched with sat.NH$_4$Cl (20 mL), and the mixture was extracted with CH$_2$Cl$_2$ (10 mL×2). The combined organic phase was washed with brine (10 mL), dried over Na$_2$SO$_4$, filtered and concentrated to give the crude product. The crude product was purified by flash chromatography on silica gel (EtOAc in PE=30% to 80%) to give impure product. The impure product was purified by Prep-HPLC (Waters Xbridge (150 mm×25 mm, 5 µm), A=H$_2$O (10 mM NH$_4$HCO$_3$), and B=CH$_3$CN; 47-77% B over 6 minutes) to give the product (12.41 mg, 0.03 mmol, 12% yield) as a solid. $^1$H NMR MeOD-d$_4$ 400 MHz $\delta_H$=7.79-7.67 (m, 3H), 7.47-7.30 (m, 4H), 4.57-4.46 (m, 1H), 4.08-3.91 (m, 2H), 3.64-3.44 (m, 2H), 2.20-1.93 (m, 7H). LCMS $R_t$=1.25 min in 2.0 min chromatography, MS ESI calcd. for $C_{21}H_{20}F_3N_2O_4$ [M+H]$^+$ 421.1, found 421.1.

Example 90. Synthesis of Compound 112

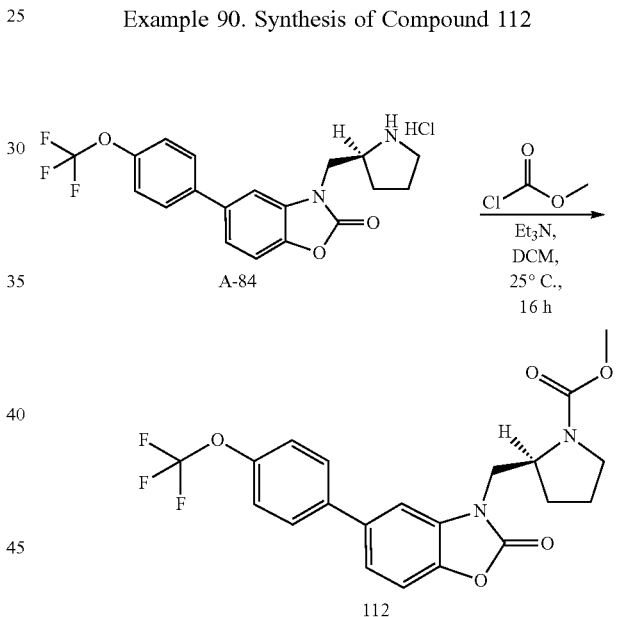

A mixture of 3-[[(2S)-pyrrolidin-2-yl]methyl]-5-[4-(trifluoromethoxy)phenyl]-1,3-benzoxazol-2-one hydrochloride (100 mg, 0.24 mmol), Et$_3$N (0.17 mL, 1.21 mmol) and methyl carbonochloridate (45.56 mg, 0.48 mmol) in CH$_2$Cl$_2$ (10 mL) was stirred at 25° C. for 16 hours. The reaction was quenched with sat NH$_4$Cl (10 mL), and the mixture was extracted with CH$_2$Cl$_2$ (10 mL×2). The combined organic phase was washed with brine (10 mL), dried over Na$_2$SO$_4$, filtered and concentrated to give the crude product. The crude product was purified by prep-HPLC (Waters Xbridge (150 mm×25 mm, 5 µm), A=H$_2$O (10 mM NH$_4$HCO$_3$) and B=CH$_3$CN; 57-77% B over 6 minutes) to give the product (71.61 mg, 0.16 mmol, 68% yield) as a solid. $^1$H NMR DMSO-d$_6$+D$_2$O 400 MHz $\delta_H$=7.80-7.71 (m, 2H), 7.59-7.38 (m, 5H), 4.30-4.17 (m, 1H), 3.99-3.83 (m, 2H), 3.40-3.17 (m, 5H), 2.02-1.73 (m, 4H). LCMS $R_t$=1.30 min in 2.0 min chromatography, MS ESI calcd. for $C_{21}H_{20}F_3N_2O_5$ [M+H]$^+$ 437.1, found 437.0.

Example 91. Synthesis of Compound 113

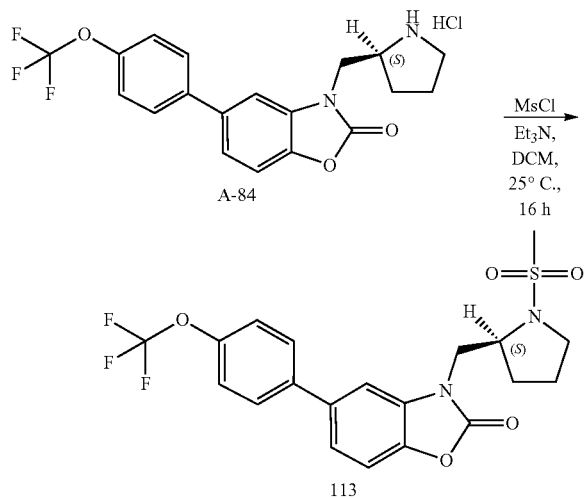

A mixture of 3-[[(2S)-pyrrolidin-2-yl]methyl]-5-[4-(trifluoromethoxy)phenyl]-1,3-benzoxazol-2-one hydrochloride (100 mg, 0.24 mmol), Et₃N (0.17 mL, 1.21 mmol) and methanesulfonyl chloride (55.23 mg, 0.48 mmol) in CH₂Cl₂ (10 mL) was stirred at 25° C. for 16 hours. The reaction was quenched with sat.NH₄Cl (10 mL), and the mixture was extracted with CH₂Cl₂ (10 mL×2). The combined organic phase was washed with brine (10 mL), dried over Na₂SO₄, filtered and concentrated to give the crude product. The crude product was purified by Prep-HPLC (Waters Xbridge (150 mm×25 mm, 5 μm), A=H₂O (10 mM NH₄HCO₃) and B=CH₃CN; 55-75% B over 6 minutes) to give the product (47.27 mg, 0.10 mmol, 43% yield) as a solid. ¹H NMR DMSO-d₆+D₂O 400 MHz $\delta_H$=7.78 (d, 2H), 7.61 (s, 1H), 7.48-7.38 (m, 4H), 4.13-4.07 (m, 1H), 3.97-3.86 (m, 2H), 3.31-3.20 (m, 2H), 2.86 (s, 3H), 2.05-1.79 (m, 4H). LCMS R$_t$=1.26 min in 2.0 min chromatography, MS ESI calcd. for C₂₀H₂₀F₃N₂O₅S [M+H]⁺ 457.1, found 457.0.

Example 92. Synthesis of Compound 114

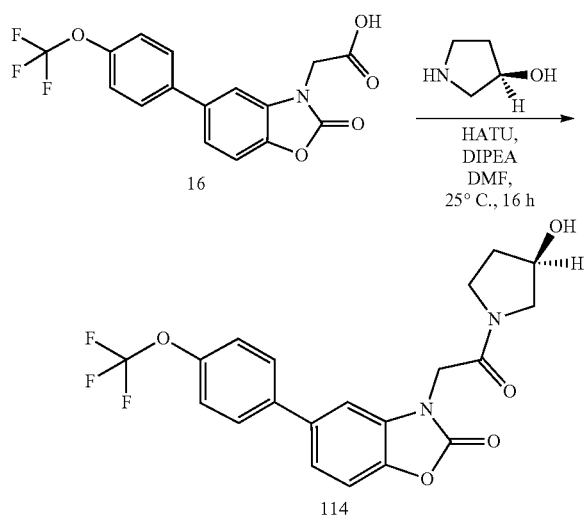

To the mixture of 2-[2-oxo-5-[4-(trifluoromethoxy)phenyl]-1,3-benzoxazol-3-yl]acetic acid (500 mg, 1.42 mmol), (3R)-pyrrolidin-3-ol (184.97 mg, 2.12 mmol) and HATU (1.61 g, 4.25 mmol) in DMF (10 mL) was added the DIPEA (0.74 mL, 4.25 mmol). And the mixture was stirred at 25° C. for 16 hours. The mixture was diluted with H₂O (10 mL), and the mixture was extracted with EtOAc (20 mL×2). The combined organic phase was washed with brine (10 mL), dried over Na₂SO₄ and filtered. The filtrate was concentrated to give the crude product. The crude product was purified by flash chromatography on silica gel (EtOAc in PE=20% to 50% to 100%) to give the impure product (300 mg, ~50% yield) as a solid.

A part of the impure product (100 mg) was triturated from i-Pr₂O (2 mL) to give the product (55 mg, 0.13 mmol, 55% yield) as a solid. ¹H NMR DMSO-d₆+D₂O 400 MHz $\delta_H$=7.72 (d, 2H), 7.49-7.37 (m, 5H), 4.79-4.61 (m, 2H), 4.43-4.25 (m, 1H), 3.69-3.23 (m, 4H), 2.09-1.70 (m, 2H). LCMS R$_t$=1.17 min in 2.0 min chromatography, MS ESI calcd. for C₂₀H₁₈F₃N₂O₅ [M+H]⁺ 423.1, found 423.1.

Example 93. Synthesis of Compound 115

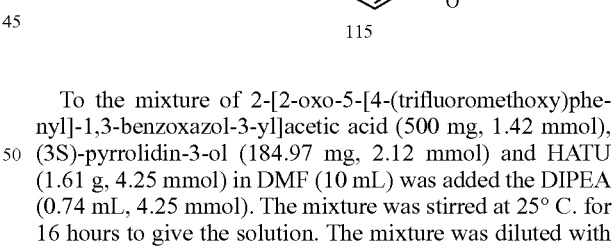

To the mixture of 2-[2-oxo-5-[4-(trifluoromethoxy)phenyl]-1,3-benzoxazol-3-yl]acetic acid (500 mg, 1.42 mmol), (3S)-pyrrolidin-3-ol (184.97 mg, 2.12 mmol) and HATU (1.61 g, 4.25 mmol) in DMF (10 mL) was added the DIPEA (0.74 mL, 4.25 mmol). The mixture was stirred at 25° C. for 16 hours to give the solution. The mixture was diluted with H₂O (20 mL), and the mixture was extracted with EtOAc (20 mL×2). The combined organic phase was washed with brine (10 mL), dried over Na₂SO₄, filtered and concentrated to give the crude product. The crude product was purified by flash chromatography on silica gel (EtOAc in PE=20% to 50% to 100%) to give the impure product (300 mg, ~50% yield) as a solid.

The impure product (100 mg) was purified by Prep-HPLC (Xtimate C18 (150 mm×25 mm 5 μm), A=H₂O (10 mM NH₄HCO₃) and B=CH₃CN; 35-65% B over 9 minutes) to give the product (43.95 mg, 0.10 mmol, 44% yield) as a solid. ¹H NMR DMSO-d₆+D₂O 400 MHz $\delta_H$=7.72 (d, 2H), 7.54-7.34 (m, 5H), 4.80-4.60 (m, 2H), 4.41-4.26 (m, 1H), 3.71-3.24 (m, 4H), 2.07-1.72 (m, 2H). LCMS R$_t$=1.22 min in 2.0 min chromatography, MS ESI calcd. for $C_{20}H_{18}F_3N_2O_5$ [M+H]$^+$ 423.1, found 423.1.

Example 94. Synthesis of Compound 116

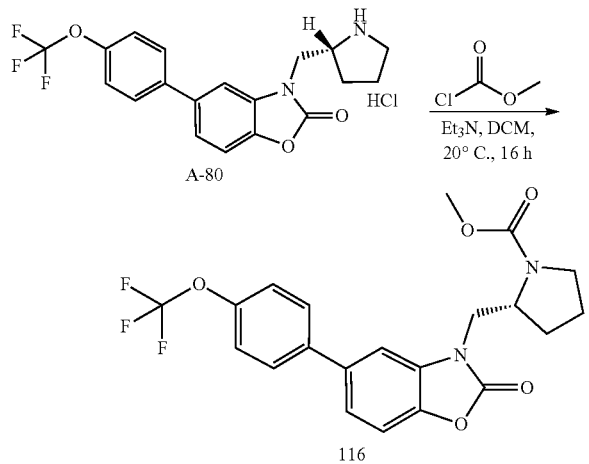

116

A mixture of 3-[[2R)-pyrrolidin-2-yl]methyl]-5-[4-(trifluoromethoxy)phenyl]-1,3-benzoxazol-2-one hydrochloride (90 mg, 0.22 mmol), Et$_3$N (0.15 mL, 1.08 mmol) and methyl carbonochloridate (41.01 mg, 0.43 mmol) in DCM (25 mL) was stirred at 20° C. for 16 hours. The reaction was diluted with sat.NH$_4$Cl (15 mL), extracted with DCM (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 59-79% B over 6 minutes) to give the product (38.68 mg, 0.09 mmol, 41% yield) as a solid. $^1$H NMR DMSO-d$_6$+D$_2$O 400 MHz $\delta_H$=7.81-7.70 (m, 2H), 7.55-7.34 (m, 5H), 4.29-4.16 (m, 1H), 3.97-3.85 (m, 2H), 3.41-3.13 (m, 5H), 2.02-1.70 (m, 4H). LCMS R$_f$=1.30 min in 2 min chromatography, MS ESI calcd. for $C_{21}H_{20}F_3N_2O_5$ [M+H]$^+$ 437.1, found 437.1.

Example 95. Synthesis of Compound 117

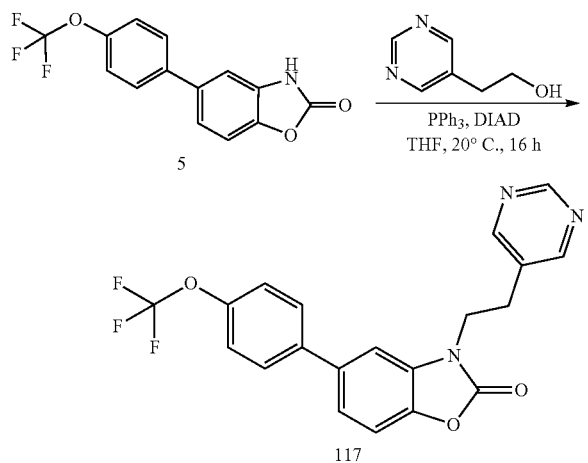

117

To a mixture of 5-[4-(trifluoromethoxy)phenyl]-3H-1,3-benzoxazol-2-one (100 mg, 0.34 mmol), 2-pyrimidin-5-ylethanol (126.15 mg, 1.02 mmol) and PPh$_3$ (177.7 mg, 0.68 mmol) in THF (6 mL) was added DIAD (136.99 mg, 0.68 mmol) and the mixture was stirred under N$_2$ at 20° C. for 16 hours to give a mixture. The mixture was concentrated to dryness, diluted with H$_2$O (10 mL), and extracted with EtOAc (10 mL×2). The combined organic phase was washed with brine (10 mL), dried over Na$_2$SO$_4$, filtered. And the filtrate was concentrated to give the crude product. The crude product was purified by Prep-HPLC (Kromasil (150 mm×25 mm, 10 μm), A=H$_2$O (0.05% NH$_3$H$_2$O) and B=CH$_3$CN; 48-78% B over 7 minutes) to give the product (49.53 mg, 123.4 μmol, 36% yield) as a solid. $^1$H NMR DMSO-d$_6$ 400 MHz $\delta_H$=9.02 (s, 1H), 8.73 (s, 2H), 7.78 (d, 2H), 7.60 (s, 1H), 7.48 (d, 2H), 7.42 (s, 2H), 4.20 (t, 2H), 3.11 (t, 2H). LCMS R$_f$=1.17 min in 2 min chromatography, MS ESI calcd. for $C_{20}H_{15}F_3N_3O_3$ [M+H]$^+$ 402.1, found 402.1.

Example 96. Synthesis of Compound 118

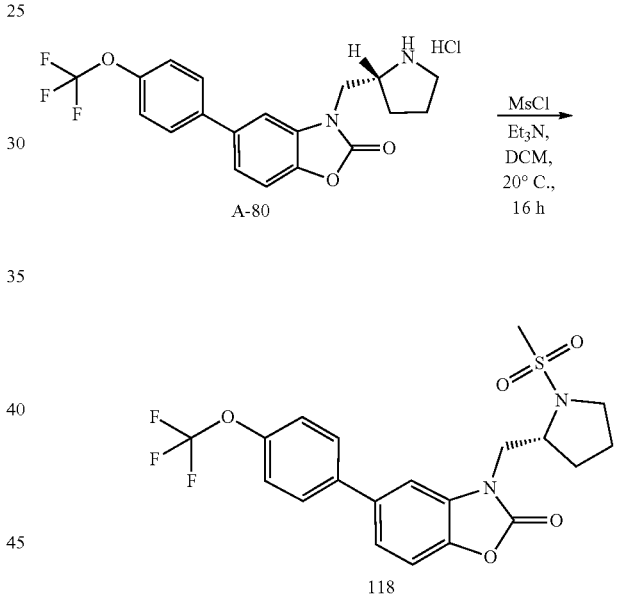

118

A mixture of 3-[[(2R)-pyrrolidin-2-yl]methyl]-5-[4-(trifluoromethoxy)phenyl]-1,3-benzoxazol-2-one hydrochloride (100 mg, 0.24 mmol), Et$_3$N (0.17 mL, 1.21 mmol) and methanesulfonyl chloride (55.23 mg, 0.48 mmol) in DCM (25 mL) was stirred at 20° C. for 16 hours. The reaction was diluted with sat.NH$_4$Cl (15 mL), and extracted with DCM (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 55-75% B over 6 minutes) to give the product (22.24 mg, 48.7 μmol, 20% yield, 100%) as a solid. $^1$H NMR DMSO-d$_6$+D$_2$O 400 MHz $\delta_H$=7.77 (d, 2H), 7.59 (s, 1H), 7.46-7.34 (m, 4H), 4.13-4.07 (m, 1H), 3.98-3.86 (m, 2H), 3.31-3.17 (m, 2H), 2.83 (s, 3H), 2.04-1.78 (m, 4H). LCMS R$_f$=1.25 min in 2 min chromatography, MS ESI calcd. for $C_{20}H_{20}F_3N_2O_5S$ [M+H]$^+$ 457.1, found 457.1.

Example 97. Synthesis of Compound 119

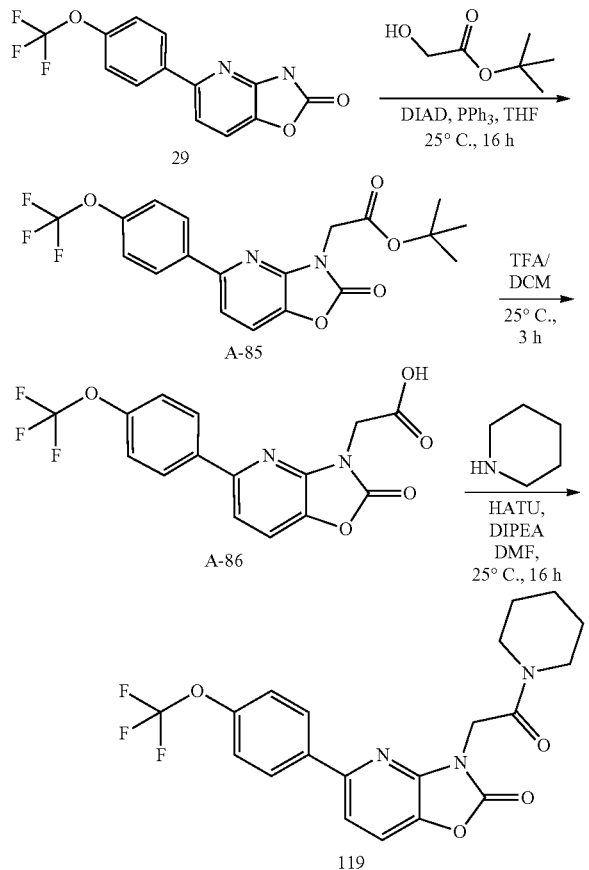

To a solution of 5-[4-(trifluoromethoxy)phenyl]-3H-oxazolo[4,5-b]pyridin-2-one (500 mg, 1.69 mmol) in THF (20 mL) was added tert-butyl 2-hydroxyacetate (669.28 mg, 5.06 mmol), PPh₃ (885.52 mg, 3.38 mmol) and DIAD (682.68 mg, 3.38 mmol). The resulting mixture was stirred at 25° C. under N₂ for 16 hours to give a solution. The reaction solution was concentrated to give the crude product. The crude product was purified by flash chromatography on silica gel (EtOAc in PE=0% to 10% to 20%) to give the product (680 mg, 1.66 mmol, 98% yield) as a solid. ¹H NMR CDCl₃, 400 MHz $\delta_H$=7.97 (d, 2H), 7.49 (s, 2H), 7.30 (d, 2H), 4.62 (s, 2H), 1.49 (s, 9H).

To a solution of tert-butyl 2-[2-oxo-5-[4-(trifluoromethoxy)phenyl]oxazolo[4,5-b]pyridin-3-yl]acetate (690 mg, 1.68 mmol) in DCM (10 mL) was added TFA (5.11 mL). The resulting mixture was stirred at 25° C. for 3 hours to give a solution. The reaction solution was concentrated to give the crude product (586 mg, 1.65 mmol, 98% yield) as a solid. ¹H NMR DMSO-d₆ 400 MHz $\delta_H$=8.17 (d, 2H), 7.92-7.79 (m, 2H), 7.48 (d, 2H), 4.67 (s, 2H).

To a solution of 2-[2-oxo-5-[4-(trifluoromethoxy)phenyl]oxazolo[4,5-b]pyridin-3-yl]acetic acid (195 mg, 0.55 mmol) in DMF (5 mL) was added HATU (313.96 mg, 0.83 mmol), DIPEA (0.48 mL, 2.75 mmol) and then piperidine (56.25 mg, 0.66 mmol). The mixture was stirred at 25° C. for 16 hours to give a solution. Saturated NH₄Cl aqueous (20 mL) and EtOAc (20 mL) were added to the reaction mixture and stirred for 5 minutes. After separated, the organic layer was washed with water (20 mL×2), brine (20 mL×2), dried over anhydrous Na₂SO₄, filtered and concentrated to give the crude product. The crude product was purified by Prep-TLC (silica gel, PE:EtOAc=1:1) to give the product (120.57 mg, 0.28 mmol, 52% yield) as a solid. ¹H NMR DMSO-d₆ 400 MHz $\delta_H$=8.15 (d, 2H), 7.88 (d, 1H), 7.80 (d, 1H), 7.49 (d, 2H), 4.86 (s, 2H), 3.59-3.51 (m, 2H), 3.46-3.41 (m, 2H), 1.67-1.58 (m, 4H), 1.50-1.42 (m, 2H). LCMS $R_t$=1.21 min in 2.0 min chromatography, MS ESI calcd. for $C_{20}H_{19}F_3N_3O_4$ [M+H]⁺ 422.1, found 422.1.

Example 98. Synthesis of Compound 120

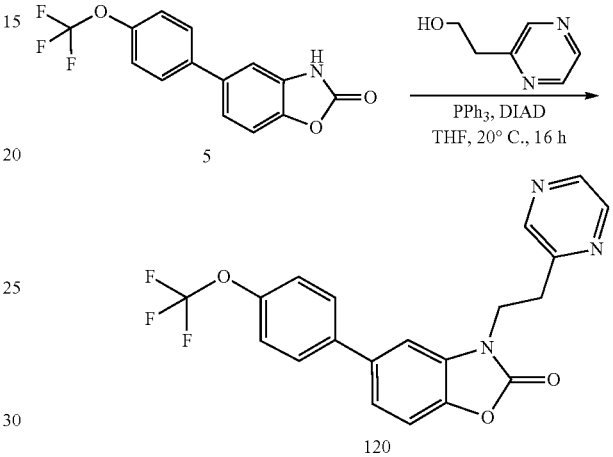

To a mixture of 5-[4-(trifluoromethoxy)phenyl]-3H-1,3-benzoxazol-2-one (100 mg, 0.34 mmol), 2-pyrazin-2-ylethanol (126.15 mg, 1.02 mmol) and PPh₃ (177.7 mg, 0.68 mmol) in THF (6 mL) was added the DIAD (136.99 mg, 0.68 mmol), and the mixture was stirred under N₂ at 20° C. for 16 hours to give the mixture. The mixture was concentrated to dryness, diluted with H₂O (10 mL), and the mixture was extracted with EtOAc (10 mL×2). The combined organic phase was washed with brine (10 mL), dried over Na₂SO₄, filtered and concentrated to give the crude product. The crude product was purified by Prep-HPLC (Kromasil (150 mm×25 mm 10 μm), A=H₂O (0.05% NH₃.H₂O) and B=CH₃CN; 50-80% B over 7 minutes) to give the product (41.28 mg, 102.9 μmol, 30% yield) as a solid. ¹H NMR DMSO-d₆ 400 MHz $\delta_H$=8.64 (d, 1H), 8.52-8.49 (m, 1H), 8.47 (d, 1H), 7.77 (d, 2H), 7.54 (s, 1H), 7.48 (d, 2H), 7.41 (s, 2H), 4.28 (t, 2H), 3.26 (t, 2H). LCMS $R_t$=1.19 min in 2 min chromatography, MS ESI calcd. for $C_{20}H_{15}F_3N_3O_3$ [M+H]⁺ 402.1, found 402.0.

Example 99. Synthesis of Compound 121

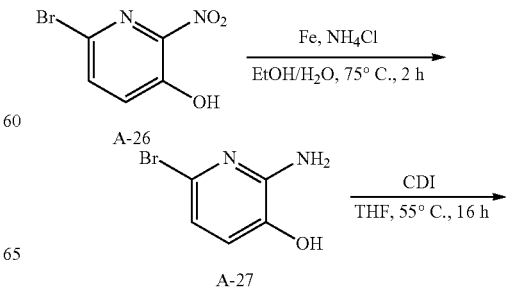

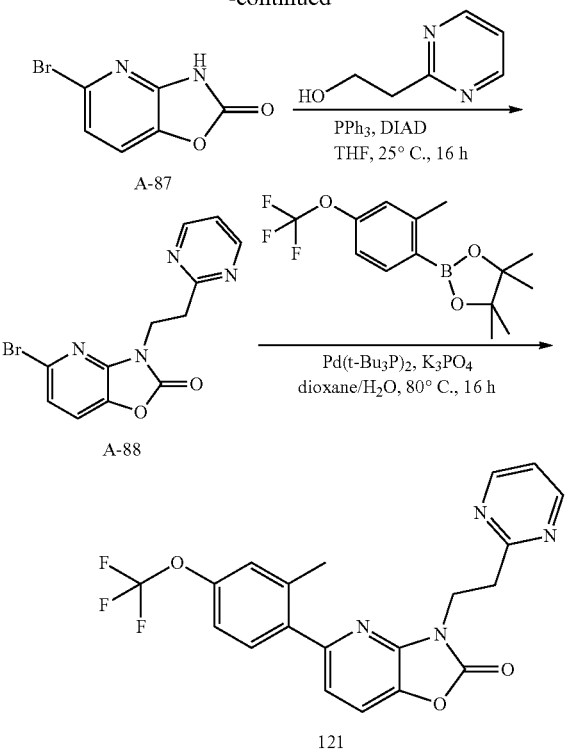

A mixture of 6-bromo-2-nitro-pyridin-3-ol (3 g, 13.7 mmol), Fe (7657.88 mg, 136.99 mmol) and NH$_4$Cl (7329.1 mg, 136.99 mmol) in Ethanol (100 mL) and Water (100 mL) was stirred at 75° C. for 2 hours to give a black suspension. The reaction mixture was cooled to room temperature and filtered through Celite. The filtrate was concentrated to give the crude product (2.5 g, 13.22 mmol, 96.55% yield) as a solid. $^1$H NMR DMSO-d$_6$ 400 MHz δ$_H$=9.71 (s, 1H), 6.74 (d, 1H), 6.50 (d, 1H), 5.92 (br s, 2H).

A mixture of 2-amino-6-bromo-pyridin-3-ol (2.5 g, 13.23 mmol) and CDI (2.24 g, 15.87 mmol) in THF (100 mL) was stirred at 55° C. for 16 hours. The reaction solution was cooled to room temperature and concentrated to give the crude product. The crude product was purified by flash chromatography on silica gel (EtOAc in PE=10% to 30% to 50%) to give the product (900 mg, 4.18 mmol, 32% yield) as a solid. $^1$H NMR DMSO-d$_6$ 400 MHz δ$_H$=12.68 (s, 1H), 7.62 (d, 1H), 7.33 (d, 1H).

To a solution of 5-bromo-3H-oxazolo[4,5-b]pyridin-2-one (200 mg, 0.93 mmol) in THF (10 mL) was added PPh$_3$ (487.98 mg, 1.86 mmol), 2-pyrimidin-2-ylethanol (230.96 mg, 1.86 mmol) and then DIAD (376.2 mg, 1.86 mmol). The resulting mixture was stirred at 25° C. under N$_2$ for 16 hours. The reaction solution was concentrated to give a residue. Water (20 mL) was added to the residue, and the mixture was extracted with EtOAc (20 mL×2). The combined organic phase was washed with brine (20 mL×2), dried over anhydrous Na$_2$SO$_4$, filtered and concentrated to give the crude product. The crude product was purified by flash chromatography on silica gel (EtOAc in PE=10% to 30% to 50%) to give the product (200 mg, 0.62 mmol, 67% yield) as a solid. $^1$H NMR (CDCl$_3$, 400 MHz) δ$_H$=8.63 (d, 2H), 7.25-7.15 (m, 3H), 4.44 (t, 2H), 3.48 (t, 2H).

A mixture of 5-bromo-3-(2-pyrimidin-2-ylethyl)oxazolo[4,5-b]pyridin-2-one (60 mg, 0.19 mmol), 4,4,5,5-tetramethyl-2-[2-methyl-4-(trifluoromethoxy)phenyl]-1,3,2-dioxaborolane (67.73 mg, 0.22 mmol), K$_3$PO$_4$ (79.33 mg, 0.37 mmol) and Pd(t-Bu$_3$P)$_2$ (14.32 mg, 0.03 mmol) in 1,4-Dioxane (4 mL) and Water (0.40 mL) was stirred at 80° C. under N$_2$ for 16 hours to give a suspension. The reaction mixture was cooled to room temperature and filtered through Celite. The filtrate was concentrated to give the crude product. The crude product was purified by Prep-TLC (silica gel, PE:EtOAc=1:1) to give the product (53.55 mg, 0.12 mmol, 68% yield) as a solid. $^1$H NMR (CDCl$_3$, 400 MHz) δ$_H$=8.61 (d, 2H), 7.46 (d, 1H), 7.37 (d, 1H), 7.15-7.08 (m, 4H), 4.49 (t, 2H), 3.51 (t, 2H), 2.38 (s, 3H). LCMS R$_t$=1.18 min in 2.0 min chromatography, MS ESI calcd. for C$_{20}$H$_{16}$F$_3$N$_4$O$_3$ [M+H]$^+$ 417.1, found 417.1.

Example 100. Synthesis of Compound 122

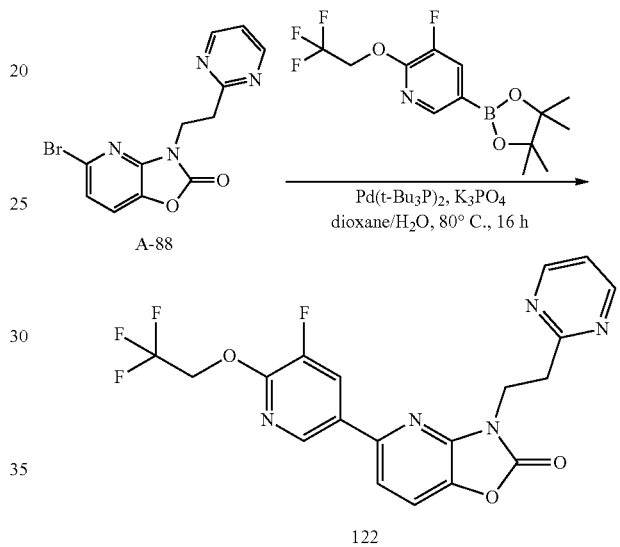

A mixture of 5-bromo-3-(2-pyrimidin-2-ylethyl)oxazolo[4,5-b]pyridin-2-one (60 mg, 0.19 mmol), 3-fluoro-5-(4,4,5,5-tetramethyl-1,3,2-dioxaborolan-2-yl)-2-(2,2,2-trifluoroethoxy)pyridine (71.99 mg, 0.22 mmol), K$_3$PO$_4$ (79.33 mg, 0.37 mmol) and Pd(t-Bu$_3$P)$_2$ (14.32 mg, 0.03 mmol) in 1,4-Dioxane (4 mL) and Water (0.40 mL) was stirred at 80° C. under N$_2$ for 16 hours to give a suspension. The reaction mixture was cooled to room temperature and filtered through Celite. The filtrate was concentrated to give the crude product. The crude product was purified by Prep-TLC (silica gel, PE:EtOAc=1:1) to give the product (57.98 mg, 0.13 mmol, 71% yield) as a solid. $^1$H NMR (CDCl$_3$, 400 MHz) δ$_H$=8.63 (d, 2H), 8.45 (d, 1H), 8.01 (dd, 1H), 7.48-7.40 (m, 2H), 7.12 (t, 1H), 4.90 (q, 2H), 4.52 (t, 2H), 3.54 (t, 2H). LCMS R$_t$=1.14 min in 2.0 min chromatography, MS ESI calcd. for C$_{19}$H$_{14}$F$_4$N$_5$O$_3$ [M+H]$^+$ 436.1, found 436.0.

Example 101. Synthesis of Compound 123

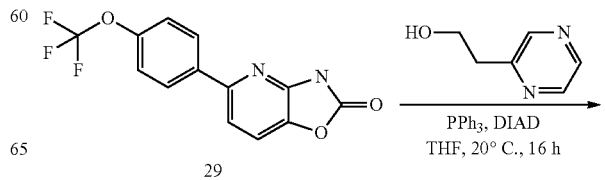

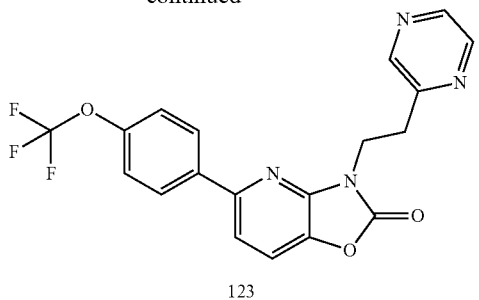

123

To a mixture of 5-[4-(trifluoromethoxy)phenyl]-3H-oxazolo[4,5-b]pyridin-2-one (100 mg, 0.34 mmol), and 2-pyrazin-2-ylethanol (125.73 mg, 1.01 mmol) in THF (10 mL) was added PPh$_3$ (177.1 mg, 0.68 mmol) and DIAD (136.54 mg, 0.68 mmol). The reaction mixture was stirred at 20° C. under N$_2$ for 16 hours. After cooling to r.t., the mixture was diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 30%) to give the product (49.1 mg, 0.12 mmol, 36% yield) as a solid. $^1$H NMR (CDCl$_3$, 400 MHz) $\delta_H$=8.50-8.46 (m, 2H), 8.39 (d, 1H), 7.94 (d, 2H), 7.46 (s, 2H), 7.32 (d, 2H), 4.46 (t, 2H), 3.43 (t, 2H). LCMS R$_t$=1.37 min in 2.0 min chromatography, MS ESI calcd. for C$_{19}$H$_{14}$F$_3$N$_4$O$_3$ [M+H]$^+$ 403.1, found 403.0.

Example 102. Synthesis of Compound 124

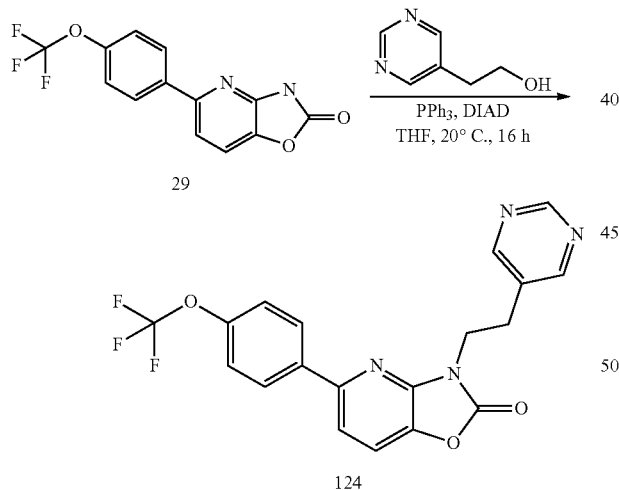

To a mixture of 5-[4-(trifluoromethoxy)phenyl]-3H-oxazolo[4,5-b]pyridin-2-one (100 mg, 0.34 mmol), 2-pyrimidin-5-ylethanol (125.73 mg, 1.01 mmol) in THF (10 mL) was added PPh$_3$ (177.1 mg, 0.68 mmol) and DIAD (136.54 mg, 0.68 mmol). The reaction mixture was stirred at 20° C. under N$_2$ for 16 hours. After cooling to r.t., the mixture was diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 30%) to give the product (23.15 mg, 0.06 mmol, 17% yield) as a solid. $^1$H NMR (CDCl$_3$, 400 MHz) $\delta_H$=9.08 (s, 1H), 8.68 (s, 2H), 7.95-7.90 (d, 2H), 7.48 (s, 2H), 7.34 (d, 2H), 4.30 (t, 2H), 3.26 (t, 2H). LCMS R$_t$=1.24 min in 2.0 min chromatography, MS ESI calcd. for C$_{19}$H$_{14}$F$_3$N$_4$O$_3$ [M+H]$^+$ 403.1, found 402.8.

Example 103. Synthesis of Compound 125

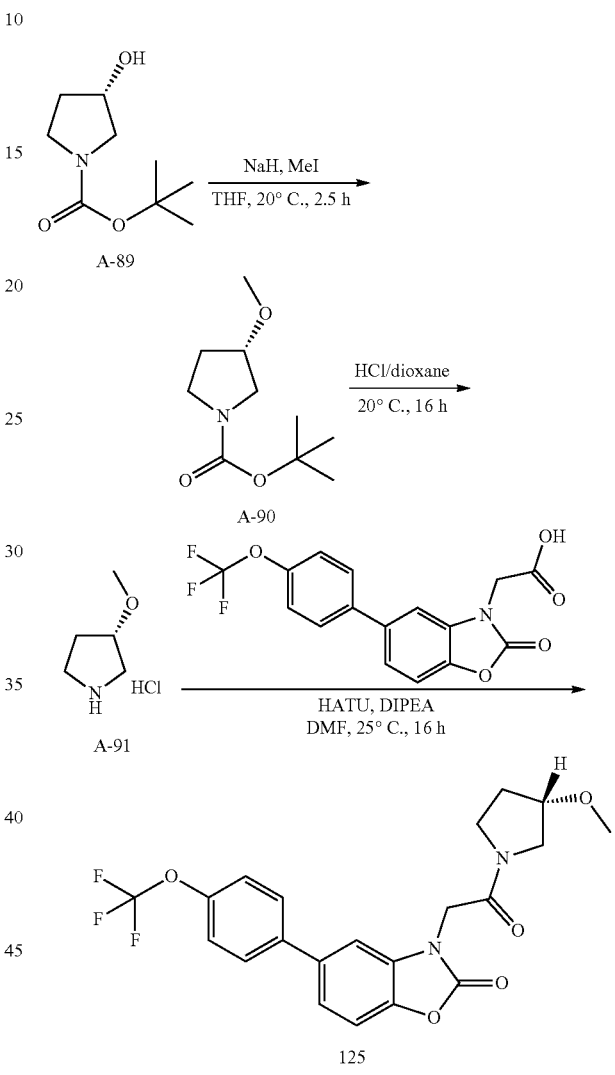

To a solution of tert-butyl (3S)-3-hydroxypyrrolidine-1-carboxylate (1000 mg, 5.34 mmol) in THF (20 mL) was added NaH (256.36 mg, 6.41 mmol). The reaction mixture was stirred at 20° C. for 0.5 hour. Then iodomethane (1516.13 mg, 10.68 mmol) was added. The reaction mixture was stirred at 20° C. for 2 hours to give a mixture. The reaction mixture was diluted with sat.NH$_4$Cl (30 mL), and the mixture was extracted with EtOAc (20 mL×2). The combined organic phase was washed with brine (15 mL), dried over Na$_2$SO$_4$, filtered and concentrated to give the crude product (1100 mg, 5.47 mmol) as an oil. $^1$H NMR (CDCl$_3$, 400 MHz) $\delta_H$=3.97-3.88 (m, 1H), 3.52-3.36 (m, 4H), 3.33 (s, 3H), 2.05-1.85 (m, 2H), 1.46 (s, 9H).

A mixture of tert-butyl (3S)-3-methoxypyrrolidine-1-carboxylate (1100 mg, 5.47 mmol) in 4M HCl/dioxane (15 mL, 60 mmol) was stirred at 20° C. for 16 hours to give a mixture. The reaction mixture was concentrated to give the crude product (1000 mg, 7.27 mmol) as an oil, which was used directly in next step. ¹H NMR (CDCl₃, 400 MHz) δ1-1=10.03-9.49 (m, 2H), 4.13-4.06 (m, 1H), 3.53-3.34 (m, 4H), 3.32 (s, 3H), 2.26-2.13 (m, 1H), 2.09-1.93 (m, 1H).

To the mixture of 2-[2-oxo-5-[4-(trifluoromethoxy)phenyl]-1,3-benzoxazol-3-yl]acetic acid (200 mg, 0.57 mmol), (3S)-3-methoxypyrrolidine hydrochloride (155.82 mg, 1.13 mmol) and HATU (645.83 mg, 1.7 mmol) in DMF (3 mL) was added the DIPEA (0.3 mL, 1.7 mmol). The mixture was stirred at 25° C. for 16 hours to give the solution. The mixture was diluted with H₂O (10 mL), and the mixture was extracted with EtOAc (20 mL×2). The combined organic phase was washed with brine (10 mL), dried over Na₂SO₄, filtered and concentrated to give the crude product. The crude product was purified by Prep-TLC (silica gel, PE:EtOAc=1:1) to give the impure product. The impure product was further purified by triturating from i-Pr₂O (2 mL) to give the product (35.39 mg, 80.5 μmol, 14% yield) as a solid. ¹H NMR DMSO-d₆+D₂O 400 MHz δ$_H$=7.71 (d, 2H), 7.47-7.36 (m, 5H), 4.81-4.60 (m, 2H), 4.08-3.93 (m, 1H), 3.70-3.40 (m, 3H), 3.34-3.17 (m, 4H), 2.13-1.82 (m, 2H). LCMS R$_t$=1.23 min in 2.0 min chromatography, MS ESI calcd. for C₂₁H₂₀F₃N₂O₅ [M+H]⁺ 437.1, found 436.8.

Example 104. Synthesis of Compound 126

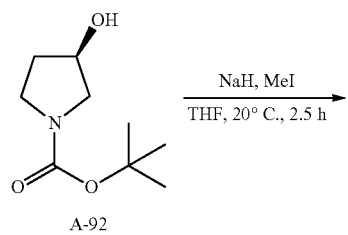

A-92

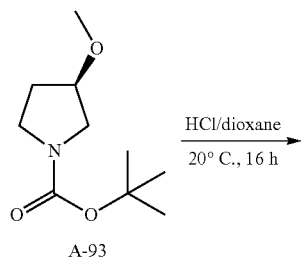

A-93

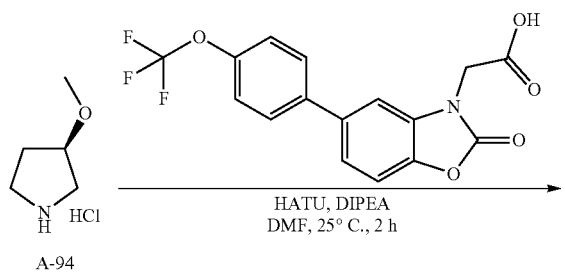

A-94

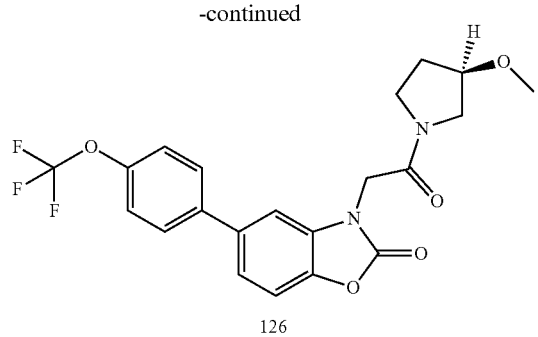

126

To a solution of tert-butyl (3R)-3-hydroxypyrrolidine-1-carboxylate (1000 mg, 5.34 mmol) in THF (20 mL) was added NaH (256.36 mg, 6.41 mmol). The reaction mixture was stirred at 20° C. for 0.5 hour. Then iodomethane (1516.13 mg, 10.68 mmol) was added. The reaction mixture was stirred at 20° C. for 2 hours to give a mixture. The reaction mixture was diluted with sat.NH₄Cl (30 mL), and the mixture was extracted with EtOAc (20 mL×2). The combined organic phase was washed with brine (15 mL), dried over Na₂SO₄, filtered and concentrated to give the crude product (1100 mg, 5.47 mmol) as an oil. ¹H NMR (CDCl₃, 400 MHz) δ$_H$=3.97-3.88 (m, 1H), 3.53-3.36 (m, 4H), 3.33 (s, 3H), 2.06-1.84 (m, 2H), 1.46 (s, 9H).

A mixture of tert-butyl (3R)-3-methoxypyrrolidine-1-carboxylate (1100 mg, 5.47 mmol) in 4M HCl/dioxane (15 mL, 60 mmol) was stirred at 20° C. for 16 hours to give a mixture. The reaction mixture was concentrated to give the crude product (1000 mg, 7.27 mmol) as an oil. ¹H NMR CDCl₃, 400 MHz δ$_H$=10.10-9.39 (m, 2H), 4.13-4.04 (m, 1H), 3.51-3.35 (m, 4H), 3.31 (s, 3H), 2.24-2.12 (m, 1H), 2.08-1.95 (m, 4H).

To the mixture of 2-[2-oxo-5-[4-(trifluoromethoxy)phenyl]-1,3-benzoxazol-3-yl]acetic acid (200 mg, 0.57 mmol), (3R)-3-methoxypyrrolidine hydrochloride (116.87 mg, 0.85 mmol) and HATU (645.83 mg, 1.7 mmol) in DMF (3 mL) was added the DIPEA (0.3 mL, 1.7 mmol). And the mixture was stirred at 25° C. for 2 hours to give the solution. The mixture was diluted with H₂O (10 mL), and the mixture was extracted with EtOAc (20 mL×2). The combined organic phase was washed with brine (10 mL), dried over Na₂SO₄, filtered. The filtrate was concentrated to give the crude product. The crude product was purified by Prep-TLC (silica gel, PE:EtOAc=1:1) to give the impure product. The impure product was further purified by triturating from i-Pr₂O (2 mL) to give the product (81.18 mg, 0.18 mmol, 33% yield) as a solid. ¹H NMR DMSO-d₆+D₂O 400 MHz δ$_H$=7.69 (d, 2H), 7.43-7.35 (m, 5H), 4.77-4.59 (m, 2H), 4.10-3.94 (m, 1H), 3.69-3.41 (m, 3H), 3.34-3.18 (m, 4H), 2.13-1.83 (m, 2H). LCMS R$_t$=1.26 min in 2.0 min chromatography, MS ESI calcd. for C₂₁H₂₀F₃N₂O₅ [M+H]⁺ 437.1, found 436.8.

Example 105. Synthesis of Compound 127

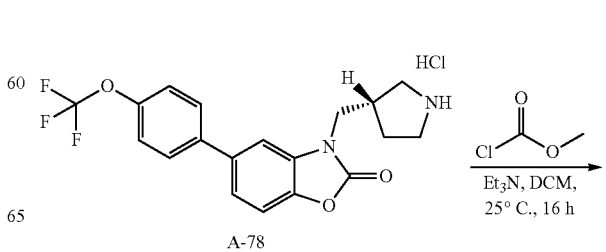

A-78

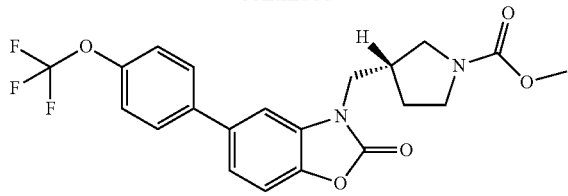

127

A mixture of 3-[[(3S)-pyrrolidin-3-yl]methyl]-5-[4-(trifluoromethoxy)phenyl]-1,3-benzoxazol-2-one hydrochloride (150 mg, 0.40 mmol), Et$_3$N (0.27 mL, 1.98 mmol) and methyl carbonochloridate (74.93 mg, 0.79 mmol) in CH$_2$Cl$_2$ (10 mL) was stirred at 25° C. for 16 hours to give a mixture. The reaction was quenched with sat.NH$_4$Cl (10 mL), and the mixture was extracted with CH$_2$Cl$_2$ (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 µm), A=H$_2$O (10 mM NH$_4$HCO$_3$) and B=CH$_3$CN; 55-75% B over 6 minutes) to give the product (58.59 mg, 0.13 mmol, 34% yield) as a solid.

1H NMR DMSO-d$_6$ 400 MHz δ$_H$=7.81 (d, 2H), 7.71 (s, 1H), 7.51-7.41 (m, 4H), 3.92 (d, 2H), 3.58-3.49 (m, 3H), 3.48-3.39 (m, 2H), 3.29-3.20 (m, 1H), 3.16-3.09 (m, 1H), 2.82-2.69 (m, 1H), 2.03-1.91 (m, 1H), 1.78-1.62 (m, 1H). LCMS R$_t$=1.40 min in 2.0 min chromatography, MS ESI calcd. for C$_{21}$H$_{20}$F$_3$N$_2$O$_5$ [M+H]$^+$ 437.1, found 437.1.

Example 106. Synthesis of Compound 128

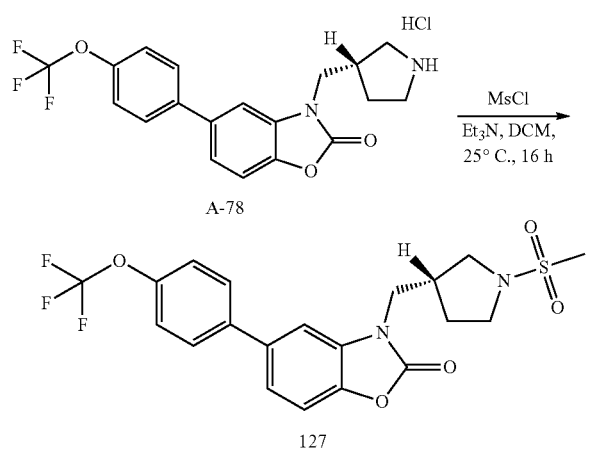

A mixture of 3-[[(3S)-pyrrolidin-3-yl]methyl]-5-[4-(trifluoromethoxy)phenyl]-1,3-benzoxazol-2-one hydrochloride (150 mg, 0.40 mmol), Et$_3$N (0.27 mL, 1.98 mmol) and methanesulfonyl chloride (90.83 mg, 0.79 mmol) in CH$_2$Cl$_2$ (10 mL) was stirred at 25° C. for 16 hours to give a mixture. The reaction was quenched with sat.NH$_4$Cl (10 mL), and the mixture was extracted with CH$_2$Cl$_2$ (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 µm), A=H$_2$O (10 mM NH$_4$HCO$_3$) and B=CH$_3$CN; 52-69% B over 6 minutes) to give the product (60.97 mg, 0.13 mmol, 34% yield) as a solid. $^1$H NMR DMSO-d$_6$+D$_2$O 400 MHz δ$_H$=7.79-7.74 (m, 2H), 7.58 (s, 1H), 7.45-7.37 (m, 4H), 3.96-3.83 (m, 2H), 3.38-3.29 (m, 2H), 3.23-3.14 (m, 1H), 3.06-3.00 (m, 1H), 2.84 (s, 3H), 2.80-2.70 (m, 1H), 2.07-1.94 (m, 1H), 1.78-1.64 (m, 1H). LCMS R$_t$=1.35 min in 2.0 min chromatograph, MS ESI calcd. for C$_{20}$H$_{20}$F$_3$N$_2$O$_5$S [M+H]$^+$ 457.1, found 457.0.

Example 107. Synthesis of Compound 129

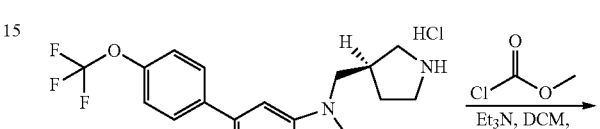

A-82

129

A mixture of 3-[[(3R)-pyrrolidin-3-yl]methyl]-5-[4-(trifluoromethoxy)phenyl]-1,3-benzoxazol-2-one hydrochloride (200 mg, 0.48 mmol), Et$_3$N (0.33 mL, 2.41 mmol) and methyl carbonochloridate (91.13 mg, 0.96 mmol) in DCM (25 mL) was stirred at 20° C. for 16 hours. The reaction was diluted with sat.NH$_4$Cl (20 mL), and extracted with DCM (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 µm), A=H$_2$O (10 mM NH$_4$HCO$_3$) and B =CH$_3$CN; 55-65% B over 7 minutes) to give the product (53.76 mg, 0.12 mmol, 25% yield) as a solid. $^1$H NMR DMSO-d$_6$+D$_2$O 400 MHz δ$_H$=7.78 (d, 2H), 7.61 (s, 1H), 7.50-7.33 (m, 4H), 3.88 (d, 2H), 3.57-3.46 (m, 3H), 3.45-3.34 (m, 2H), 3.28-3.18 (m, 1H), 3.15-3.03 (m, 1H), 2.80-2.68 (m, 1H), 2.03-1.90 (m, 1H), 1.78-1.61 (m, 1H). LCMS R$_t$=1.41 min in 2 min chromatography, MS ESI calcd. for C$_{21}$H$_{20}$F$_3$N$_2$O$_5$ [M+H]$^+$ 437.1, found 437.1.

Example 108. Synthesis of Compound 130

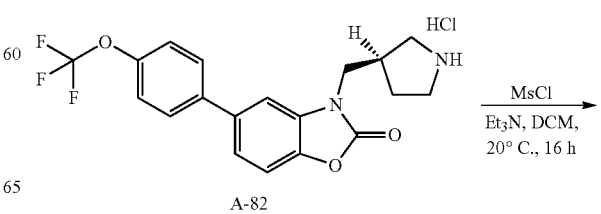

A-82

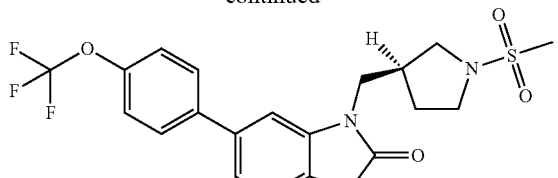

130

A mixture of 3-[[(3R)-pyrrolidin-3-yl]methyl]-5-[4-(trifluoromethoxy)phenyl]-1,3-benzoxazol-2-one hydrochloride (200 mg, 0.48 mmol), Et₃N (0.33 mL, 2.41 mmol) and methanesulfonyl chloride (110.46 mg, 0.96 mmol) in DCM (25 mL) was stirred at 20° C. for 16 hours. The reaction was diluted with sat.NH₄Cl (20 mL), and the mixture was extracted with DCM (10 mL×2). The combined organic phase was washed with brine (10 mL), dried over Na₂SO₄, filtered and concentrated to give the crude product. The crude product was purified by Prep-HPLC (Waters Xbridge (150 mm×25 mm, 5 μm), A=H₂O (10 mM NH₄HCO₃) and B=CH₃CN; 51-71% B over 6 minutes) to give the product (68.23 mg, 0.15 mmol, 31% yield) as a solid. $^1$H NMR DMSO-d₆+D₂O 400 MHz $\delta_H$=7.79 (d, 2H), 7.66-7.60 (m, 1H), 7.47-7.39 (m, 4H), 3.94-3.86 (m, 2H), 3.41-3.30 (m, 2H), 3.24-3.15 (m, 1H), 3.09-3.01 (m, 1H), 2.86 (s, 3H), 2.80-2.70 (m, 1H), 2.07-1.93 (m, 1H), 1.79-1.66 (m, 1H). LCMS $R_t$=1.28 min in 2 min chromatography, MS ESI calcd. for $C_{20}H_{20}F_3N_2O_5S$ [M+H]⁺ 457.1, found 456.8.

Example 109. Synthesis of Compound 131

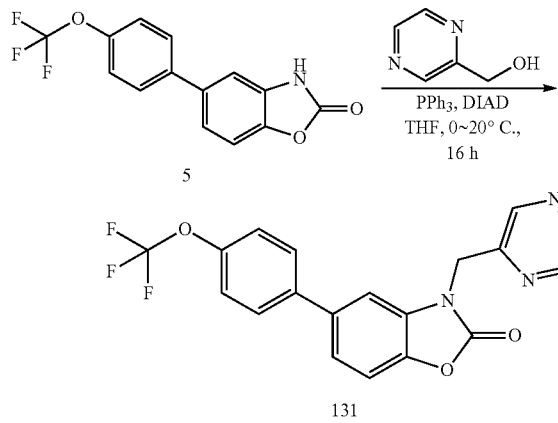

131

To a mixture of 5-[4-(trifluoromethoxy)phenyl]-3H-1,3-benzoxazol-2-one (100 mg, 0.34 mmol), pyrazin-2-ylmethanol (111.9 mg, 1.02 mmol) and PPh₃ (177.7 mg, 0.68 mmol) in THF (6 mL) was added DIAD (136.99 mg, 0.68 mmol) at 0° C. and the mixture was stirred under N₂ at 20° C. for 16 hours to give the mixture. The mixture was concentrated to dryness, diluted with H₂O (10 mL), and extracted with EtOAc (10 mL×2). The combined organic phase was washed with brine (10 mL), dried over Na₂SO₄, filtered and the filtrate was concentrated to give the crude product. The crude product was purified by flash chromatography on silica gel (EtOAc in PE=0% to 35% to 45% to 60%) to give the product (100.9 mg, 260.4 μmol, 77% yield) as an oil. $^1$H NMR DMSO-d₆ 400 MHz $\delta_H$=8.83 (s, 1H), 8.60-8.53 (m, 2H), 7.74 (d, 2H), 7.63 (s, 1H), 7.50-7.42 (m, 4H), 5.35 (s, 2H). LCMS $R_t$=1.52 min in 2 min chromatography, MS ESI calcd. for $C_{19}H_{13}F_3N_3O_3$ [M+H]⁺ 388.1, found 388.1.

Example 110. Synthesis of Compound 132

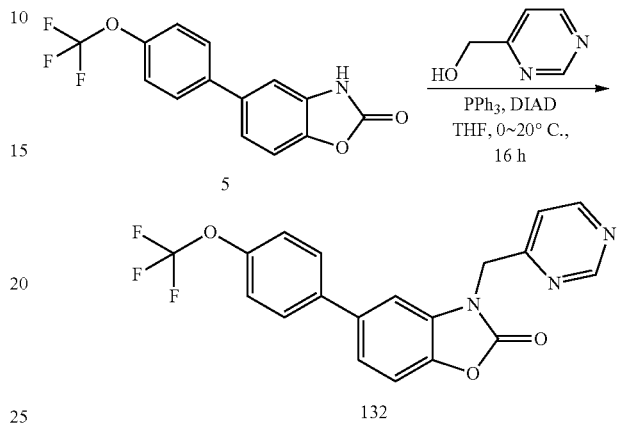

132

To a mixture of 5-[4-(trifluoromethoxy)phenyl]-3H-1,3-benzoxazol-2-one (100 mg, 0.34 mmol), pyrimidin-4-ylmethanol (111.9 mg, 1.02 mmol) and PPh₃ (177.7 mg, 0.68 mmol) in THF (6 mL) was added the DIAD (136.99 mg, 0.68 mmol) at 0° C. and the mixture was stirred under N₂ at 20° C. for 16 hours. The mixture was concentrated to dryness, diluted with H₂O (10 mL), and the mixture was extracted with EtOAc (10 mL×2). The combined organic phase was washed with brine (10 mL), dried over Na₂SO₄, filtered and the filtrate was concentrated to give the crude product. The crude product was purified by flash chromatography on silica gel (EtOAc in PE=0% to 30% to 40% to 55%) to give the product (62.94 mg, 160.4 μmol, 47% yield) as colorless oil. $^1$H NMR DMSO-d₆ 400 MHz $\delta_H$=9.09 (s, 1H), 8.79 (d, 1H), 7.74 (d, 2H), 7.63-7.59 (m, 2H), 7.51-7.41 (m, 4H), 5.30 (s, 2H). LCMS $R_t$=1.27 min in 2 min chromatography, MS ESI calcd. for $C_{19}H_{13}F_3N_3O_3$ [M+H]⁺ 388.1, found 387.8.

Example 111. Synthesis of Compound 133

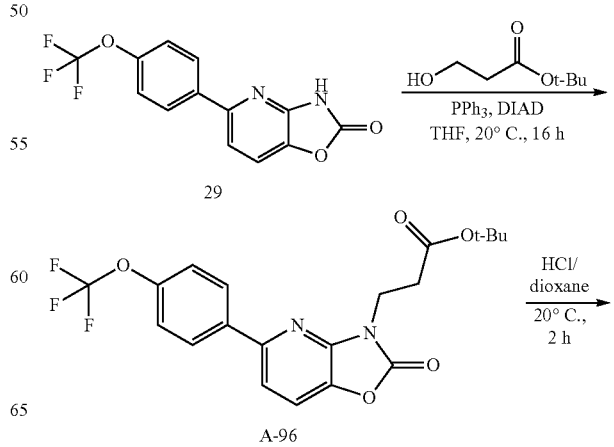

A-96

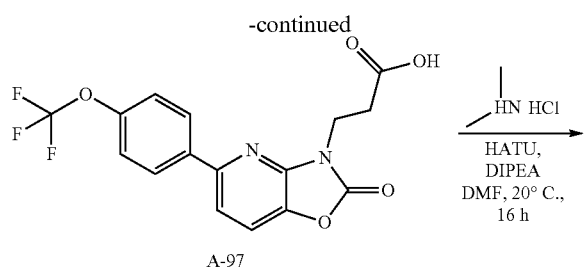

The combined organic phase was washed with brine (10 mL), dried over $Na_2SO_4$, filtered and concentrated to give the crude product. The crude product was purified by flash chromatography on silica gel (DCM) to give the product (25.31 mg, 62.4 μmol, 16% yield) as a solid. $^1$H NMR DMSO-$d_6$ 400 MHz $\delta_H$=8.18 (d, 2H), 7.84-7.73 (m, 2H), 7.48 (d, 2H), 4.09 (t, 2H), 2.99-2.87 (m, 5H), 2.80 (s, 3H). LCMS $R_t$=1.27 min in 2 min chromatography, MS ESI calcd. for $C_{18}H_{17}F_3N_3O_4$ [M+H]$^+$ 396.1, found 396.1.

Example 112. Synthesis of Compound 134

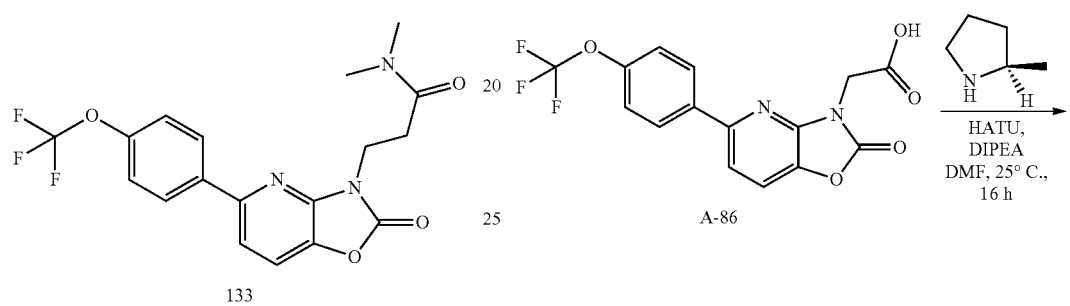

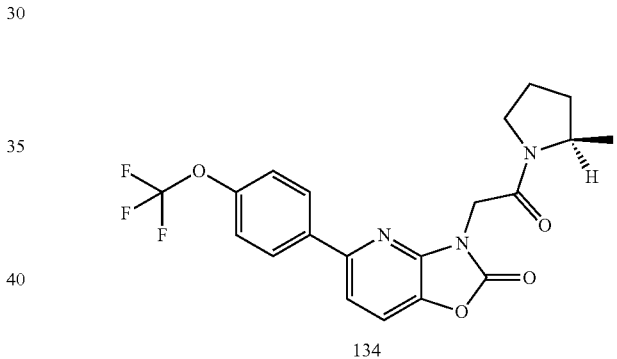

To a mixture of 5-[4-(trifluoromethoxy)phenyl]-3H-oxazolo[4,5-b]pyridin-2-one (200 mg, 0.68 mmol), tert-butyl 3-hydroxypropanoate (296.11 mg, 2.03 mmol) and PPh$_3$ (354.21 mg, 1.35 mmol) in THF (5 mL) was added the DIAD (273.07 mg, 1.35 mmol) at 0° C. and the mixture was stirred under N$_2$ at 20° C. for 16 hours. The mixture was concentrated to dryness, diluted with H$_2$O (10 mL), and the mixture was extracted with EtOAc (10 mL×2). The combined organic phase was washed with brine (10 mL), dried over Na$_2$SO$_4$, filtered and concentrated to give the crude product. The crude product was purified by flash chromatography on silica gel (EtOAc in PE=0% to 20% to 30% to 45%) to give the product (255 mg, 0.49 mmol, 72% yield) as an oil. LCMS $R_t$=0.93 min in 1.5 min chromatography, MS ESI calcd. for $C_{20}H_{19}F_3N_2O_5Na$ [M+Na]$^+$ 447.1, found 447.1.

A mixture of tert-butyl 3-[2-oxo-5-[4-(trifluoromethoxy)phenyl]oxazolo[4,5-b]pyridin-3-yl]propanoate (250 mg, 0.59 mmol) in TFA (3 mL) and DCM (6 mL) was stirred at 20° C. for 2 hour. From LCMS, desired MS was observed, and no starting material was remained. The mixture was concentrated to dryness to give the crude product (210 mg, 0.33 mmol) as an oil, which was used directly without any further purification. LCMS $R_t$=0.94 min in 1.5 min chromatography, MS ESI calcd. for $C_{16}H_{12}F_3N_2O_5$ [M+H]$^+$ 369.1, found 369.1.

To a mixture of 3-[2-oxo-5-[4-(trifluoromethoxy)phenyl]oxazolo[4,5-b]pyridin-3-yl]propanoic acid (210.01 mg, 0.57 mmol), HATU (216.83 mg, 0.57 mmol), DIPEA (0.33 mL, 1.9 mmol) in DMF (6 mL) was added N-methylmethanamine hydrochloride (31 mg, 0.38 mmol), and the mixture was stirred at 20° C. for 4 hours. The mixture was diluted with H$_2$O (10 mL) and extracted with EtOAc (10 mL×3).

To a solution of 2-[2-oxo-5-[4-(trifluoromethoxy)phenyl]oxazolo[4,5-b]pyridin-3-yl]acetic acid (195 mg, 0.55 mmol) in DMF (5 mL) was added HATU (313.96 mg, 0.83 mmol), DIPEA (0.48 mL, 2.75 mmol) and (2R)-2-methylpyrrolidine (56.25 mg, 0.66 mmol). The resulting mixture was stirred at 25° C. for 16 hours to give a solution. Saturated NH$_4$Cl aqueous (20 mL) and EtOAc (20 mL) were added to the reaction mixture and stirred for 5 minutes. After separated, the organic layer was washed with water (20 mL×2) and brine (20 mL×2), dried over anhydrous Na$_2$SO$_4$, filtered and concentrated to give the crude product. The crude product was purified by Prep-TLC (silica gel, PE:EtOAc=1:1) to give the product (145.29 mg, 0.34 mmol, 63% yield) as a solid. $^1$H NMR DMSO-$d_6$ 400 MHz $\delta_H$=8.19-8.11 (m, 2H), 7.91-7.85 (m, 1H), 7.84-7.77 (m, 1H), 7.49 (d, 2H), 4.74 (s, 2H), 4.37-4.29 (m, 0.3H), 4.08-3.96 (m, 0.7H), 3.76-3.55 (m, 1.4H), 3.41-3.35 (m, 0.6H), 2.10-1.79 (m, 3H), 1.76-1.50 (m, 1H), 1.31 (d, 1H), 1.10 (d, 2H). LCMS $R_t$=1.20 min in 2.0 min chromatography, MS ESI calcd. for $C_{20}H_{19}F_3N_3O_4$ [M+H]$^+$ 422.1, found 422.1.

Example 113. Synthesis of Compound 135

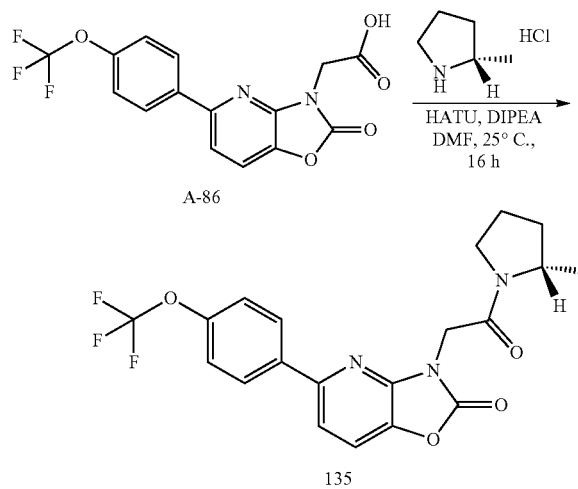

To a solution of 2-[2-oxo-5-[4-(trifluoromethoxy)phenyl] oxazolo[4,5-b]pyridin-3-yl]acetic acid (195 mg, 0.55 mmol) in DMF (5 mL) was added HATU (313.96 mg, 0.83 mmol), DIPEA (0.48 mL, 2.75 mmol) and (2S)-2-methylpyrrolidine hydrochloride (80.33 mg, 0.66 mmol). The resulting mixture was stirred at 25° C. for 16 hours to give a solution. Saturated NH$_4$Cl aqueous (20 mL) and EtOAc (20 mL) were added to the reaction mixture and stirred for 5 minutes. After separated, the organic layer was washed with water (20 mL×2), brine (20 mL×2), dried over anhydrous Na$_2$SO$_4$, filtered and concentrated to give the crude product. The crude product was purified by Prep-TLC (silica gel, PE:E-tOAc=1:1) to give the product (77.38 mg, 0.18 mmol, 33% yield) as a solid. $^1$H NMR DMSO-d$_6$ 400 MHz $\delta_H$=8.18-8.12 (m, 2H), 7.91-7.86 (m, 1H), 7.83-7.78 (m, 1H), 7.49 (d, 2H), 4.95-4.65 (m, 2H), 4.37-4.29 (m, 0.3H), 4.08-3.96 (m, 0.7H), 3.75-3.54 (m, 1.4H), 3.40-3.35 (m, 0.6H), 2.11-1.79 (m, 3H), 1.76-1.50 (m, 1H), 1.31 (d, 1H), 1.10 (d, 2H). LCMS R$_t$=1.20 min in 2.0 min chromatography, MS ESI calcd. for C$_{20}$H$_{19}$F$_3$N$_3$O$_4$ [M+H]$^+$ 422.1, found 422.1.

Example 114. Synthesis of Compound 136

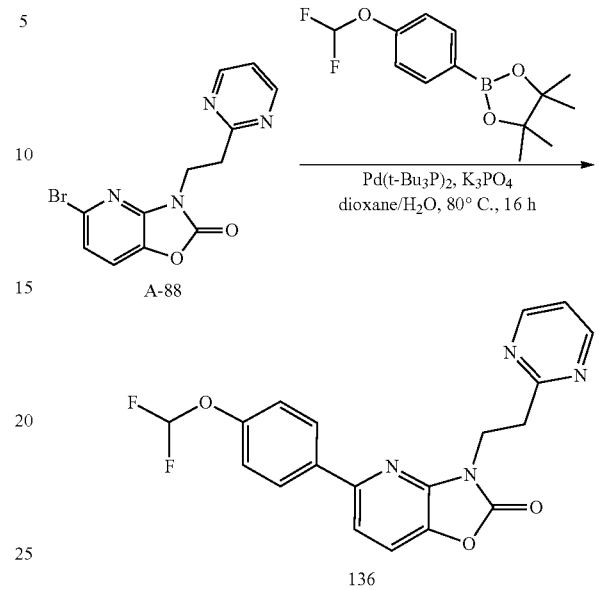

A mixture of 5-bromo-3-(2-pyrimidin-2-ylethyl)oxazolo [4,5-b]pyridin-2-one (40 mg, 0.12 mmol), 2-[4-(difluoromethoxy)phenyl]-4,4,5,5-tetramethyl-1,3,2-dioxaborolane (168.21 mg, 0.62 mmol), K$_3$PO$_4$ (52.89 mg, 0.25 mmol) and Pd(t-Bu$_3$P)$_2$ (9.55 mg, 0.02 mmol) in 1,4-Dioxane (4 mL) and Water (0.40 mL) was stirred at 80° C. under N$_2$ for 16 hours to give a suspension. The reaction mixture was cooled to room temperature and filtered through Celite. The filtrate was concentrated to give the crude product. The crude product was purified by Prep-TLC (silica gel, PE:E-tOAc=1:1) to give the product (14.82 mg, 38.6 μmol, 31% yield) as a solid. $^1$H NMR CDCl$_3$, 400 MHz $\delta_H$=8.62 (d, 2H), 7.93 (d, 2H), 7.43 (s, 2H), 7.20 (d, 2H), 7.09 (t, 1H), 6.57 (t, 1H), 4.53 (t, 2H), 3.56 (t, 2H). LCMS R$_t$=1.22 min in 2.0 min chromatography, MS ESI calcd. for C$_{19}$H$_{15}$F$_2$N$_4$O$_3$ [M+H]$^+$ 385.1, found 385.1.

Example 115. Synthesis of Compound 137

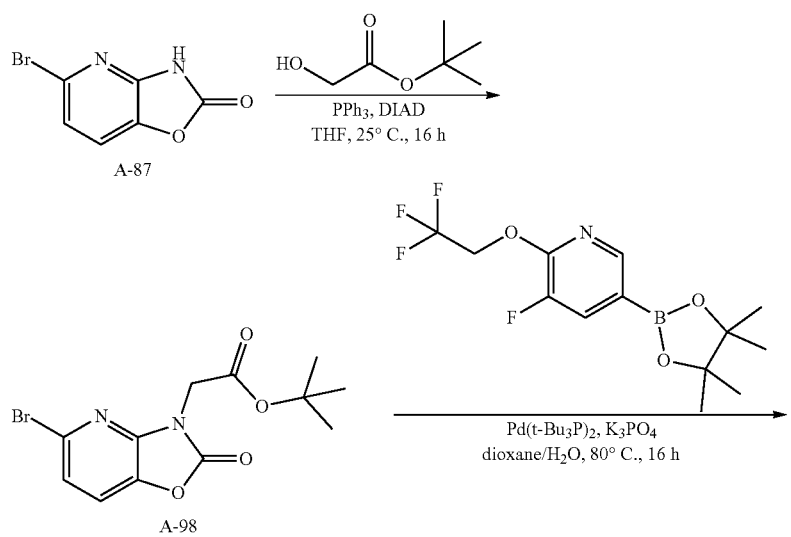

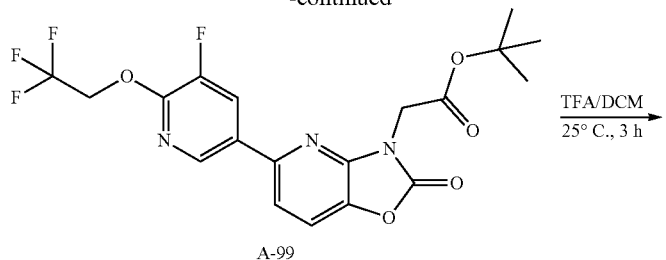

A-99

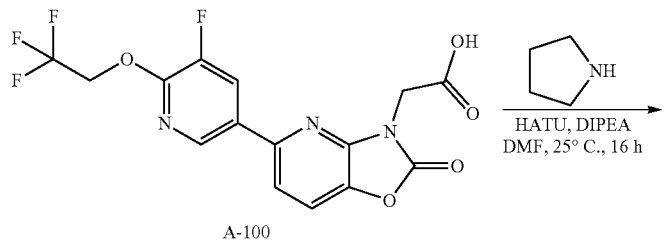

A-100

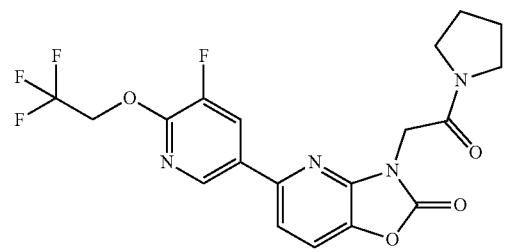

137

To a solution of 5-bromo-3H-oxazolo[4,5-b]pyridin-2-one (300 mg, 1.4 mmol) in THF (5 mL) was added tert-butyl 2-hydroxyacetate (553.23 mg, 4.19 mmol), PPh$_3$ (731.97 mg, 2.79 mmol) and then DIAD (564.31 mg, 2.79 mmol). The resulting mixture was stirred at 25° C. under N$_2$ for 16 hours to give a solution. The reaction solution was concentrated to give a residue. Water (20 mL) was added to the residue, and the mixture was extracted with EtOAc (20 mL×2). The combined organic layer was washed with brine (20 mL×2), dried over anhydrous Na$_2$SO$_4$, filtered and concentrated to give the crude product. The crude product was purified by flash chromatography on silica gel (EtOAc in PE=0% to 10% to 30%) to give the product (400 mg, 1.22 mmol, 87% yield) as a solid. $^1$H NMR CDCl$_3$, 400 MHz $\delta_H$=7.33-7.29 (m, 1H), 7.27-7.24 (m, 1H), 4.55 (s, 2H), 1.48 (s, 9H).

A mixture of tert-butyl 2-(5-bromo-2-oxo-oxazolo[4,5-b]pyridin-3-yl)acetate (100 mg, 0.30 mmol), 3-fluoro-5-(4,4,5,5-tetramethyl-1,3,2-dioxaborolan-2-yl)-2-(2,2,2-trifluoroethoxy)pyridine (117.06 mg, 0.36 mmol), K$_3$PO$_4$ (129 mg, 0.61 mmol) and Pd(t-Bu$_3$P)$_2$ (23.29 mg, 0.05 mmol) in 1,4-Dioxane (10 mL) and Water (1 mL) was stirred at 80° C. under N$_2$ for 16 hours to give a suspension. The reaction mixture was cooled to room temperature and filtered through Celite. The filtrate was concentrated to give the crude product. The crude product was purified by flash chromatography on silica gel (EtOAc in PE=0% to 10% to 20%) to give the product (120 mg, 0.27 mmol, 89% yield) as a solid. 1H NMR (CDCl$_3$, 400 MHz) δ=8.47 (s, 1H), 8.03 (d, 1H), 7.55-7.40 (m, 2H), 4.90 (q, 2H), 4.62 (s, 2H), 1.50 (s, 9H).

To a solution of tert-butyl 2-[5-[5-fluoro-6-(2,2,2-trifluoroethoxy)-3-pyridyl]-2-oxo-oxazolo[4,5-b]pyridin-3-yl]acetate (120 mg, 0.27 mmol) in DCM (5 mL) was added TFA (2.78 mL). The resulting mixture was stirred at 25° C. for 2 hours to give a solution. The reaction solution was concentrated to give the crude product (100 mg, 0.25 mmol, 95.40% yield) as a solid. $^1$H NMR DMSO-d$_6$ 400 MHz S=8.75 (d, 1H), 8.47 (d, 1H), 7.96-7.85 (m, 2H), 5.15 (q, 2H), 4.71 (s, 2H).

To a solution of 2-[5-[5-fluoro-6-(2,2,2-trifluoroethoxy)-3-pyridyl]-2-oxo-oxazolo[4,5-b]pyridin-3-yl]acetic acid (100 mg, 0.26 mmol) in DMF (5 mL) was added HATU (147.28 mg, 0.39 mmol), DIPEA (0.14 mL, 0.77 mmol) and pyrrolidine (27.55 mg, 0.39 mmol). The resulting mixture was stirred at 25° C. for 16 hours to give a solution. Saturated NH$_4$Cl aqueous (20 mL) was added to the reaction mixture, and the mixture was extracted with EtOAc (20 mL×2). The combined organic phase was washed with brine (20 mL×2), dried over anhydrous Na$_2$SO$_4$, filtered and concentrated to give the crude product. The crude product was purified by Prep-TLC (silica gel, PE:EtOAc=1:1) to give the product (34.11 mg, 75.5 μmol, 29% yield) as a solid. $^1$H NMR (CDCl$_3$, 400 MHz) $\delta_H$=8.44 (d, 1H), 8.03 (dd, 1H), 7.50 (d, 1H), 7.43 (d, 1H), 4.89 (q, 2H), 4.69 (s, 2H), 3.62 (t, 2H), 3.54 (t, 2H), 2.11 (quin, 2H), 1.94 (quin, 2H). LCMS R$_t$=1.27 min in 2.0 min chromatography, MS ESI calcd. for C$_{19}$H$_{17}$F$_4$N$_4$O$_4$ [M+H]$^+$ 441.1, found 441.0.

Example 116. Synthesis of Compound 138 and Compound 139

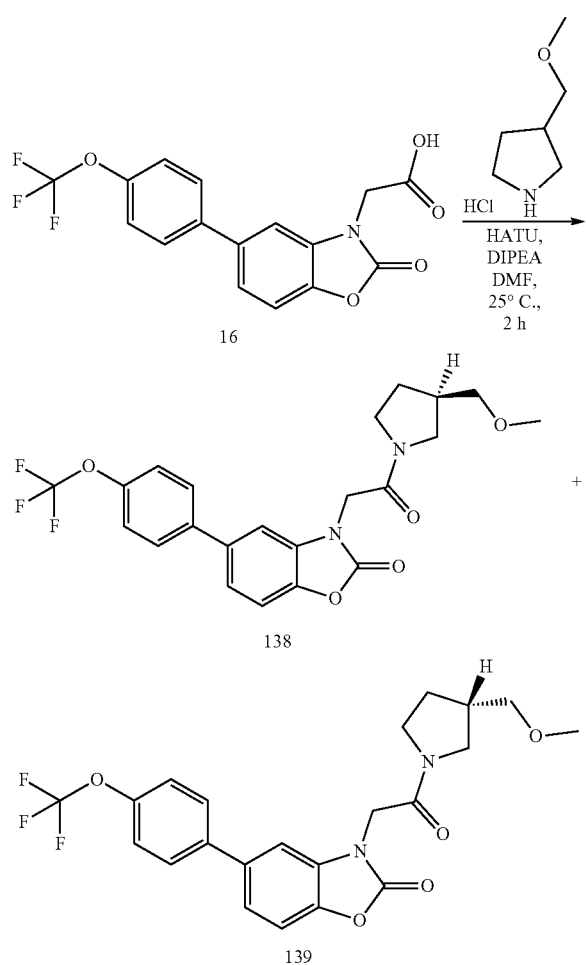

Compound 138:
¹H NMR DMSO-$d_6$+$D_2O$ 400 MHz $δ_H$=7.71 (d, 2H), 7.45-7.36 (m, 5H), 4.76-4.59 (m, 2H), 3.72-3.59 (m, 1H), 3.57-3.16 (m, 8H), 3.04-2.98 (m, 0.5H), 2.41-2.36 (m, 0.5H), 2.07-1.86 (m, 1H), 1.73-1.50 (m, 1H). LCMS $R_t$=1.28 min in 2.0 min chromatography, MS ESI calcd. for $C_{22}H_{22}F_3N_2O_5$ [M+H]⁺ 451.1, found 451.0.

Compound 139:
¹H NMR DMSO-$d_6$+$D_2O$ 400 MHz $δ_H$=7.72 (d, 2H), 7.50-7.36 (m, 5H), 4.79-4.61 (m, 2H), 3.75-3.59 (m, 1H), 3.55-3.12 (m, 8H), 3.06-2.97 (m, 0.5H), 2.41-2.36 (m, 0.5H), 2.09-1.86 (m, 1H), 1.75-1.47 (m, 1H). LCMS $R_t$=1.27 min in 2.0 min chromatography, MS ESI calcd. for $C_{22}H_{22}F_3N_2O_5$ [M+H]⁺ 451.1, found 451.1.

Example 117. Synthesis of Compound 140

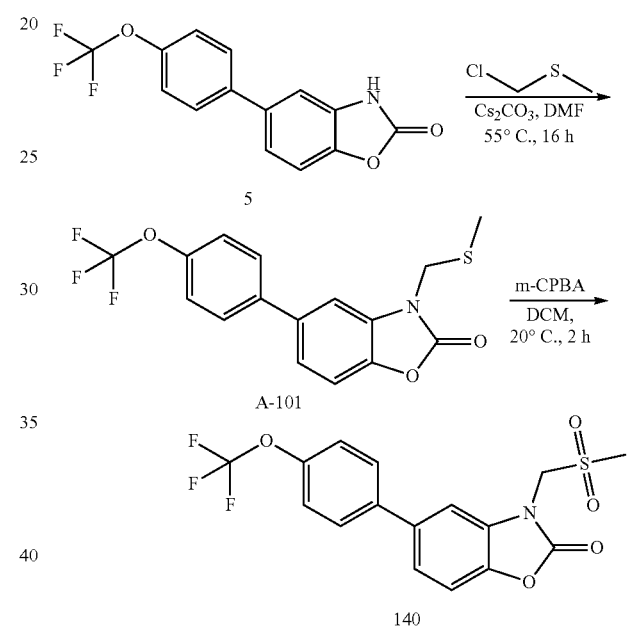

To the mixture of 2-[2-oxo-5-[4-(trifluoromethoxy)phenyl]-1,3-benzoxazol-3-yl]acetic acid (500 mg, 1.42 mmol), DIPEA (0.74 mL, 4.25 mmol) and HATU (1.61 g, 4.25 mmol) in DMF (10 mL) was added the 3-(methoxymethyl)pyrrolidine hydrochloride (321.93 mg, 2.12 mmol), and the mixture was stirred at 25° C. for 2 hours to give the solution. The mixture was diluted with $H_2O$ (10 mL) and extracted with EtOAc (20 mL×2). The combined organic phase was washed with brine (10 mL), dried over $Na_2SO_4$, filtered and concentrated to give the crude product. The crude product was purified by flash chromatography on silica gel (EtOAc in PE=20% to 50% to 100%) to give the impure product. The impure product was further purified by Prep-HPLC (Waters Xbridge (150 mm×25 mm, 5 μm), A=$H_2O$ (0.05% $NH_4OH$) and B=$CH_3CN$; 50-80% B over 8 minutes) to give the product (150 mg).

The product was separated by SFC (OJ(250 mm×30 mm, 5 μm); A=$CO_2$ and B=EtOH (0.1% $NH_3H_2O$); 20° C.; 50 mL/min; 30% B; 7 min run; 14 injections, $R_t$ of peak 1=4.90 min, $R_t$ of Peak 2=5.82 min) to give the compound 138 (35.08 mg, 77.9 μmol) (Peak1, $R_t$=2.90 min in SFC) as a solid and compound 139 (42.87 mg, 95.2 μmol) (Peak2, $R_t$=3.21 min in SFC) as a solid. Note: the enantiomers were randomly assigned.

A mixture of 5-[4-(trifluoromethoxy)phenyl]-3H-1,3-benzoxazol-2-one (100 mg, 0.34 mmol), chloro(methylsulfanyl)methane (65.43 mg, 0.68 mmol) and $Cs_2CO_3$ (220.72 mg, 0.68 mmol) in DMF (2 mL) was stirred at 55° C. for 16 hours to give a mixture. After cooling to r.t., the mixture was diluted with $H_2O$ (20 mL), and the mixture was extracted with EtOAc (20 mL×2). The combined organic phase was washed with brine (15 mL), dried over $Na_2SO_4$, filtered and concentrated. The residue was purified by flash chromatography on silica gel (EtOAc in PE=0% to 10% to 30%) to give the product 110 mg, 0.31 mmol, 91% yield) as a solid. ¹H NMR DMSO-$d_6$ 400 MHz $δ_H$=7.83-7.75 (m, 3H), 7.52-7.44 (m, 4H), 5.11 (s, 2H), 2.17 (s, 3H).

To a solution of 3-(methylsulfanylmethyl)-5-[4-(trifluoromethoxy)phenyl]-1,3-benzoxazol-2-one (110 mg, 0.31 mmol) in DCM (10 mL) was added m-CPBA (160.27 mg, 0.93 mmol). The reaction mixture was stirred at 20° C. for 2 hours to give a solution. The reaction mixture was quenched with sat.$NaHCO_3$ (20 mL), extracted with DCM (10 mL×3). The combined organic phase was washed with brine (10 mL), dried over $Na_2SO_4$, filtered and concentrated. The residue was purified by flash chromatography on silica gel (EtOAc in PE=0% to 15% to 30%) to give the product (69.04 mg, 0.18 mmol, 57% yield) as a solid. $^1$H NMR DMSO-$d_6$ 400 MHz $\delta_H$=7.83-7.75 (m, 3H), 7.54-7.47 (m, 4H), 5.49 (s, 2H), 3.15 (s, 3H). LCMS $R_f$=1.27 min in 2.0 min chromatography. MS MS ESI calcd. for $C_{16}H_{12}F_3NO_5SNa$ [M+Na]$^+$ 410.0286, found 410.0282.

Example 118. Synthesis of Compound 141

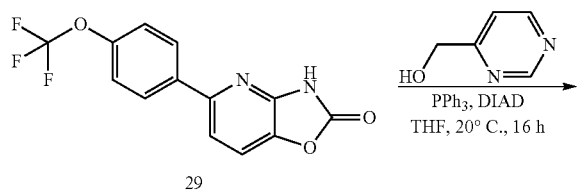

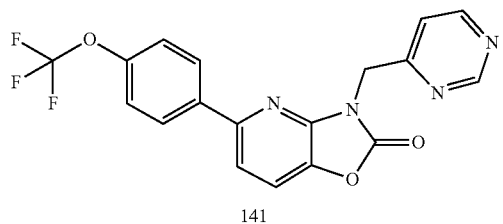

A mixture of 5-[4-(trifluoromethoxy)phenyl]-3H-oxazolo[4,5-b]pyridin-2-one (100 mg, 0.34 mmol), pyrimidin-4-ylmethanol (74.35 mg, 0.68 mmol), PPh$_3$ (177.1 mg, 0.68 mmol) and DIAD (136.54 mg, 0.68 mmol) in THF (3 mL) was stirred at 20° C. under N$_2$ for 16 hours. The reaction was quenched with sat.NH$_4$Cl (10 mL), and the mixture was extracted with EtOAc (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 45-75% B over 7 minutes) to give the product (68.81 mg, 0.18 mmol, 52% yield) as a solid. $^1$H NMR DMSO-$d_6$ 400 MHz $\delta_H$=9.10 (d, 1H), 8.81 (d, 1H), 8.07 (d, 2H), 7.90 (d, 1H), 7.81 (d, 1H), 7.74-7.70 (m, 1H), 7.44 (d, 2H), 5.27 (s, 2H). LCMS $R_f$=1.27 min in 2.0 min chromatography, MS ESI calcd. for $C_{18}H_{12}F_3N_4O_3$ [M+H]$^+$ 389.1, found 389.0.

Example 119. Synthesis of Compound 142

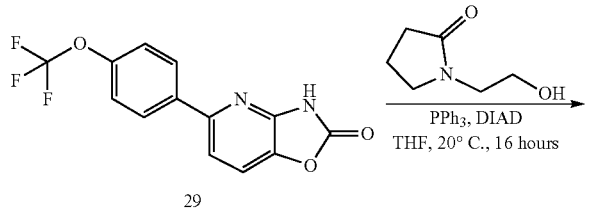

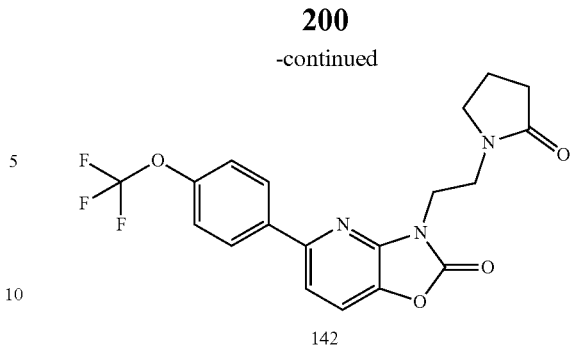

To the mixture of 5-[4-(trifluoromethoxy)phenyl]-3H-oxazolo[4,5-b]pyridin-2-one (200 mg, 0.68 mmol), 1-(2-hydroxyethyl)pyrrolidin-2-one (261.63 mg, 2.03 mmol) and PPh$_3$ (354.21 mg, 1.35 mmol) in THF (6 mL) was added DIAD (273.07 mg, 1.35 mmol) at 0° C. and the mixture was stirred under N$_2$ at 20° C. for 16 hours to give the mixture. The mixture was concentrated to dryness, diluted with H$_2$O (10 mL), and the mixture was extracted with EtOAc (20 mL×2). The combined organic phase was washed with brine (10 mL), dried over Na$_2$SO$_4$, filtered and the filtrate was concentrated to give the crude product. The crude product was purified by flash chromatography on silica gel (EtOAc in PE=0% to 30% to 40% to 55%) to give the product (127.94 mg, 0.31 mmol, 47% yield) as a solid. $^1$H NMR DMSO-$d_6$ 400 MHz $\delta_H$=8.21 (d, 2H), 7.84-7.73 (m, 2H), 7.50 (d, 2H), 4.11-4.02 (m, 2H), 3.60 (t, 2H), 3.51 (t, 2H), 1.89-1.79 (m, 2H), 1.75-1.60 (m, 2H). LCMS $R_f$=1.14 min in 2 min chromatography, MS ESI calcd. for $C_{19}H_{17}F_3N_3O_4$ [M+H]$^+$ 408.1, found 408.0.

Example 120. Synthesis of Compound 143

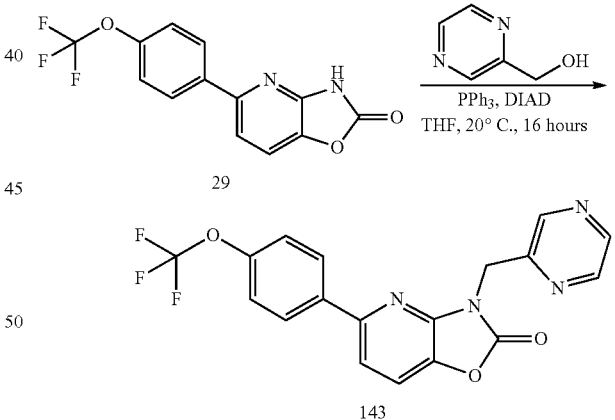

A mixture of pyrazin-2-ylmethanol (74.35 mg, 0.68 mmol), 5-[4-(trifluoromethoxy)phenyl]-3H-oxazolo[4,5-b]pyridin-2-one (100 mg, 0.34 mmol), PPh$_3$ (177.10 mg, 0.68 mmol) and DIAD (136.54 mg, 0.68 mmol) in THF (3 mL) was stirred at 20° C. for 16 hours. The reaction was diluted with sat.NH$_4$Cl (20 mL), and the mixture was extracted with DCM (20 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 42-72% B over 7 minutes) to give the product (64.4 mg, 0.17 mmol, 49% yield) as a solid. ¹H NMR (DMSO-d₆ 400 MHz) δ$_H$=8.91 (s, 1H), 8.64-8.54 (m, 2H), 8.08 (d, 2H), 7.89-7.78 (m, 2H), 7.44 (d, 2H), 5.32 (s, 2H). LCMS R$_f$=1.17 min in 2 min chromatography, MS ESI calcd. for $C_{18}H_{12}F_3N_4O_3$ [M+H]⁺ 389.1, found 389.0.

Example 121. Synthesis of Compound 144

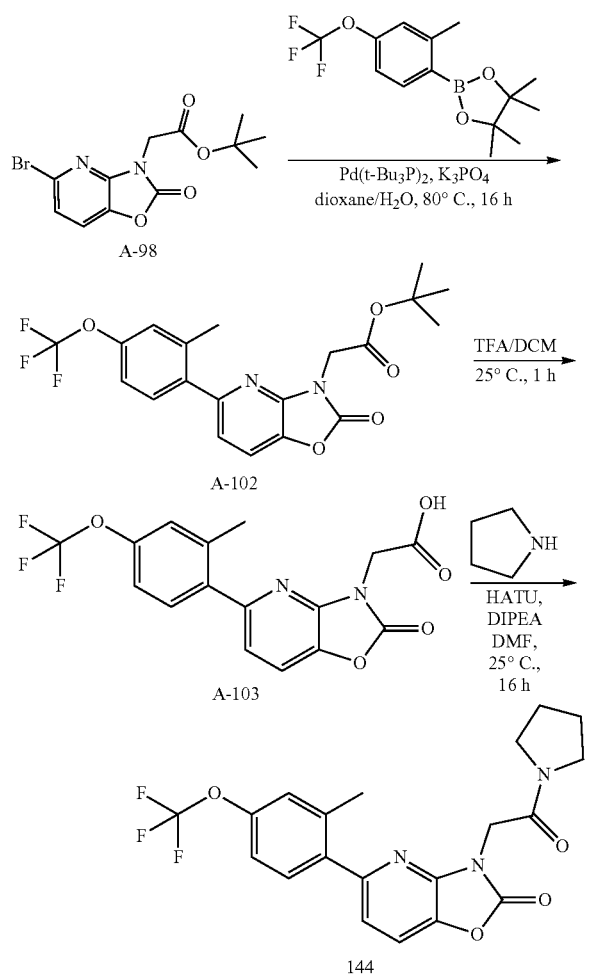

A mixture of tert-butyl 2-(5-bromo-2-oxo-oxazolo[4,5-b]pyridin-3-yl)acetate (100 mg, 0.30 mmol), 4,4,5,5-tetramethyl-2-[2-methyl-4-(trifluoromethoxy)phenyl]-1,3,2-dioxaborolane (110.14 mg, 0.36 mmol), K₃PO₄ (129 mg, 0.61 mmol) and Pd(t-Bu₃P)₂ (23.29 mg, 0.05 mmol) in 1,4-Dioxane (5 mL) and water (0.50 mL) was stirred at 80° C. under N₂ for 16 hours to give a suspension. The reaction mixture was cooled to room temperature and filtered through Celite. The filtrate was concentrated to give the residue (120 mg). Water (15 mL) was added to the residue, and the resulting mixture was extracted with EtOAc (20 mL×2). The combined organic phase was washed with brine (15 mL×2), dried over anhydrous Na₂SO₄, filtered and concentrated to give the crude product (110 mg). The crude product was purified by flash chromatography on silica gel (EtOAc in PE=0% to 10% to 20%) to give the product (100 mg, 0.21 mmol, 71% yield) as colorless oil. ¹H NMR (CDCl₃, 400 MHz) δ$_H$=7.51 (d, 1H), 7.38 (d, 1H), 7.18-7.09 (m, 3H), 4.59 (s, 2H), 2.37 (s, 3H), 1.48 (s, 9H).

To a solution of tert-butyl 2-[5-[2-methyl-4-(trifluoromethoxy)phenyl]-2-oxo-oxazolo[4,5-b]pyridin-3-yl]acetate (100 mg, 0.24 mmol) in DCM (5 mL) was added TFA (2.5 mL). The resulting solution was stirred at 25° C. for 1 hour to give a solution. The reaction solution was concentrated to give the crude product (86 mg, 0.23 mmol, 99% yield) as a grey solid which was used to next step directly without further purification. LCMS R$_f$=0.94 min in 1.5 min chromatography, MS ESI calcd. for $C_{16}H_{12}F_3N_2O_5$ [M+H]⁺ 369.1, found 369.0.

To a solution of 2-[5-[2-methyl-4-(trifluoromethoxy)phenyl]-2-oxo-oxazolo[4,5-b]pyridin-3-yl]acetic acid (86 mg, 0.23 mmol) in DMF (5 mL) was added HATU (133.19 mg, 0.35 mmol), DIPEA (0.12 mL, 0.70 mmol) and pyrrolidine (19.93 mg, 0.28 mmol). The resulting mixture was stirred at 25° C. for 16 hours to give a solution. Water (20 mL) was added to the reaction solution, and the mixture was extracted with EtOAc (30 mL×2). The combined organic phase was washed with water (20 mL×2) and brine (20 mL×2), dried over anhydrous Na₂SO₄, filtered and concentrated to give the crude product. The crude product was purified by Prep-TLC (silica gel, PE:EtOAc=1:1) to give the product (41.09 mg, 95.4 μmol, 41% yield) as a solid. ¹H NMR (CDCl₃, 400 MHz) δ$_H$=7.50 (d, 1H), 7.39 (d, 1H), 7.15-7.09 (m, 3H), 4.66 (s, 2H), 3.67-3.45 (m, 4H), 2.35 (s, 3H), 2.04 (quin, 2H), 1.89 (quin, 2H). LCMS R$_f$=1.35 min in 2.0 min chromatography, MS ESI calcd. for $C_{20}H_{19}F_3N_3O_4$ [M+H]⁺ 422.1, found 422.0.

Example 122. Synthesis of Compound 145

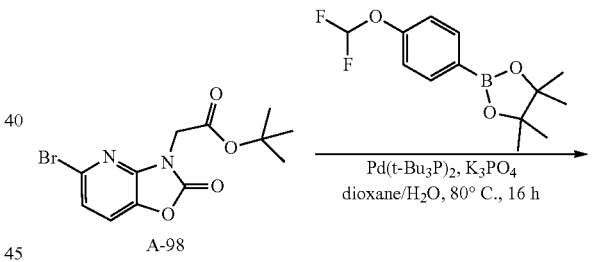

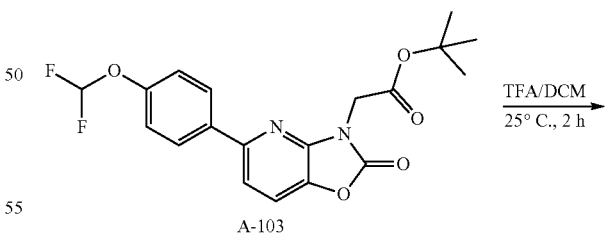

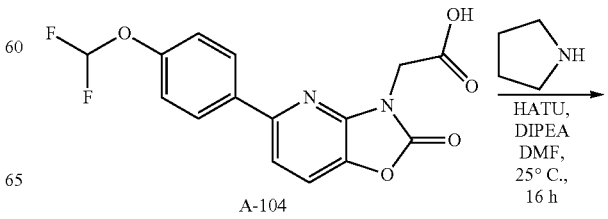

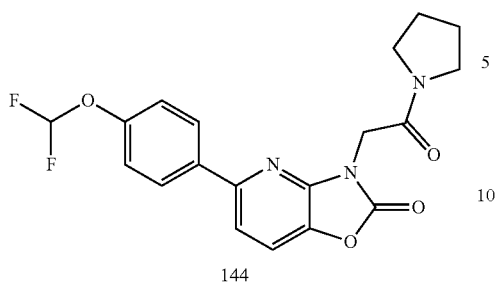

144

A mixture of tert-butyl 2-(5-bromo-2-oxo-oxazolo[4,5-b]pyridin-3-yl)acetate (100 mg, 0.30 mmol), 2-[4-(difluoromethoxy)phenyl]-4,4,5,5-tetramethyl-1,3,2-dioxaborolane (98.46 mg, 0.36 mmol), $K_3PO_4$ (129 mg, 0.61 mmol) and Pd(t-Bu$_3$P)$_2$ (23.29 mg, 0.05 mmol) in 1,4-dioxane (5 mL) and water (0.50 mL) was stirred at 80° C. under $N_2$ for 16 hours. The reaction mixture was cooled to room temperature and filtered through Celite. The filtrate was concentrated to give the residue (90 mg). Water (15 mL) was added to the residue, and the resulting mixture was extracted with EtOAc (20 mL×2). The combined organic phase was washed with brine (15 mL×2), dried over anhydrous $Na_2SO_4$, filtered and concentrated. The crude product was purified by flash chromatography on silica gel (EtOAc in PE=0% to 10% to 20%) to give the product (90 mg, 0.22 mmol, 73% yield) as a solid. $^1$H NMR (CDCl$_3$, 400 MHz) $\delta_H$=7.95 (d, 2H), 7.48 (s, 2H), 7.21 (d, 2H), 6.81-6.34 (m, 1H), 4.63 (s, 2H), 1.49 (s, 9H).

To a solution of tert-butyl 2-[5-[4-(difluoromethoxy)phenyl]-2-oxo-oxazolo[4,5-b]pyridin-3-yl]acetate (90 mg, 0.23 mmol) in DCM (5 mL) was added TFA (2.5 mL). The resulting solution was stirred at 25° C. for 2 hours. The reaction solution was concentrated to give the crude product (75 mg, 0.22 mmol, 99% yield) as a grey solid, which was used to the next step directly without further purification. LCMS R$_t$=0.76 min in 1.5 min chromatography, MS ESI calcd. for $C_{15}H_{11}F_2N_2O_5$ [M+H]$^+$ 337.1, found 336.9.

To a solution of 2-[5-[4-(difluoromethoxy)phenyl]-2-oxo-oxazolo[4,5-b]pyridin-3-yl]acetic acid (75 mg, 0.22 mmol) in DMF (3 mL) was added HATU (127.21 mg, 0.33 mmol), DIPEA (0.12 mL, 0.67 mmol) and pyrrolidine (31.73 mg, 0.45 mmol). The resulting mixture was stirred at 25° C. for 16 hours. Water (15 mL) was added to the reaction solution, and the mixture was extracted with EtOAc (20 mL×2). The combined organic layer was washed with brine (20 mL×2), dried over anhydrous $Na_2SO_4$, filtered and concentrated to give the crude product. The crude product was purified by flash chromatography on silica gel (EtOAc in PE=10% to 30% to 50%) to give the product (24.63 mg, 0.06 mmol, 27% yield) as a solid. $^1$H NMR (CDCl$_3$, 400 MHz) $\delta_H$=7.92 (d, 2H), 7.50-7.42 (m, 2H), 7.20 (d, 2H), 6.56 (t, 1H), 4.70 (s, 2H), 3.61 (t, 2H), 3.54 (t, 2H), 2.09 (quin, 2H), 1.92 (quin, 2H). LCMS R$_t$=1.17 min in 2.0 min chromatography, MS ESI calcd. for $C_{19}H_{18}F_2N_3O_4$ [M+H]$^+$ 390.1, found 390.0.

Example 123. Synthesis of Compound 146

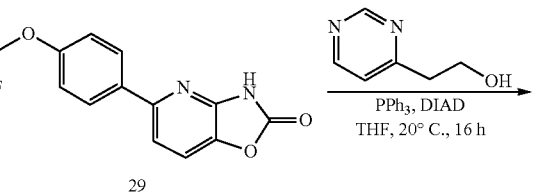

29

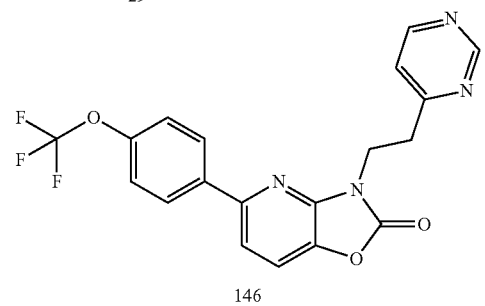

146

A mixture of 5-[4-(trifluoromethoxy)phenyl]-3H-oxazolo[4,5-b]pyridin-2-one (100 mg, 0.34 mmol), 2-pyrimidin-4-ylethanol (83.82 mg, 0.68 mmol), PPh$_3$ (177.10 mg, 0.68 mmol) and DIAD (136.54 mg, 0.68 mmol) in THF (3 mL) was stirred at 20° C. under $N_2$ for 16 hours. The reaction was diluted with sat.NH$_4$Cl (10 mL), and the mixture was extracted with EtOAc (10 mL×2). The combined organic phase was washed with brine (10 mL), dried over $Na_2SO_4$, filtered and concentrated to give the crude product. The crude product was purified by flash chromatography on silica gel (EtOAc in PE=40% to 70%) to give the product (53.90 mg, 0.13 mmol, 39% yield) as solid. $^1$H NMR (DMSO-d$_6$+D$_2$O 400 MHz) $\delta_H$=8.94 (s, 1H), 8.59 (d, 1H), 8.03 (d, 2H), 7.76-7.63 (m, 2H), 7.52-7.40 (m, 3H), 4.28 (t, 2H), 3.26 (t, 2H). LCMS R$_t$=1.28 min in 2 min chromatography, MS ESI calcd. for $C_{19}H_{14}F_3N_4O_3$ [M+H]$^+$ 403.1, found 403.1.

Example 124. Synthesis of Compound 147

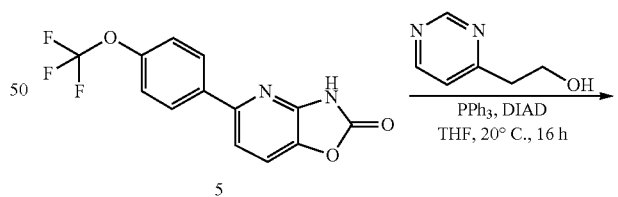

5

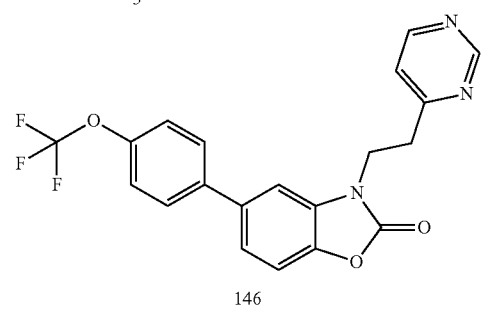

146

A mixture of 5-[4-(trifluoromethoxy)phenyl]-3H-1,3-benzoxazol-2-one (100 mg, 0.34 mmol), 2-pyrimidin-4-ylethanol (83.82 mg, 0.68 mmol), PPh$_3$ (177.1 mg, 0.68 mmol) and DIAD (136.54 mg, 0.68 mmol) in THF (3 mL) was stirred at 20° C. under N$_2$ for 16 hours. The reaction was quenched with sat.NH$_4$Cl (10 mL), and the mixture was extracted with EtOAc (10 mL×2). The combined organic phase was washed with brine (10 mL), dried over Na$_2$SO$_4$, filtered and concentrated to give the crude product. The crude product was purified by flash chromatography on silica gel (EtOAc in PE=40% to 80%) to give the impure product. The impure product was purified by Prep-HPLC (Waters Xbridge (150 mm×25 mm, 5 μm) A=H$_2$O (10 mM NH$_4$HCO$_3$) and B=CH$_3$CN; 43-73% B over 6 minutes) to give the product (17.19 mg, 42.8 μmol, 13% yield) as a solid. $^1$H NMR (DMSO-d$_6$ 400 MHz) δ$_H$=9.06 (d, 1H), 8.68 (d, 1H), 7.78 (d, 2H), 7.59 (s, 1H), 7.52 (dd, 1H), 7.47 (d, 2H), 7.42 (d, 2H), 4.30 (t, 2H), 3.23 (t, 2H). LCMS R$_t$=1.18 min in 2.0 min chromatography, MS ESI calcd. for C$_{20}$H$_{15}$F$_3$N$_3$O$_3$ [M+H]$^+$ 402.1, found 402.1.

Example 125. Synthesis of Compound 148

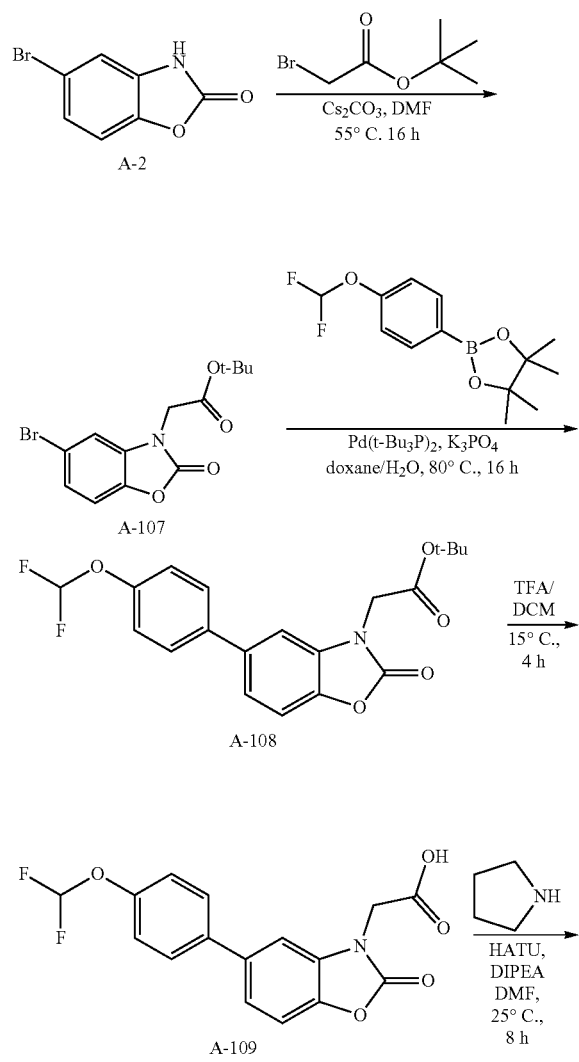

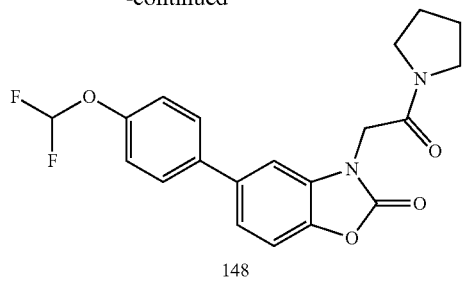

148

To a mixture of 5-bromo-3H-1,3-benzoxazol-2-one (500 mg, 2.34 mmol) and Cs$_2$CO$_3$ (1.52 g, 4.67 mmol) in DMF (10 mL) was added tert-butyl 2-bromoacetate (911.36 mg, 4.67 mmol). The reaction mixture was stirred at 55° C. for 16 hours to give a mixture. After cooling to r.t., the mixture was diluted with H$_2$O (20 mL), and the mixture was extracted with EtOAc (20 mL×2). The combined organic phase was washed with brine (20 mL), dried over Na$_2$SO$_4$, filtered and concentrated to give the crude product. The crude product was triturated from PE (5 mL) to give the product (660 mg, 2.01 mmol, 86% yield) as a solid. $^1$H NMR (DMSO-d$_6$ 400 MHz) δ$_H$=7.66 (d, 1H), 7.41-7.27 (m, 2H), 4.65 (s, 2H), 1.42 (s, 9H).

To a mixture of tert-butyl 2-(5-bromo-2-oxo-1,3-benzoxazol-3-yl)acetate (200 mg, 0.61 mmol), [4-(difluoromethoxy)phenyl]-4,4,5,5-tetramethyl-1,3,2-dioxaborolane (197.52 mg, 0.73 mmol), K$_3$PO$_4$ (258.78 mg, 1.22 mmol) and Pd(t-Bu$_3$P)$_2$ (62.29 mg, 0.12 mmol) in 1,4-dioxane (4 mL) and water (0.4 mL) was stirred at 80° C. for 16 hours under N$_2$. After cooling to r.t., the mixture was diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0% to 4% to 8% to 15%) to give the product (180 mg, 0.46 mmol, 75% yield) as a solid. $^1$H NMR (DMSO-d$_6$ 400 MHz) δ$_H$=7.83-7.61 (m, 3H), 7.55-7.04 (m, 5H), 4.72 (s, 2H), 1.43 (s, 9H).

A mixture of tert-butyl 2-[5-[4-(difluoromethoxy)phenyl]-2-oxo-1,3-benzoxazol-3-yl]acetate (180 mg, 0.46 mmol) in TFA (3 mL) and DCM (6 mL) was stirred at 15° C. for 4 hours. The mixture was concentrated to dryness to give the product (150 mg, 0.45 mmol, 97% yield) as a solid. $^1$H NMR (DMSO-d$_6$ 400 MHz) δ$_H$=7.80-7.66 (m, 3H), 7.55-7.04 (m, 5H), 4.71 (s, 2H).

A mixture of 2-[5-[4-(difluoromethoxy)phenyl]-2-oxo-1,3-benzoxazol-3-yl]acetic acid (130 mg, 0.39 mmol), HATU (294.88 mg, 0.78 mmol), and DIPEA (0.27 mL, 1.55 mmol) in DMF (6 mL) was stirred at 25° C. for 10 min. Then to the mixture was added pyrrolidine (41.37 mg, 0.58 mmol), and the mixture was stirred at 25° C. for 8 hours. The mixture was diluted with H$_2$O (10 mL) and extracted with DCM (10 mL×2). The combined organic phase was washed with brine (10 mL), dried over Na$_2$SO$_4$, filtered and concentrated to give the crude product. The crude product was purified by prep-HPLC (Kromasil (150 mm×25 mm, 5 μm), A=H$_2$O (0.05% NH$_4$OH) and B=CH$_3$CN; 40-70% B over 7 minutes) to give the product (23.5 mg, 60.5 μmol, 16% yield) as a solid. $^1$H NMR (DMSO-d$_6$ 400 MHz) δ$_H$=7.69 (d, 2H), 7.53 (s, 1H), 7.47-6.97 (m, 5H), 4.73 (s, 2H), 3.56 (t, 2H), 3.30 (t, 2H), 2.00-1.87 (m, 2H), 1.86-1.70 (m, 2H). LCMS R$_t$=1.11 min in 2 min chromatography, MS ESI calcd. for C$_{20}$H$_{19}$F$_2$N$_2$O$_4$ [M+H]$^+$ 389.1, found 389.1.

Example 126. Synthesis of Compound 149 and Compound 150

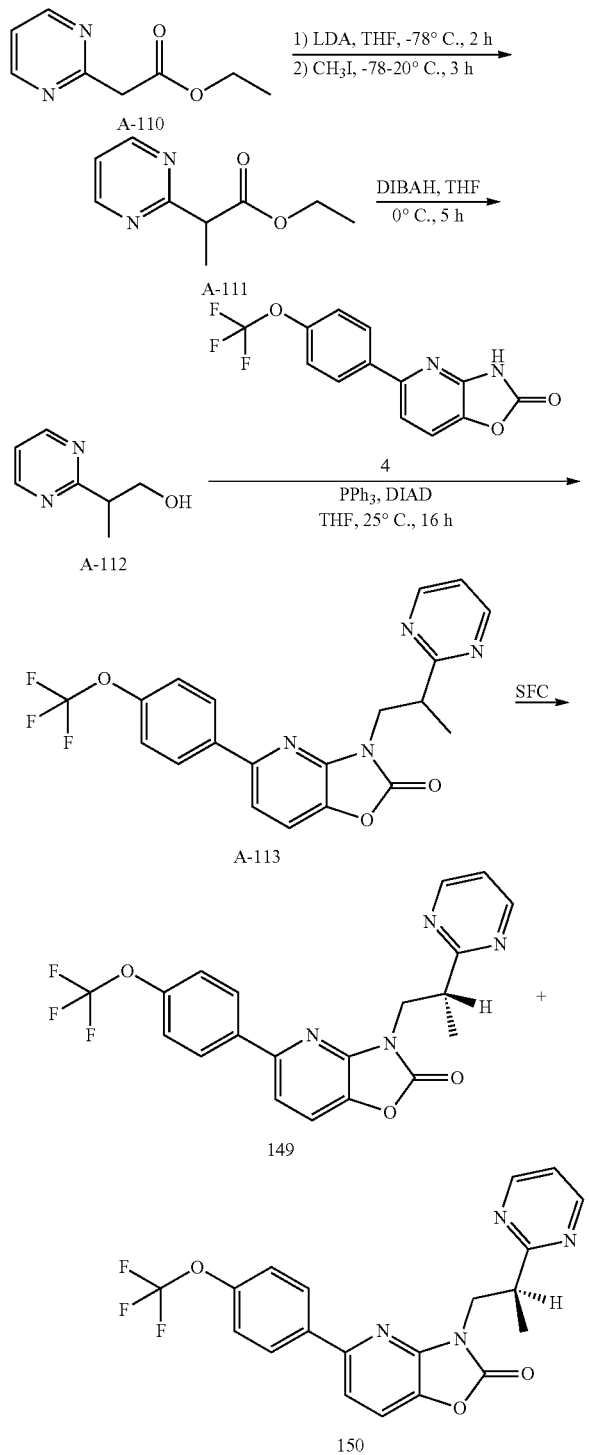

To a mixture of ethyl 2-pyrimidin-2-ylacetate (900 mg, 5.42 mmol) in THF (20 mL) was added LDA (3.25 mL, 6.5 mmol) at −78° C., then the mixture was stirred at −78° C. for 2 hours. To the mixture was added iodomethane (922.46 mg, 6.5 mmol), then the mixture was stirred at −78° C. to 20° C. for 3 hours. The mixture was quenched with sat. NH$_4$Cl (30 mL), then the mixture was extracted with EtOAc (50 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 20% to 45%) to give the product (730 mg, 4.05 mmol, 75% yield) as oil. $^1$H NMR (CDCl$_3$, 400 MHz) δ$_H$=8.72 (d, 2H), 7.19 (t, 1H), 4.19 (q, 2H), 4.14-4.07 (m, 1H), 1.62 (d, 3H), 1.22 (t, 3H).

To a mixture of ethyl 2-pyrimidin-2-ylpropanoate (650 mg, 3.61 mmol) in THF (20 mL) was added DIBAL-H (10.82 mL, 10.82 mmol) at 0° C., then the mixture was stirred at 0° C. for 5 hours. The mixture was quenched with Na$_2$SO$_4$.10H$_2$O (20 g). The mixture was filtered through Celite, eluted with THF (30 mL×2), the filtrate was concentrated to give the crude product. The crude product was purified by flash chromatography on silica gel (EtOAc in PE=0% to 50% to 100%) to give the product (150 mg, 1.06 mmol, 29% yield) as an oil. $^1$H NMR (CDCl$_3$, 400 MHz) δ$_H$=8.70 (d, 2H), 7.20 (t, 1H), 4.03-3.96 (m, 1H), 3.95-3.86 (m, 1H), 3.33-3.21 (m, 1H), 1.39 (d, 3H). LCMS R$_t$=0.12 min in 1.5 min chromatography, MS ESI calcd. for C$_7$H$_{11}$N$_2$O [M+H]$^+$ 139.1, found 138.9.

To a solution of 5-[4-(trifluoromethoxy)phenyl]-3H-oxazolo[4,5-b]pyridin-2-one (100 mg, 0.34 mmol) in THF (5 mL) was added PPh$_3$ (177.1 mg, 0.68 mmol), 2-pyrimidin-2-ylpropan-1-ol (139.94 mg, 1.01 mmol) and DIAD (136.54 mg, 0.68 mmol). The resulting mixture was stirred at 25° C. under N$_2$ for 16 hours to give a solution. The reaction solution was concentrated to give a residue. To the residue was added water (20 mL), and the mixture was extracted with EtOAc (20 mL×2). The combined organic phase was washed with water (15 mL×2) and brine (15 mL×2), dried over anhydrous Na$_2$SO$_4$, filtered and concentrated to give the crude product. The crude product was purified by flash chromatography on silica gel (EtOAc in PE=0% to 10% to 20%) to give the product (130 mg) as a solid. LCMS R$_t$=1.38 min in 2.0 min chromatography, MS ESI calcd. for C$_{20}$H$_{16}$F$_3$N$_4$O$_3$ [M+H]$^+$ 417.1, found 417.1.

The product was separated by SFC (Column: DAICEL CHIRALCEL OJ-H (250 mm×30 mm, 5 μm); A=CO$_2$ and B=Neu-ETOH; 40° C.; 60 mL/min; 15% B; 11 min run; 17 injections, R$_t$ of peak 1=8.43 min, R$_t$ of Peak 2=9.53 min) to give the Compound 149 (37.47 mg, 0.09 mmol, 27% yield, Peak 1) as a solid and Compound 150 (52.19 mg, 0.13 mmol, 37% yield, Peak 2) as a solid.

Compound 149

$^1$H NMR (CDCl$_3$, 400 MHz) δ$_H$=8.61 (d, 2H), 7.94 (d, 2H), 7.42 (s, 2H), 7.30 (d, 2H), 7.04 (t, 1H), 4.45-4.28 (m, 2H), 3.90-3.78 (m, 1H), 1.52 (d, 3H). LCMS R$_t$=1.25 min in 2.0 min chromatography, MS ESI calcd. for C$_{20}$H$_{16}$F$_3$N$_4$O$_3$ [M+H]$^+$ 417.1, found 417.0.

Compound 150

$^1$H NMR (CDCl$_3$, 400 MHz) δ$_H$=8.61 (d, 2H), 7.94 (d, 2H), 7.42 (s, 2H), 7.30 (d, 2H), 7.04 (t, 1H), 4.46-4.26 (m, 2H), 3.91-3.77 (m, 1H), 1.52 (d, 3H). LCMS R$_t$=1.25 min in 2.0 min chromatography, MS ESI calcd. for C$_{20}$H$_{16}$F$_3$N$_4$O$_3$ [M+H]$^+$ 417.1, found 417.1.

Example 127. Synthesis of Compound 151

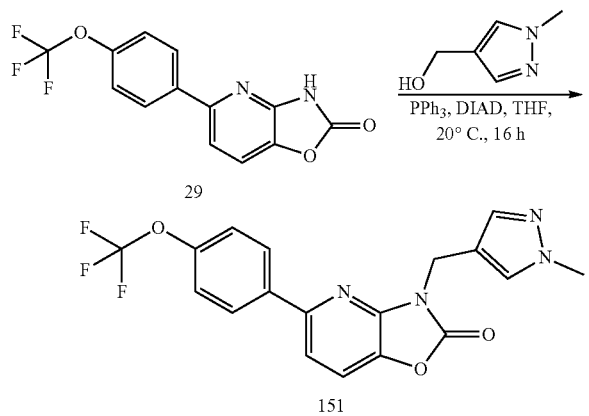

To a solution of 5-[4-(trifluoromethoxy)phenyl]-3H-oxazolo[4,5-b]pyridin-2-one (60 mg, 0.20 mmol), (1-methylpyrazol-4-yl)methanol (68.14 mg, 0.61 mmol) and PPh₃ (106.26 mg, 0.41 mmol) in THF (3 mL) was added DIAD (81.92 mg, 0.41 mmol). The resulting mixture was stirred at 20° C. under N₂ for 16 hours to give a solution. The reaction solution was concentrated to give a residue. The residue was diluted with water (5 mL), extracted with EtOAc (10 mL×2). The combined organic layer was washed with water (5 mL×2), brine (5 mL×2), dried over anhydrous Na₂SO₄, filtered and concentrated to give the crude product.

The crude product was purified by flash chromatography on silica gel (EtOAc in PE=0% to 20% to 30%) to give the product (31.82 mg, 81.5 µmol, 40% yield) as a solid. $^1$H NMR (400 Mz, CDCl₃) $\delta_H$=8.03 (d, 2H), 7.67 (s, 1H), 7.57 (s, 1H), 7.50-7.42 (m, 2H), 7.35 (d, 2H), 5.03 (s, 2H), 3.87 (s, 3H). LCMS $R_t$=1.26 min in 2.0 min chromatography, MS ESI calcd. for $C_{18}H_{14}F_3N_4O_3$ [M+H]$^+$ 391.1, found 390.9.

Example 128. Synthesis of Compound 152

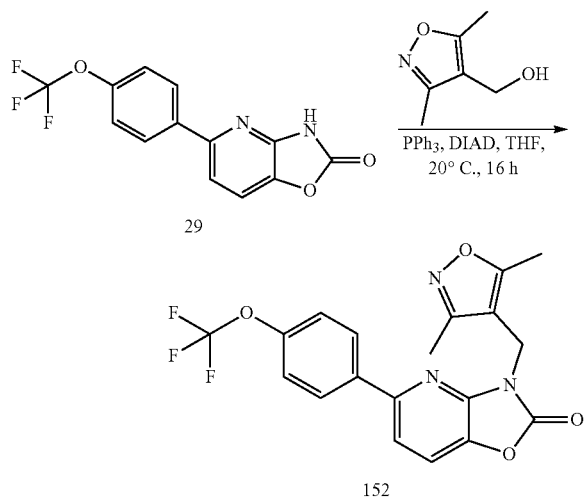

To a solution of 5-[4-(trifluoromethoxy)phenyl]-3H-oxazolo[4,5-b]pyridin-2-one (60 mg, 0.20 mmol), (3,5-dimethylisoxazol-4-yl)methanol (77.26 mg, 0.61 mmol) and PPh₃ (106.26 mg, 0.41 mmol) in THF (3 mL) was added DIAD (81.92 mg, 0.41 mmol). The resulting mixture was stirred at 20° C. under N₂ for 16 hours to give a solution. The reaction solution was concentrated to give a residue. The residue was diluted with water (5 mL), extracted with EtOAc (10 mL×2). The combined organic layer was washed with water (5 mL×2), brine (5 mL×2), dried over anhydrous Na₂SO₄, filtered and concentrated to give the crude product. The crude product was purified by flash chromatography on silica gel (EtOAc in PE=0% to 20% to 30%) to give the product (51.04 mg, 125.9 µmol, 62% yield) as a solid. $^1$H NMR (400 MHz, CDCl₃) $\delta_H$=7.95 (d, 2H), 7.49 (s, 2H), 7.34 (d, 2H), 4.90 (s, 2H), 2.61 (s, 3H), 2.43 (s, 3H). LCMS $R_t$=1.35 min in 2.0 min chromatography, MS ESI calcd. for $C_{19}H_{15}F_3N_3O_4$ [M+H]$^+$ 406.1, found 405.9.

Example 129. Synthesis of Compound 153

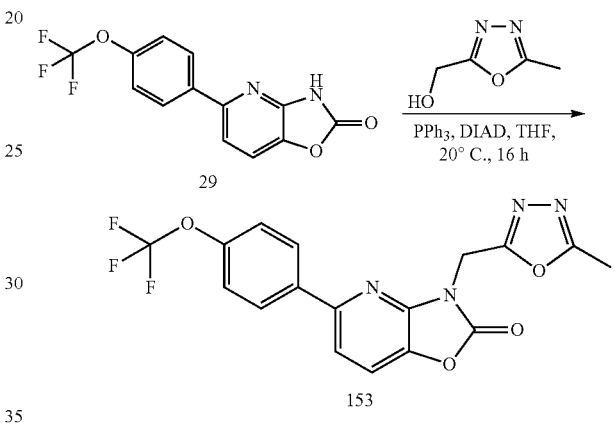

To a mixture of 5-[4-(trifluoromethoxy)phenyl]-3H-oxazolo[4,5-b]pyridin-2-one (60 mg, 0.20 mmol), PPh₃ (106.26 mg, 0.41 mmol) and (5-methyl-1,3,4-oxadiazol-2-yl)methanol (46.23 mg, 0.41 mmol) in THF (1 mL) was added DIAD (81.92 mg, 0.41 mmol). The mixture was stirred at 20° C. under N₂ for 16 hours. The reaction was diluted with sat.NH₄Cl (10 mL), and the mixture was extracted with EtOAc (15 mL×2). Then the combined organic phase was washed with brine (10 mL), dried over Na₂SO₄, filtered and concentrated to give the crude product. The crude product was purified by Prep-HPLC (Waters Xbridge (150 mm×25 mm, 5 µm) A=H₂O (10 mM NH₄HCO₃) and B=CH₃CN; 47-67% B over 6 minutes) to give the product (23.49 mg, 58.60 µmol, 29% yield) as a solid. $^1$H NMR (CDCl₃, 400 MHz) $\delta_H$=7.96 (d, 2H), 7.54 (s, 2H), 7.32-7.28 (m, 2H), 5.37 (s, 2H), 2.54 (s, 3H). LCMS $R_t$=1.12 min in 2 min chromatography, MS ESI calcd. for $C_{17}H_{12}F_3N_4O_4$ [M+H]$^+$ 393.1, found 393.0.

Example 130. Synthesis of Compound 154

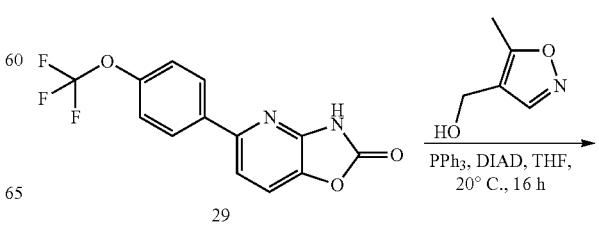

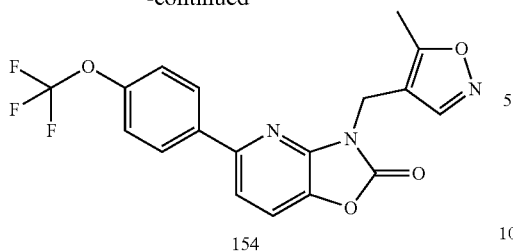

154

To a mixture of (5-methylisoxazol-4-yl)methanol (45.82 mg, 0.41 mmol), 5-[4-(trifluoromethoxy)phenyl]-3H-oxazolo[4,5-b]pyridin-2-one (60 mg, 0.20 mmol) and PPh₃ (106.26 mg, 0.41 mmol) in THF (1 mL) was added DIAD (81.92 mg, 0.41 mmol). The mixture was stirred at 20° C. under N₂ for 16 hours. The reaction was diluted with sat.NH₄Cl (10 mL), and the mixture was extracted with EtOAc (10 mL×2). Then the combined organic phase was washed with brine (10 mL), dried over Na₂SO₄, filtered and concentrated to give the crude product. The crude product was purified by flash chromatography on silica gel (EtOAc in PE=0% to 30%) to give the product (48.92 mg, 0.12 mmol, 62% yield) as a solid. ¹H NMR (CDCl₃, 400 MHz,) $δ_H$=8.43 (s, 1H), 7.99 (d, 2H), 7.49 (d, 2H), 7.35 (d, 2H), 4.96 (s, 2H), 2.63 (s, 3H). LCMS $R_t$=1.25 min in 2.0 min chromatography, MS ESI calcd. for $C_{13}H_{13}F_3N_3O_4$ [M+H]⁺ 392.1, found 392.1.

Example 131. Synthesis of Compound 155

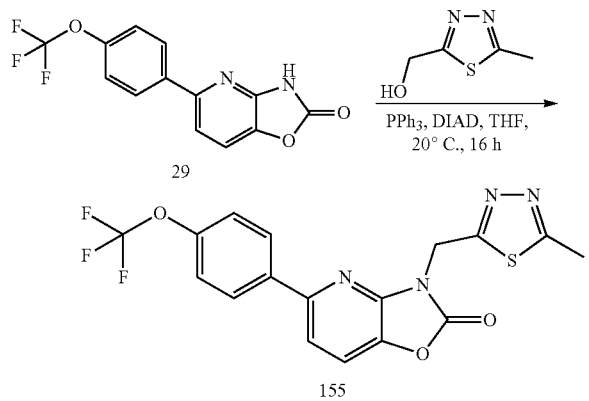

155

To a mixture of 5-[4-(trifluoromethoxy)phenyl]-3H-oxazolo[4,5-b]pyridin-2-one (60 mg, 0.20 mmol), PPh₃ (106.26 mg, 0.41 mmol) and (5-methyl-1,3,4-thiadiazol-2-yl)methanol (52.74 mg, 0.41 mmol) in THF (1 mL) was added DIAD (81.92 mg, 0.41 mmol). The mixture was stirred at 20° C. under N₂ for 16 hours. The reaction was diluted with sat.NH₄Cl (10 mL), and the mixture was extracted with EtOAc (15 mL×2). Then the combined organic phase was washed with brine (10 mL), dried over Na₂SO₄, filtered and concentrated to give the crude product. The crude product was purified by Prep-HPLC (Waters Xbridge (150 mm×25 mm, 5 μm) A=H₂O (10 mM NH₄HCO₃) and B=CH₃CN; 49-69% B over 6 minutes) to give the product (36.17 mg, 87.40 mmol, 43% yield) as a solid. ¹H NMR (DMSO-d₆ 400 MHz) $δ_H$=8.17 (d, 2H), 7.92-7.80 (m, 2H), 7.49 (d, 2H), 5.52 (s, 2H), 2.69 (s, 3H). LCMS $R_t$=1.15 min in 2 min chromatography, MS ESI calcd. for $C_{17}H_{12}F_3N_4O_3S$ [M+H]⁺ 409.1, found 409.0.

Example 132. Synthesis of Compound 156

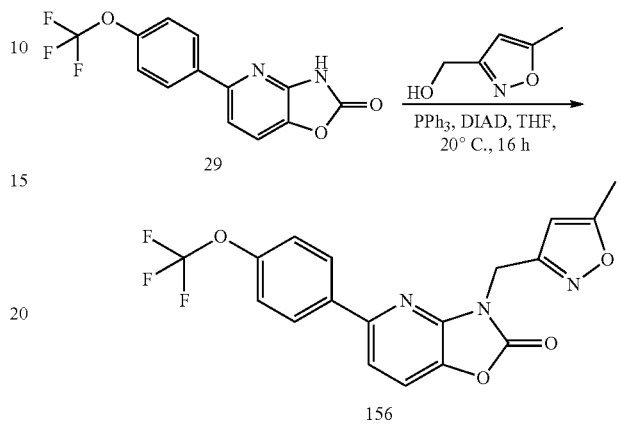

156

To a mixture of (5-methylisoxazol-3-yl)methanol (45.82 mg, 0.41 mmol), 5-[4-(trifluoromethoxy)phenyl]-3H-oxazolo[4,5-b]pyridin-2-one (60 mg, 0.20 mmol) and PPh₃ (106.26 mg, 0.41 mmol) in THF (3 mL) was added DIAD (81.92 mg, 0.41 mmol). The mixture was stirred at 20° C. under N₂ for 16 hours. The reaction was diluted with sat.NH₄Cl (10 mL), and the mixture was extracted with EtOAc (10 mL×2). Then the combined organic phase was washed with brine (10 mL), dried over Na₂SO₄, filtered and concentrated to give the crude product. The crude product was purified by flash chromatography on silica gel (EtOAc in PE=0% to 30%) to give the product (52.56 mg, 0.13 mmol, 66% yield) as a solid. ¹H NMR (CDCl₃, 400 MHz,) $δ_H$=8.01 (d, 2H), 7.46-7.54 (m, 2H), 7.31 (d, 2H), 6.12 (s, 1H), 5.22 (s, 2H), 2.40 (s, 3H). LCMS $R_t$=1.22 min in 2.0 min chromatography, MS ESI calcd. for $C_{18}H_{13}F_3N_3O_4$ [M+H]⁺ 392.1, found 392.0.

Example 133. Synthesis of Compound 157

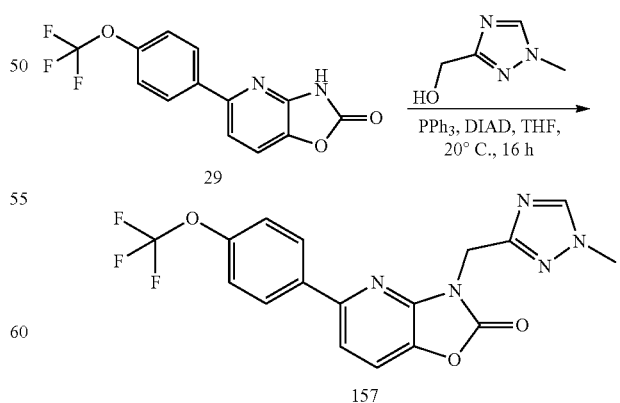

157

To a mixture of 5-[4-(trifluoromethoxy)phenyl]-3H-oxazolo[4,5-b]pyridin-2-one (60 mg, 0.2 mmol), (1-methyl-1,2,4-triazol-3-yl)methanol (45.83 mg, 0.41 mmol) and PPh₃

(106.26 mg, 0.41 mmol) in THF (1 mL) was added the DIAD (81.92 mg, 0.41 mmol), and the mixture was stirred at 20° C. under N₂ for 16 hours. The reaction was diluted with sat.NH₄Cl (10 mL), and the mixture was extracted with EtOAc (10 mL×2). Then the combined organic phase was washed with brine (10 mL), dried over Na₂SO₄, filtered and concentrated to give the crude product. The crude product was purified by purified by prep-HPLC [Kromasil (150 mm×25 mm, 5 μm) A=H₂O (0.05% NH₄OH) and B=CH₃CN; 47-87% B over 7 minutes] to give the product (21.81 mg, 0.06 mmol, 28% yield) as a solid. ¹H NMR (DMSO-d₆ 400 MHz) δ$_H$=8.40 (s, 1H), 8.12 (d, 2H), 7.87 (d, 1H), 7.80 (d, 1H), 7.47 (d, 2H), 5.13 (s, 2H), 3.80 (s, 3H). LCMS R$_t$=1.12 min in 2 min chromatography, MS ESI calcd. for C₁₇H₁₃F₃N₅O₃ [M+H]⁺ 392.1, found 392.0.

Example 134. Synthesis of Compound 158

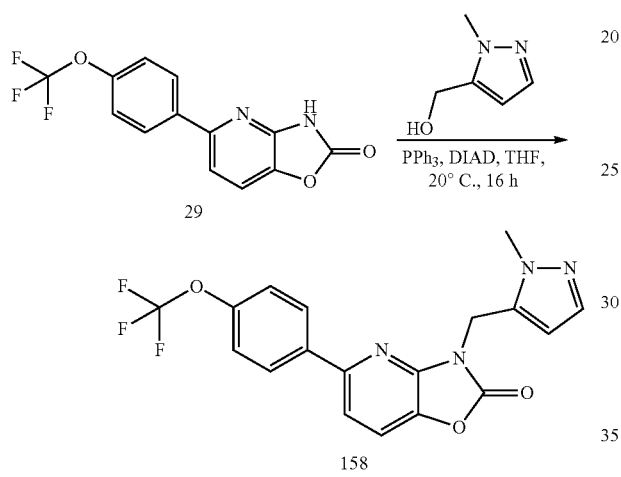

To a mixture of 5-[4-(trifluoromethoxy)phenyl]-3H-oxazolo[4,5-b]pyridin-2-one (60 mg, 0.2 mmol), (2-methylpyrazol-3-yl)methanol (45.43 mg, 0.41 mmol) and PPh₃ (106.26 mg, 0.41 mmol) in THF (1 mL) was added the DIAD (81.92 mg, 0.41 mmol), and the mixture was stirred at 20° C. under N₂ for 16 hours. The reaction was diluted with sat.NH₄Cl (10 mL), and the mixture was extracted with EtOAc (10 mL×2). Then the combined organic phase was washed with brine (10 mL), dried over Na₂SO₄, filtered and concentrated to give the crude product. The crude product was purified by flash chromatography on silica gel (EtOAc in PE=20% to 70%) to give the product (9.03 mg, 23.1 mol, 11% yield) as a solid. ¹H NMR (DMSO-d₆ 400 MHz) δ$_H$=8.18 (d, 2H), 7.88-7.77 (m, 2H), 7.50 (d, 2H), 7.35 (d, 1H), 6.38 (d, 1H), 5.18 (s, 2H), 3.97 (s, 3H). LCMS R$_t$=1.20 min in 2.0 min chromatography, MS ESI calcd. for C₁₈H₁₄F₃N₄O₃ [M+H]⁺ 391.1, found 391.1.

Example 135. Synthesis of Compound 159

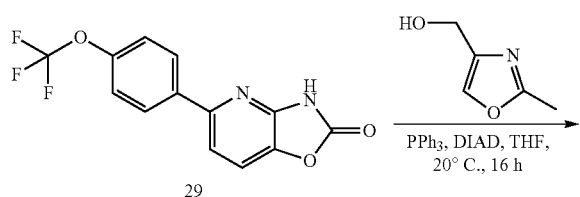

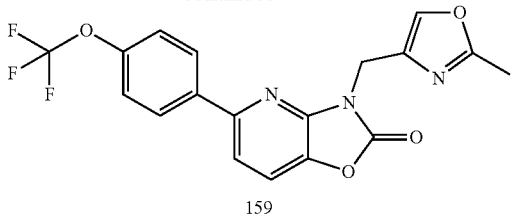

To a mixture of 5-[4-(trifluoromethoxy)phenyl]-3H-oxazolo[4,5-b]pyridin-2-one (60 mg, 0.2 mmol), (2-methyloxazol-4-yl)methanol (45.82 mg, 0.41 mmol) and PPh₃ (106.26 mg, 0.41 mmol) in THF (2 mL) was added the DIAD (81.92 mg, 0.41 mmol), and the mixture was stirred at 20° C. under N₂ for 16 hours. The reaction was diluted with sat.NH₄Cl (10 mL), and the mixture was extracted with EtOAc (10 mL×2). Then the combined organic phase was washed with brine (10 mL), dried over Na₂SO₄, filtered and concentrated to give the crude product. The crude product was purified by flash chromatography on silica gel (EtOAc in PE=0 to 40% to 70%) to give the product (36.56 mg, 0.09 mmol, 46% yield) as a solid. ¹H NMR (CDCl₃, 400 MHz) δ$_H$=8.00 (d, 2H), 7.66 (s, 1H), 7.50-7.45 (m, 2H), 7.32 (d, 2H), 5.07 (s, 2H), 2.43 (s, 3H). LCMS R$_t$=1.18 min in 2 min chromatography, MS ESI calcd. for C₁₈H₁₃F₃N₃O₄ [M+H]⁺ 392.1, found 392.0.

Example 136. Synthesis of Compound 160

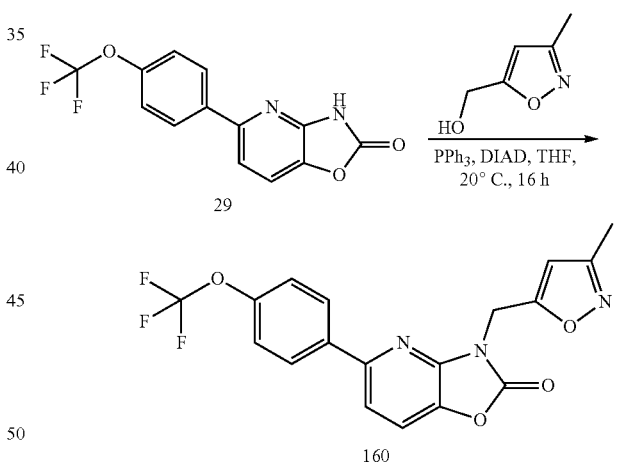

To a mixture of 5-[4-(trifluoromethoxy)phenyl]-3H-oxazolo[4,5-b]pyridin-2-one (60 mg, 0.2 mmol), (3-methylisoxazol-5-yl)methanol (45.82 mg, 0.41 mmol) and PPh₃ (106.26 mg, 0.41 mmol) in THF (1 mL) was added the DIAD (81.92 mg, 0.41 mmol), and the mixture was stirred at 20° C. under N₂ for 16 hours. The reaction was diluted with sat.NH₄Cl (10 mL), and the mixture was extracted with EtOAc (10 mL×2). Then the combined organic phase was washed with brine (10 mL), dried over Na₂SO₄, filtered and concentrated to give the crude product. The crude product was purified by flash chromatography on silica gel (EtOAc in PE=20% to 70%) to give the product (43.59 mg, 0.11 mmol, 55% yield) as solid. ¹H NMR (DMSO-d₆ 400 MHz) δ$_H$=8.17 (d, 2H), 7.89-7.81 (m, 2H), 7.48 (d, 2H), 6.50 (s, 1H), 5.23 (s, 2H), 2.20 (s, 3H). LCMS $R_t$=1.21 min in 2.0 min chromatography, MS ESI calcd. for $C_{18}H_{13}F_3N_3O_4$ [M+H]$^+$ 392.1, found 392.0.

Example 137. Synthesis of Compound 161

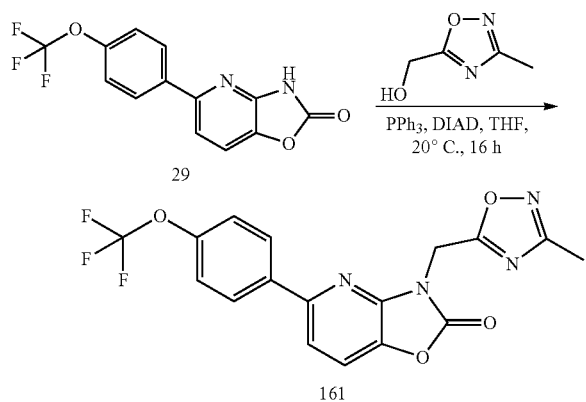

To a mixture of 5-[4-(trifluoromethoxy)phenyl]-3H-oxazolo[4,5-b]pyridin-2-one (60 mg, 0.20 mmol), PPh$_3$ (106.26 mg, 0.41 mmol) and (3-methyl-1,2,4-oxadiazol-5-yl)methanol (46.23 mg, 0.41 mmol) in THF (1 mL) was added DIAD (81.92 mg, 0.41 mmol). The mixture was stirred at 20° C. under N$_2$ for 16 hours. The mixture was diluted with NH$_4$Cl (20 mL), and extracted with EtOAc (20 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN; 52-72% B over 7 minutes) to give the product (34.48 mg, 85.80 μmol, 42% yield) as a solid. $^1$H NMR (DMSO-d$_6$ 400 MHz) $\delta_H$=8.13 (d, 2H), 7.95-7.81 (m, 2H), 7.48 (d, 2H), 5.49 (s, 2H), 2.32 (s, 3H). LCMS $R_t$=1.17 min in 2 min chromatography, MS ESI calcd. for $C_{17}H_{12}F_3N_4O_4$ [M+H]$^+$ 393.1, found 393.0.

Example 138. Synthesis of Compound 162

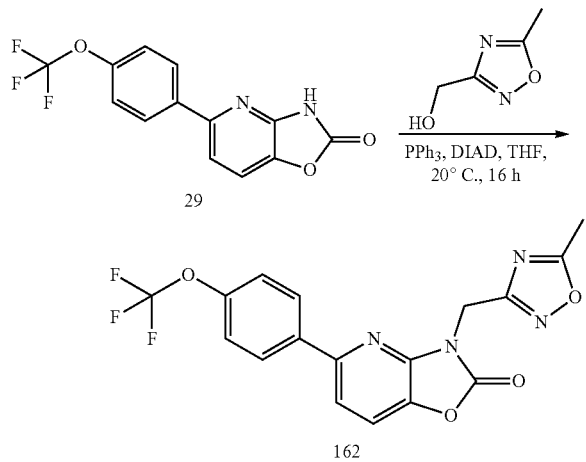

To a mixture of 5-[4-(trifluoromethoxy)phenyl]-3H-oxazolo[4,5-b]pyridin-2-one (60 mg, 0.20 mmol), PPh$_3$ (106.26 mg, 0.41 mmol) and (5-methyl-1,2,4-oxadiazol-3-yl)methanol (46.23 mg, 0.41 mmol) in THF (1 mL) was added DIAD (81.92 mg, 0.41 mmol). The mixture was stirred at 20° C. under N$_2$ for 16 hours. The reaction was diluted with sat.NH$_4$Cl (20 mL), and the mixture was extracted with EtOAc (15 mL×2). Then the combined organic phase was washed with brine (10 mL), dried over Na$_2$SO$_4$, filtered and concentrated to give the crude product. The crude product was purified by Prep-HPLC (Waters Xbridge (150 mm×25 mm, 5·μm) A=H$_2$O (10 mM NH$_4$HCO$_3$) and B=CH$_3$CN; 52-72% B over 6 minutes) to give the product (18.43 mg, 46.80 mmol, 23% yield) as a solid. $^1$H NMR DMSO-d$_6$ 400 MHz $\delta_H$=8.14 (d, 2H), 7.95-7.80 (m, 2H), 7.48 (d, 2H), 5.26 (s, 2H), 2.56 (s, 3H). LCMS $R_t$=1.16 min in 2 min chromatography, MS ESI calcd. for $C_{17}H_{12}F_3N_4O_4$ [M+H]$^+$ 393.1, found 393.0.

Example 139. Synthesis of Compound 163

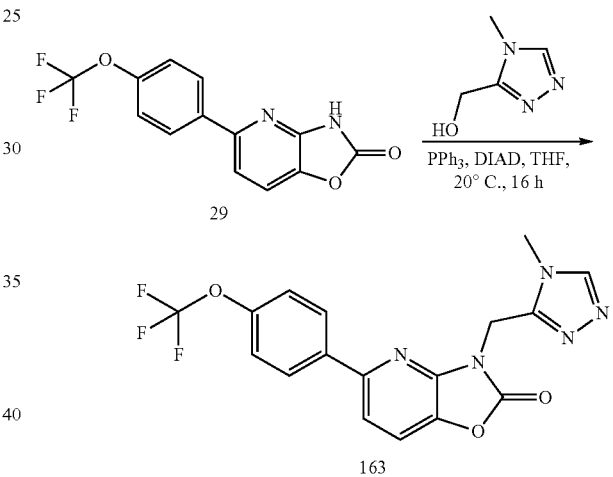

A mixture of (4-methyl-1,2,4-triazol-3-yl)methanol (45.83 mg, 0.41 mmol), 5-[4-(trifluoromethoxy)phenyl]-3H-oxazolo[4,5-b]pyridin-2-one (60 mg, 0.20 mmol), PPh$_3$ (106.26 mg, 0.41 mmol) and DIAD (81.92 mg, 0.41 mmol) in THF (3 mL) was stirred at 20° C. under N$_2$ for 16 hours. The reaction was diluted with sat.NH$_4$Cl (10 mL), and the mixture was extracted with EtOAc (10 mL×2). Then the combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN; 32-47% B over 8 minutes) to give the impure product. The impure product was triturated from i-Pr$_2$O (10 mL) and purified by Prep-HPLC (Waters Xbridge (150 mm×25 mm, 5 μm) A=H$_2$O (10 mM NH$_4$HCO$_3$) and B=CH$_3$CN; 33-63% B over 6 minutes) to give the product (16.59 mg, 41.1 μmol, 20% yield) as a solid. $^1$H NMR (DMSO-d$_6$ 400 MHz) $\delta_H$=8.48 (s, 1H), 8.14 (d, 2H), 7.88 (d, 1H), 7.81 (d, 1H), 7.48 (d, 2H), 5.30 (s, 2H), 3.79 (s, 3H). LCMS $R_t$=1.10 min in 2.0 min chromatography, MS ESI calcd. for $C_{17}H_{13}F_3N_5O_3$ [M+H]$^+$ 392.1, found 391.9.

Example 140. Synthesis of Compound 164

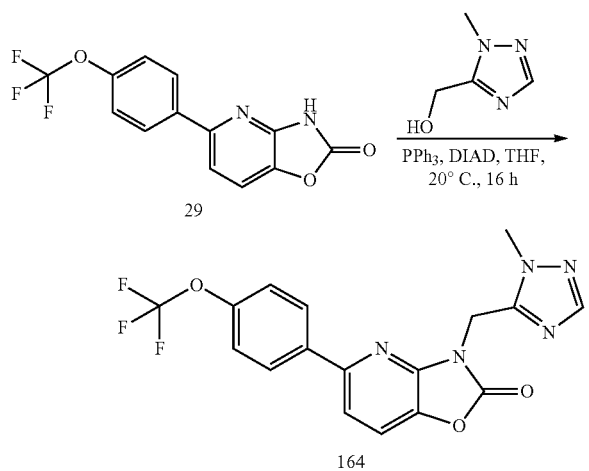

A mixture of (2-methyl-1,2,4-triazol-3-yl)methanol (45.83 mg, 0.41 mmol), 5-[4-(trifluoromethoxy)phenyl]-3H-oxazolo[4,5-b]pyridin-2-one (60 mg, 0.20 mmol), PPh$_3$ (106.26 mg, 0.41 mmol) and DIAD (81.92 mg, 0.41 mmol) in THF (3 mL) was stirred at 20° C. under N$_2$ for 16 hours. The reaction was diluted with sat.NH$_4$Cl (10 mL), and the mixture was extracted with EtOAc (10 mL×2). Then the combined organic phase was washed with brine (10 mL), dried over Na$_2$SO$_4$, filtered and concentrated to give the crude product. The crude product was purified by flash chromatography on silica gel (EtOAc in PE=10% to 40%) to give impure product. The impure product was purified by Prep-HPLC (Xbridge BEH C18 (250 mm×50 mm, 10 μm) A=H$_2$O (10 mM NH$_4$HCO$_3$) and B=CH$_3$CN; 38-68% B over 9 minutes) to give the product (20.82 mg, 52.6 μmol, 26% yield) as a solid. $^1$H NMR (DMSO-d$_6$ 400 MHz) $\delta_H$=8.12 (d, 2H), 7.90-7.86 (m, 1H), 7.84-7.79 (m, 2H), 7.48 (d, 2H), 5.34 (s, 2H), 4.01 (s, 3H). LCMS R$_t$=1.09 min in 2.0 min chromatography, MS ESI calcd. for C$_{17}$H$_{13}$F$_3$N$_5$O$_3$ [M+H]$^+$ 392.1, found 392.0.

Example 141. Synthesis of Compound 165

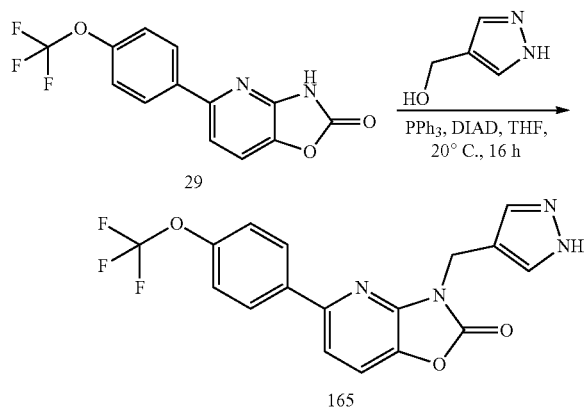

A mixture of 5-[4-(trifluoromethoxy)phenyl]-3H-oxazolo[4,5-b]pyridin-2-one (60 mg, 0.20 mmol), 1H-pyrazol-4-ylmethanol (39.74 mg, 0.41 mmol), PPh$_3$ (106.26 mg, 0.41 mmol) and DIAD (81.92 mg, 0.41 mmol) in THF (3 mL) was stirred at 20° C. under N$_2$ for 16 hours. The reaction was diluted with sat.NH$_4$Cl (10 mL), and the mixture was extracted with EtOAc (10 mL×2). Then the combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN; 46-66% B over 6 minutes) to give the product (23.1 mg, 61.4 μmol, 30% yield) as a solid. $^1$H NMR (DMSO-d$_6$ 400 MHz) $\delta_H$=12.83 (br s, 1H), 8.22 (d, 2H), 7.87-7.77 (m, 3H), 7.59 (s, 1H), 7.50 (d, 2H), 4.97 (s, 2H). LCMS R$_t$=1.13 min in 2.0 min chromatography, MS ESI calcd. for C$_{17}$H$_{12}$F$_3$N$_4$O$_3$ [M+H]$^+$ 377.1, found 377.1.

Example 142. Synthesis of Compound 166

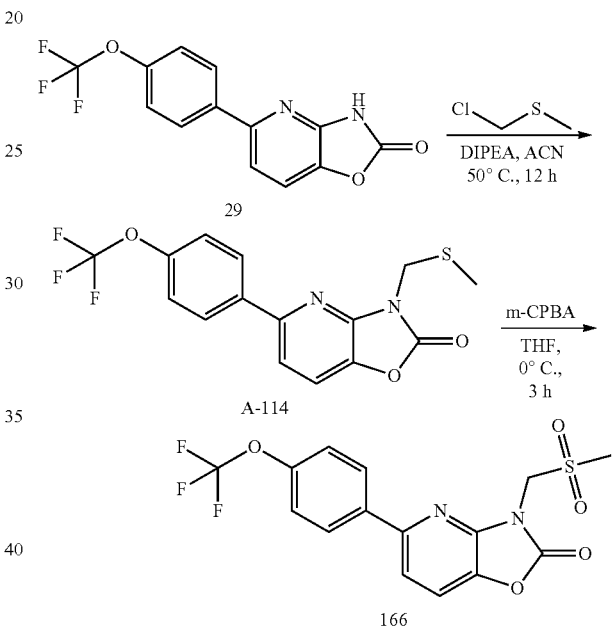

A mixture of 5-[4-(trifluoromethoxy)phenyl]-3H-oxazolo[4,5-b]pyridin-2-one (150 mg, 0.51 mmol), chloro(methylsulfanyl)methane (244.55 mg, 2.53 mmol) and DIPEA (0.44 mL, 2.53 mmol) in MeCN (10 mL) was stirred at 50° C. for 12 hours. After cooling to r.t., the mixture was diluted with H$_2$O (30 mL), and the mixture was extracted with EtOAc (50 mL×2). The combined organic phase was washed with water (30 mL) and brine (30 mL), dried over Na$_2$SO$_4$, filtered and concentrated to give the crude product. The crude product was purified by flash chromatography on silica gel (EtOAc in PE=0% to 15% to 30%) to give the product (110 mg, 0.31 mmol, 61% yield) as a solid. LCMS R$_t$=0.97 min in 1.5 min chromatography, MS ESI calcd. for C$_{15}$H$_{12}$F$_3$N$_3$O$_3$S [M+H]$^+$ 357.0, found 357.0. To a mixture of 3-(methylsulfanylmethyl)-5-[4-(trifluoromethoxy)phenyl]oxazolo[4,5-b]pyridin-2-one (60 mg, 0.17 mmol) in THF (10 mL) was added m-CPBA (102.56 mg, 0.51 mmol) at 0° C., then the mixture was stirred at 0° C. for 3 hours. The mixture was quenched with sat.Na$_2$CO$_3$ (10 mL), then the mixture was extracted with EtOAc (30 mL×2). The combined organic phase was washed with brine (15 mL), dried over Na$_2$SO$_4$, filtered and concentrated to give the crude product. The crude product was purified by Prep-TLC (silica gel, PE:EtOAc=1:1) to give the product (52.19 mg, 134.4 μmol, 80% yield) as a solid. $^1$H NMR (CDCl$_3$, 400 MHz) $\delta_H$=7.99 (d, 2H), 7.62-7.55 (m, 2H), 7.33 (d, 2H), 5.23 (s, 2H), 3.17 (s, 3H). LCMS R$_t$=1.11 min in 2.0 min chromatography, MS ESI calcd. for C$_{15}$H$_{12}$F$_3$N$_2$O$_5$S [M+H]$^+$ 389.0, found 388.9.

Example 143. Synthesis of Compound 167

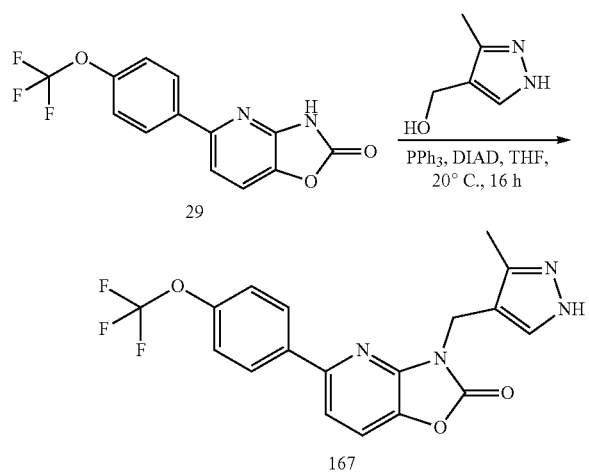

To a mixture of 5-[4-(trifluoromethoxy)phenyl]-3H-oxazolo[4,5-b]pyridin-2-one (100 mg, 0.34 mmol), (3-methyl-1H-pyrazol-4-yl)methanol (75.71 mg, 0.68 mmol) and PPh$_3$ (265.65 mg, 1.01 mmol) in THF (3 mL) was added DIAD (204.8 mg, 1.01 mmol). The mixture was stirred at 20° C. for 16 hours. The reaction was quenched with sat.NH$_4$Cl (10 mL), and the mixture was extracted with EtOAc (20 mL×2). The combined organic phase was washed with brine (10 mL), dried over Na$_2$SO$_4$, filtered and concentrated to give the crude product. The crude product was purified by prep-HPLC (Xbridge (150 mm×30 mm, 10 μm) A=H$_2$O (0.05% NH$_4$OH) and B=CH$_3$CN; 48-78% B over 7 minutes) to give the product (33.96 mg, 87.00 mol, 26% yield) as a solid. $^1$H NMR (CDCl$_3$, 400 MHz) $\delta_H$=10.00-9.24 (m, 1H), 8.02 (d, 2H), 7.79 (s, 1H), 7.50-7.41 (m, 2H), 7.34 (d, 2H), 5.02 (s, 2H), 2.49 (s, 3H). LCMS R$_t$=1.12 min in 2.0 min chromatography, MS ESI calcd. for C$_{18}$H$_{14}$F$_3$N$_4$O$_3$ [M+H]$^+$ 391.1, found 391.0.

Example 144: Efficacy of Exemplary Compounds in the Modulation of Late Sodium Current (INaL)

Functional characterization of exemplary compounds to modulate INaL expressed by the Nav1.6 voltage-gated sodium channel was accomplished using the PatchXpress™ high throughput electrophysiology platform (Molecular Devices, Sunnyvale, Calif.). HEK-293 cells expressing recombinant, human Nav1.6 (hNav1.6) were grown in DMEM/high-glucose Dulbecco's modified, 10% FBS, 2 mM sodium pyruvate, 10 mM HEPES and 400 μg/mL G418. Cells were grown to 50%-80% confluency prior to harvesting. Trypsinized cells were washed, allowed to recover for 1 hour and then resuspended in extracellular recording solution at a concentration of 1×10$^6$ cells/ml. The onboard liquid handling facility of the PatchXpress was used for dispensing cells and applying test compounds. Nav late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a Na free solution containing an impermeant cation (e.g., Choline or NDMG) was added to confirm the identify of the sodium current. Percent steady-state inhibition of INaL was calculated as: [(INaL_compound)/(INaL_control)]*100, where INaL_compound and INaL_control represent INaL recorded in the presence or absence of compound, respectively.

Results from this assay relating to percent inhibition of INaL at hNav1.5 (measured using procedure similar to described above but using HEK-293 cells expressing recombinant, human Nav1.5 (hNav1.5) at 1 μM are summarized in Table 1 below. In this table, "A" indicates inhibition of less than 30%; "B" indicates inhibition of between about 30% to about 70%; and "C" indicates inhibition of greater than 70%.

TABLE 1

| Compound | INaL v1.6 (1 μM, % Inhibition) |
|---|---|
| 1 | C |
| 2 | B |
| 3 | C |
| 4 | C |
| 5 | C |
| 6 | B |
| 7 | C |
| 8 | A |
| 9 | A |
| 10 | C |
| 11 | C |
| 12 | C |
| 13 | C |
| 14 | B |
| 15 | A |
| 16 | A |
| 17 | B |
| 18 | A |
| 19 | C |
| 20 | B |
| 21 | B |
| 22 | A |
| 23 | A |
| 24 | A |
| 25 | C |
| 26 | C |
| 27 | B |
| 28 | C |
| 29 | A |
| 30 | B |
| 31 | B |
| 32 | B |
| 33 | C |
| 34 | B |
| 35 | C |
| 36 | A |
| 37 | B |
| 38 | B |
| 39 | C |
| 40 | B |
| 41 | A |
| 42 | A |
| 43 | A |
| 44 | A |
| 45 | A |
| 46 | A |
| 47 | A |
| 48 | B |
| 49 | A |
| 50 | B |
| 51 | B |
| 52 | B |

TABLE 1-continued

| Compound | INaL v1.6 (1 µM, % Inhibition) |
|---|---|
| 53 | C |
| 54 | B |
| 55 | B |
| 56 | C |
| 57 | C |
| 58 | C |
| 59 | B |
| 61 | C |
| 62 | C |
| 64 | C |
| 65 | B |
| 66 | C |
| 67 | C |
| 68 | C |
| 69 | C |
| 70 | B |
| 71 | A |
| 72 | C |
| 73 | C |
| 75 | C |
| 76 | C |
| 77 | B |
| 78 | C |
| 79 | B |
| 80 | B |
| 81 | C |
| 84 | C |
| 85 | B |
| 86 | C |
| 87 | B |
| 88 | A |
| 89 | C |
| 90 | B |
| 91 | B |
| 92 | A |
| 93 | C |
| 96 | B |
| 97 | C |
| 98 | B |
| 99 | C |
| 100 | C |
| 101 | C |
| 102 | C |
| 103 | C |
| 104 | C |
| 105 | C |
| 106 | C |
| 107 | B |
| 108 | B |
| 109 | C |
| 110 | B |
| 111 | B |
| 112 | C |
| 113 | B |
| 114 | A |
| 115 | A |
| 116 | C |
| 117 | C |
| 118 | A |
| 119 | C |
| 120 | C |
| 121 | B |
| 122 | A |
| 123 | C |
| 124 | C |
| 125 | A |
| 126 | B |
| 127 | C |
| 128 | B |
| 129 | C |
| 130 | A |
| 131 | C |
| 132 | C |
| 133 | C |
| 134 | C |
| 135 | B |
| 136 | A |
| 137 | A |
| 138 | B |
| 139 | B |
| 140 | B |
| 141 | B |
| 142 | A |
| 143 | C |
| 144 | A |
| 145 | A |
| 146 | C |
| 147 | C |
| 148 | A |
| 149 | C |
| 150 | B |
| 151 | C |
| 152 | A |
| 153 | B |
| 154 | C |
| 155 | C |
| 156 | C |
| 157 | B |
| 158 | B |
| 159 | C |
| 160 | C |
| 161 | C |
| 162 | C |
| 163 | A |
| 164 | B |
| 165 | B |
| 166 | B |
| 167 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A compound of Formula (I-1):

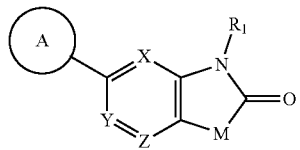

(I)

or a pharmaceutically acceptable salt thereof, wherein:
each of X, Y, and Z is independently N or CR';
M is O or $C(R^{2a})(R^{2b})$;
A is phenyl or 5-6 membered heteroaryl, wherein phenyl and 5-6 membered heteroaryl are substituted by one or more $R^3$;
R' is selected from the group consisting of hydrogen, $C_{1-6}$ alkyl, $OR^c$, and halogen;
$R^1$ is selected from the group consisting of hydrogen, $C_{1-6}$ alkyl, $C_{3-8}$ carbocyclyl, and 3-10 membered heterocyclyl, wherein $C_{1-6}$alkyl, $C_{3-8}$ carbocyclyl, and 3-10 membered heterocyclyl are optionally substituted with one or more $R^4$;
each of $R^{2a}$ and $R^{2b}$ is independently hydrogen or $C_{1-6}$ alkyl, wherein $C_{1-6}$ alkyl is optionally substituted by one or more $R^4$;
each $R^3$ is independently selected from the group consisting of $C_{1-6}$alkyl, $C_{3-8}$ carbocyclyl, 3-10 membered heterocyclyl, halo, cyano, nitro, and —$OR^c$, wherein $C_{1-6}$alkyl, $C_{3-8}$ carbocyclyl, and 3-10 membered heterocyclyl are optionally substituted with one or more $R^5$;
each of $R^4$ and $R^5$ is independently selected from the group consisting of deuterium, $C_{1-6}$alkyl, $C_{3-8}$ carbocyclyl, 3-10 membered heterocyclyl, phenyl, 5-6 membered heteroaryl, halo, oxo, cyano, nitro, —$OR^c$, —$N(R^d)_2$, —$C(O)R^c$, —$C(O)OR^c$, —$S(O)_2$—$R^c$, —$S(O)_2N(R^d)_2$, and —$C(O)N(R^d)_2$, wherein $C_{1-6}$alkyl, $C_{3-8}$ carbocyclyl, 3-10 membered heterocyclyl, phenyl, and 5-6 membered heteroaryl is optionally substituted by one or more $R^7$;

each $R^C$ is independently selected from the group consisting of hydrogen, $C_{1-6}$alkyl, $C_{3-8}$carbocyclyl, 3-10 membered heterocyclyl, phenyl, and 5-6 membered heteroaryl, wherein $C_{1-6}$alkyl, $C_{3-8}$ carbocyclyl, 3-10 membered heterocyclyl, phenyl, and 5-6 membered heteroaryl is optionally substituted by one or more $R^6$;

each $R^d$ is independently hydrogen or $C_{1-6}$ alkyl, wherein each $C_{1-6}$ alkyl is optionally substituted by one or more $R^6$; or two $R^d$, taken together with the atoms to which they are attached, form a 3-10 membered heterocyclyl optionally substituted with —OH, $C_{1-6}$alkoxy, or $C_{1-6}$alkyl optionally substituted with $C_{1-6}$alkoxy;

each $R^e$ is $C_{1-6}$alkyl;

each $R^6$ is independently selected from the group consisting of $C_{1-6}$alkyl, $C_{3-8}$carbocyclyl, 3-10 membered heterocyclyl, halo, cyano, nitro, and —OH; and each $R^7$ is independently selected from the group consisting of $C_{1-6}$alkyl, halo, oxo, —$C(O)R^c$, and —$C(O)OR^c$;

wherein the compound is not one of the following:

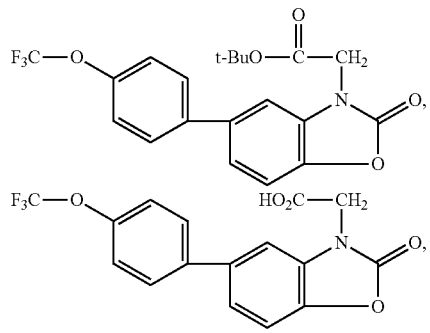

or a pharmaceutically acceptable salt thereof.

2. The compound of claim 1, wherein each of X, Y, and Z is independently CR'.

3. The compound of claim 1, wherein M is O.

4. The compound of claim 1, wherein A is phenyl substituted by 1 $R^3$.

5. The compound of claim 1, wherein $R^3$ is —$OR^c$.

6. The compound of claim 5, wherein $R^3$ is —$OCF_3$.

7. The compound of claim 1, wherein $R^1$ is $C_{1-6}$alkyl, wherein $C_{1-6}$alkyl is optionally substituted with one or more $R^4$.

8. The compound of claim 1, wherein $R^4$ is selected from the group consisting of deuterium, halo, —$OR^c$, oxo, $C_{3-8}$carbocyclyl, 5-6 membered heteroaryl, —$C(O)OR^c$, and —$C(O)N(R^d)_2$.

9. The compound of claim 8, wherein $R^4$ is selected from the group consisting of deuterium, fluoro, tetrahydrofuranyl, tetrahydropyranyl, pyrimidinyl, OH, $C(O)N(CH_3)_2$, $C(O)N(CH_3)(CH_2CH_3)$, $C(O)N(CH_3)(CH_2CF_3)$, and C(O)N-tetrahydropyrrolyl.

10. The compound of claim 1, wherein the compound of Formula (I-1) is a compound of Formula (I-2):

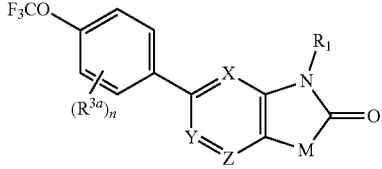

(I-2)

or a pharmaceutically acceptable salt thereof, wherein:
each of X, Y, and Z is independently N or CR';
M is O or $C(R^{2a})(R^{2b})$;
R' is selected from the group consisting of hydrogen, $C_{1-6}$ alkyl, $-OR^c$, and halogen;
$R^1$ is selected from the group consisting of hydrogen, $C_{1-6}$ alkyl, $C_{3-8}$carbocyclyl, and 3-10 membered heterocyclyl, wherein $C_{1-6}$alkyl, $C_{3-8}$ carbocyclyl, and 3-10 membered heterocyclyl are optionally substituted with one or more $R^4$;
each of $R^{2a}$ and $R^{2b}$ is independently hydrogen or $C_{1-6}$ alkyl, wherein $C_{1-6}$ alkyl is optionally substituted by one or more $R^4$;
each $R^{3a}$ is independently selected from the group consisting of $C_{1-6}$alkyl, $C_{3-8}$carbocyclyl, 3-10 membered heterocyclyl, halo, cyano, nitro, and $-OR^c$, wherein $C_{1-6}$ alkyl, $C_{3-8}$carbocyclyl, and 3-10 membered heterocyclyl are optionally substituted with one or more $R^5$;
each of $R^4$ and $R^5$ is independently selected from the group consisting of deuterium, $C_{1-6}$alkyl, $C_{3-8}$carbocyclyl, 3-10 membered heterocyclyl, phenyl, 5-6 membered heteroaryl, halo, cyano, nitro, $-C(O)N(R^d)_2$, $-C(O)R^c$, $-C(O)OR^c$, $-S(O)_2N(R^d)_2$, and $-OR^c$, wherein $C_{1-6}$alkyl, $C_{3-8}$carbocyclyl, 3-10 membered heterocyclyl, phenyl, and 5-6 membered heteroaryl is optionally substituted by one or more $R^7$;
each $R^C$ is independently selected from the group consisting of hydrogen, $C_{1-6}$alkyl, $C_{3-8}$carbocyclyl, 3-10 membered heterocyclyl, phenyl, and 5-6 membered heteroaryl, wherein $C_{1-6}$alkyl, $C_{3-8}$ carbocyclyl, 3-10 membered heterocyclyl, phenyl, and 5-6 membered heteroaryl is optionally substituted by one or more $R^6$;
each $R^d$ is independently hydrogen or $C_{1-6}$alkyl optionally substituted with one or more halogen;
or two $R^d$, taken together with the atoms to which they are attached, form a 3-10 membered heterocyclyl optionally substituted with $-OH$, $C_{1-6}$ alkoxy, or $C_{1-6}$alkyl optionally substituted with $C_{1-6}$ alkoxy;
each $R^c$ is $C_{1-6}$alkyl;
each $R^6$ is independently selected from the group consisting of $C_{1-6}$alkyl, $C_{3-8}$carbocyclyl, 3-10 membered heterocyclyl, halo, cyano, nitro, and $-OH$;
each $R^7$ is independently selected from the group consisting of $C_{1-6}$alkyl, oxo, halo, $-C(O)R^c$, and $-C(O)R^c$;
n is selected from the group consisting of 0, 1, 2, 3, and 4, wherein the compound is not one of the following:

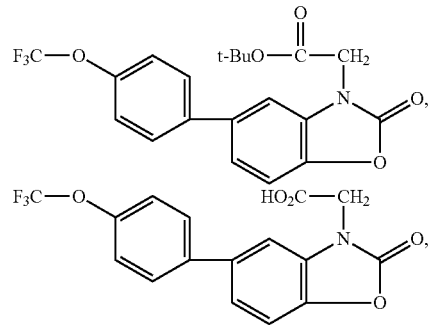

or a pharmaceutically acceptable salt thereof.

11. The compound of claim 10, wherein the compound of formula 1-2 is a compound of formula 1-3:

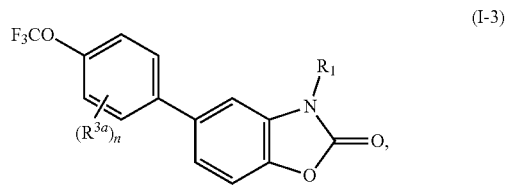

(I-3)

or a pharmaceutically acceptable salt thereof.

12. The compound of claim 10, wherein each of X, Y, and Z is CR', wherein R' is hydrogen.

13. The compound of claim 10, wherein M is O.

14. The compound of claim 10, wherein $R^1$ is $C_{1-6}$alkyl, wherein $C_{1-6}$alkyl is optionally substituted with one or more $R^4$.

15. The compound of claim 10, wherein each of $R^4$ and $R^5$ is independently selected from the group consisting of deuterium, $C_{1-6}$alkyl, $C_{3-8}$carbocyclyl, 3-10 membered heterocyclyl, phenyl, 5-6 membered heteroaryl, halo, cyano, nitro, $-C(O)N(R^d)_2$, $-C(O)CH_3$, $-C(O)OCH_3$, $-SO_2CH_3$, $-S(O)_2N(R^d)_2$, and $-OR^c$, wherein $C_{1-6}$ alkyl, $C_{3-8}$carbocyclyl, 3-10 membered heterocyclyl, phenyl, and 5-6 membered heteroaryl is optionally substituted by one or more $R^7$.

16. The compound of claim 10, wherein each of $R^4$ and $R^5$ is independently selected from the group consisting of deuterium, $C_{1-6}$alkyl, $C_{3-8}$carbocyclyl, 3-10 membered heterocyclyl, phenyl, 5-6 membered heteroaryl, halo, cyano, nitro, $-C(O)N(R^d)_2$, $-SO_2CH_3$, $-S(O)_2N(R^d)_2$, and $-OR^c$, wherein $C_{1-6}$alkyl, $C_{3-8}$carbocyclyl, 3-10 membered heterocyclyl, phenyl, and 5-6 membered heteroaryl is optionally substituted by one or more $R^7$.

17. The compound of claim 10, wherein each of $R^4$ and $R^5$ is independently selected from the group consisting of deuterium, $C_{1-6}$alkyl, $C_{3-8}$carbocyclyl, 3-10 membered heterocyclyl, phenyl, 5-6 membered heteroaryl, halo, cyano, nitro, and $-OR^c$, wherein $C_{1-6}$ alkyl, $C_{3-8}$carbocyclyl, 3-10 membered heterocyclyl, phenyl, and 5-6 membered heteroaryl is optionally substituted by one or more $R^7$.

18. A compound selected from the group consisting of:

229
-continued
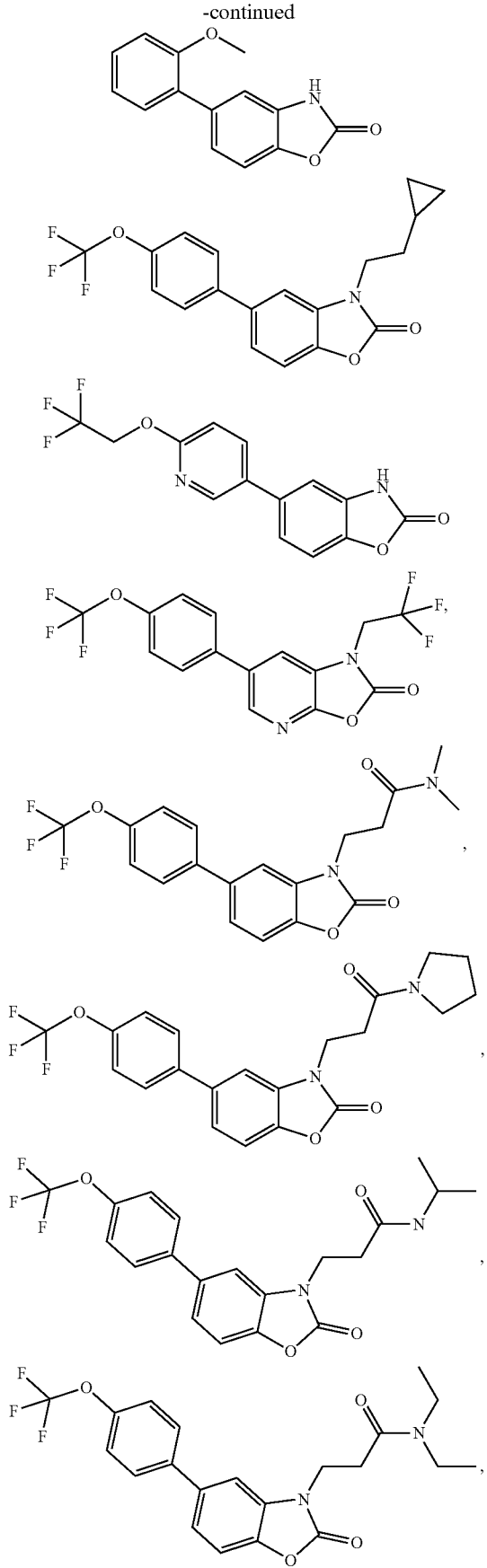
230
-continued
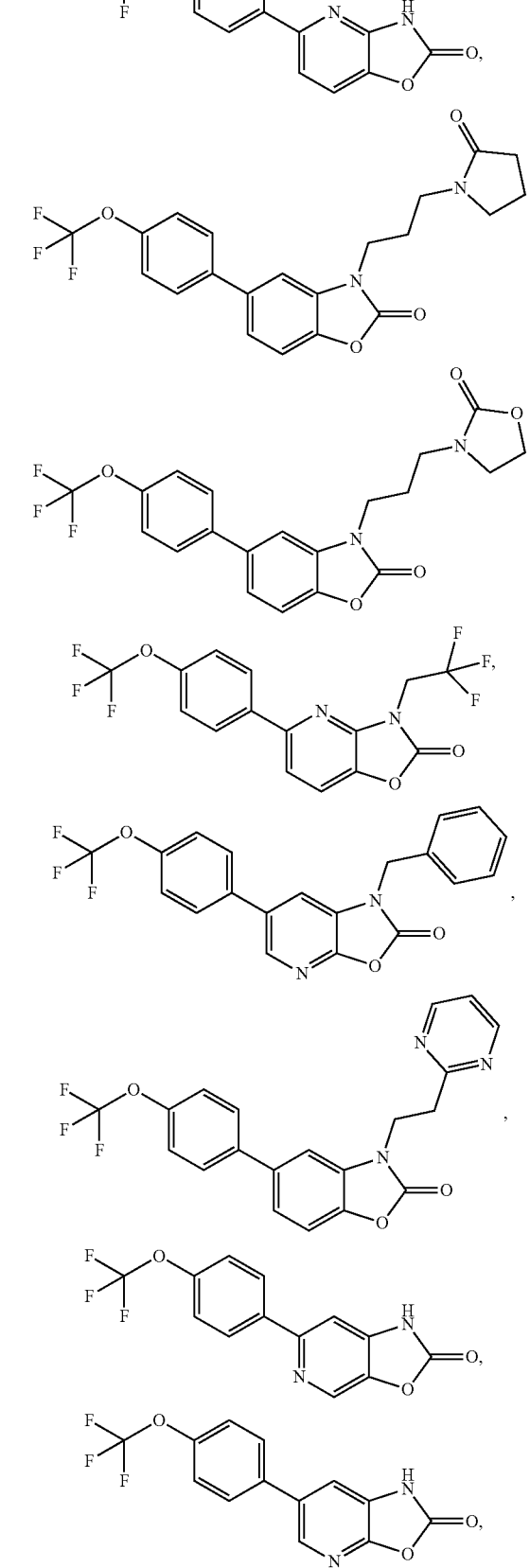

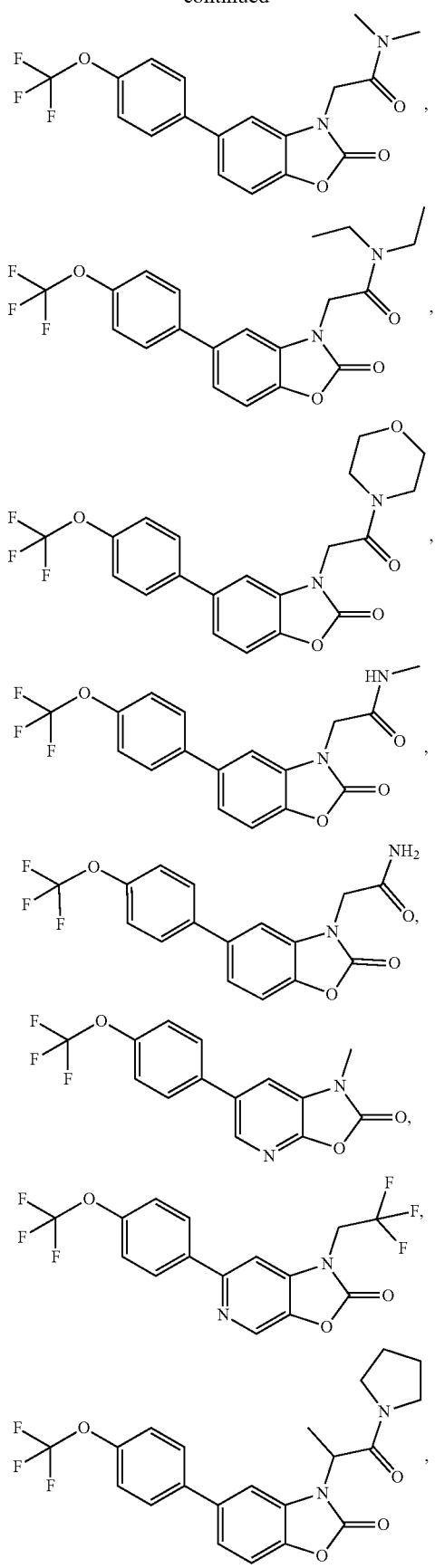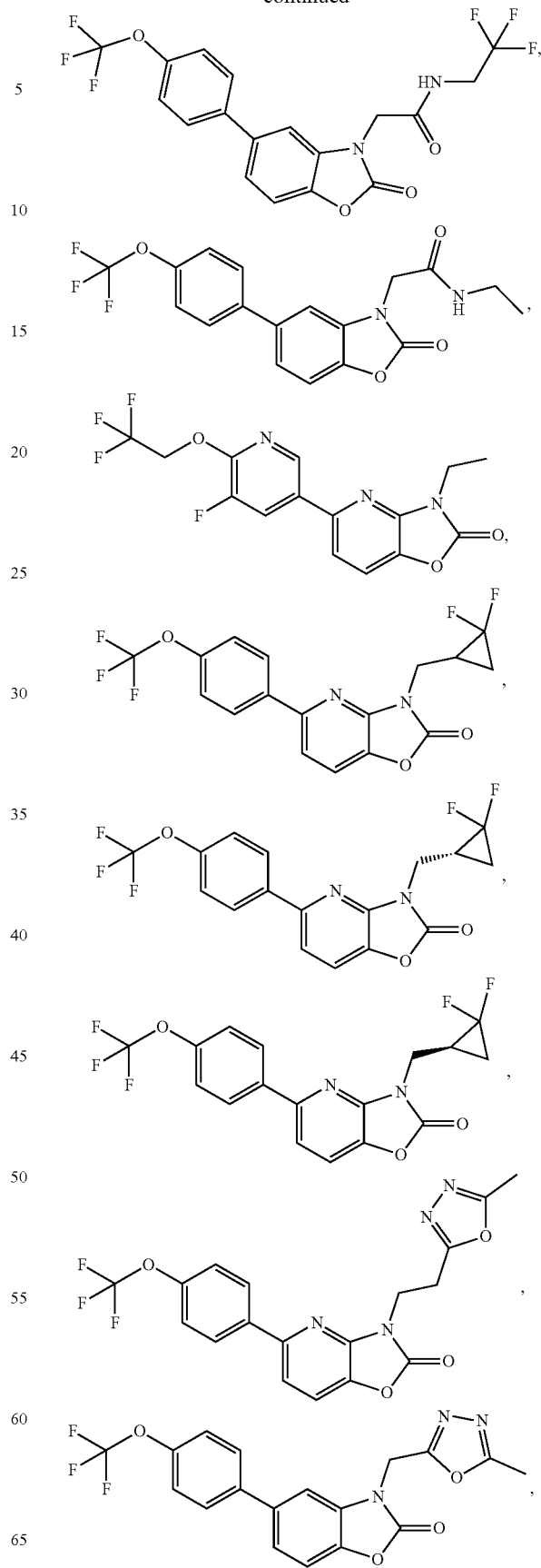

233
-continued
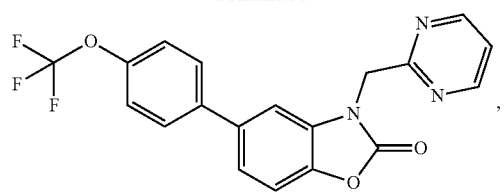,
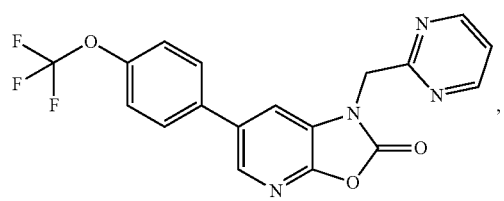,
,
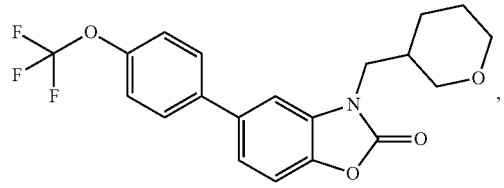,
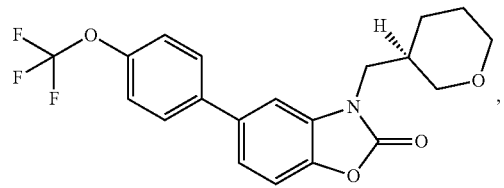,
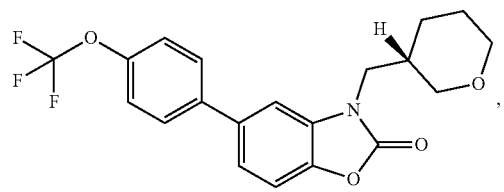,
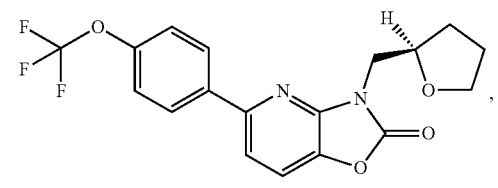,
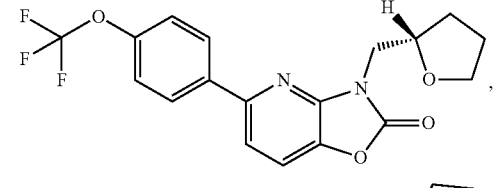,
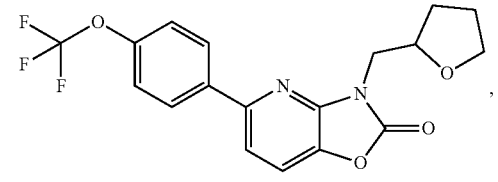,
234
-continued
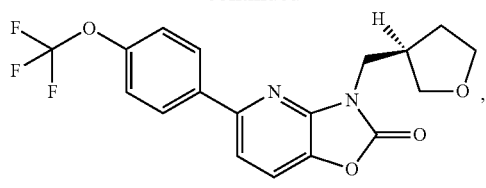,
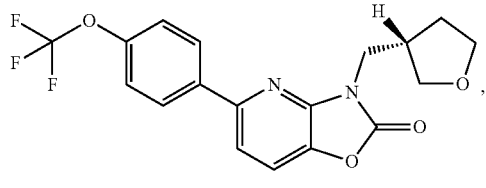,
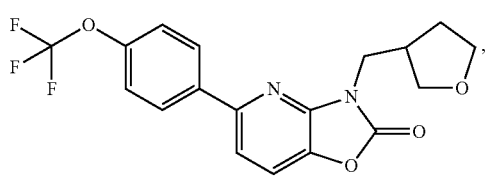,
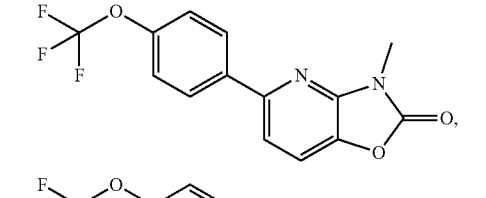,
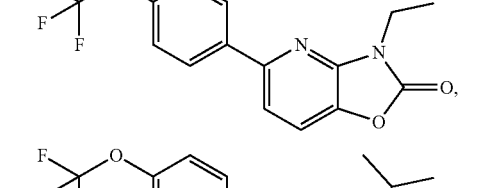,
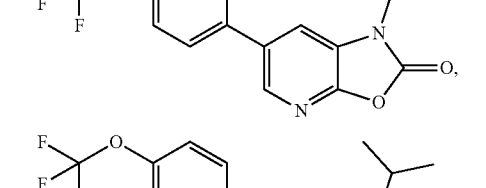,
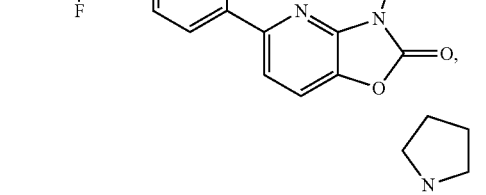,
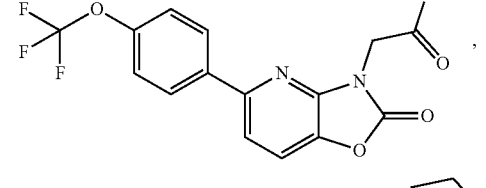,
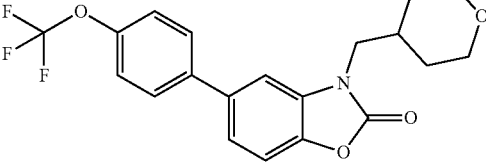,

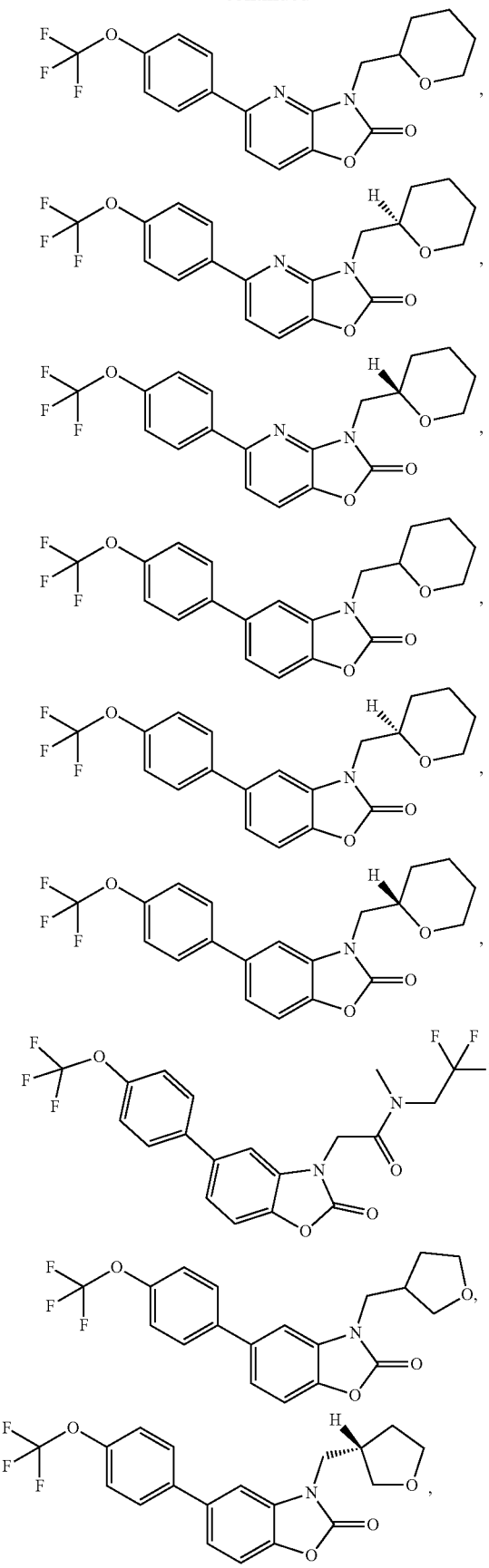
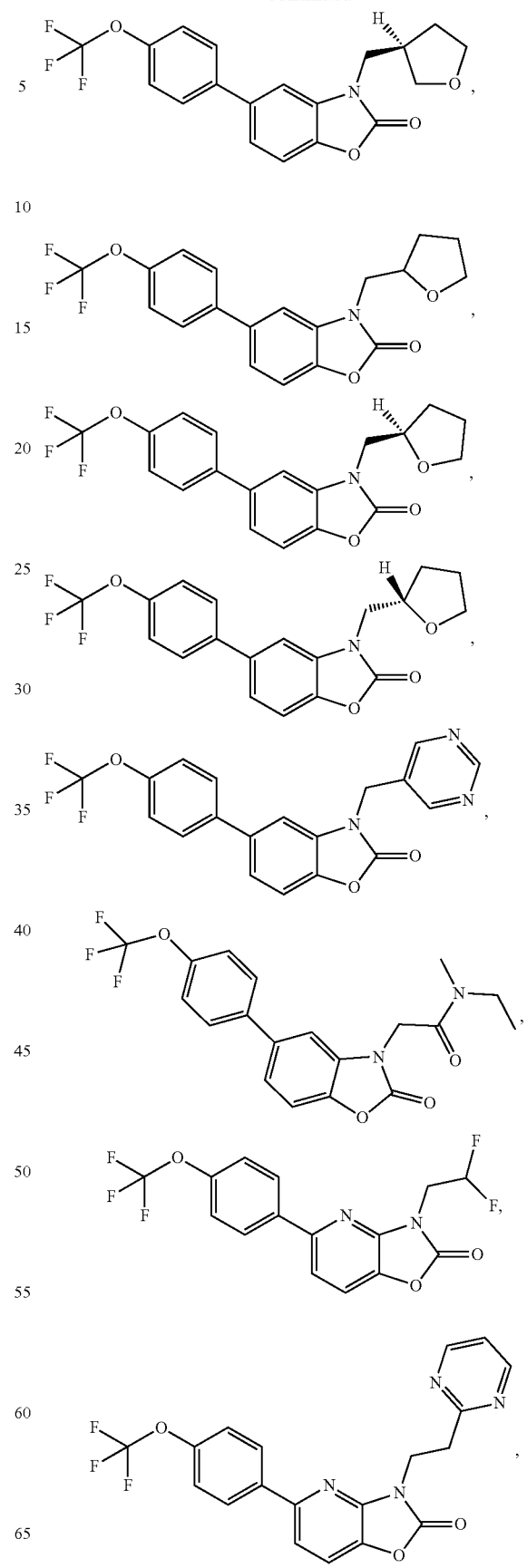

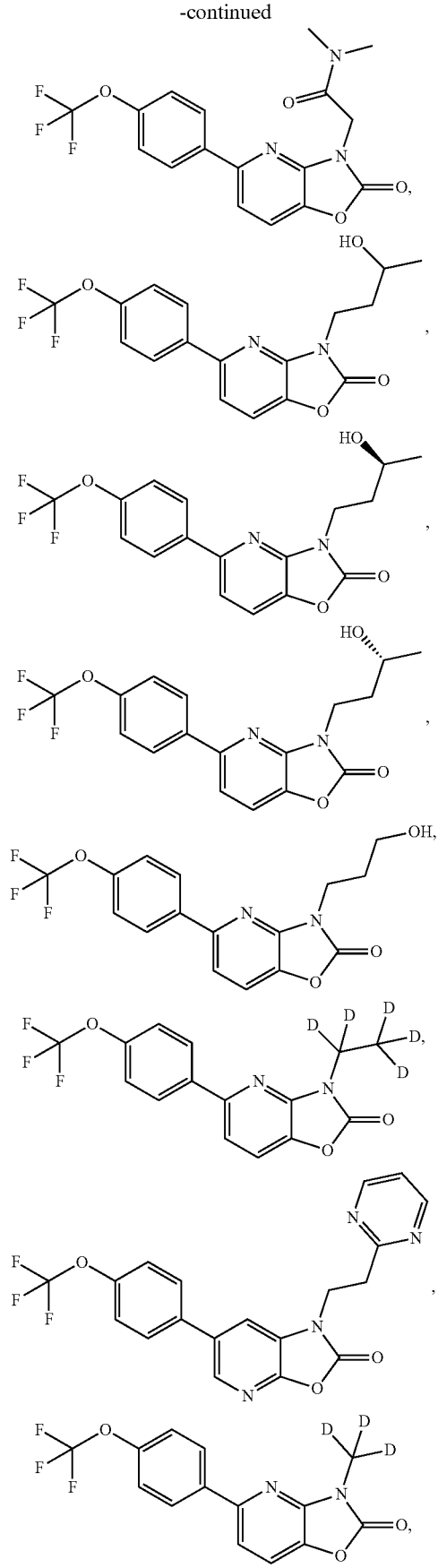
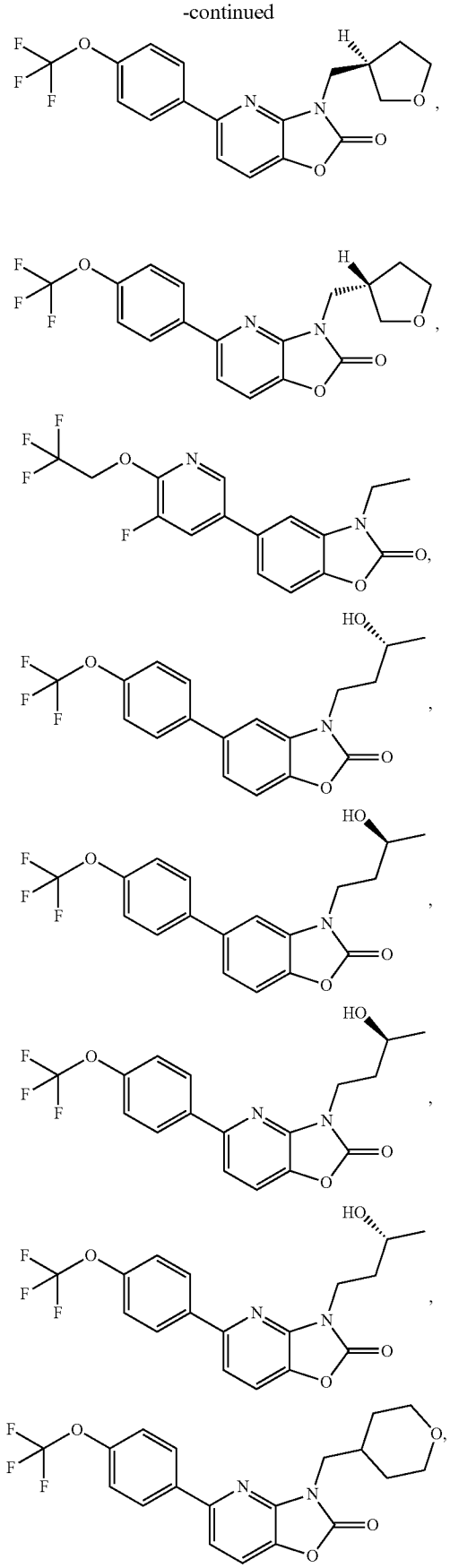

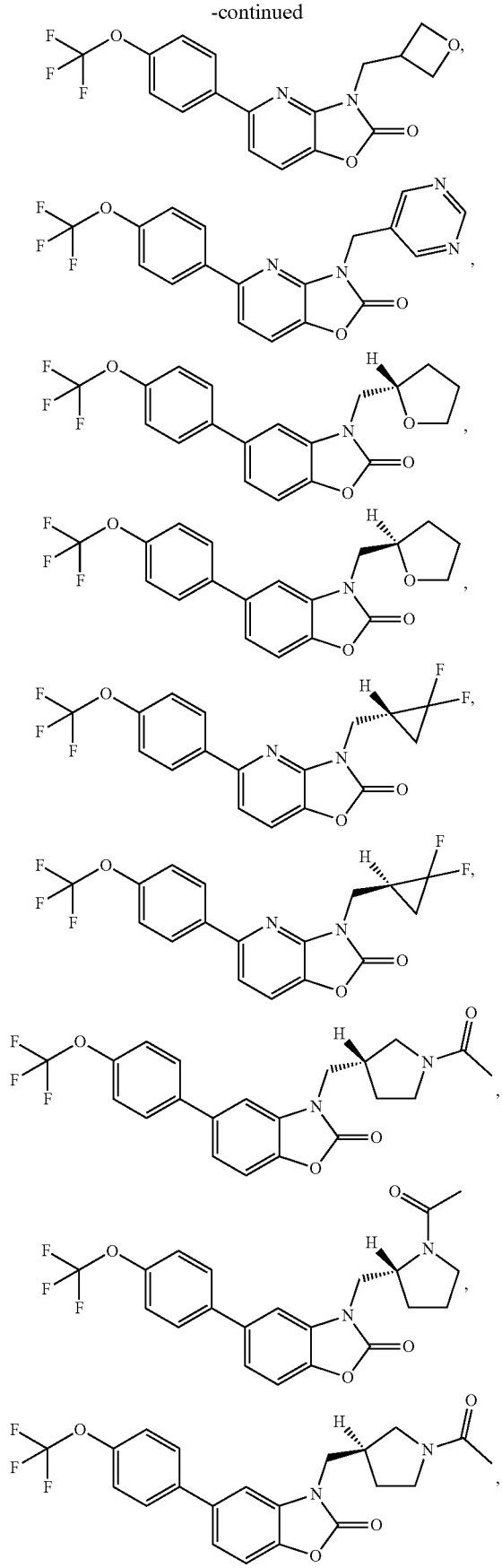
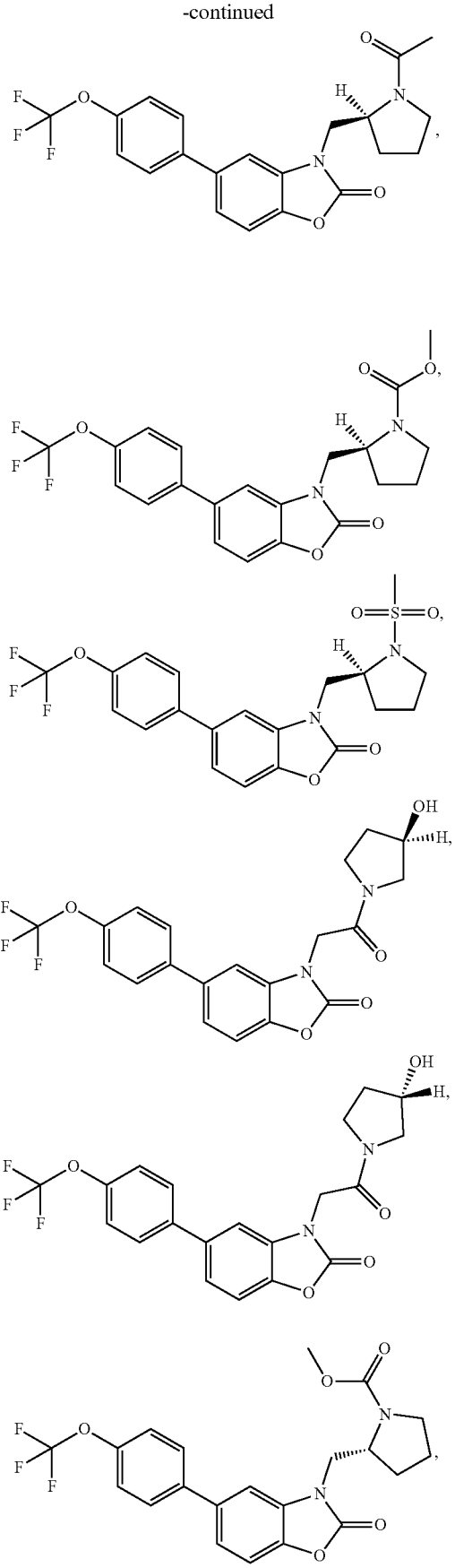

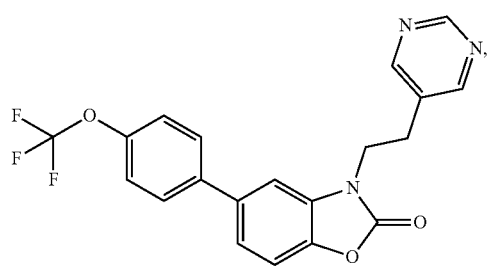
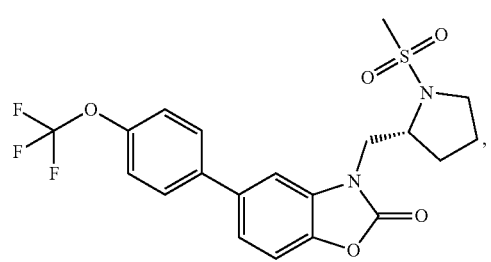
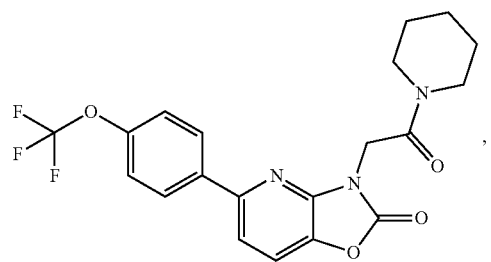
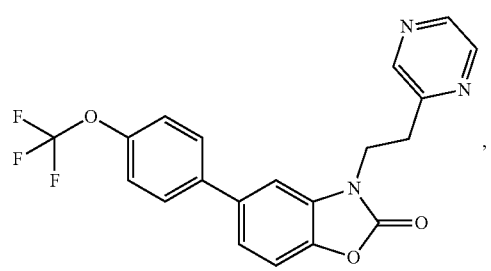
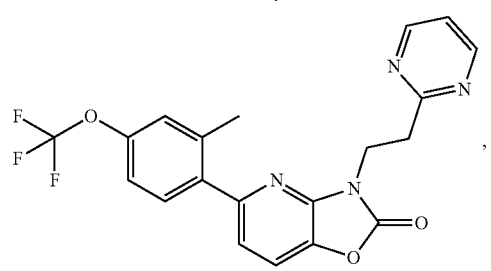
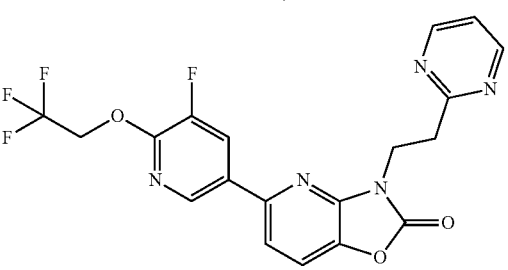
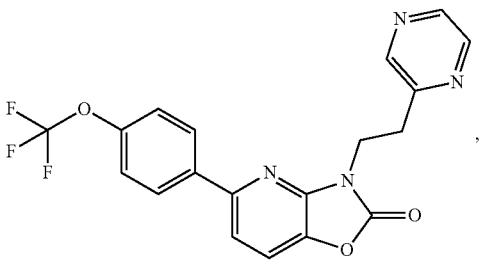
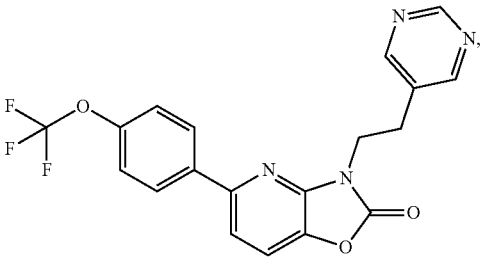
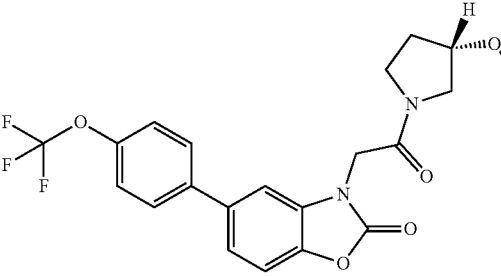
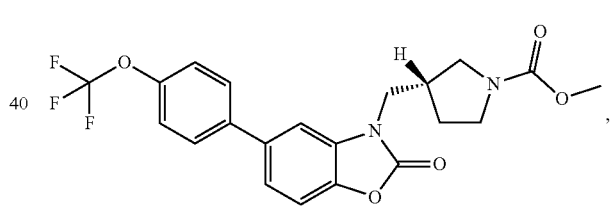
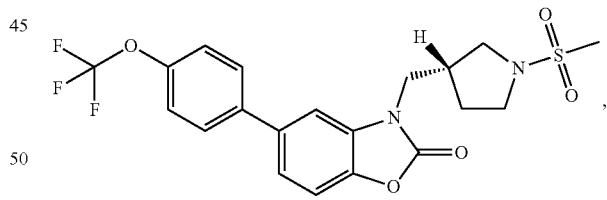
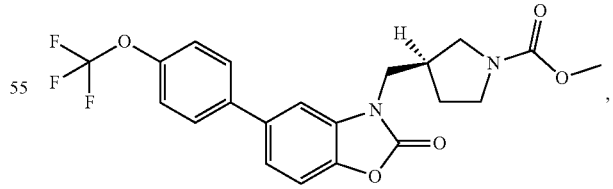
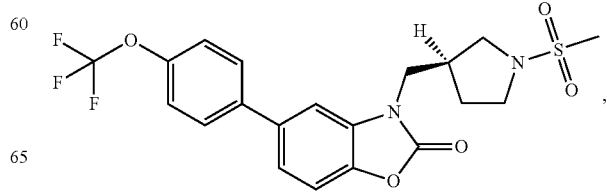

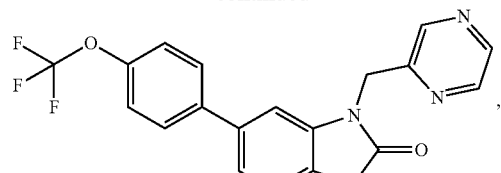
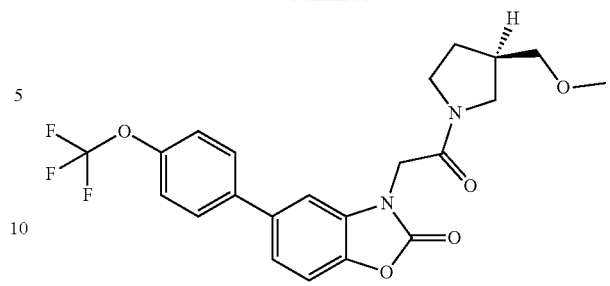
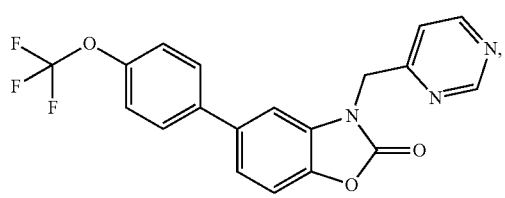
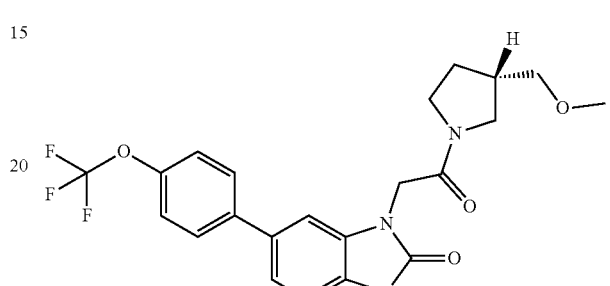
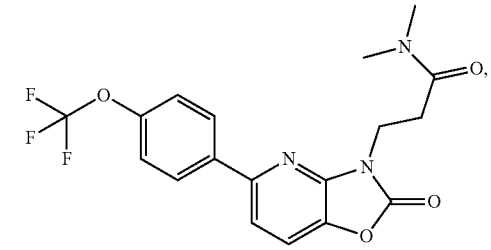
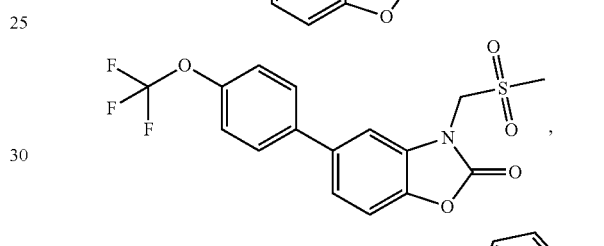
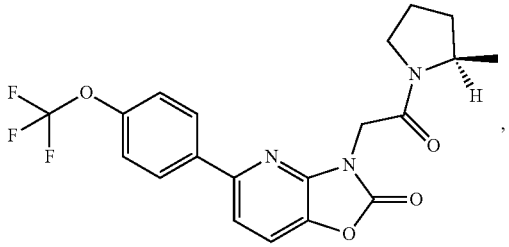
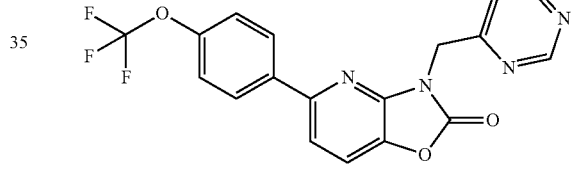
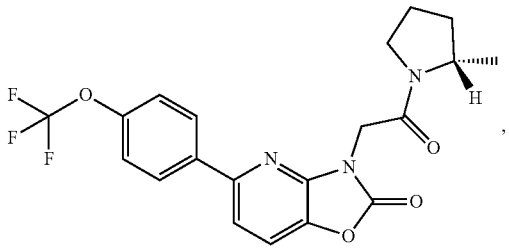
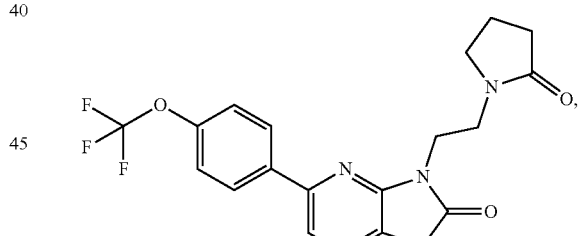
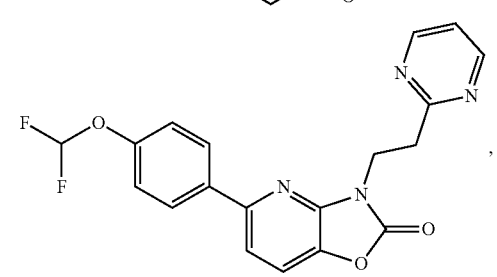
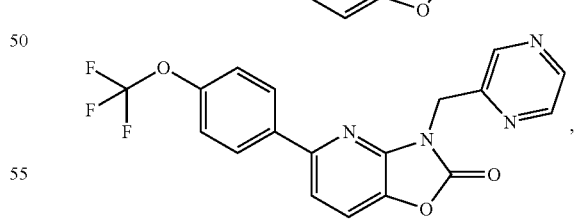
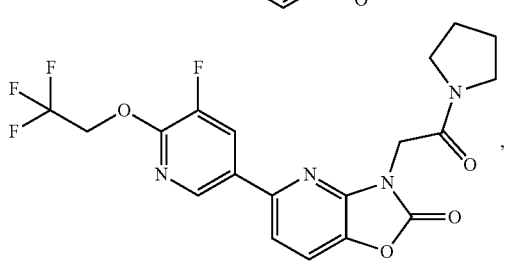
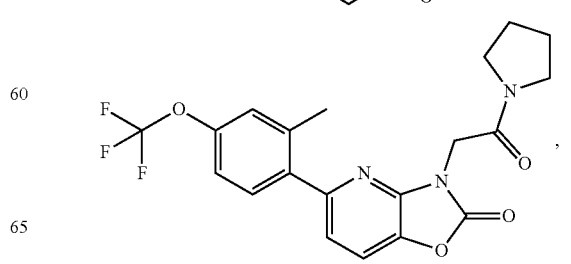

245
-continued
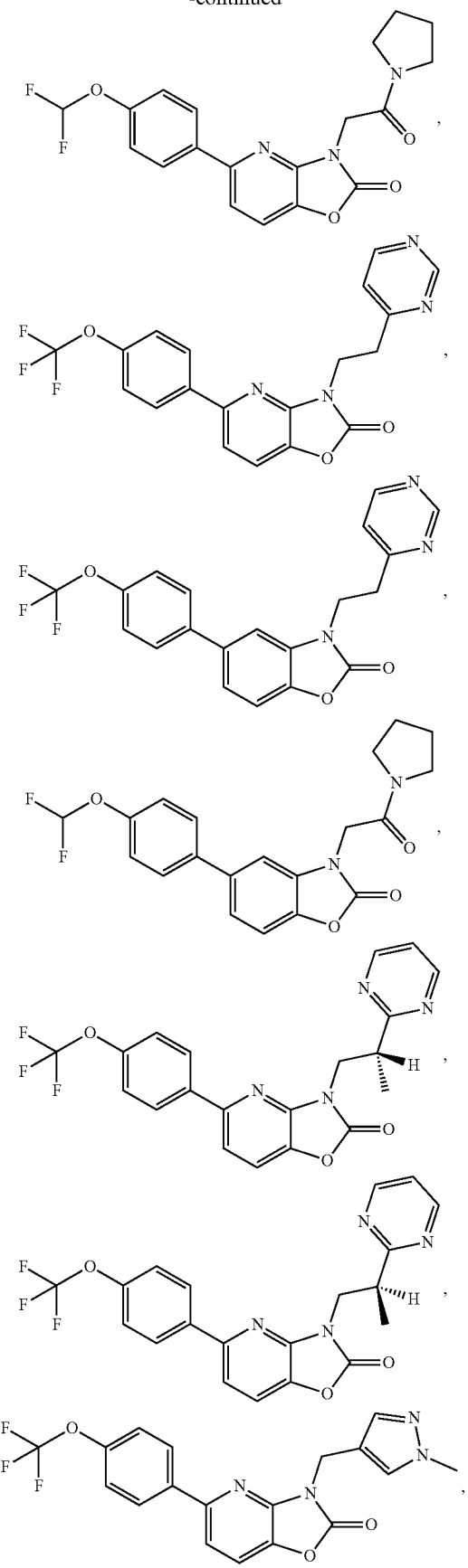
246
-continued
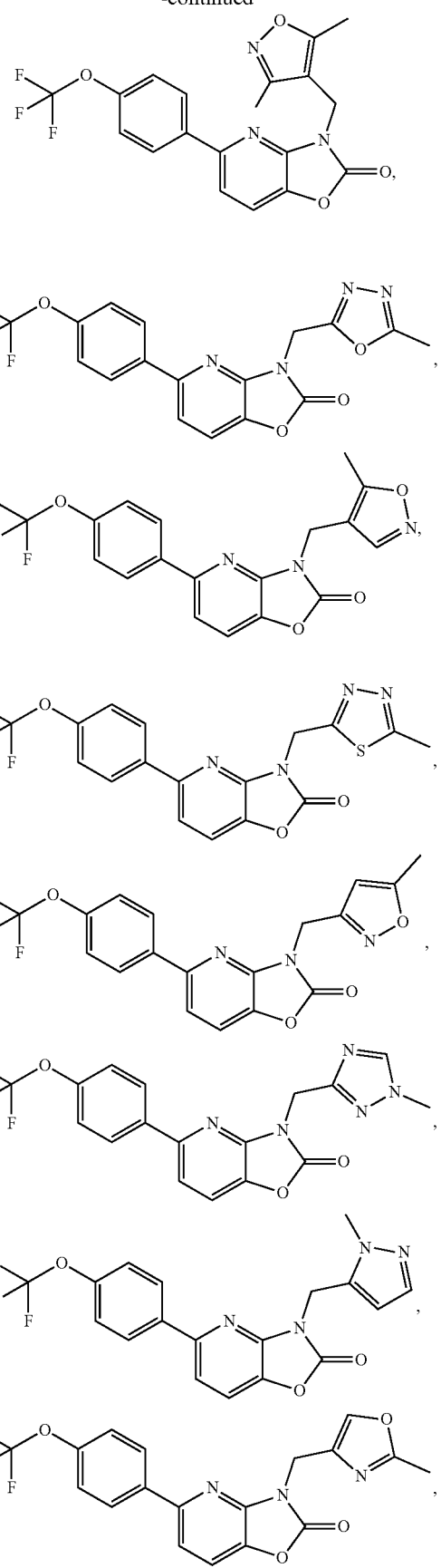

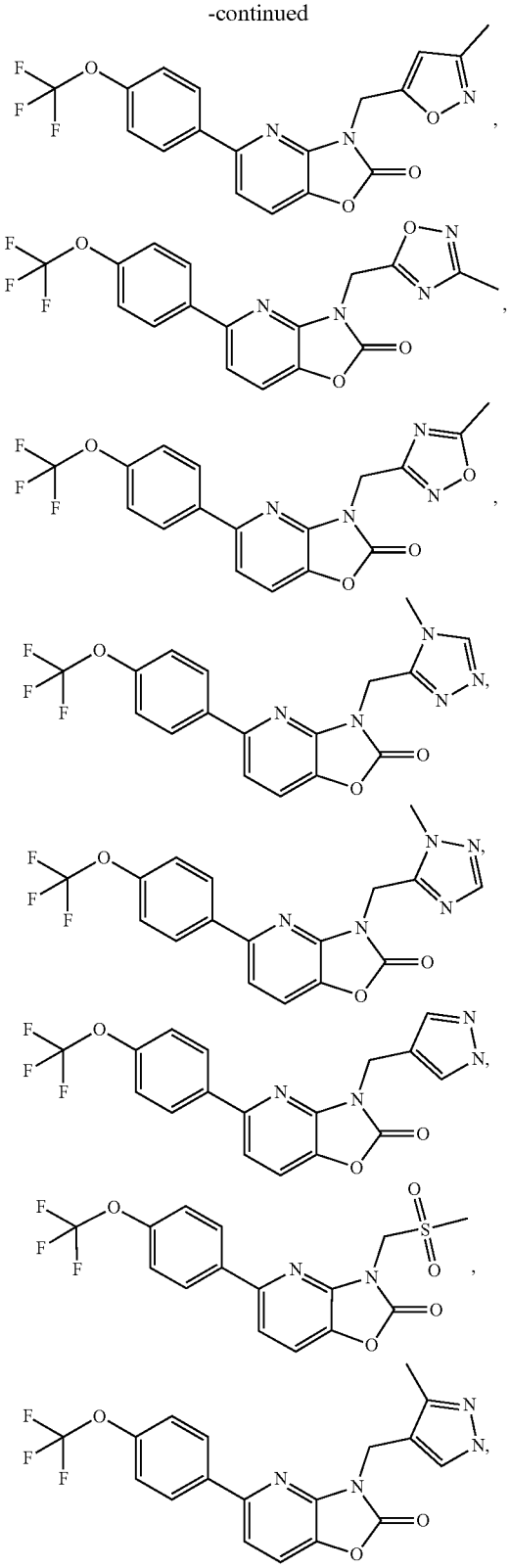

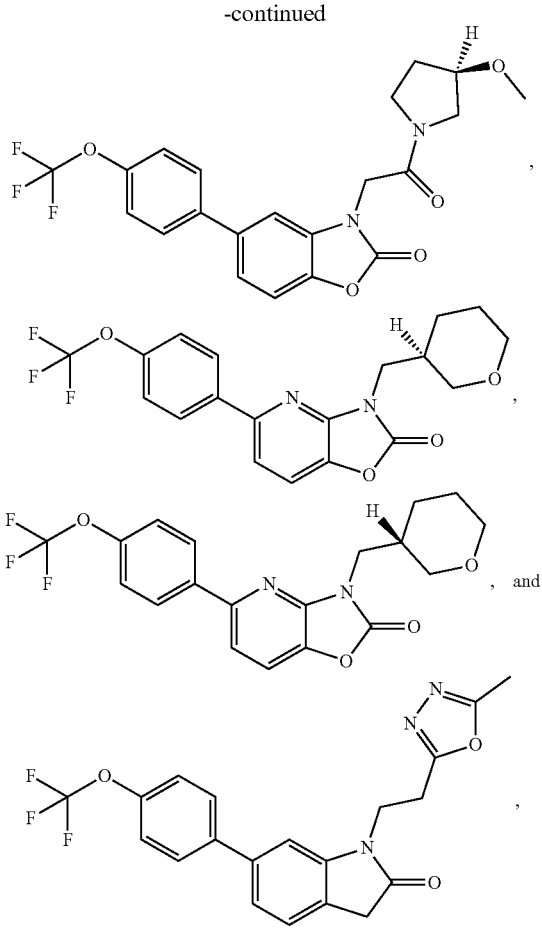

or a pharmaceutically acceptable salt thereof.

19. A pharmaceutical composition comprising a compound of claim 1, or a pharmaceutically acceptable salt thereof, and a pharmaceutically acceptable carrier.

20. A method of treating a neurological disorder or a psychiatric disorder, wherein the method comprises administering to a subject in need thereof a compound of claim 1, or a pharmaceutically acceptable salt thereof.

21. The method of claim 20, wherein the neurological disorder is epilepsy, an epilepsy syndrome, a neurodevelopmental disorder, or a neuromuscular disorder.

22. A pharmaceutical composition comprising a compound of claim 18, or a pharmaceutically acceptable salt thereof, and a pharmaceutically acceptable carrier.

23. A method of treating a neurological disorder or a psychiatric disorder,
wherein the method comprises administering to a subject in need thereof a compound of claim 18, or a pharmaceutically acceptable salt thereof.

24. The method of claim 23, wherein the neurological disorder is epilepsy, an epilepsy syndrome, a neurodevelopmental disorder, or a neuromuscular disorder.

* * * * *